(12) United States Patent
Connor

(10) Patent No.: US 10,607,507 B2
(45) Date of Patent: Mar. 31, 2020

(54) ARCUATE WEARABLE DEVICE WITH A CIRCUMFERENTIAL OR ANNULAR ARRAY OF SPECTROSCOPIC SENSORS FOR MEASURING HYDRATION LEVEL

(71) Applicant: Robert A. Connor, St. Paul, MN (US)

(72) Inventor: Robert A. Connor, St. Paul, MN (US)

(73) Assignee: Medibotics, St. Paul, MN (US)

(*) Notice: Subject to any disclaimer, the term of this patent is extended or adjusted under 35 U.S.C. 154(b) by 351 days.

(21) Appl. No.: 15/725,330

(22) Filed: Oct. 5, 2017

(65) Prior Publication Data
US 2018/0042513 A1    Feb. 15, 2018

Related U.S. Application Data

(63) Continuation-in-part of application No. 15/431,769, filed on Feb. 14, 2017, and a continuation-in-part of
(Continued)

(51) Int. Cl.
| | |
|---|---|
| *G01N 21/27* | (2006.01) |
| *G01N 21/3554* | (2014.01) |
| *G01J 3/10* | (2006.01) |
| *G01J 3/02* | (2006.01) |
| *A61B 5/00* | (2006.01) |
| *A61B 5/1455* | (2006.01) |
| *A61B 5/145* | (2006.01) |
| *G09B 23/28* | (2006.01) |

(Continued)

(52) U.S. Cl.
CPC .......... *G09B 23/28* (2013.01); *A61B 5/0075* (2013.01); *A61B 5/1455* (2013.01); *A61B 5/4875* (2013.01); *A61B 5/681* (2013.01); *A61B 5/6824* (2013.01); *A61B 5/6831* (2013.01); *G01J 3/0264* (2013.01); *G01J 3/108* (2013.01); *G01N 21/27* (2013.01); *G01N 21/3554* (2013.01); *G06K 9/2018* (2013.01); *G09B 19/00* (2013.01); *A61B 2562/04* (2013.01)

(58) Field of Classification Search
CPC combination set(s) only.
See application file for complete search history.

(56) References Cited

U.S. PATENT DOCUMENTS

| | | |
|---|---|---|
| 6,614,238 B1 | 9/2003 | Jean et al. |
| 6,987,393 B2 | 1/2006 | Jean et al. |
| | (Continued) | |

OTHER PUBLICATIONS

Babajanyan et al., 2010, "Real-Time Noninvasive Measurement of Glucose Concentration Using a Microwave Biosensor," Journal of Sensors, vol. 2010, Dec. 29, 2010.
(Continued)

*Primary Examiner* — Jacqueline Cheng
*Assistant Examiner* — Tho Q Tran

(57) ABSTRACT

This invention is an arcuate wearable device with a circumferential or annular array of spectroscopic sensors which measures a person's body hydration. In an example, this invention can be embodied in a modular smart watch band, a specialized hydration-monitoring band, or a finger ring. A circumferential or annular array of spectroscopic sensors helps to ensure continuous measurement of body hydration, even if a wearable device shifts and/or rotates on a person's wrist, arm, or finger.

1 Claim, 52 Drawing Sheets

Related U.S. Application Data application No. 14/951,475, filed on Nov. 24, 2015, now Pat. No. 10,314,492.

(60) Provisional application No. 62/549,587, filed on Aug. 24, 2017, provisional application No. 62/439,147, filed on Dec. 26, 2016.

(51) Int. Cl.
*G09B 19/00* (2006.01)
*G06K 9/20* (2006.01)

(56) References Cited

U.S. PATENT DOCUMENTS

| | | | |
|---|---|---|---|
| 7,371,217 B2 | 5/2008 | Kim et al. | |
| 7,627,357 B2 | 12/2009 | Zribi et al. | |
| 7,680,522 B2 | 3/2010 | Andersohn et al. | |
| 8,199,007 B2 | 6/2012 | Coakley et al. | |
| 8,515,517 B2 | 8/2013 | Hayter et al. | |
| 8,613,892 B2 | 12/2013 | Stafford | |
| 8,868,147 B2 | 10/2014 | Stippick et al. | |
| 8,930,145 B2 | 1/2015 | Li et al. | |
| 8,961,415 B2 | 2/2015 | LeBoeuf et al. | |
| 8,989,230 B2 | 3/2015 | Dummer et al. | |
| 9,037,204 B2 | 5/2015 | Schlottau | |
| 9,061,899 B2 | 6/2015 | Rowe et al. | |
| 9,134,175 B2 | 9/2015 | Matsushita | |
| 10,271,745 B2 * | 4/2019 | Gu | A61B 5/02433 |
| 2008/0200790 A1 | 8/2008 | Kim et al. | |
| 2008/0319299 A1 | 12/2008 | Stippick et al. | |
| 2009/0018420 A1 | 1/2009 | White | |
| 2009/0105605 A1 | 4/2009 | Abreu | |
| 2010/0249546 A1 | 9/2010 | White | |
| 2010/0268056 A1 * | 10/2010 | Picard | A61B 5/0531 600/388 |
| 2012/0056289 A1 | 3/2012 | Tian et al. | |
| 2012/0310055 A1 | 12/2012 | Jean | |
| 2013/0041235 A1 | 2/2013 | Rogers et al. | |
| 2013/0197319 A1 | 8/2013 | Monty et al. | |
| 2013/0199822 A1 | 8/2013 | Fan et al. | |
| 2013/0248380 A1 | 9/2013 | Cui | |
| 2014/0009638 A1 | 1/2014 | Baraniuk et al. | |
| 2014/0058220 A1 | 2/2014 | LeBoeuf et al. | |
| 2014/0064315 A1 | 3/2014 | Dummer et al. | |
| 2014/0107493 A1 * | 4/2014 | Yuen | A61B 5/0205 600/473 |
| 2014/0148658 A1 | 5/2014 | Zalevsky et al. | |
| 2014/0221792 A1 | 8/2014 | Miller et al. | |
| 2014/0316230 A1 | 10/2014 | Denison et al. | |
| 2014/0339438 A1 | 11/2014 | Correns et al. | |
| 2015/0005644 A1 | 1/2015 | Rhoads | |
| 2015/0015888 A1 | 1/2015 | Gulati et al. | |
| 2015/0018647 A1 * | 1/2015 | Mandel | A61B 5/14552 600/323 |
| 2015/0036138 A1 | 2/2015 | Watson et al. | |
| 2015/0073723 A1 | 3/2015 | Mulligan et al. | |
| 2015/0094551 A1 | 4/2015 | Frix et al. | |
| 2015/0099943 A1 | 4/2015 | Russell | |
| 2015/0112170 A1 | 4/2015 | Amerson et al. | |
| 2015/0126824 A1 | 5/2015 | LeBoeuf et al. | |
| 2015/0126825 A1 | 5/2015 | LeBoeuf et al. | |
| 2015/0130633 A1 | 5/2015 | Grubstein et al. | |
| 2015/0130634 A1 | 5/2015 | Grubstein et al. | |
| 2015/0135118 A1 | 5/2015 | Grubstein et al. | |
| 2015/0141769 A1 | 5/2015 | Mulligan et al. | |
| 2015/0148623 A1 | 5/2015 | Benaron | |
| 2015/0148624 A1 | 5/2015 | Benaron | |
| 2015/0148632 A1 | 5/2015 | Benaron | |
| 2015/0148636 A1 | 5/2015 | Benaron | |
| 2015/0157219 A1 * | 6/2015 | Lee | A61B 5/0531 600/393 |
| 2015/0168217 A1 | 6/2015 | Englund et al. | |
| 2015/0192462 A1 | 7/2015 | Schiering et al. | |
| 2015/0216454 A1 | 8/2015 | Kasahara et al. | |
| 2015/0216479 A1 | 8/2015 | Abreu | |
| 2015/0216484 A1 | 8/2015 | Kasahara et al. | |
| 2015/0224275 A1 | 8/2015 | Pastoor et al. | |
| 2015/0233762 A1 | 8/2015 | Goldring et al. | |
| 2015/0238083 A1 | 8/2015 | Faubert et al. | |
| 2015/0260573 A1 | 9/2015 | Ishimaru | |
| 2015/0305674 A1 | 10/2015 | McPherson et al. | |
| 2017/0014040 A1 * | 1/2017 | Shim | A61B 5/7221 |
| 2017/0071518 A1 | 3/2017 | Da Silveira et al. | |
| 2017/0079535 A1 * | 3/2017 | Tchertkov | A61B 5/02427 |
| 2017/0188668 A1 * | 7/2017 | Watterson | A44C 5/0015 |

OTHER PUBLICATIONS

Caduff et al., 2009, "Non-Invasive Glucose Monitoring in Patients with Type 1 Diabetes: A Multisensor System Combining Sensors for Dielectric and Optical Characterisation of Skin," Biosensors and Bioelectronics, 24, 2009, 2778-2784.

Caduff et al., 2011, "Characteristics of a Multisensor System for Non-Invasive Glucose Monitoring with External Validation and Prospective Evaluation," Biosensors and Bioelectronics, 26, 2011, 3794-3800.

Caduff et al., 2015, "Glucose Detection from Skin Dielectric Measurements," Dielectric Relaxation in Biological Systems, Oxford University Press, 2015.

Chien et al., 2015, "A Microwave Reconfigurable Dielectric-Based Glucose Sensor with 20 mg/dL Sensitivity at Sub-nL Sensing Volume in CMOS," IEEE, 2015.

Choi et al., 2014, "Design of Continuous Non-Invasive Blood Glucose Monitoring Sensor Based on a Microwave Split Ring Resonator," RF Wireless Technology Biomedical Healthcare Applications; IEEE MTT-S International Microwave Workshop Series, London, Dec. 8-10, 2014, 1-3.

Choi et al., 2015, "Design and In Vitro Interference Test of Microwave Noninvasive Blood Glucose Monitoring Sensor," IEEE Transactions on Microwave Theory and Techniques, 63(10), Oct. 2015.

Fallon, 2013, "Wearable Tech Company Revolutionizes Health Monitor," Business News Daily, Oct. 29, 2013.

Fu et al., 2015, "Study on a Glucose Concentration Measurement System Based on Microwave Perturbation Technique," Journal of Microwave Power and Electromagnetic Energy, 49(4), 2015, 215-224.

Gadawe et al., 2015, "Non Invasive Microwave Sensor for Near Field Biological Applications," Intl. Journal of Innovative Research in Computer and Communication Engineering, 3(5), May 2015, 4641-4647.

Green, et al., 2005, "Design of a Microwave Sensor for Non-Invasive Determination of Blood-Glucose Concentration," MS Thesis, Dept. of Electrical and Computer Engineering, Baylor University, 2005.

Guarin et al., 2013, "Microwave-Based Noninvasive Concentration Measurements for Biomedical Applications," IEEE Newsletter, Jul. 2013, http://lifesciences.ieee.org/publications/newsletter/july-2013/374-microwave-based-noninvasive-sensors-for-biomedical-applications.

Hadkar et al., 2015, "Design of Square Shaped Miniaturized Split Ring Resonators," Int. Journal of Engineering Research and Applications, 5(5), Part 4, May 2015, 11-14.

Jean et al., 2008, "A Microwave Frequency Sensor for Non-Invasive Blood-Glucose Measurement," IEEE Sensors Applications Symposium, Atlanta, GA, Feb. 12-14, 2008, 4-7.

Jean, B., 2016, "Non-Invasive Blood Glucose Analysis Through Use of High Frequency Measurement of the Dielectric Constant," http://web.ecs.baylor.edu/faculty/jean/research/blood.htm.

Kim et al., 2008, "Microwave Dielectric Resonator Biosensor for Aqueous Glucose Solution," Review of Scientific Instruments, 79(8), 2008, 1-3.

Kim et al., 2014, "A Reusable Robust Radio Frequency Biosensor Using Microwave Resonator by Integrated Passive Device Technology for Quantitative Detection of Glucose Level," Biosensors and Bioelectronics, vol. 67, May 15, 2015, 687-693.

(56) References Cited

OTHER PUBLICATIONS

Kim et al., 2015, "Rapid, Sensitive, and Reusable Detection of Glucose by a Robust Radiofrequency Integrated Passive Device Biosensor Chip," Scientific Reports, 5, 7807, Jan. 15, 2015.
Kumar et al., 2013, "Measuring Blood Glucose Levels with Microwave Sensor," International Journal of Computer Applications, 72(15), Jun. 4-9, 2013.
Mazady, A., 2014, "Non-Invasive Glucose Meter," Electrical and Computer Engineering Department, University of Connecticut, Nov. 15, 2014, http://www.engr.uconn.edu/~mam10069/Docs/NonInvasiveGlucoseMeasurement.pdf.
Tao et al., 2011, "Metamaterials on Paper as a Sensing Platform," Advanced Materials, 23(28), Jul. 26, 2011, 3197-3201.
VRBA et al., 2015, "A Microwave Metamaterial Inspired Sensor for Non-Invasive Blood Glucose Monitoring," Radioengineering, 24(4), Dec. 2015, 877.
Wellenzohn et al., 2015, "A Theoretical Design of a Biosensor Device Based on Split Ring Resonators for Operation in the Microwave Regime," Procedia Engineering, 120, 2015, 865-869.

\* cited by examiner

ARCUATE WEARABLE DEVICE WITH A CIRCUMFERENTIAL OR ANNULAR ARRAY OF SPECTROSCOPIC SENSORS FOR MEASURING HYDRATION LEVEL

CROSS-REFERENCE TO RELATED APPLICATIONS

This patent application:

[A] is a CIP (continuation in part) of U.S. patent application Ser. No. 15/431,769 by Robert A. Connor entitled "Wearable Technology for Non-Invasive Glucose Monitoring" filed on Feb. 13, 2017 which—

(a) was a CIP of application Ser. No. 14/330,649 "Eyewear System for Monitoring and Modifying Nutritional Intake" filed Jul. 14, 2014 which was:
  (1) a CIP of application Ser. No. 13/523,739 "The Willpower Watch™: A Wearable Food Consumption Monitor" filed Jun. 14, 2012; and
  (2) a CIP of application Ser. No. 13/797,955 "Device for Selectively Reducing Absorption of Unhealthy Food" filed Mar. 12, 2013 which claimed the priority benefit of the priority benefit of provisional application 61/729,494 "Device for Selectively Reducing Absorption of Unhealthy Food" filed Nov. 23, 2012;

(b) was a CIP of application Ser. No. 14/992,073 "Wearable Device for the Ear with Electroencephalographic and Spectroscopic Sensors" filed Jan. 11, 2016 which was:
  (1) a CIP of application Ser. No. 14/599,522 "Mobile Wearable Electromagnetic Brain Activity Monitor" filed Jan. 18, 2015 which in turn was: a CIP of application Ser. No. 14/562,719 "Willpower Glasses™: A Wearable Food Consumption Monitor" filed Dec. 7, 2014 which claimed the priority benefit of provisional application 61/932,517 "Nutrode™: Wearable EEG Monitor for Modifying Food Consumption" filed Jan. 28, 2014; claimed the priority benefit of provisional application 61/932,517 "Nutrode™: Wearable EEG Monitor for Modifying Food Consumption" filed Jan. 28, 2014; claimed the priority benefit of provisional application 61/939,244 "Brainwave-Controlled Eyewear" filed Feb. 12, 2014; claimed the priority benefit of provisional application 62/017,615 "Nervision™ Integrated Eyewear and EEG Monitor" filed Jun. 26, 2014; and claimed the priority benefit of provisional application 62/089,696 "Electroencephalographic Eyewear" filed Dec. 6, 2014;
  (2) a CIP of application Ser. No. 14/550,953 "Wearable Food Consumption Monitor" filed Nov. 22, 2014; and
  (3) a CIP of application Ser. No. 13/616,238 "Interactive Voluntary and Involuntary Caloric Intake Monitor" filed Sep. 14, 2012;

(c) was a CIP of application Ser. No. 15/206,215 "Finger Ring with Electromagnetic Energy Sensor for Monitoring Food Consumption" filed Jul. 8, 2016 which
  (1) was a CIP of application Ser. No. 14/948,308 "Spectroscopic Finger Ring for Compositional Analysis of Food or Other Environmental Objects" filed Nov. 21, 2015 which, in turn, was: a CIP of application Ser. No. 13/901,099 "Smart Watch and Food-Imaging Member for Monitoring Food Consumption" filed May 23, 2013; a CIP of application Ser. No. 14/132,292 "Caloric Intake Measuring System using Spectroscopic and 3D Imaging Analysis" filed Dec. 18, 2013; and a CIP of application Ser. No. 14/449,387 "Wearable Imaging Member and Spectroscopic Optical Sensor for Food Identification and Nutrition Modification" filed Aug. 1, 2014;
  (2) was a CIP of application Ser. No. 14/951,475 "Wearable Spectroscopic Sensor to Measure Food Consumption Based on Interaction Between Light and the Human Body" filed Nov. 24, 2015 which, in turn, was: a CIP of application Ser. No. 13/901,131 "Smart Watch and Food Utensil for Monitoring Food Consumption" filed May 23, 2013; a CIP of application Ser. No. 14/071,112 "Wearable Spectroscopy Sensor to Measure Food Consumption" filed Nov. 4, 2013; a CIP of application Ser. No. 14/623,337 "Wearable Computing Devices and Methods for the Wrist and/or Forearm" filed Feb. 16, 2015; and claimed the priority benefit of provisional application 62/245,311 "Wearable Device for the Arm with Close-Fitting Biometric Sensors" filed Oct. 23, 2015; and
  (3) claimed the priority benefit of provisional application 62/349,277 "Glucowear™ System for Monitoring and Managing Intra-body Glucose Levels" filed Jun. 13, 2016;

(d) was a CIP of application Ser. No. 15/236,401 "Wearable Brain Activity Monitor" filed Aug. 13, 2016 which:
  (1) was a CIP of application Ser. No. 15/136,948 "Wearable and Mobile Brain Computer Interface (BCI) Device and Method" filed Apr. 24, 2016 which: was a CIP of application Ser. No. 14/599,522 "Mobile Wearable Electromagnetic Brain Activity Monitor" filed Jan. 18, 2015 which: was a CIP of application Ser. No. 14/562,719 "Willpower Glasses™: A Wearable Food Consumption Monitor" filed Dec. 7, 2014 which claimed the priority benefit of provisional application 61/932,517 "Nutrode™: Wearable EEG Monitor for Modifying Food Consumption" filed Jan. 28, 2014; claimed the priority benefit of provisional application 61/932,517 "Nutrode™: Wearable EEG Monitor for Modifying Food Consumption" filed Jan. 28, 2014; claimed the priority benefit of provisional application 61/939,244 "Brainwave-Controlled Eyewear" filed Feb. 12, 2014; claimed the priority benefit of provisional application 62/017,615 "Nervision™ Integrated Eyewear and EEG Monitor" filed Jun. 26, 2014; and claimed the priority benefit of provisional application 62/089,696 "Electroencephalographic Eyewear" filed Dec. 9, 2014;
  (2) claimed the priority benefit of provisional application 62/160,172 "Hair-Engaging Mobile Brain Activity Monitor" filed May 12, 2015;
  (3) claimed the priority benefit of provisional application 62/169,661 "Internet of Thinks (IoT): A Brain Computer Interface (BCI) Using EEG Patterns Associated with the Same Command Across Different Action Modes" filed Jun. 2, 2015;
  (4) claimed the priority benefit of provisional application 62/303,126 "Undulating Mobile EEG Monitor Spanning a Portion of the Forehead" filed Mar. 3, 2016;
  (5) claimed the priority benefit of provisional application 62/322,594 "Halo-Style Mobile Electroencephalographic (EEG) Monitor" filed Apr. 14, 2016; and (6) was a CIP of application Ser. No. 14/599,522 "Mobile Wearable Electromagnetic Brain Activity Monitor" filed Jan. 18, 2015 which: was a CIP of application Ser. No. 14/562,719 "Willpower Glasses™: A Wearable Food Consumption Monitor" filed Dec. 7, 2014 which claimed the priority benefit of provisional application 61/932,517 "Nutrode™: Wearable EEG Monitor for Modifying Food Consumption" filed Jan. 28, 2014; claimed the priority benefit of provisional application 61/932,517 "Nutrode™: Wearable EEG Monitor for Modifying Food Consumption" filed Jan. 28, 2014; claimed the priority benefit of provisional application 61/939,244 "Brainwave-Controlled Eyewear" filed Feb. 12, 2014; claimed the priority benefit of provisional application 62/017,615 "Nervision™ Integrated Eyewear and EEG Monitor" filed Jun. 26, 2014; and claimed the priority benefit of provisional application 62/089,696 "Electroencephalographic Eyewear" filed Dec. 9, 2014;

(e) was a CIP of application Ser. No. 15/294,746 "Wearable Device for the Arm with Close-Fitting Biometric Sensors" filed Oct. 16, 2016 which:
  (1) was a CIP of application Ser. No. 14/623,337 "Wearable Computing Devices and Methods for the Wrist and/or Forearm" filed Feb. 16, 2015 which, in turn, claimed the priority benefit of: provisional application 61/944,090 "Wearable Computing Device for the Wrist and/or Arm" filed Feb. 25, 2014; provisional application 61/948,124 "Wearable Computing Device for the Wrist and/or Arm" filed Mar. 5, 2014; provisional application 62/100,217 "Forearm Wearable Device with Distal-to-Proximal Flexibly-Connected Display Modules" filed Jan. 6, 2015; provisional application 62/106,856 "Forearm Wearable Computing Device with Proximal and Distal Arcuate Bands" filed Jan. 23, 2015; provisional application 62/111,163 "Forearm-Wearable Computing Device with Large Display Area" filed Feb. 3, 2015; provisional application 62/113,423 "Sensor-Informed Modification of the Interface Modality Between a Human and a Wearable Computing Device" filed Feb. 7, 2015; and provisional application 62/115,691 "Adjustment of Wearable Computer-to-Human Interface Based on Environmental and/or Physiological Sensors" filed Feb. 13, 2015;
  (2) was a CIP of application Ser. No. 14/951,475 "Wearable Spectroscopic Sensor to Measure Food Consumption Based on Interaction Between Light and the Human Body" filed Nov. 24, 2015 which, in turn: (a) is a CIP of application Ser. No. 13/901,131 "Smart Watch and Food Utensil for Monitoring Food Consumption" filed May 23, 2013; (b) is a CIP of application Ser. No. 14/071,112 "Wearable Spectroscopy Sensor to Measure Food Consumption" filed Nov. 4, 2013; (c) is a CIP of application Ser. No. 14/623,337 "Wearable Computing Devices and Methods for the Wrist and/or Forearm" filed Feb. 16, 2015; and (d) claimed the priority benefit of provisional application 62/245,311 "Wearable Device for the Arm with Close-Fitting Biometric Sensors" filed Oct. 23, 2015;
  (3) claimed the priority benefit of provisional application 62/245,311 "Wearable Device for the Arm with Close-Fitting Biometric Sensors" filed Oct. 23, 2015; and
  (4) claimed the priority benefit of provisional application 62/349,277 "Glucowear™ System for Monitoring and Managing Intra-body Glucose Levels" filed Jun. 13, 2016;
  (f) claimed the priority benefit of provisional application 62/311,462 "Glucowear™ Automated Closed-Loop System for Glycemic Control" filed Mar. 22, 2016;
  (g) claimed the priority benefit of provisional application 62/349,277 "Glucowear™ System for Monitoring and Managing Intra-body Glucose Levels" filed Jun. 13, 2016; and
  (h) claimed the priority benefit of provisional application 62/439,147 "Arcuate Wearable Device for Measuring Body Hydration and/or Glucose Level" filed Dec. 26, 2016;

[B] is a CIP of U.S. patent application Ser. No. 14/951,475 by Robert A. Connor entitled "Wearable Spectroscopic Sensor to Measure Food Consumption Based on Interaction Between Light and the Human Body" filed on Nov. 24, 2015 which:
  (a) was a CIP of U.S. patent application Ser. No. 13/901,131 by Robert A. Connor entitled "Smart Watch and Food Utensil for Monitoring Food Consumption" filed on May 23, 2013;
  (b) was a CIP of U.S. patent application Ser. No. 14/071,112 by Robert A. Connor entitled "Wearable Spectroscopy Sensor to Measure Food Consumption" filed on Nov. 4, 2013;
  (c) was a CIP of U.S. patent application Ser. No. 14/623,337 by Robert A. Connor entitled "Wearable Computing Devices and Methods for the Wrist and/or Forearm" filed on Feb. 16, 2015; and
  (d) claimed the priority benefit of U.S. provisional patent application 62/245,311 by Robert A. Connor entitled "Wearable Device for the Arm with Close-Fitting Biometric Sensors" filed on Oct. 23, 2015;

[C] claims the priority benefit of U.S. provisional patent application 62/439,147 by Robert A. Connor entitled "Arcuate Wearable Device for Measuring Body Hydration and/or Glucose Level" filed on Dec. 26, 2016; and

[D] claims the priority benefit of U.S. provisional patent application 62/549,587 by Robert A. Connor entitled "Wearable Band with a Circumferential Array of Sequentially-Activated Light Emitters for Biometric Measurement" filed on Aug. 24, 2017.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable devices for measuring a person's body hydration level.

INTRODUCTION

Maintaining proper body hydration is important for a person's health, especially during times of intense physical exertion or high ambient temperature. Body dehydration can cause significant health problems such as: heat injury ranging from mild cramps to heatstroke; urinary tract infections and kidney failure; electrolyte imbalance leading to muscle contractions and loss of consciousness; and hypovolemic shock with decreased blood pressure and low blood oxygenation. Many people, especially older people, do not realize that they are becoming dehydrated until an adverse health event occurs.

REVIEW OF THE RELEVANT ART

There is considerable prior art focused toward non-invasive measurement of body glucose level. Some of the work toward glucose measurement can also be applicable for measuring body hydration, so some key disclosures in the field of non-invasive glucose measurement are included in this review. There is also some, albeit less, relevant art which is explicitly focused on measuring body hydration level. This includes U.S. patent applications 20140221792 (Miller et al., Aug. 7, 2014, "Hydration Monitoring Apparatus"), 20150305674 (McPherson et al., Oct. 29, 2015, "Systems and Methods for Measuring Hydration in a Human Subject"), and 20170071518 (Xavier Da Silveira et al., Mar. 16, 2017, "Apparatus and Method for Optical Tissue Detection"). However, the prior art does not appear to disclose an arcuate wearable device with a circumferential or annular array of spectroscopic sensors for measuring a person's hydration level.

Relevant art in the patent literature, sorted by date, includes the following:

U.S. Pat. No. 6,614,238 (Jean et al., Sep. 2, 2003, "A Microwave Sensor Having Improved Sensitivity") discloses the use of a microwave sensor for measuring the permittivity of tested material. U.S. Pat. No. 6,987,393 (Jean et al., Jan. 17, 2006, "Ultra Wideband Pulse Dispersion Spectrometry Method and Apparatus Providing Multi-Component Composition Analysis") and U.S. Patent Application 20120310055 (Jean, B., Dec. 6, 2012, "Ultra-Wide Band Non-Invasive Biological Sensor and Method") disclose the use of microwave spectroscopy for measuring the permittivity of tested material. U.S. Pat. No. 7,371,217 (Kim et al., May 13, 2008, "Device for the Non-Invasive Measurement of Blood Glucose Concentrations by Millimeter Waves and Method Thereof") discloses the use of a rectangular waveguide for measuring glucose concentration.

U.S. Patent Application 20080200790 (Kim et al., Aug. 21, 2008, "Apparatus for Measuring Blood Sugar and Apparatus for Monitoring Blood Sugar Comprising the Same") discloses the use of finger-contact microwave sensor to measure blood sugar. U.S. Patent Application 20080319299 (Stippick et al., Dec. 25, 2008, "Method and Apparatus for Controlling Positioning of a Noninvasive Analyzer Sample Probe") discloses a probe interface method and apparatus for use in conjunction with an optical based noninvasive analyzer, wherein an algorithm controls a sample probe position and attitude relative to a skin sample site before and/or during sampling. U.S. Patent Application 20090018420 (White, Jan. 15, 2009, "Apparatus for Non-Invasive Spectroscopic Measurement of Analytes, and Method of Using the Same") discloses an apparatus for spectroscopic evaluation of a subject's body fluids at the interstitial region adjacent to or in between a subject's extremities.

U.S. Patent Application 20090105605 (Abreu, Apr. 23, 2009, "Apparatus and Method for Measuring Biologic Parameters") discloses a sensor fitted on support structures using a special geometry for acquiring continuous and undisturbed data on the physiology of the body. U.S. Pat. No. 7,627,357 (Zribi et al., Dec. 1, 2009, "System and Method for Non-Invasive Glucose Monitoring") discloses a method for determining analyte concentration levels by scattering radiation off, or through, a target. U.S. Pat. No. 7,680,522 (Andersohn et al., Mar. 16, 2010, "Method and Apparatus for Detecting Misapplied Sensors") discloses a method and system for determining whether a spectrophotometric sensor is misapplied.

U.S. Patent Application 20100249546 (White, Sep. 30, 2010, "Apparatus for Non-Invasive Spectroscopic Measurement of Analytes, and Method of Using the Same") discloses an apparatus for spectroscopic evaluation of a subject's body fluids at the interstitial region adjacent to or in between a subject's extremities. U.S. Patent Application 20120056289 (Tian et al., Mar. 8, 2012, "Materials, Systems and Methods for Optoelectronic Devices") discloses a photodetector comprising an integrated circuit and at least two optically sensitive layers. U.S. Pat. No. 8,199,007 (Coakley et al., Jun. 12, 2012, "Flex Circuit Snap Track for a Biometric Sensor") discloses a sensor assembly configured to house an optical component.

U.S. Patent Application 20130041235 (Rogers et al., Feb. 14, 2013, "Flexible and Stretchable Electronic Systems for Epidermal Electronics") discloses skin-mounted biomedical devices and methods of making and using biomedical devices for sensing and actuation applications. U.S. Patent Application 20130197319 (Monty et al., Aug. 1, 2013, "Flexible Electrode for Detecting Changes in Temperature, Humidity, and Sodium Ion Concentration in Sweat") discloses a flexible sensor suitable for contact with skin comprising: a nanocomposite; and a top layer; where the sensor provides in-situ detection in sweat or other aqueous body fluids at the skin surface of at least one physiological parameter selected from the group consisting of a physiological salt component, temperature, moisture, humidity, or combinations thereof.

U.S. Patent Application 20130199822 (Fan et al., Aug. 8, 2013, "Flexible, Permeable, Electrically Conductive and Transparent Textiles and Methods for Making Them") discloses methods for forming a flexible, permeable, electrically conductive and substantially transparent textile utilizing vapor phase deposition. U.S. Pat. No. 8,515,517 (Hayter et al., Aug. 20, 2013, "Method and System for Dynamically Updating Calibration Parameters for an Analyte Sensor") discloses methods and apparatuses for determining and dynamically updating a calibration parameter. U.S. Patent Application 20130248380 (Cui, Sep. 26, 2013, "Flexible Graphene Biosensor") discloses a biosensor comprising a graphene electrode linked to a biosensing element a linker, wherein the biosensing element is bonded to a flexible substrate. U.S. Pat. No. 8,613,892 (Stafford, Dec. 24, 2013, "Analyte Meter with a Moveable Head and Methods of Using the Same") discloses in vitro analyte meters with moveable meter portions.

U.S. Patent Application 20140009638 (Baraniuk et al., Jan. 9, 2014, "Dual-Port Measurements of Light Reflected from Micromirror Array") discloses an imaging system and method that captures compressive sensing (CS) measurements of a received light stream and also obtains samples of background light level (BGLL). U.S. Patent Application 20140058220 (LeBoeuf et al., Feb. 7, 2014, "Apparatus, Systems and Methods for Obtaining Cleaner Physiological Information Signals") discloses real-time, noninvasive health and environmental monitors including a plurality of compact sensors integrated within small, low-profile devices, such as earpiece modules. U.S. Patent Application 20140064315 (Dummer et al., Mar. 6, 2014, "Method and Apparatus Including Movable-Mirror MEMS-Tuned Surface-Emitting Lasers") discloses a VCSEL apparatus having a substrate, a solid-state gain medium, a reflective mirror on one side of the medium, a movable reflective mirror on an opposite side of the medium, and a mechanism configured to move the movable mirror to tune a characteristic wavelength.

U.S. Patent Application 20140148658 (Zalevsky et al., May 29, 2014, "Method and System for Non-Invasively Monitoring Biological or Biochemical Parameters of Individual") discloses a system and method which measures speckle patterns generated by a portion of a person's body. U.S. Patent Application 20140221792 (Miller et al., Aug. 7, 2014, "Hydration Monitoring Apparatus") discloses a hydration monitoring apparatus that uses biometric, biological, and/or physiological measurements to estimate a person's hydration level and notifies the person if they are getting dehydrated. U.S. Pat. No. 8,868,147 (Stippick et al., Oct. 21, 2014, "Method and Apparatus for Controlling Positioning of a Noninvasive Analyzer Sample Probe") discloses a probe interface method and apparatus for use in conjunction with an optical based noninvasive analyzer.

U.S. Patent Application 20140316230 (Denison et al., Oct. 23, 2014, "Methods and Devices for Brain Activity Monitoring Supporting Mental State Development and Training") discloses an electromagnetic brain activity sensors in contact with a person's head via an arcuate member which loops around the rear portion of a person's head, from one side to the other side. U.S. Patent Application 20140339438 (Correns et al., Nov. 20, 2014, "Devices and Methods for Spectroscopic Analysis") discloses devices and methods for spectrometric analysis of light-emitting samples. U.S. Patent Application 20150005644 (Rhoads, Jan. 1, 2015, "Dermoscopic Data Acquisition Employing Display Illumination") discloses use of a smartphone camera to gather skin imagery while controlled spectral illumination is emitted from the smartphone display.

U.S. Pat. No. 8,930,145 (Li et al., Jan. 6, 2015, "Light Focusing Continuous Wave Photoacoustic Spectroscopy and Its Applications to Patient Monitoring") discloses systems and methods that use spatial modulation to focus continuous wave light into a localized region of interest such as an individual blood vessel. U.S. Patent Application 20150015888 (Gulati et al., Jan. 15, 2015, "Dynamic Radially Controlled Light Input to a Noninvasive Analyzer Apparatus and Method of Use Thereof") discloses an analyzer apparatus and method to dynamically irradiate a sample with incident light where the incident light is varied in time in terms of any of: position, radial position relative to a point of the skin of a subject, solid angle, incident angle, depth of focus, energy, and/or intensity. U.S. Patent Application 20150036138 (Watson et al., Feb. 5, 2015, "Analyzing and Correlating Spectra, Identifying Samples and Their Ingredients, and Displaying Related Personalized Information") describes obtaining two spectra from the same sample under two different conditions at about the same time for comparison.

U.S. Pat. No. 8,961,415 (LeBoeuf et al., Feb. 24, 2015, "Methods and Apparatus for Assessing Physiological Conditions") discloses monitoring apparatuses and methods to detect physiological information from a subject such as heart rate, subject activity level, subject tympanic membrane temperature, and subject breathing rate. U.S. Patent Application 20150073723 (Mulligan et al., Mar. 12, 2015, "Non-invasive Hydration Monitoring") discloses novel tools and techniques for assessing, predicting and/or estimating the hydration of a patient and/or an amount of fluid needed for effective hydration of the patient. U.S. Pat. No. 8,989,230 (Dummer et al., Mar. 24, 2015, "Method and Apparatus Including Movable-Mirror MEMS-Tuned Surface-Emitting Lasers") discloses an apparatus having a substrate, a solid-state gain medium, a reflective mirror on one side of the medium, a movable reflective mirror on an opposite side of the medium, and a mechanism configured to move the movable mirror to tune a characteristic wavelength.

U.S. Patent Application 20150094551 (Frix et al., Apr. 2, 2015, "Continuous Transdermal Monitoring System and Method") discloses methods and systems for continuous transdermal monitoring ("CTM") with a pulse oximetry sensor having a plurality of light detectors arranged as an array. U.S. Patent Application 20150099943 (Russell, Apr. 9, 2015, "Wearable Physiological Sensing Device with Optical Pathways") discloses a wearable physiological sensing device may with at least one light source; a first light pipe coupled with the at least one light source, the first light pipe at least partially circumscribing an extremity of a patient, and at least one aperture for radiating light from the light source into the extremity. U.S. Patent Application 20150112170 (Amerson et al., Apr. 23, 2015, "Device and Method for Non-Invasive Glucose Monitoring") discloses a device and method for non-invasively measuring analytes and physiological parameters measuring terahertz radiation emitted though biological tissue.

U.S. Patent Application 20150126824 (LeBoeuf et al., May 7, 2015, "Apparatus for Assessing Physiological Conditions") discloses monitoring apparatuses and methods for assessing a physiological condition of a subject including at least two types of physiological information and possibly also environmental information. U.S. Patent Application 20150126825 (LeBoeuf et al., May 7, 2015, "Physiological Monitoring Apparatus") discloses wearable apparatuses including a plurality of compact sensors integrated within small, low-profile devices such as earpiece modules for monitoring various physiological and environmental factors. U.S. Patent Application 20150130633 (Grubstein et al., May 14, 2015) and 20150130634 (Grubstein et al., May 14, 2015, "Indicator and Analytics for Sensor Insertion in a Continuous Analyte Monitoring System and Related Methods") disclose systems and methods for tracking sensor insertion locations in a continuous analyte monitoring system.

U.S. Patent Application 20150135118 (Grubstein et al., May 14, 2015, "Indicator and Analytics for Sensor Insertion in a Continuous Analyte Monitoring System and Related Methods") discloses systems and methods for, among others, tracking sensor insertion locations in a continuous analyte monitoring system. U.S. Pat. No. 9,037,204 (Schlottau, May 19, 2015, "Filtered Detector Array for Optical Patient Sensors") discloses optical patient monitoring systems including a broadband emitter configured to emit two or more wavelengths of light into the tissue of a patient. U.S. Patent Application 20150141769 (Mulligan et al., May 21, 2015, "Noninvasive Monitoring for Fluid Resuscitation") discloses novel tools and techniques for assessing, predicting and/or estimating the effectiveness of fluid resuscitation of a patient and/or an amount of fluid needed for effective resuscitation of the patient.

U.S. Patent Application 20150148623 (Benaron, May 28, 2015, "Hydration Monitoring Sensor and Method for Cell Phones, Smart Watches, Occupancy Sensors, and Wearables") discloses a sensor for hydration monitoring in mobile devices, wearables, security, illumination, photography, and other devices and systems using an optional phosphor-coated broadband white LED to produce broadband light which is then transmitted along with any ambient light to a body target. U.S. Patent Application 20150148624 (Benaron, May 28, 2015, "Method for Detecting Physiology at Distance or During Movement for Mobile Devices, Illumination, Security, Occupancy Sensors, and Wearables") discloses a sensor which uses broadband light transmitted to a target such as the ear, face, or wrist of a living subject. U.S. Patent Application 20150148632 (Benaron, May 28, 2015, "Calorie Monitoring Sensor and Method for Cell Phones, Smart Watches, Occupancy Sensors, and Wearables") discloses a sensor for calorie monitoring in mobile devices, wearables, security, illumination, photography, and other devices and systems which uses an optional phosphor-coated broadband white LED to produce broadband light, which is then transmitted along with any ambient light to a target such as the ear, face, or wrist of a living subject. Calorie monitoring systems incorporating the sensor as well as methods are also disclosed. U.S. Patent Application 20150148636 (Benaron, May 28, 2015, "Ambient Light Method for Cell Phones, Smart Watches, Occupancy Sensors, and Wearables") discloses a sensor for respiratory and metabolic monitoring in mobile devices, wearables, security, illumination, photography, and other devices and systems that uses a broadband ambient light. The sensor can provide identifying features of type or status of a tissue target, such as calories used or ingested.

U.S. Patent Application 20150168217 (Englund et al., Jun. 18, 2015, "Methods and Apparatus for Spectrometry") discloses how multimode interference can be used to achieve ultra-high resolving powers and a broad spectroscopy range within a monolithic, millimeter-scale device. U.S. Pat. No. 9,061,899 (Rowe et al., Jun. 23, 2015, "Apparatus and Method of Biometric Determination Using Specialized Optical Spectroscopy Systems") discloses methods and apparatuses for performing biometric determinations using optical spectroscopy of tissue including include determination or verifications of identity, estimation of age, estimation of sex, determination of sample liveness and sample authenticity. U.S. Patent Application 20150192462 (Schiering et al., Jul. 9, 2015, "Dual Spectrometer") discloses systems and techniques for optical spectrometer detection using IR spectroscopy components and Raman spectroscopy components.

U.S. Patent Application 20150216454 (Kasahara et al., Aug. 6, 2015, "Biological Information Measurement Apparatus and Biological Information Measurement Method") discloses a blood glucose level measurement apparatus which is mounted on the wrist or the like of a user and performs a measurement using light. U.S. Patent Application 20150216479 (Abreu, Aug. 6, 2015, "Apparatus and Method for Measuring Biologic Parameters") discloses support structures for positioning sensors on a physiologic tunnel for measuring physical, chemical and biological parameters of the body. U.S. Patent Application 20150216484 (Kasahara et al., Aug. 6, 2015, "Biological Information Processing Apparatus, and Biological Information Processing Method") discloses a measurement method selection unit which selects one measurement method on the basis of a detection result from a body motion detection unit, from among a plurality of measurement methods of measuring a blood glucose level applying irradiation waves toward a living body of the subject.

U.S. Patent Application 20150224275 (Pastoor et al., Aug. 13, 2015, "Customization or Adjustment of Patient Interfaces") discloses a sensor device in the form of a patient interface which has a sensor arrangement for determining a degree of fitting of a contact surface to the patient. U.S. Patent Application 20150233762 (Goldring et al., Aug. 20, 2015, "Spectrometry System with Illuminator") discloses a spectrometer comprising a plurality of isolated optical channels. U.S. Patent Application 20150238083 (Faubert et al., Aug. 27, 2015, "Method and System for Optically Investigating a Tissue of a Subject") discloses a probe device for optically investigating a tissue of a subject, comprising: a first probe element, a second probe element, and a third probe element each to be positioned at a respective vertex of a triangle for sensing the tissue, the first probe element each comprising a first light source for emitting light having a first wavelength, the second probe element each comprising a second light source for emitting light having a second wavelength and a first photodetector for detecting light having the first wavelength and scattered the tissue, and the third probe element comprising a second photodetector for detecting light having the first and second wavelengths and scattered the tissue.

U.S. Pat. No. 9,134,175 (Matsushita, Sep. 15, 2015, "Measurement Device") discloses a spectrometry device including a wavelength-tunable interference filter that is provided with a stationary reflection film, a movable reflection film and an electrostatic actuator which changes a gap dimension between the stationary reflection film and the movable reflection film. U.S. Patent Application 20150260573 (Ishimaru, Sep. 17, 2015, "Spectroscopic Measurement Device") discloses a spectroscopic measurement device including a dark filter that is arranged on an optical path between an imaging optical system and a light detection unit and includes a plurality of regions having different transmittances. U.S. Patent Application 20150305674 (McPherson et al., Oct. 29, 2015, "Systems and Methods for Measuring Hydration in a Human Subject") discloses a wearable system for determining a person's hydration status using light sources and photodetectors to extract a plethysmographic waveforms. U.S. Patent Application 20170071518 (Xavier Da Silveira et al., Mar. 16, 2017, "Apparatus and Method for Optical Tissue Detection") discloses an apparatus for optical tissue detection and discrimination between a tissue of a user and non-tissue materials.

Relevant non-patent literature includes the following:

(Green, et al., 2005, "Design of a Microwave Sensor for Non-Invasive Determination of Blood-Glucose Concentration," MS Thesis, Dept. of Electrical and Computer Engineering, Baylor University, 2005) discloses the use of microwave sensors and resonators for measuring glucose concentrations. (Jean et al., 2008, "A Microwave Frequency Sensor for Non-Invasive Blood-Glucose Measurement," IEEE Sensors Applications Symposium, Atlanta, Ga., Feb. 12-14, 2008, 4-7) and (Jean, B., 2016, "Non-Invasive Blood Glucose Analysis Through Use of High Frequency Measurement of the Dielectric Constant," http://web.ecs.baylor.edu/faculty/jean/research/blood.htm) disclose the use of microwaves to measure glucose concentration. (Kim et al., 2008, "Microwave Dielectric Resonator Biosensor for Aqueous Glucose Solution," Review of Scientific Instruments, 79(8), 2008, 1-3) discloses the use of a microwave resonator to measure glucose level.

(Caduff et al., 2009, "Non-Invasive Glucose Monitoring in Patients with Type 1 Diabetes: A Multisensor System Combining Sensors for Dielectric and Optical Characterisation of Skin," Biosensors and Bioelectronics, 24, 2009, 2778-2784) and (Caduff et al., 2011, "Characteristics of a Multisensor System for Non-Invasive Glucose Monitoring with External Validation and Prospective Evaluation," Biosensors and Bioelectronics, 26, 2011, 3794-3800) disclose a device with a combination of dielectric and optical sensors for monitoring glucose levels. (Babajanyan et al., 2010, "Real-Time Noninvasive Measurement of Glucose Concentration Using a Microwave Biosensor," Journal of Sensors, Vol. 2010, Dec. 29, 2010) discloses a real-time glucose sensor using a microwave resonator with a probe.

(Tao et al., 2011, "Metamaterials on Paper as a Sensing Platform," Advanced Materials, 23(28), Jul. 26, 2011, 3197-3201) discloses the use of split-ring resonators in biosensors. (Guarin et al., 2013, "Microwave-Based Noninvasive Concentration Measurements for Biomedical Applications," IEEE Newsletter, July, 2013, http://lifesciences.ieee.org/publications/newsletter/july-2013/374-microwave-based-noninvasive-sensors-for-biomedical-applications) discloses the use of microwave spectroscopy for measuring glucose concentration levels. (Kumar et al., 2013, "Measuring Blood Glucose Levels with Microwave Sensor," International Journal of Computer Applications, 72(15), June, 2013, 4-9) discloses the use of a spiral resonator to measure glucose levels.

(Choi et al., 2014, "Design of Continuous Non-Invasive Blood Glucose Monitoring Sensor Based on a Microwave Split Ring Resonator," RF Wireless Technology Biomedical Healthcare Applications; IEEE MTT-S International Microwave Workshop Series, London, Dec. 8-10, 2014, 1-3) and (Choi et al., 2015, "Design and In Vitro Interference Test of Microwave Noninvasive Blood Glucose Monitoring Sensor," IEEE Transactions on Microwave Theory and Techniques, 63(10), October, 2015) disclose a glucose monitor that includes a pair of microwave split-ring resonators. (Kim et al., 2014, "A Reusable Robust Radio Frequency Biosensor Using Microwave Resonator by Integrated Passive Device Technology for Quantitative Detection of Glucose Level," Biosensors and Bioelectronics, Vol. 67, May 15, 2015, 687-693) discloses the use of a rectangular microwave resonator to measure glucose level. (Mazady, A., 2014, "Non-Invasive Glucose Meter," Electrical and Computer Engineering Department, University of Connecticut, Nov. 15, 2014, http://www.engr.uconn.edu/~mam10069/Docs/NonInvasiveGlucoseMeasurement.pdf) discloses the use of impedance spectroscopy for measuring glucose levels.

(Caduff et al., 2015, "Glucose Detection from Skin Dielectric Measurements," Dielectric Relaxation in Biological Systems, Oxford University Press, 2015) discusses the theory and selected evidence concerning the use of dielectric sensors for measuring glucose levels. (Chien et al., 2015, "A Microwave Reconfigurable Dielectric-Based Glucose Sensor with 20 mg/dL Sensitivity at Sub-nL Sensing Volume in CMOS," IEEE, 2015) discloses a dielectric-based glucose sensor. (Fu et al., 2015, "Study on a Glucose Concentration Measurement System Based on Microwave Perturbation Technique," Journal of Microwave Power and Electromagnetic Energy, 49(4), 2015, 215-224) discloses measurement of glucose concentration using microwave perturbation. (Gadawe et al., 2015, "Non Invasive Microwave Sensor for Near Field Biological Applications," Intl. Journal of Innovative Research in Computer and Communication Engineering, 3(5), May, 2015, 4641-4647) discloses a spiral microwave sensor for glucose monitoring.

(Hadkar et al., 2015, "Design of Square Shaped Miniaturized Split Ring Resonators," Int. Journal of Engineering Research and Applications, 5(5), Part 4, May, 2015, 11-14) discloses the use of square split-ring resonators. (Kim et al., 2015, "Rapid, Sensitive, and Reusable Detection of Glucose by a Robust Radiofrequency Integrated Passive Device Biosensor Chip," Scientific Reports, 5, 7807, Jan. 15, 2015) discloses the use of an intertwined spiral inductor to measure glucose concentration. (VRBA et al., 2015, "A Microwave Metamaterial Inspired Sensor for Non-Invasive Blood Glucose Monitoring," Radioengineering, 24(4), December, 2015, 877) discloses the use of inter-digitated sensors for measuring glucose levels. (Wellenzohn et al., 2015, "A Theoretical Design of a Biosensor Device Based on Split Ring Resonators for Operation in the Microwave Regime," Procedia Engineering, 120, 2015, 865-869) discloses the use of nested split-ring resonators for measuring glucose levels.

SUMMARY OF THE INVENTION

Maintaining proper body hydration is important for a person's health, especially during times of intense physical exertion or high ambient temperature. Body dehydration can cause significant health problems such as: heat injury ranging from mild cramps to heatstroke; urinary tract infections and kidney failure; electrolyte imbalance leading to muscle contractions and loss of consciousness; and hypovolemic shock with decreased blood pressure and low blood oxygenation. Many people, especially older people, do not realize that they are becoming dehydrated until an adverse health event occurs.

To address the problem of body dehydration, this invention discloses an arcuate wearable device with a circumferential or annular array of spectroscopic sensors which measures a person's body hydration level and/or water consumption so that the person can maintain their proper body hydration. A circumferential or annular array of spectroscopic sensors helps to ensure continuous measurement of body hydration, even if a wearable device shifts and/or rotates on a person's wrist, arm, or finger. For example, even if a first sensor on a first portion of an arcuate device shifts out of contact with a person's body, a second sensor on a second portion of the device remains in contact with the person's body. This ensures continuous measurement of body hydration level which is not possible without such a circumferential or annular array of light emitters.

Also, if a particular tissue area or anatomic feature of a person's finger, wrist, and/or arm (such as a particular blood vessel) is especially useful for body hydration measurement, then a circumferential or annular array of spectroscopic sensors can help to maintain analysis of this tissue area or feature even if a wearable device shifts and/or rotates on a person's body. Even if device shifting and/or rotation causes a first spectroscopic sensor in the circumferential or annular array to move further away from the desired tissue area or anatomic feature, a second spectroscopic sensor in the array will move closer to the desired tissue area or anatomic feature. This can help to ensure continuous measurement of that tissue area or anatomic feature which would not be possible without such a circumferential or annular array of spectroscopic sensors.

In an example, this invention can be embodied in a modular smart watch band, a specialized hydration-monitoring band, or a finger ring with a circumferential or annular array of spectroscopic sensors for measuring a person's body hydration level. This invention enables greater continuity of contact with a person's body and more accurate continuous measurement of body hydration levels. This appears to be a significant improvement over wearable devices for body hydration measurement in the prior art, especially wearable devices with sensors limited to a single dorsal housing.

INTRODUCTION TO THE FIGURES

Figure 30:
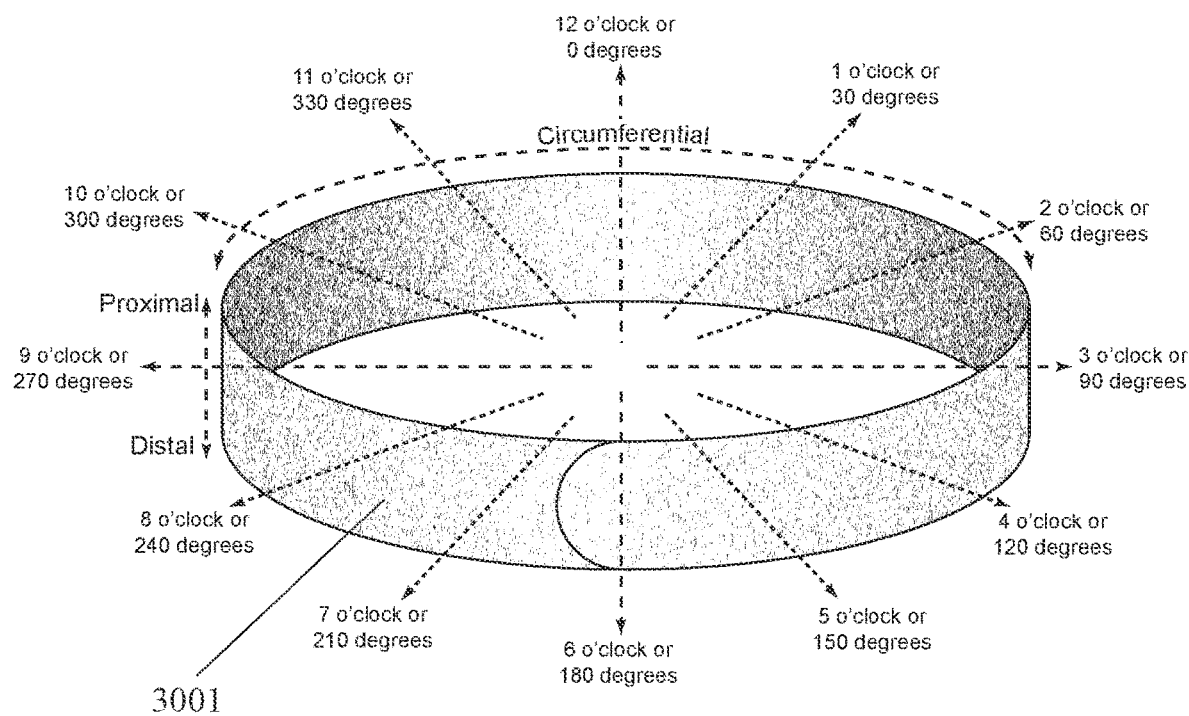

FIG. 30 defines "proximal-to-distal" and "circumferential" axes on a wearable band.

Figure 31:
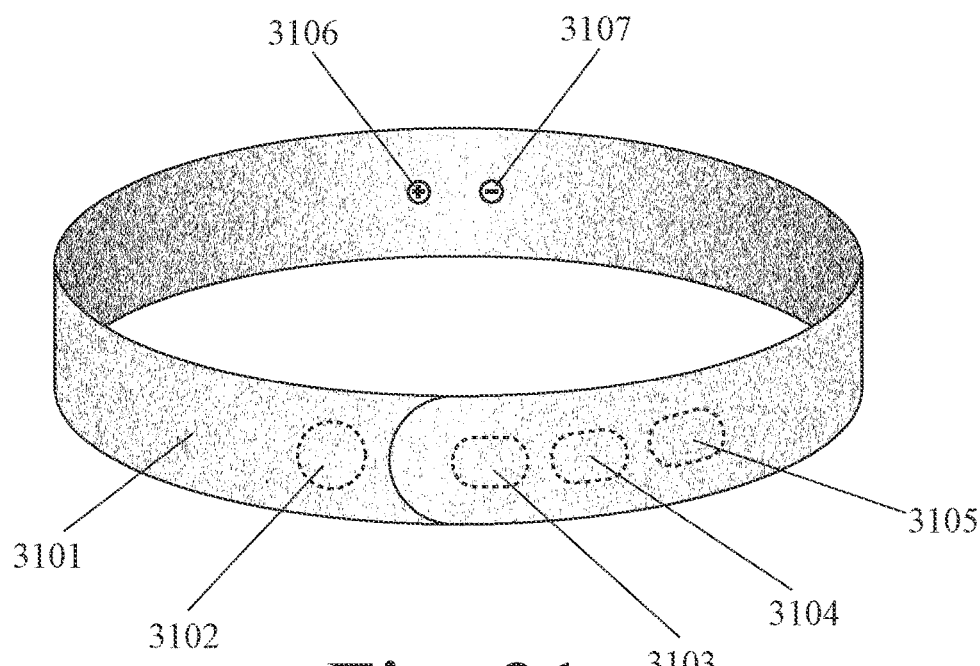

FIG. 31 shows a device with an energy emitter and receiver along the same circumference.

Figure 32:
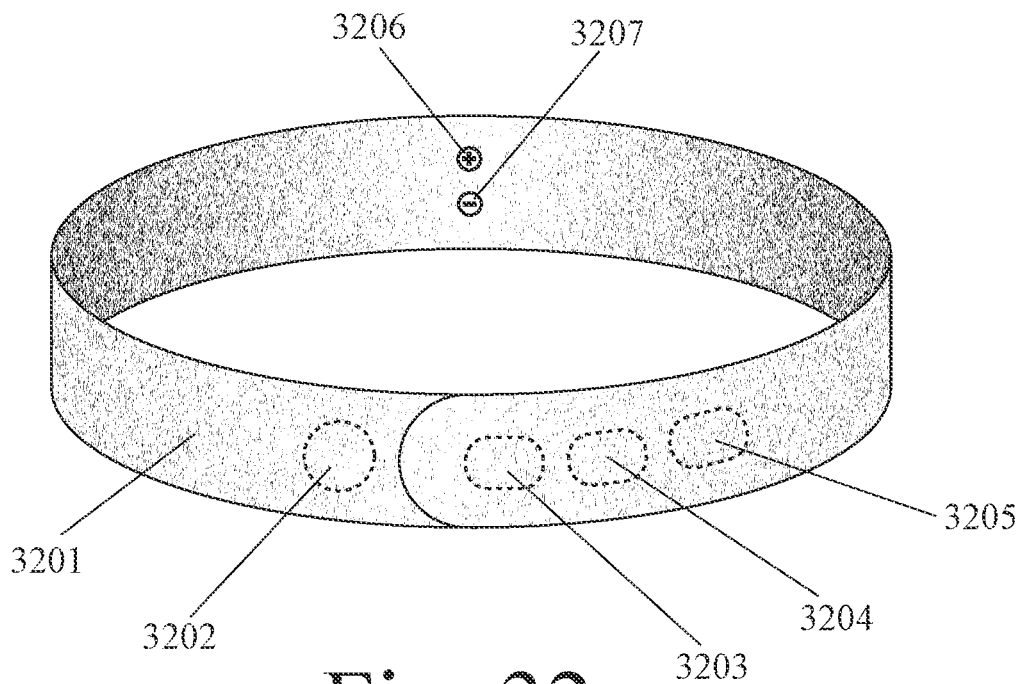

FIG. 32 shows a device with an energy emitter and receiver along the same proximal-to-distal line.

Figure 33:
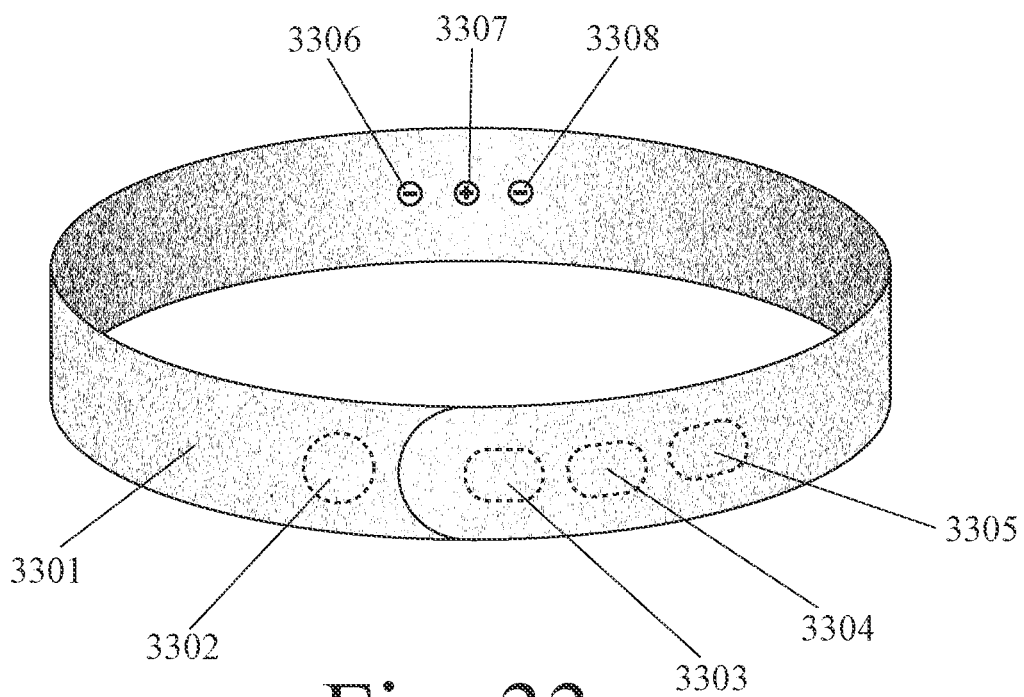

FIG. 33 shows a first device with an emitter and two receivers along the same circumference.

Figure 34:
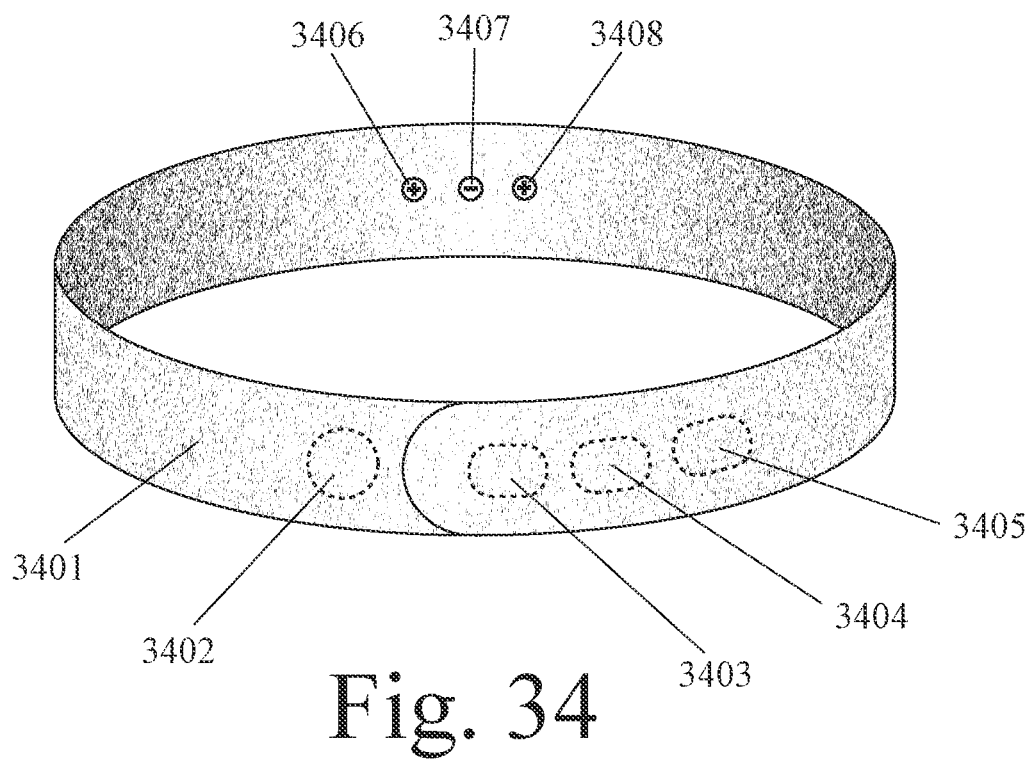

FIG. 34 shows a first device with two emitters and a receiver along the same circumference.

Figure 35:
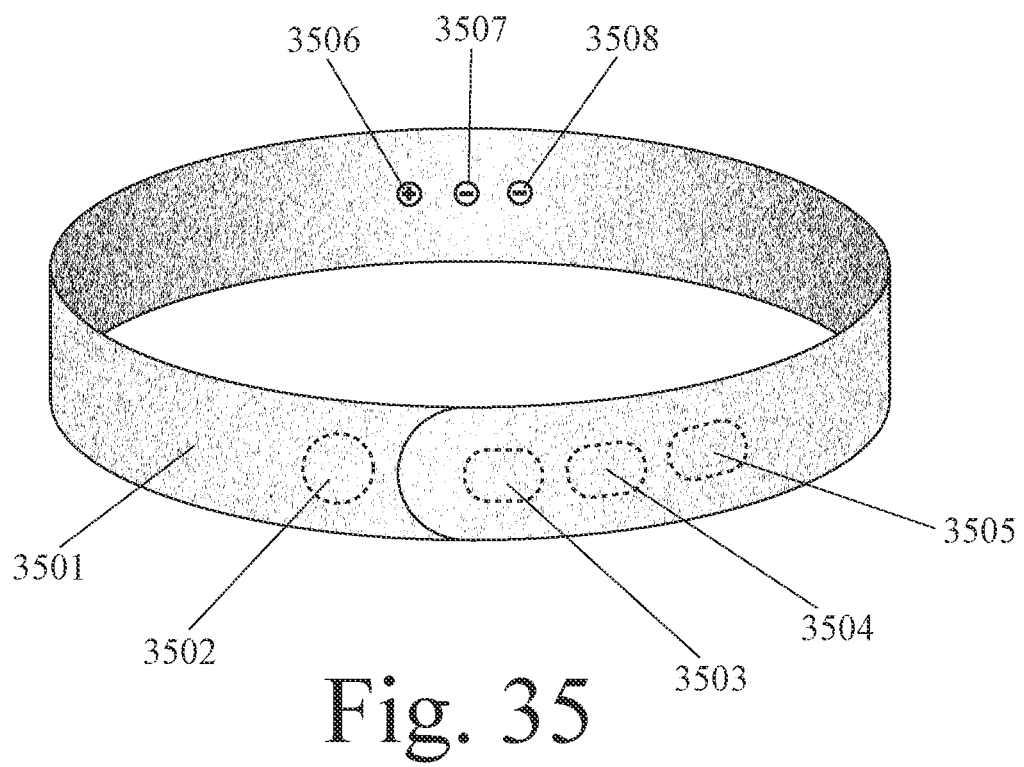

FIG. 35 shows a second device with an emitter and two receivers along the same circumference.

Figure 36:
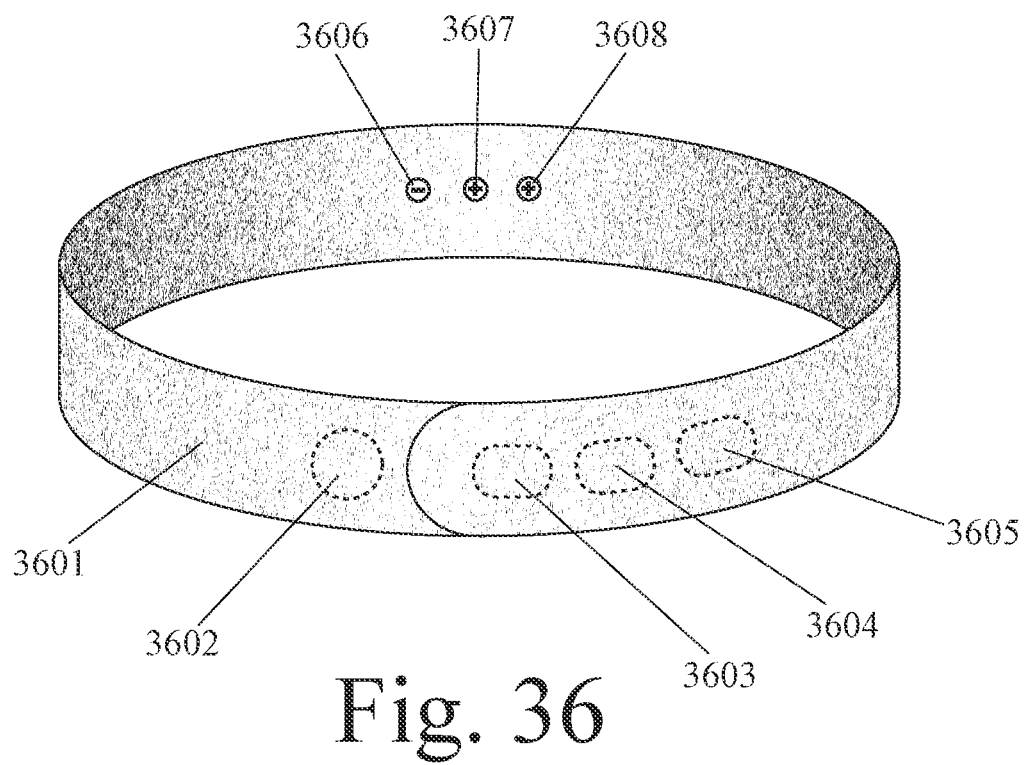

FIG. 36 shows a second device with two emitters and a receiver along the same circumference.

Figure 37:
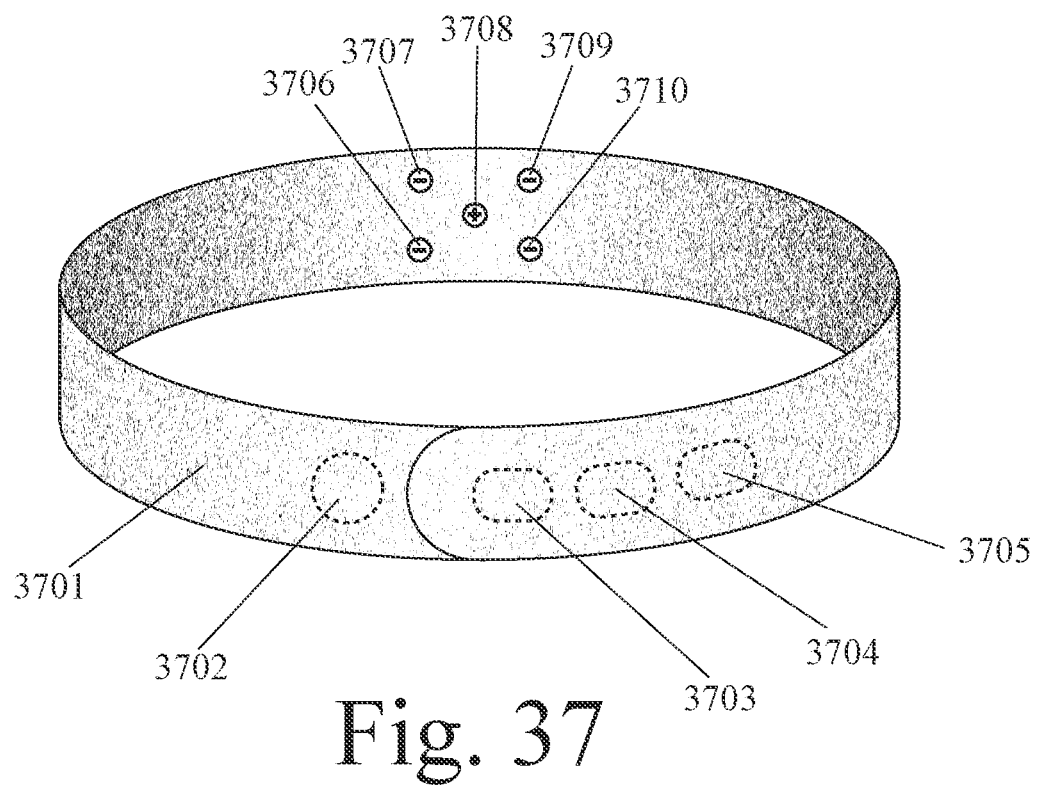

FIG. 37 shows a device with a central emitter and receivers around it.

Figure 38:
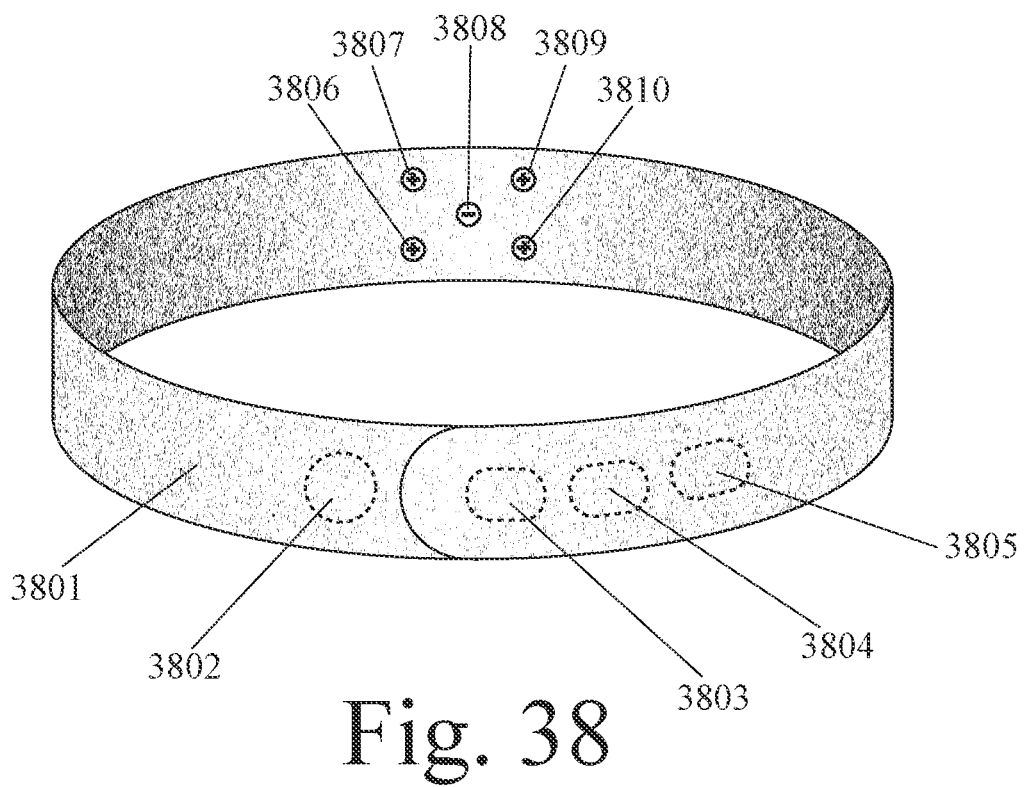

FIG. 38 shows a device with a central receiver and emitters around it.

Figure 39:
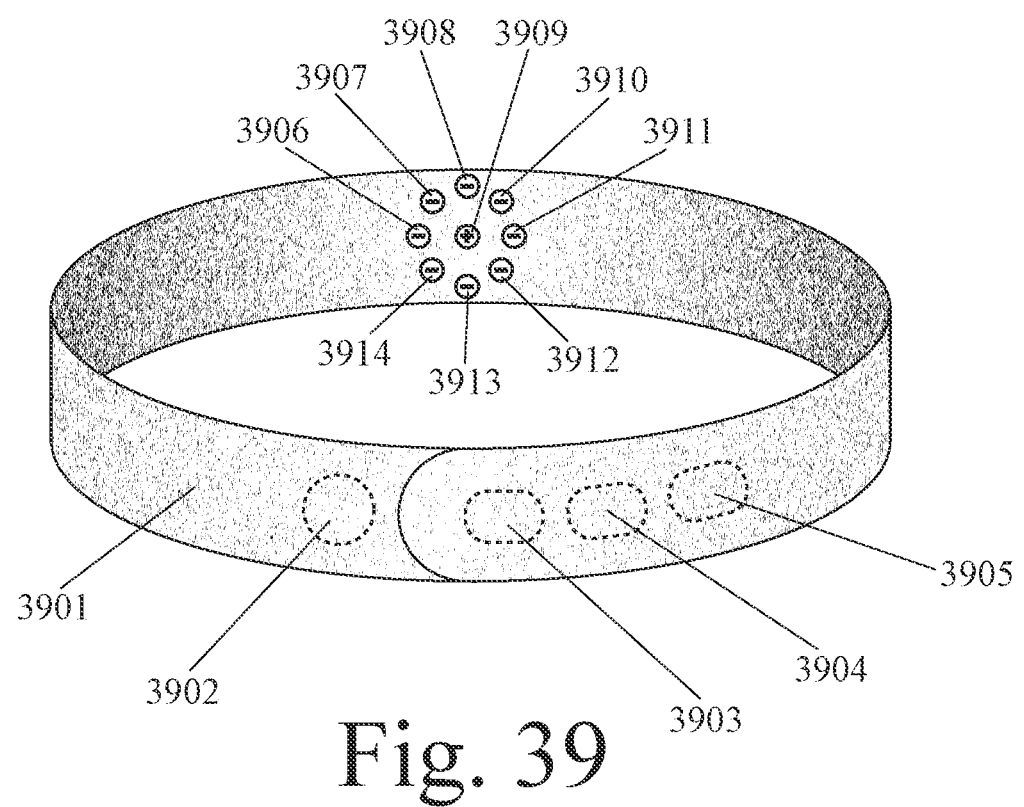

FIG. 39 shows a device with a central emitter and eight receivers around it.

Figure 40:
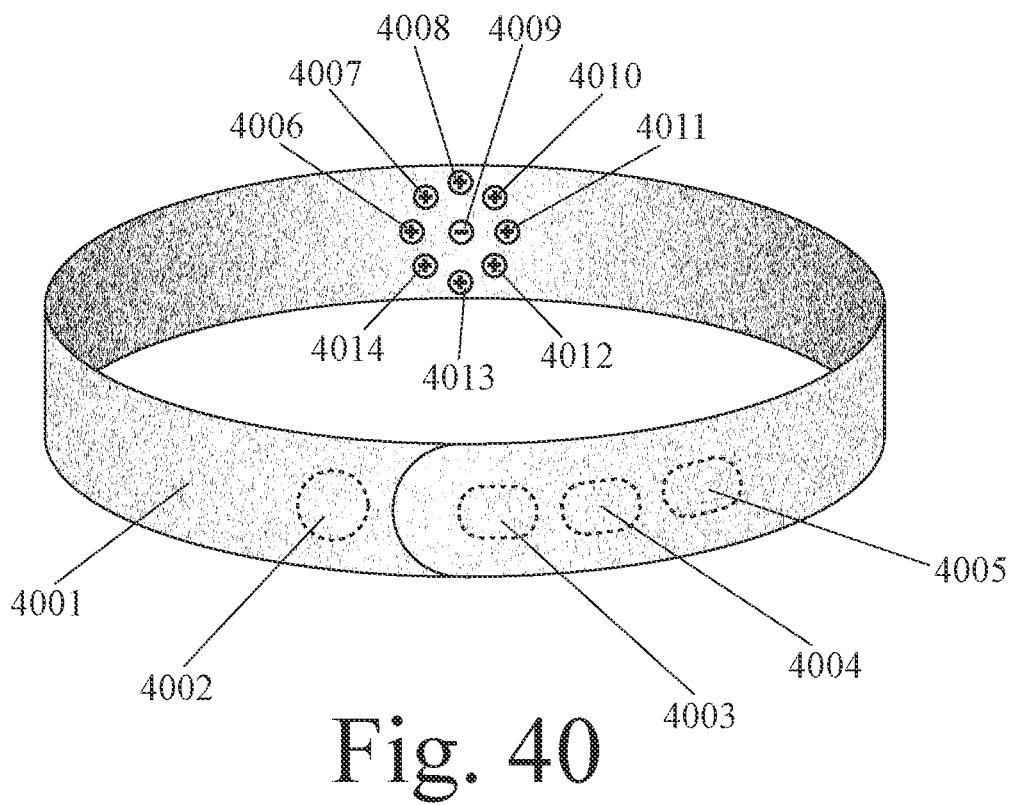

FIG. 40 shows a device with a central receiver and eight emitters around it.

Figure 41:
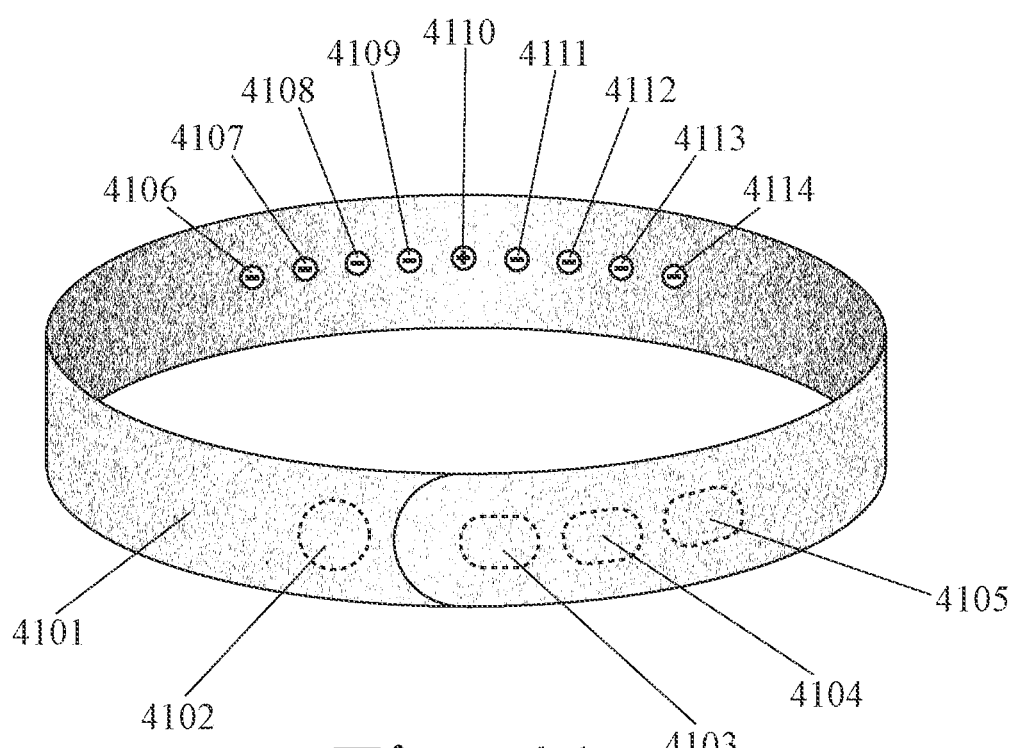

FIG. 41 shows a device with an emitter and receivers on either side along the same circumference.

Figure 42:
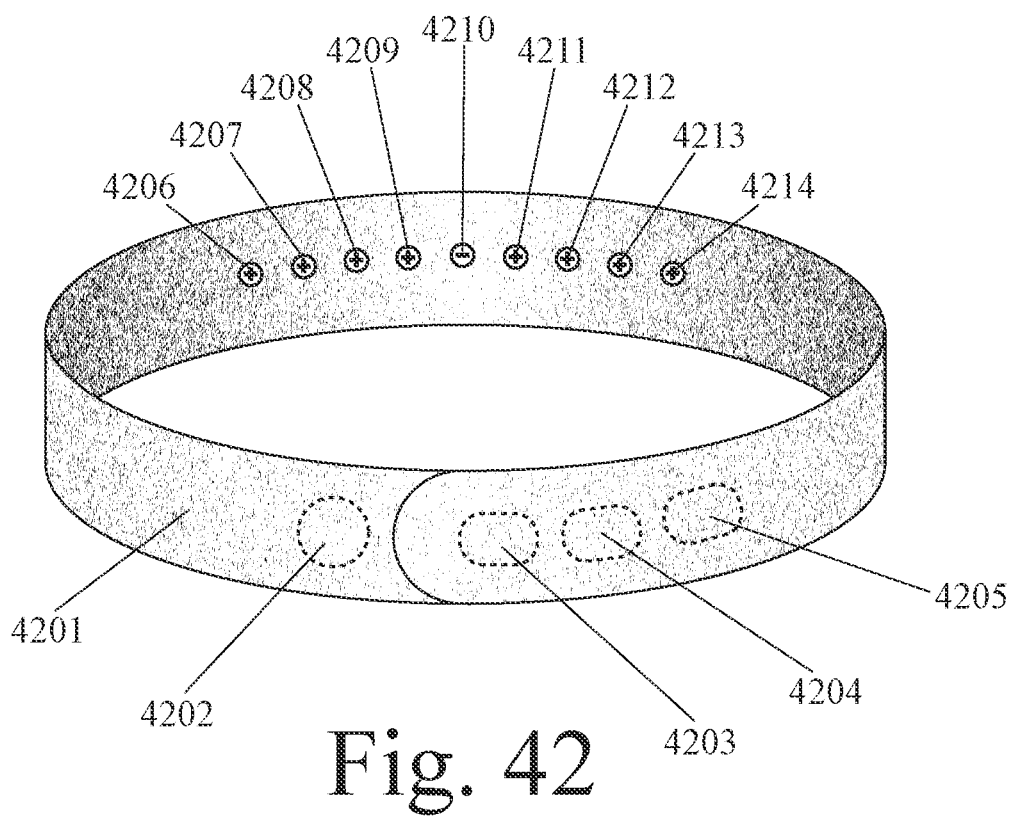

FIG. 42 shows a device with a receiver and emitters on either side along the same circumference.

Figure 43:
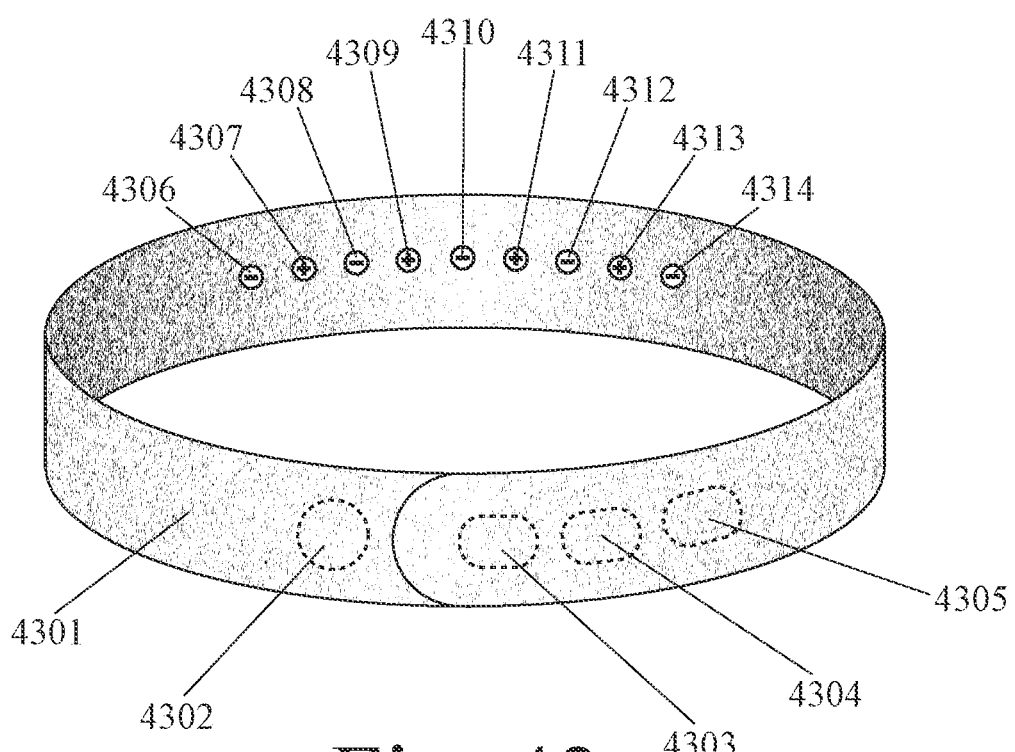

FIG. 43 shows a device with pairs of emitters and receivers along the same circumference.

Figure 44:
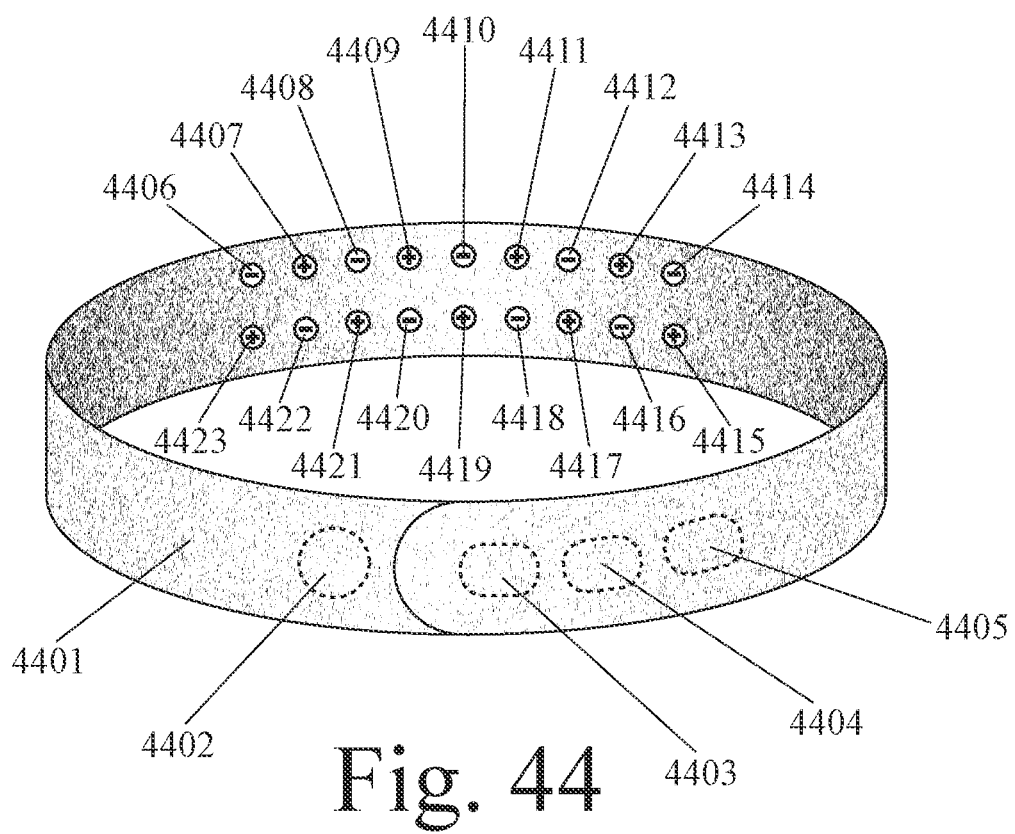

FIG. 44 shows a first device with emitters and receivers along different circumferences.

Figure 45:
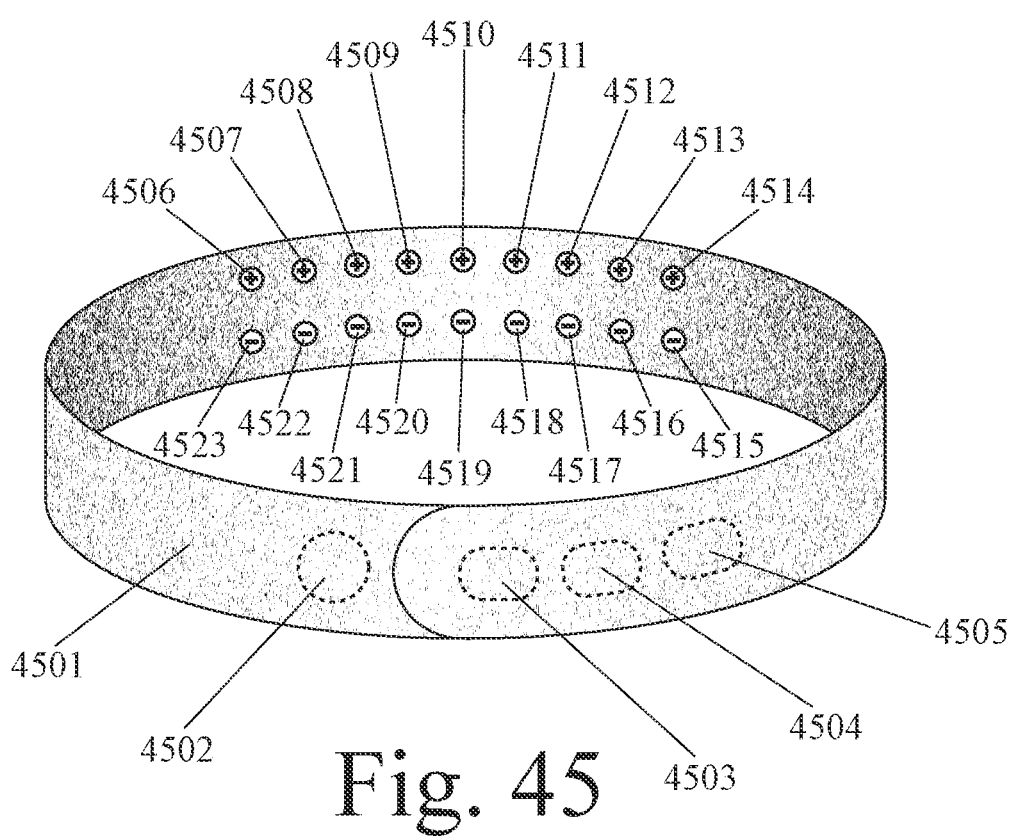

FIG. 45 shows a second device with emitters and receivers along different circumferences.

Figure 46:
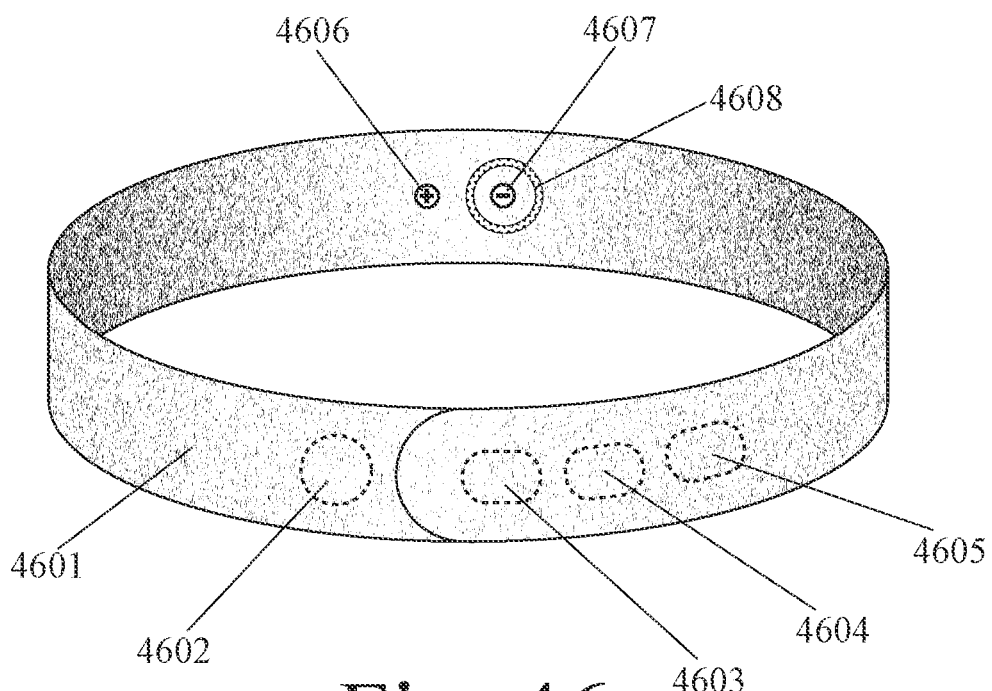

FIG. 46 shows a device with an emitter, and receiver, and a barrier around the receiver.

Figure 47:
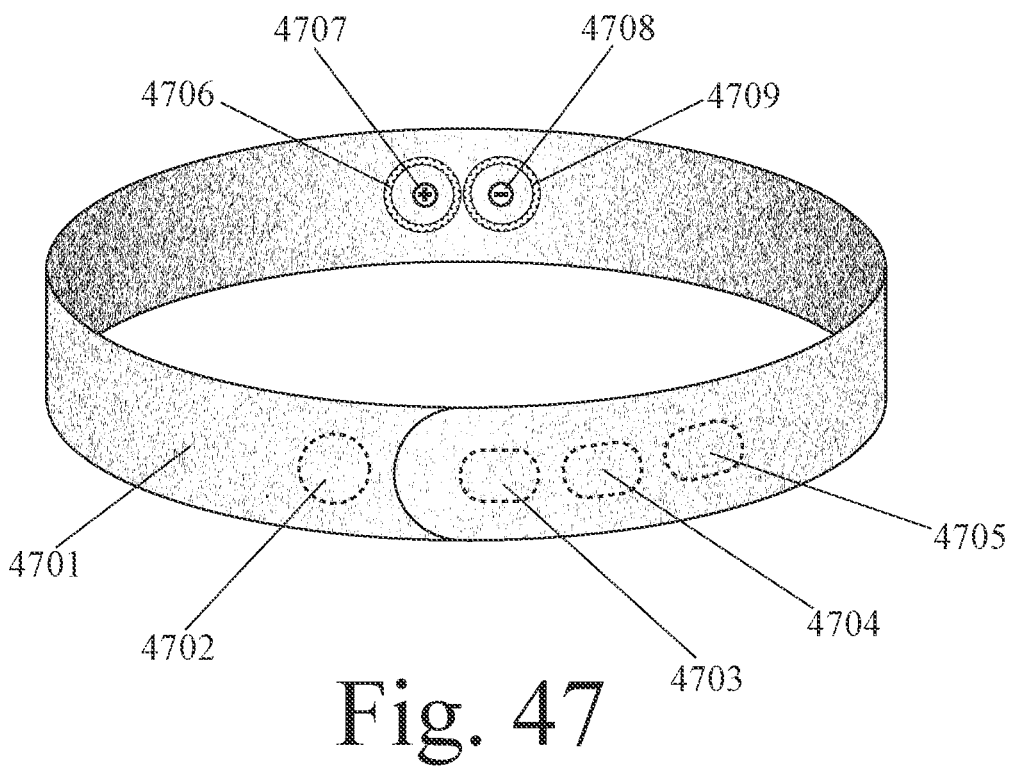

FIG. 47 shows a device with an emitter, and receiver, and barriers around both.

Figure 48:
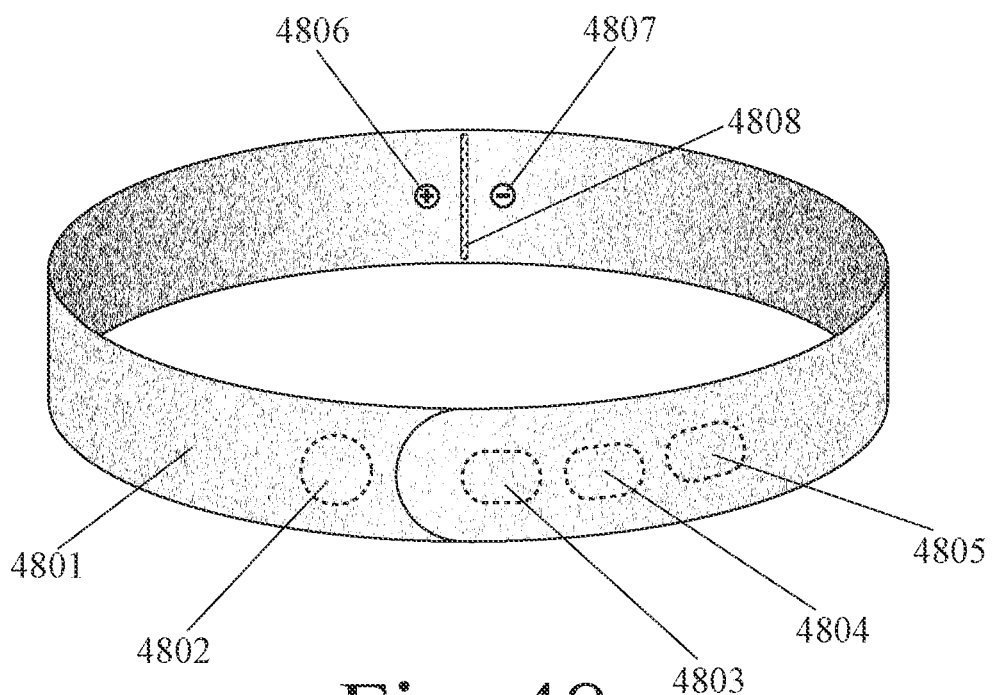

FIG. 48 shows a device with an emitter, and receiver, and a straight barrier between them.

Figure 49:
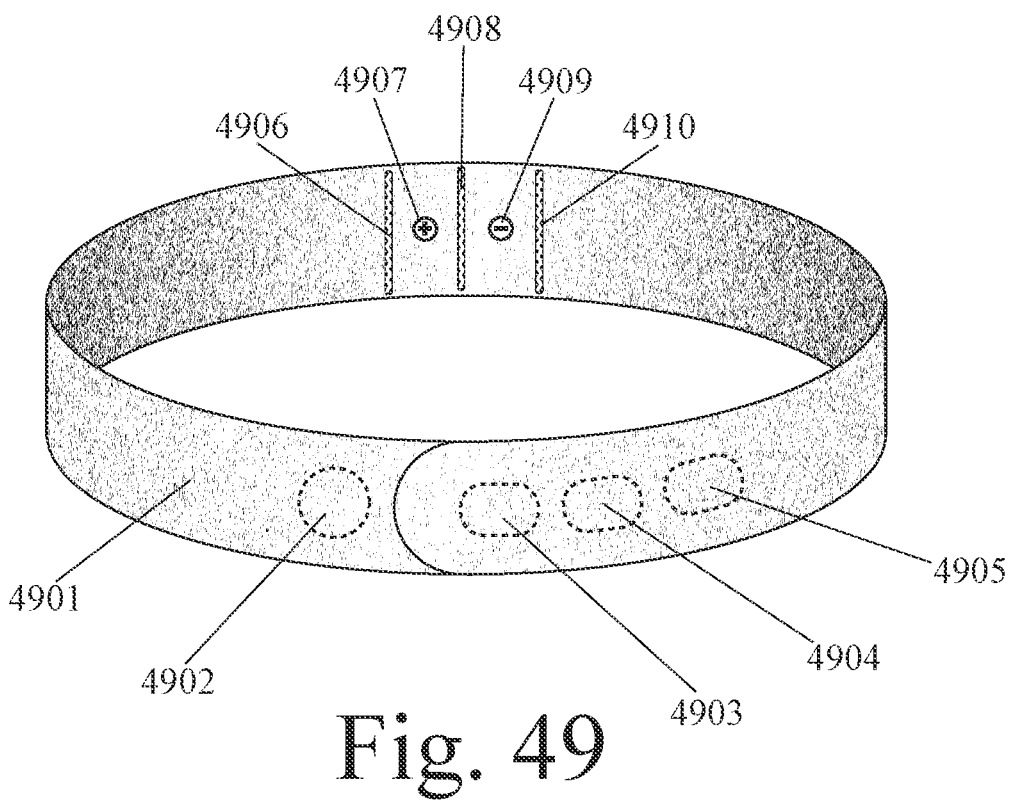

FIG. 49 shows a device with an emitter, and receiver, and a straight barriers on both sides of them.

Figure 50:
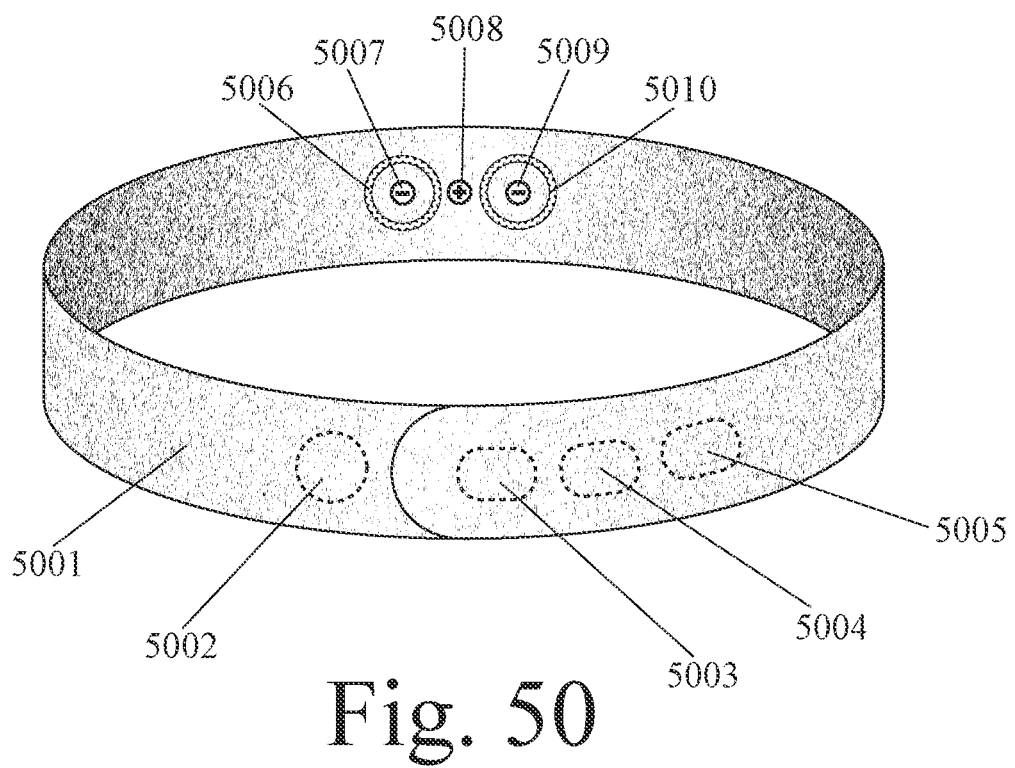

FIG. 50 shows a device with an emitter, two receivers, and barriers around both receivers.

Figure 51:
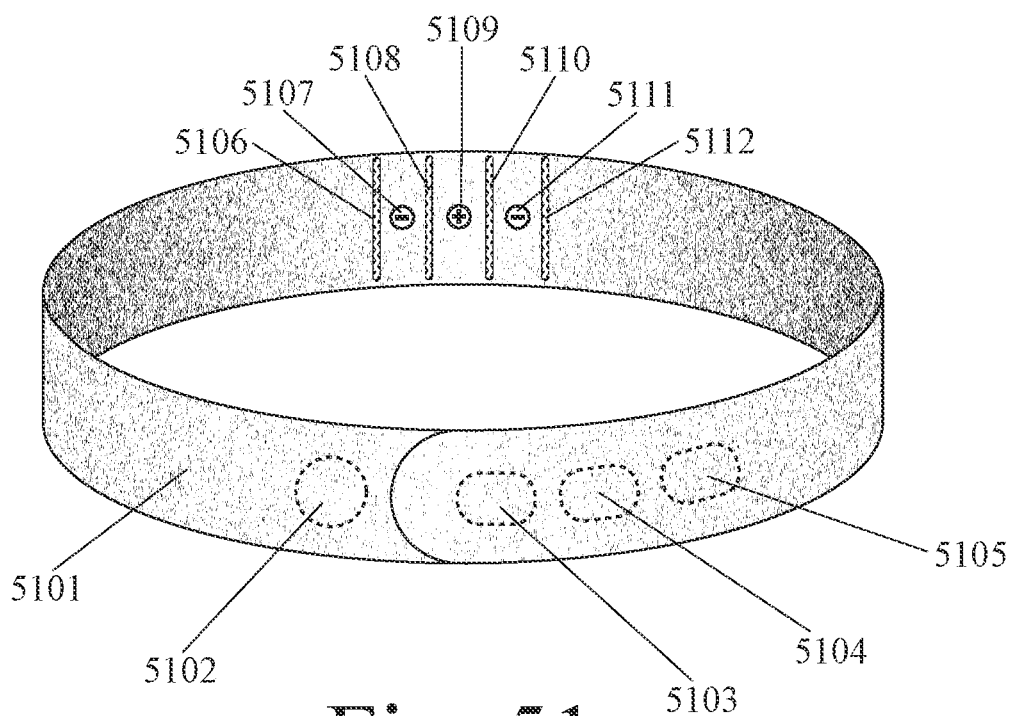

FIG. 51 shows a device with an emitter, two receivers, and straight barriers on both sides of them.

Figure 52:
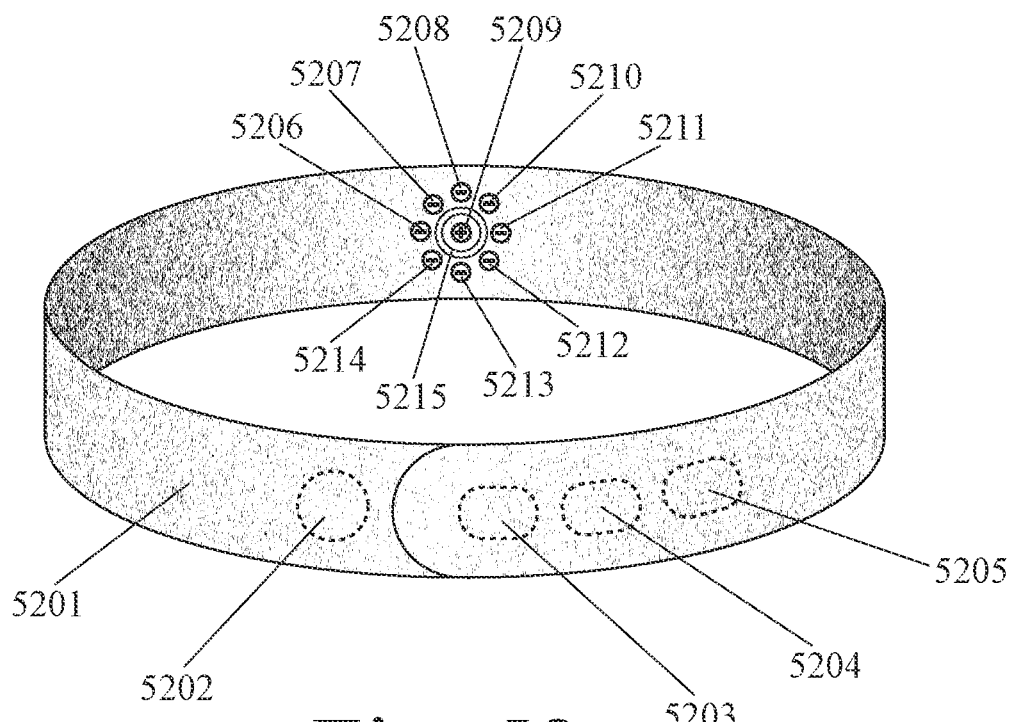

FIG. 52 shows a device with an emitter with a barrier around it and receivers around the barrier.

Figure 53:
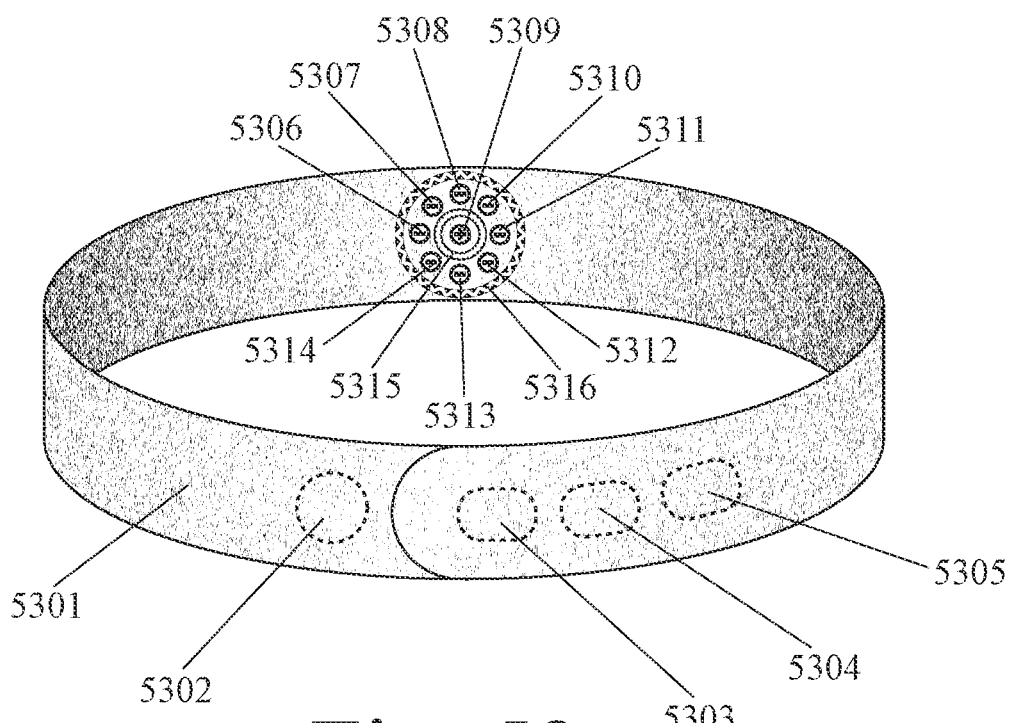

FIG. 53 shows a device with an emitter, barrier around it, receivers around the barrier, and another barrier.

Figure 54:
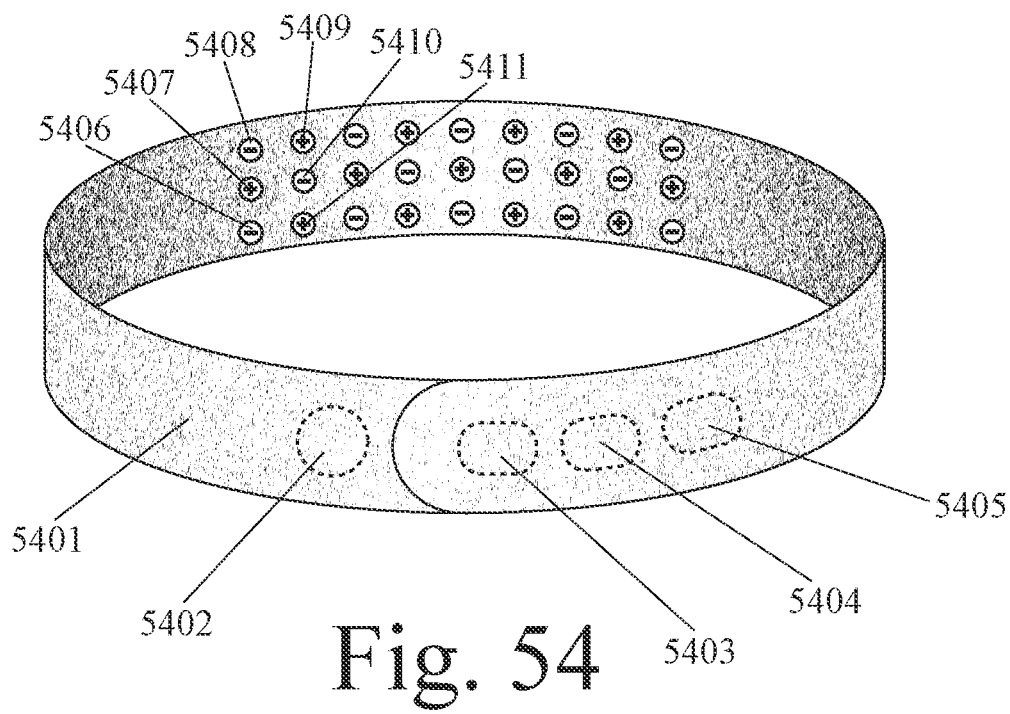

FIG. 54 shows a device with emitters and receivers along three circumferences.

Figure 55:
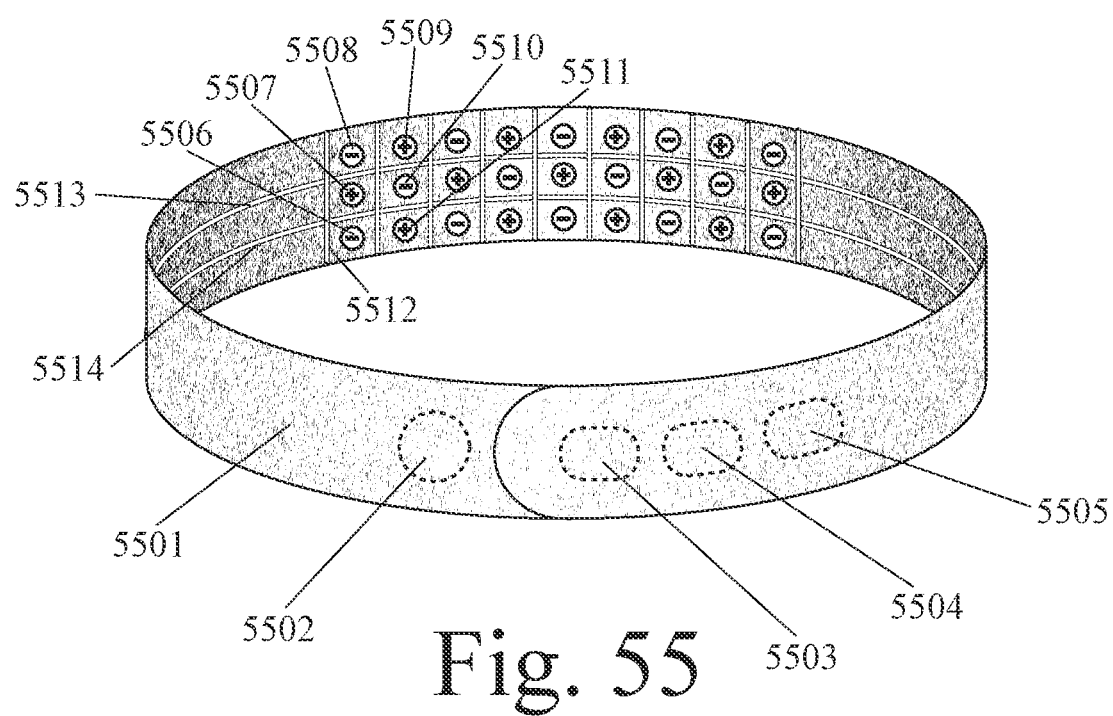

FIG. 55 shows a device with emitters and receivers along three circumferences with barriers between them.

Figure 56:
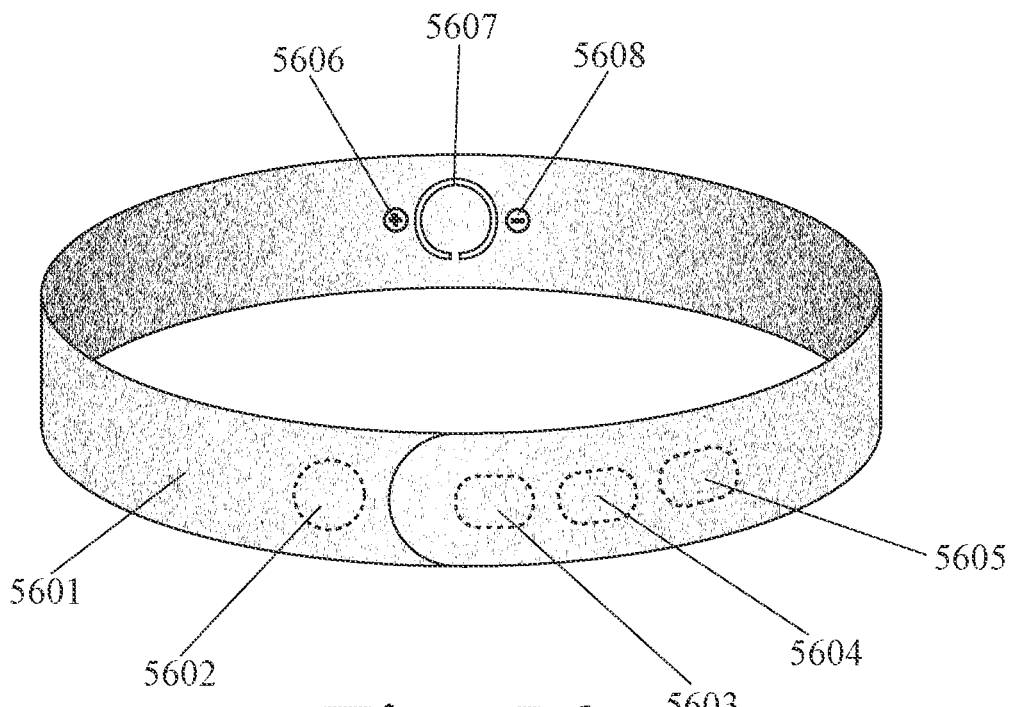

FIG. 56 shows a device with an emitter, a receiver, and a split-ring resonator between them.

Figure 57:
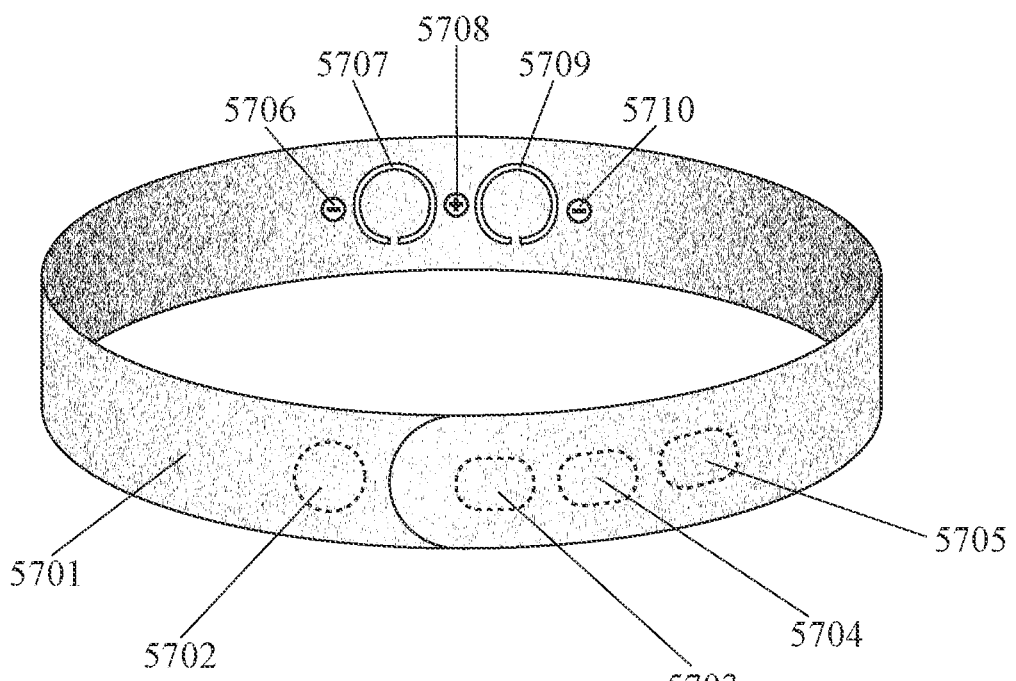

FIG. 57 shows a device with an emitter, two receivers, and two split-ring resonators between them.

Figure 58:
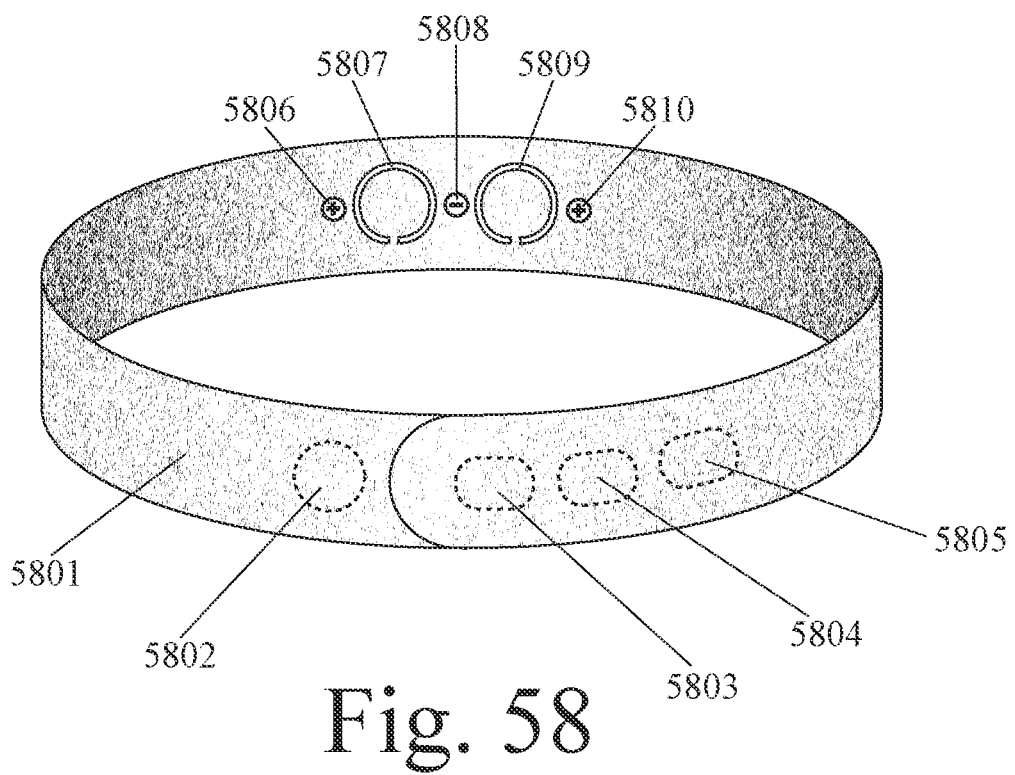

FIG. 58 shows a device with a receiver, two emitters, and two split-ring resonators between them.

Figure 59:
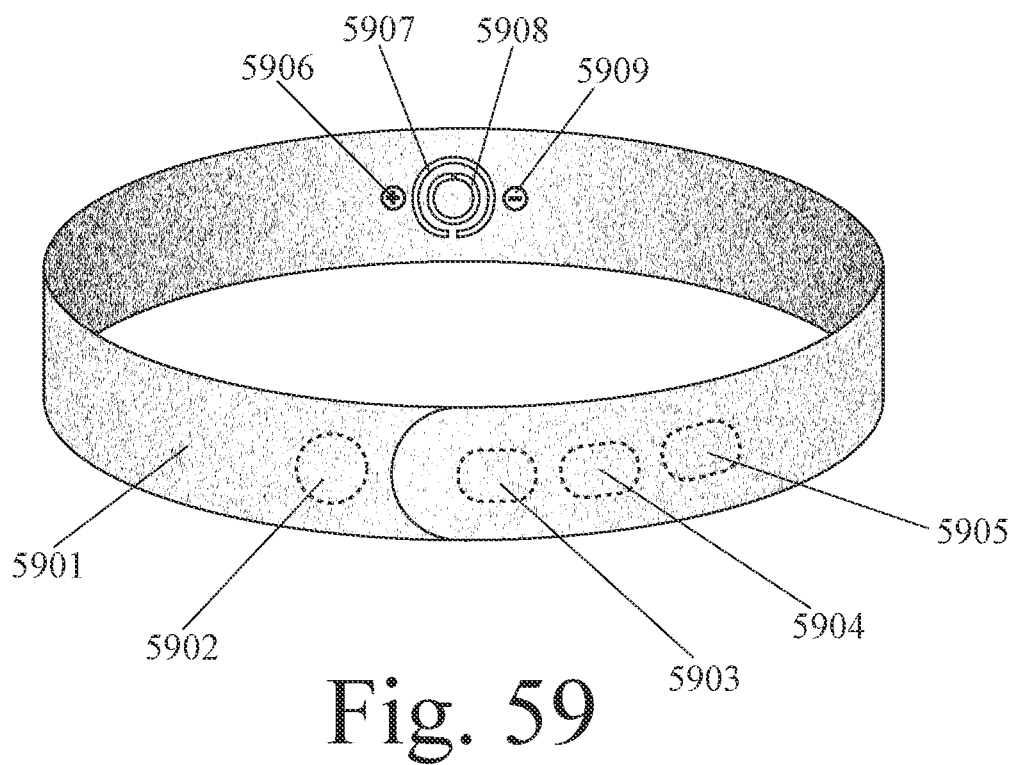

FIG. 59 shows a device with an emitter, a receiver, and nested split-ring resonators between them.

Figure 60:
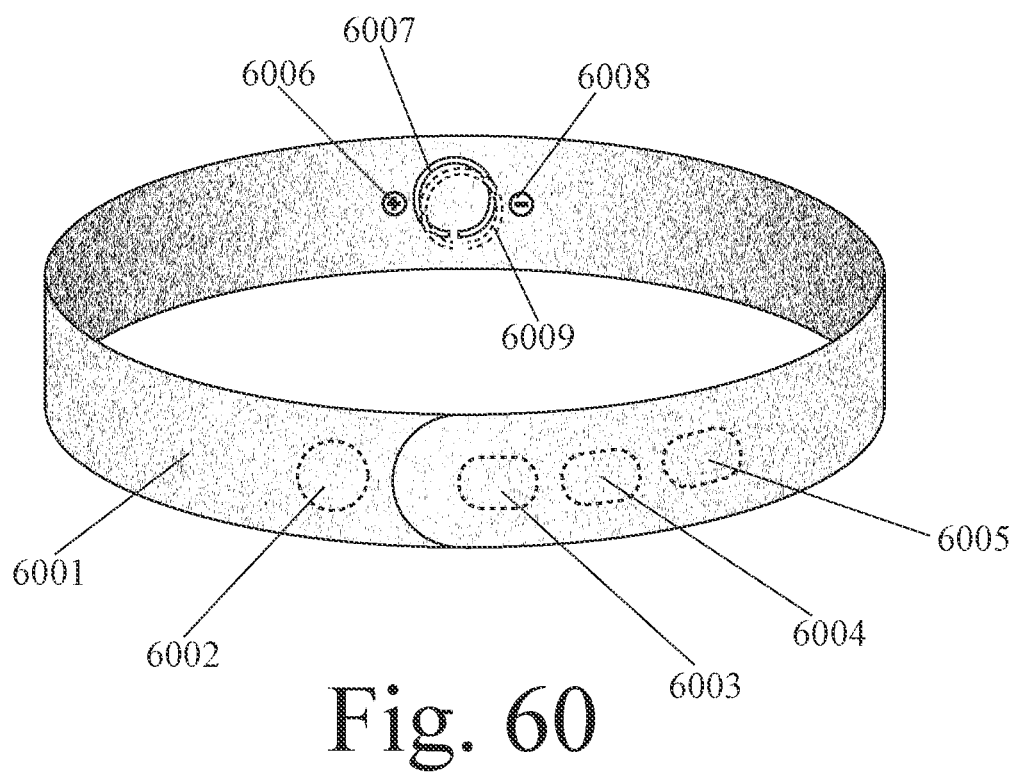

FIG. 60 shows a device with an emitter, a receiver, and stacked split-ring resonators between them.

Figure 61:
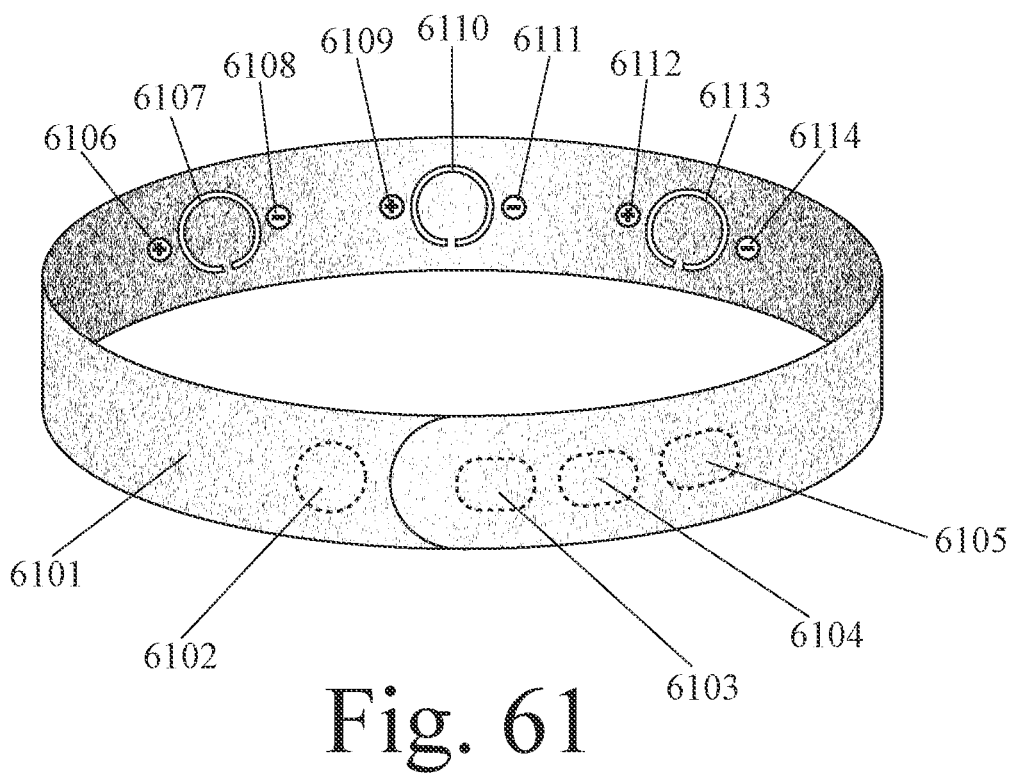

FIG. 61 shows a device with pairs of emitters and receivers with split-ring resonators between them.

Figure 62:
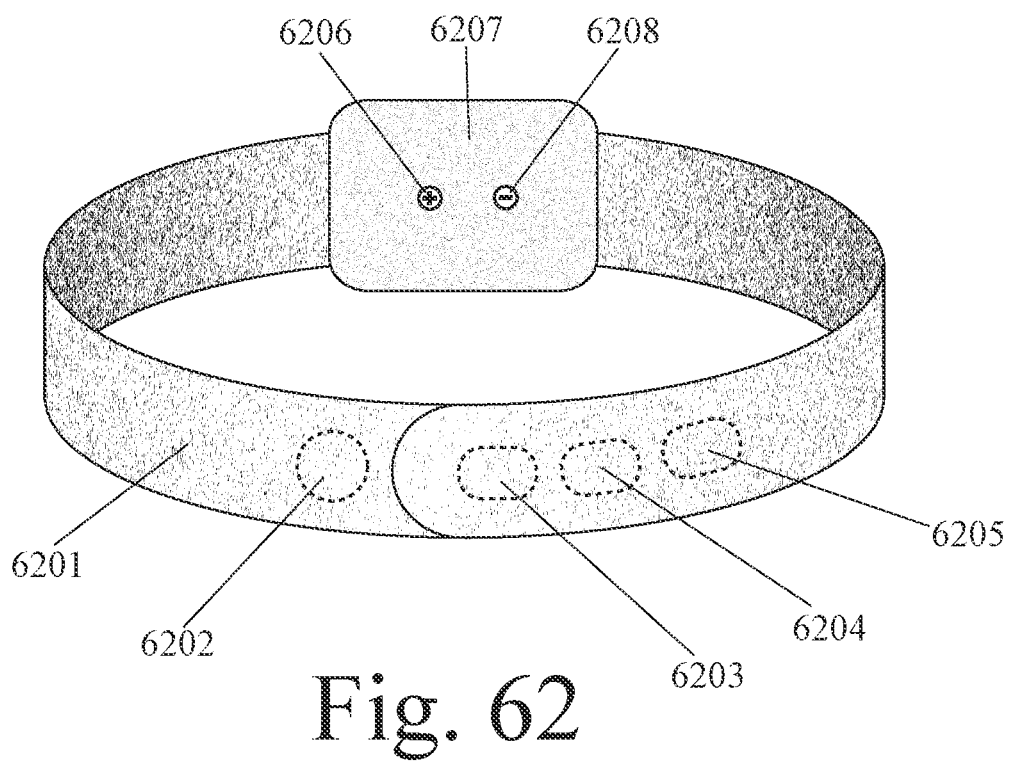

FIG. 62 shows a first device with a housing with an emitter and receiver.

Figure 63:
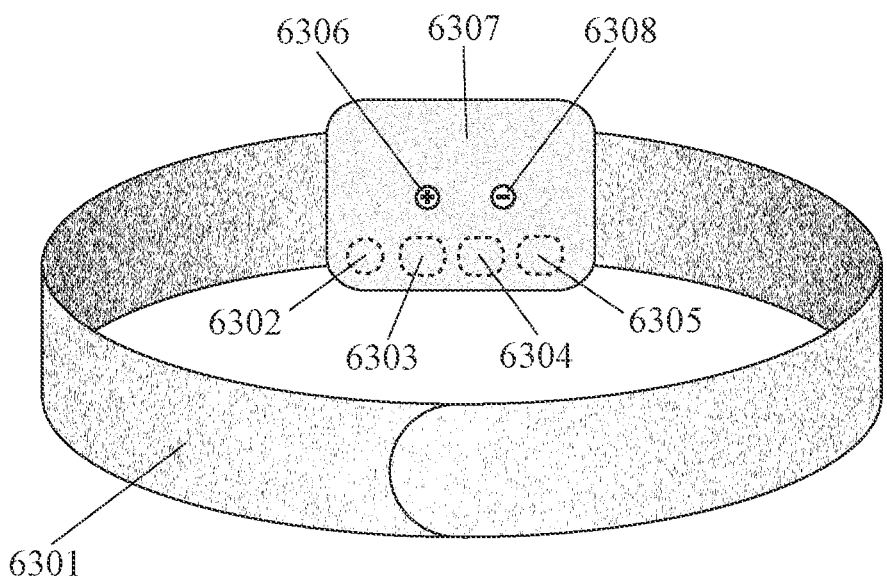

FIG. 63 shows a second device with a housing with an emitter and receiver.

Figure 64:
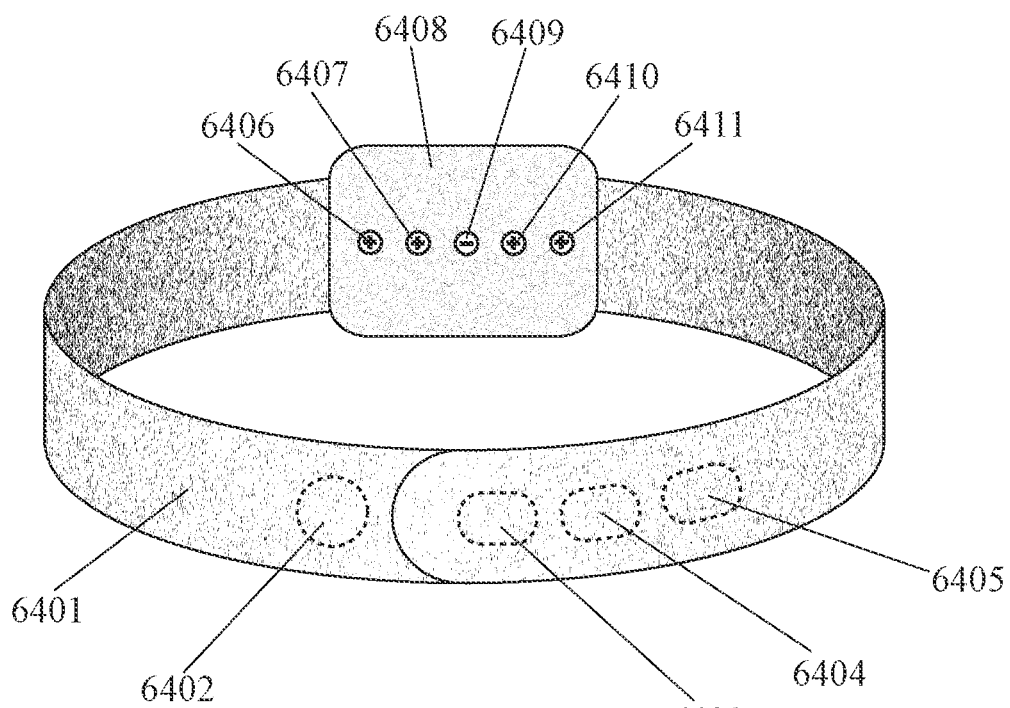

FIG. 64 shows a device with a housing with emitters and a receiver in a line.

Figure 65:
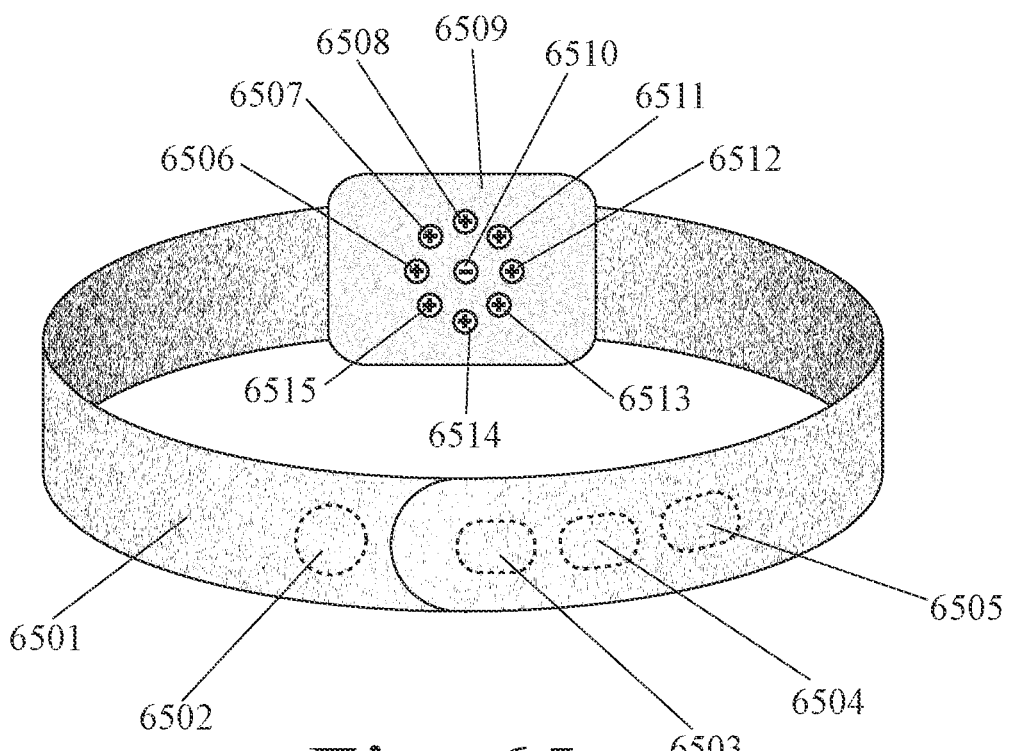

FIG. 65 shows a device with a housing with emitters in a circle around a receiver.

Figure 66:
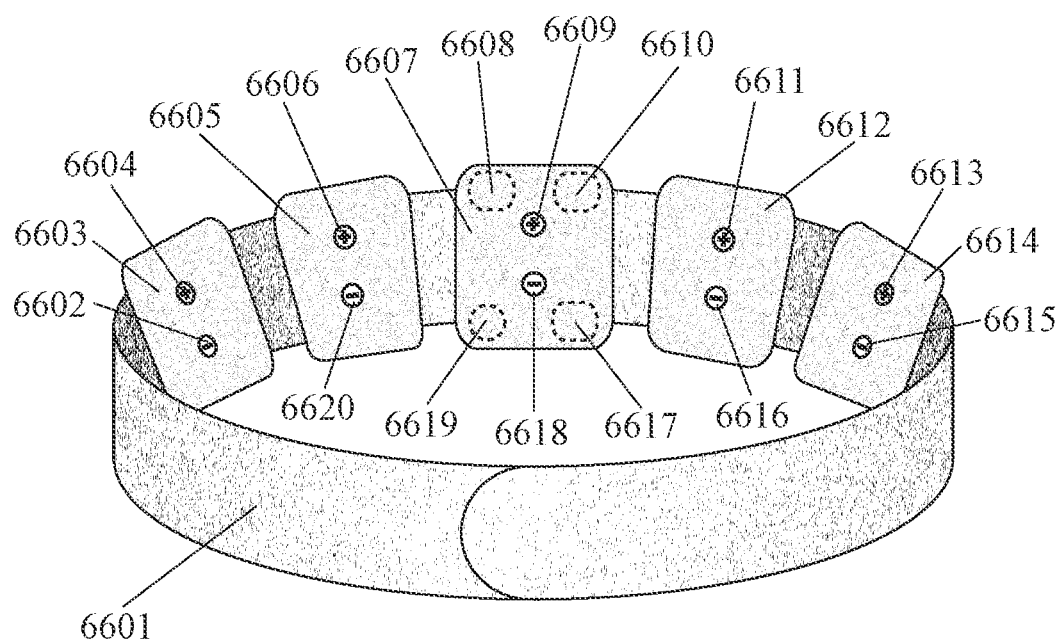

FIG. 66 shows multiple housings each with an emitter and receiver.

Figure 67:
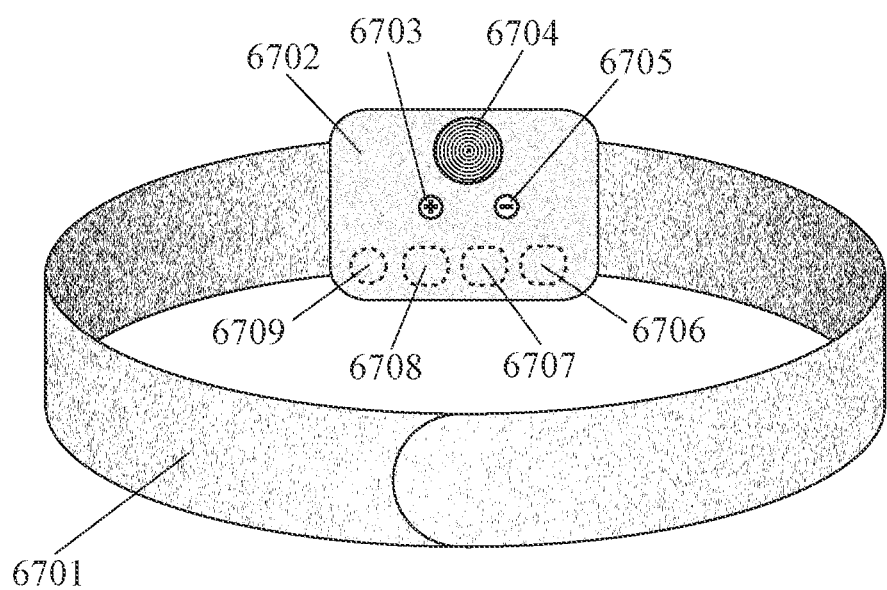

FIG. 67 shows a device with an emitter, a receiver, and a fluid-based glucose sensor.

Figure 68:
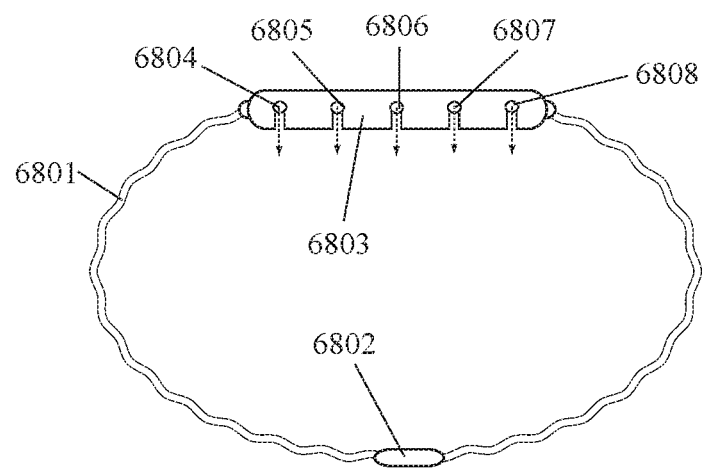

FIG. 68 shows a device with sensors at different circumferential locations.

Figure 69:
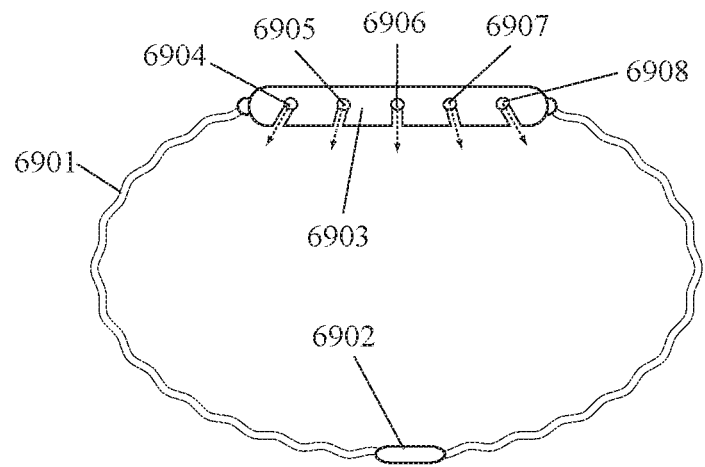

FIG. 69 shows a device projecting light at different angles.

Figure 70:
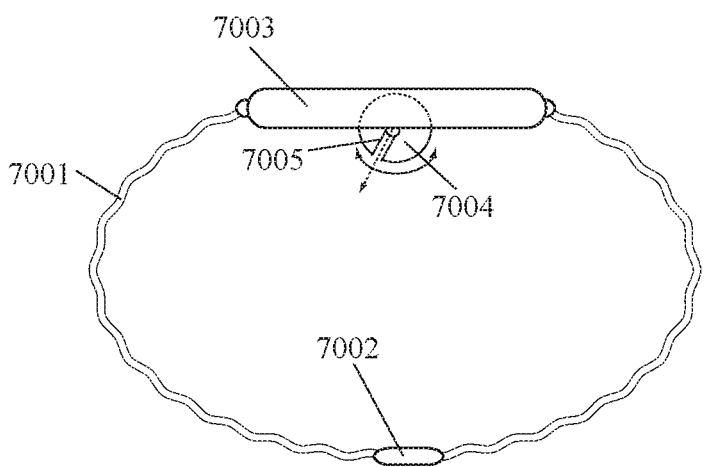

FIG. 70 shows a device with a rotating sensor.

Figure 71:
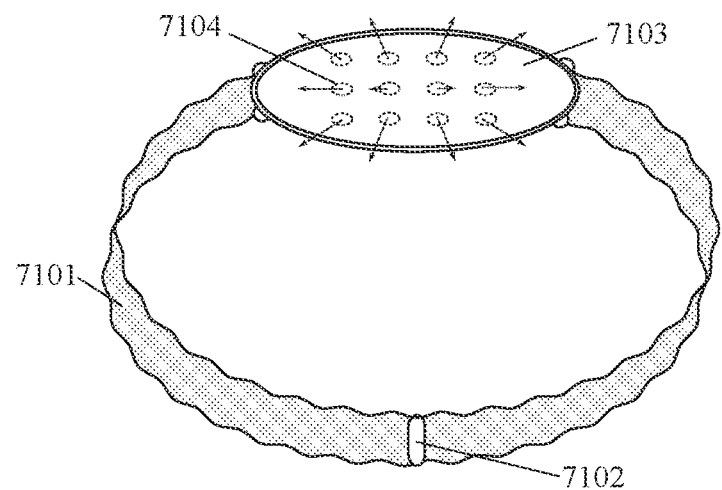

FIG. 71 shows a device with a two-dimensional array of sensors.

Figure 72:
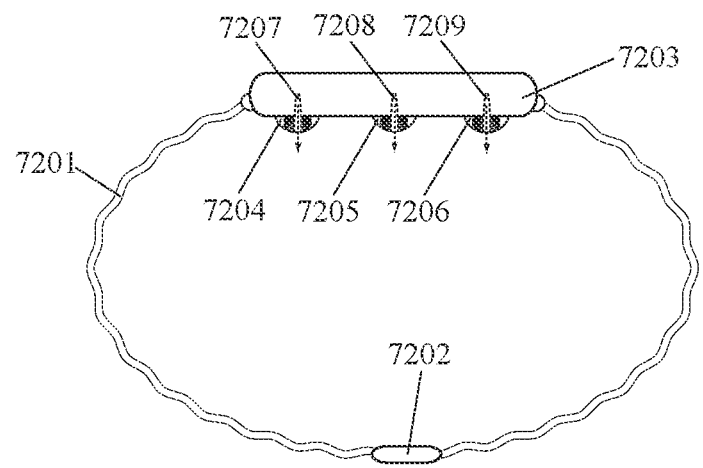

FIG. 72 shows a device with sensors which press toward the body from a flat enclosure.

Figure 73:
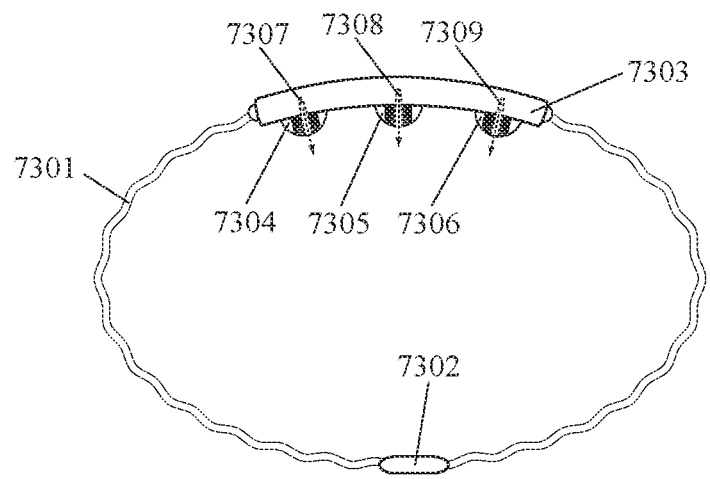

FIG. 73 shows a device with sensors which press toward the body from a curved enclosure.

Figure 74:
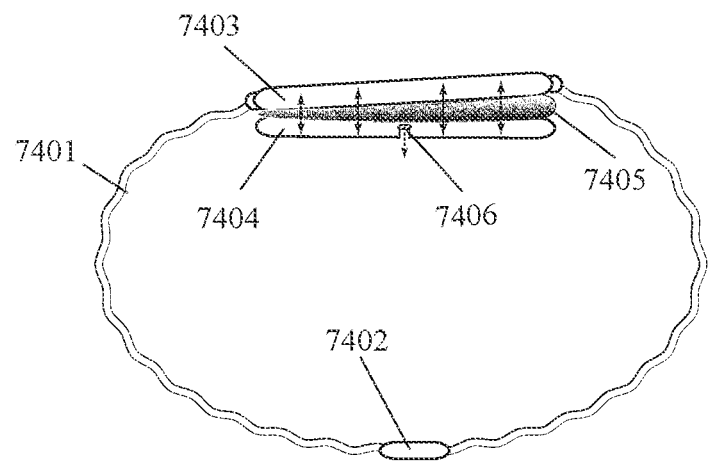

FIG. 74 shows a device with sensors on an enclosure which tilts on an inflated member.

Figure 75:
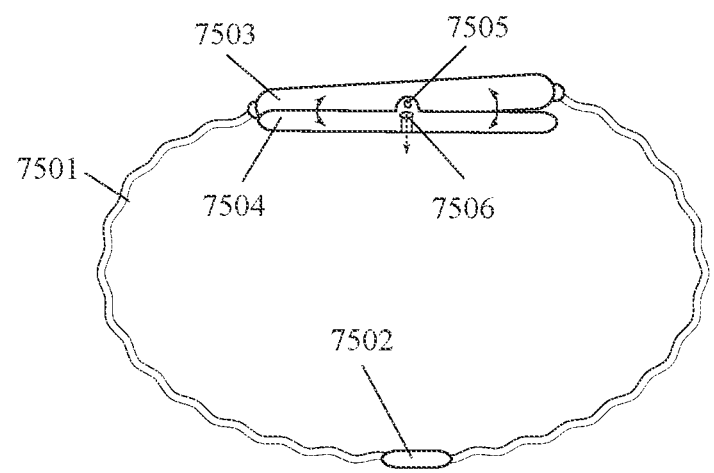

FIG. 75 shows a device with sensors on an enclosure which tilts on a rigid member.

Figure 76:
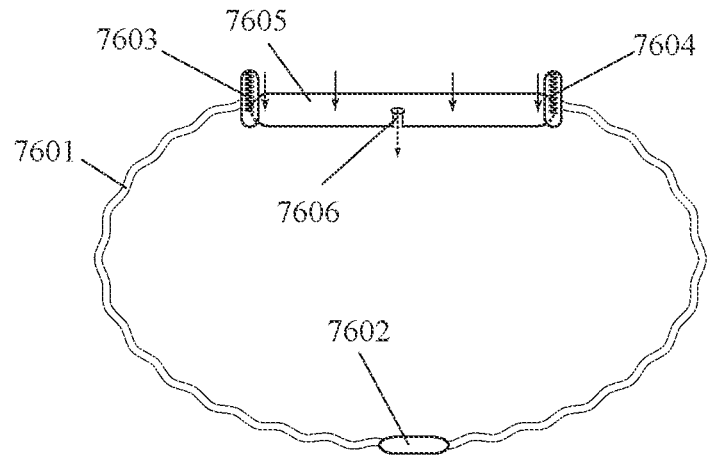

FIG. 76 shows a device with sensors on an enclosure pushed toward the body by a spring mechanism.

Figure 77:
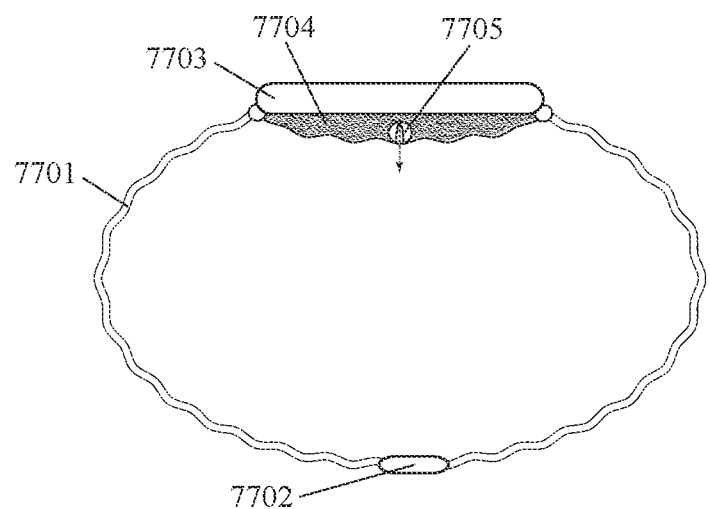

FIG. 77 shows a device with a sensor pushed toward the body by an inflated member.

Figure 78:
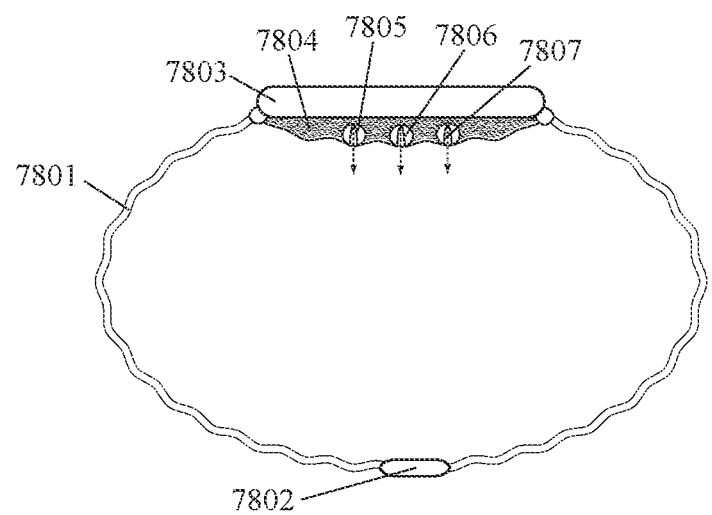

FIG. 78 shows a device with sensors pushed toward the body by an inflated member.

Figure 79:
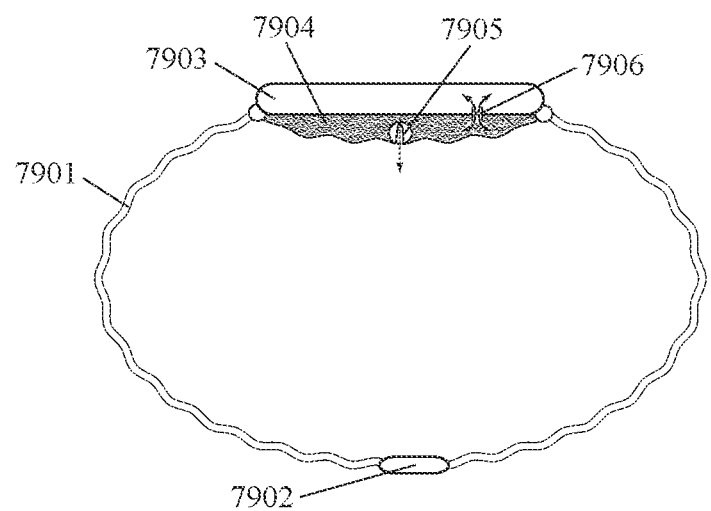

FIG. 79 shows a device with a sensor pushed toward the body by an adjustable inflated member.

Figure 80:
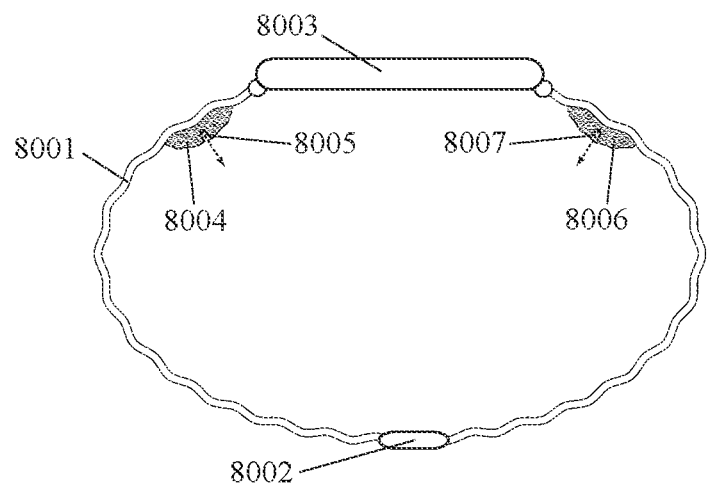

FIG. 80 shows a device with sensors pushed toward the body by inflated members.

Figure 81:
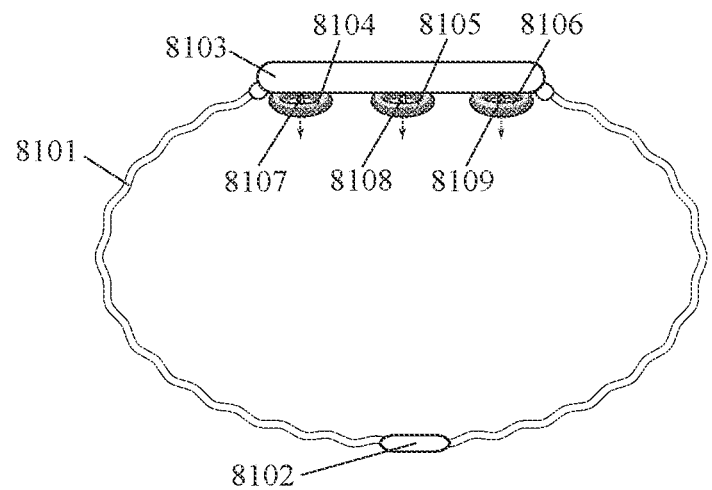

FIG. 81 shows a device with sensors pushed toward the body by toroidal inflated members.

Figure 82:
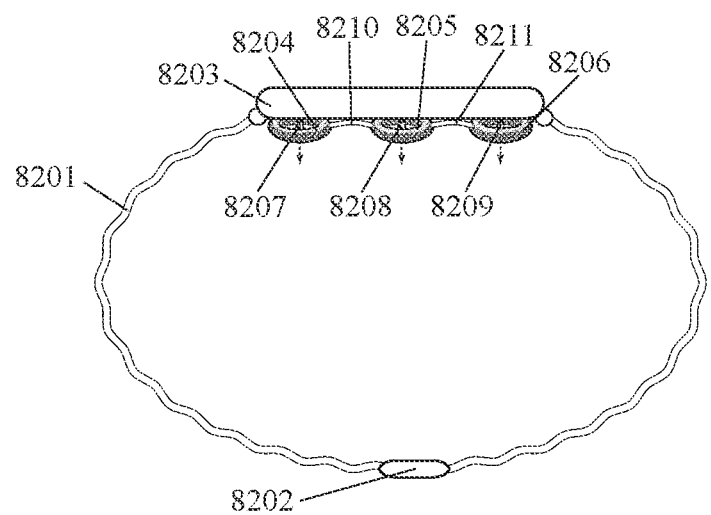

FIG. 82 shows a device with sensors pushed toward the body by connected toroidal members.

Figure 83:
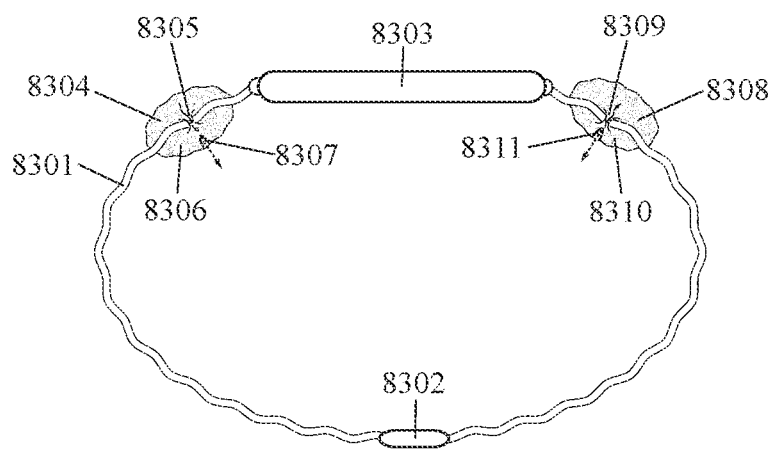

FIG. 83 shows a device with sensors pushed toward the body by adjustable inflated members.

Figure 84:
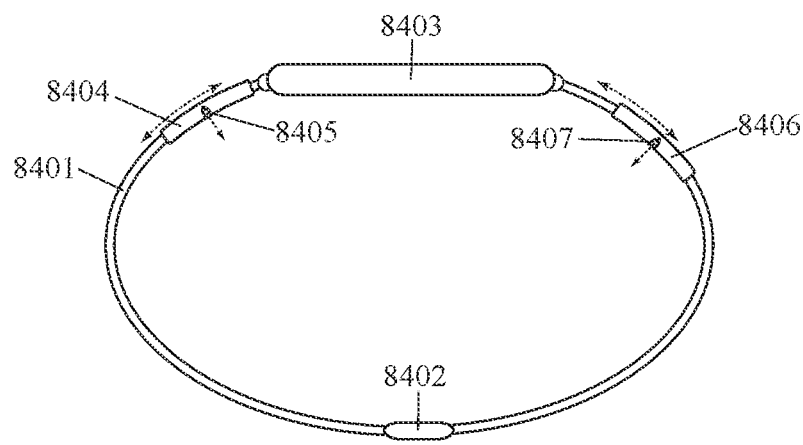

FIG. 84 shows a device with sensors on two circumferentially-sliding members.

Figure 85:
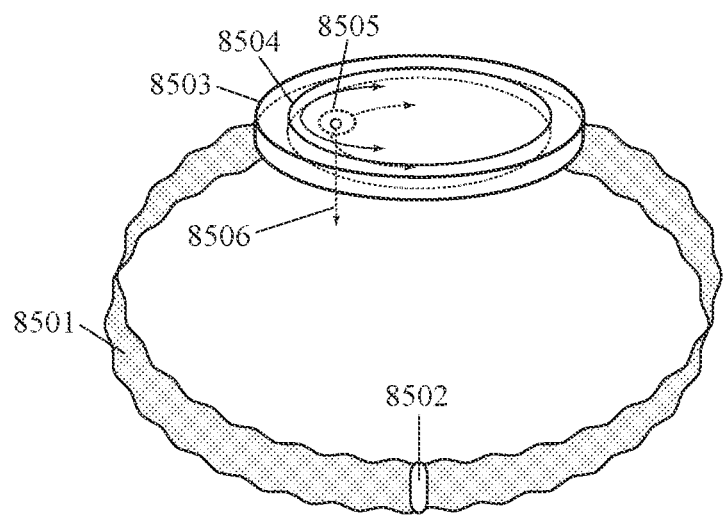

FIG. 85 shows a device with sensors on a non-threaded rotating member.

Figure 86:
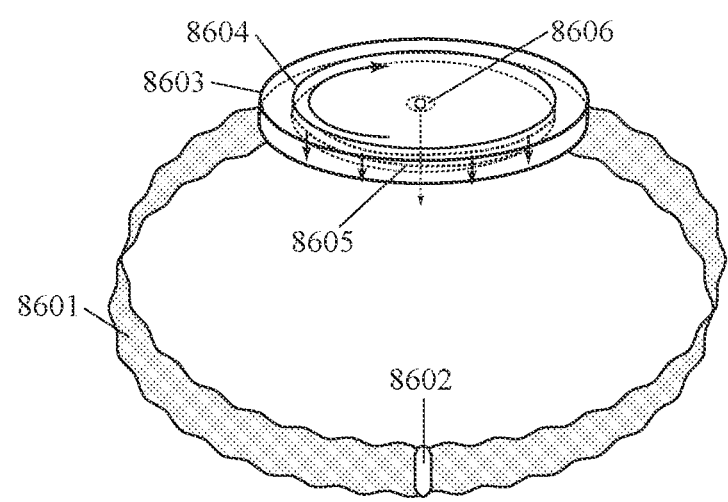

FIG. 86 shows a device with sensors on a threaded rotating member.

Figure 87:
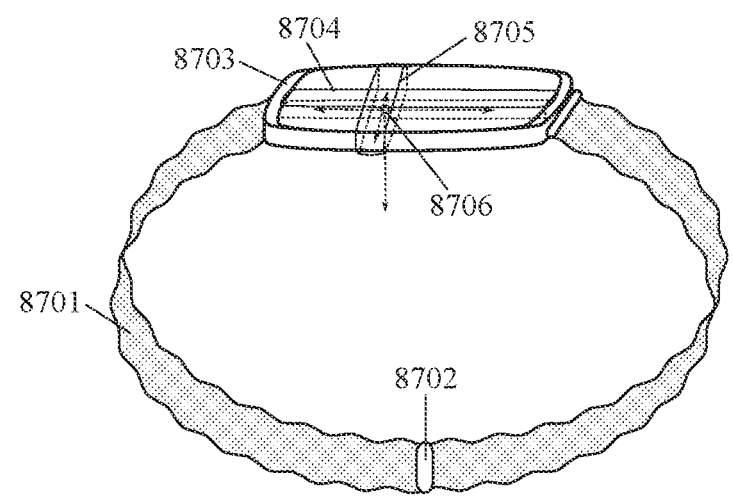

FIG. 87 shows a device with sensors which can be moved along an X and Y axes.

Figure 88:
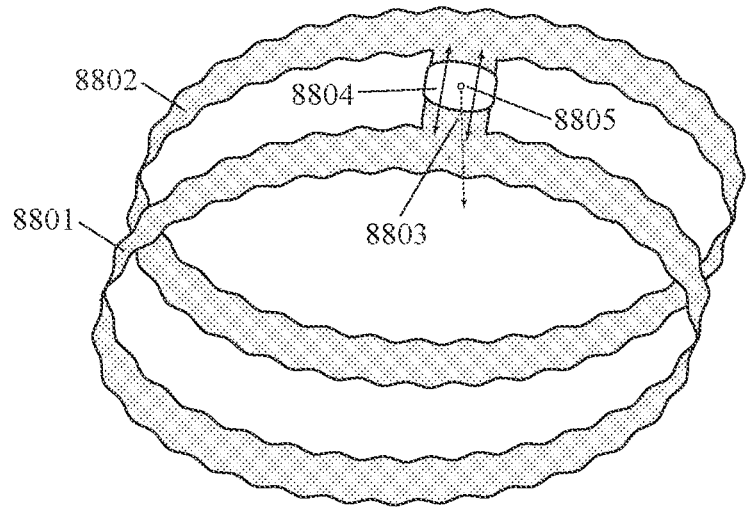

FIG. 88 shows a device with two parallel bands and a sensor which slides between them.

Figure 89:
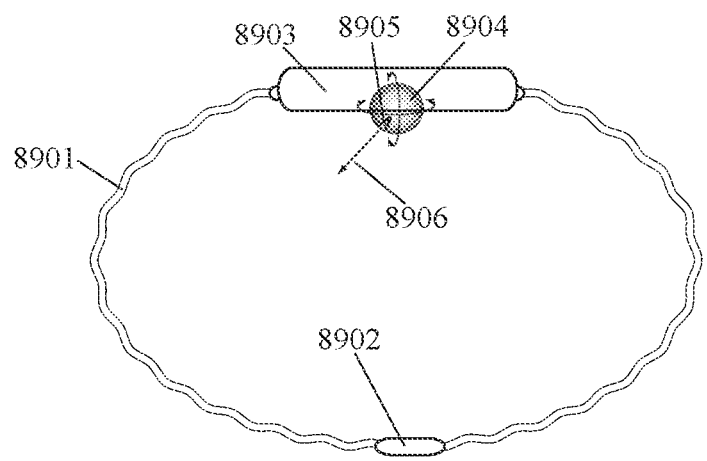

FIG. 89 shows a device with a sensor on a rotating ball.

Figure 90:
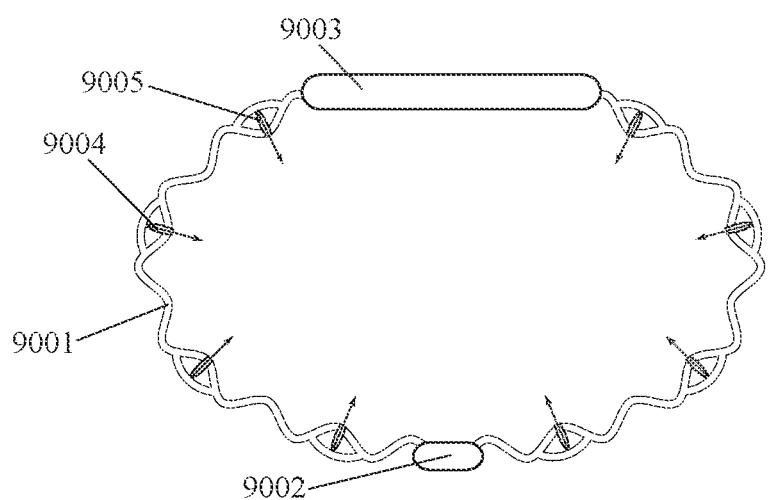

FIG. 90 shows a first device with sensors on a radially-undulating strap.

Figure 91:
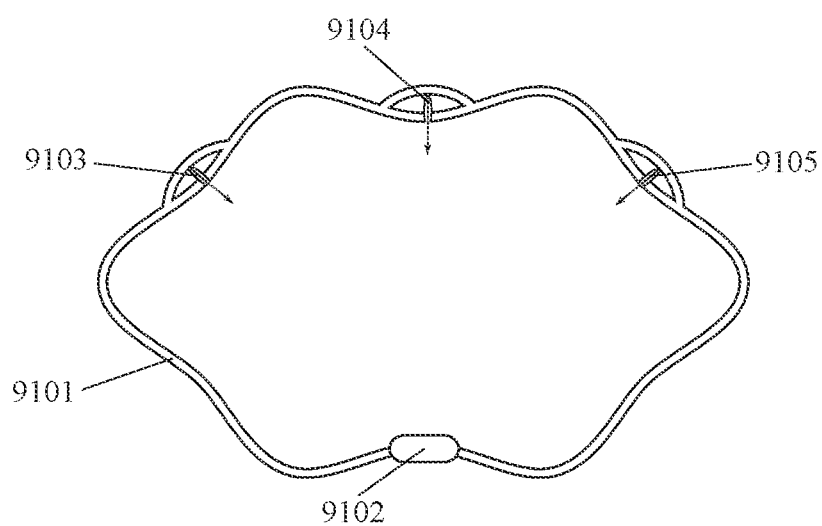

FIG. 91 shows a second device with sensors on a radially-undulating strap.

Figure 92:
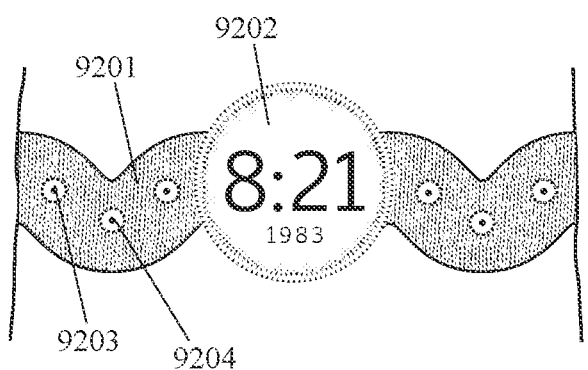

FIG. 92 shows a device with sensors on a laterally-undulating strap.

Figure 93:
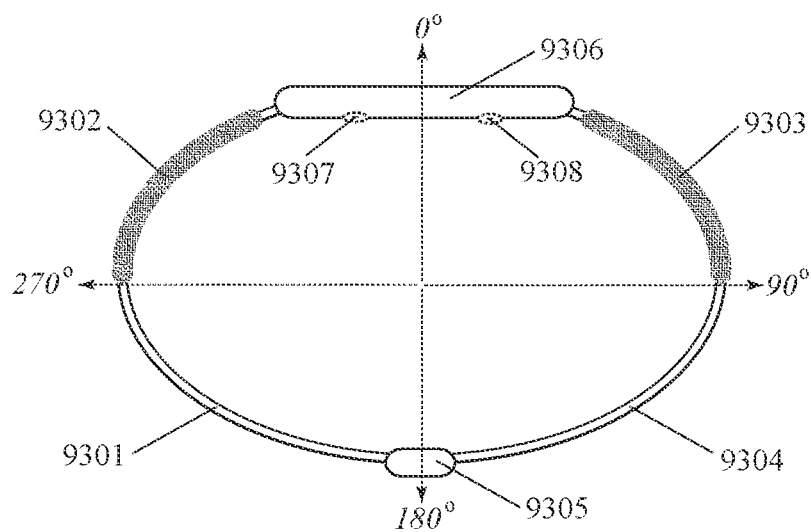

FIG. 93 shows a first device with sensors on a strap with elastic portions.

Figure 94:
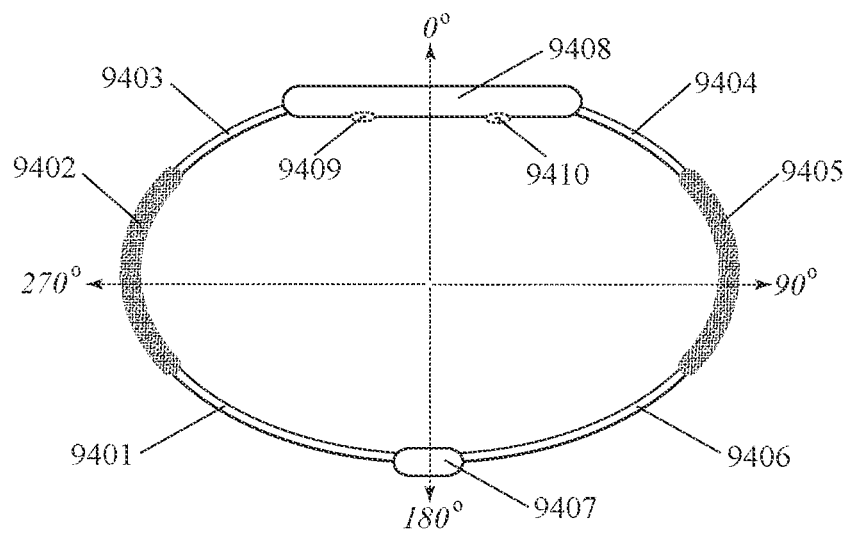

FIG. 94 shows a second device with sensors on a strap with elastic portions.

Figure 95:
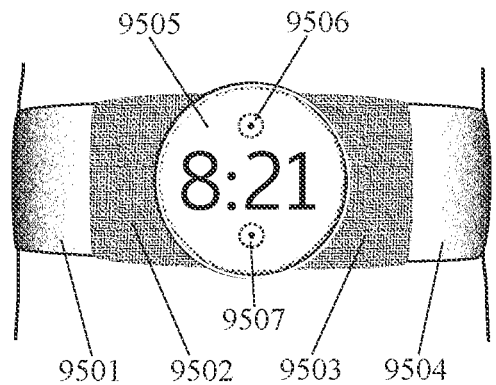

FIG. 95 shows a device with sensors on an enclosure connected to a strap by planoconvex elastic members.

Figure 96:
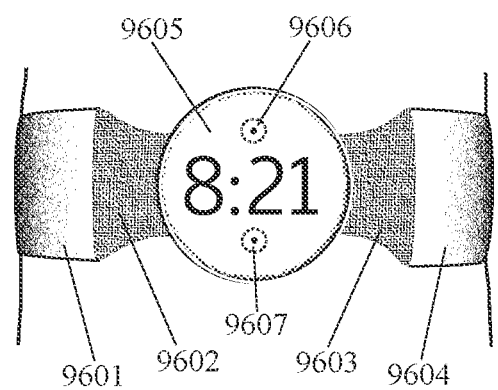

FIG. 96 shows a device with sensors on an enclosure connected to a strap by tapered elastic members.

Figure 97:
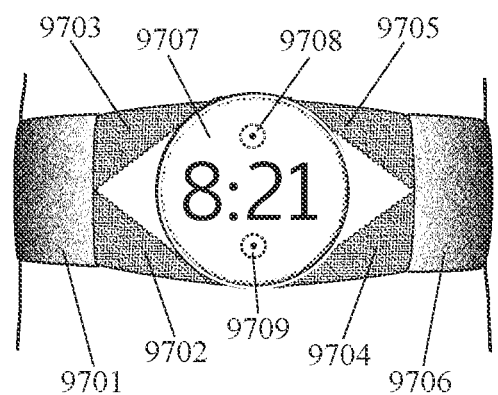

FIG. 97 shows a device with sensors on an enclosure connected to a strap by pennant-shaped elastic members.

Figure 98:
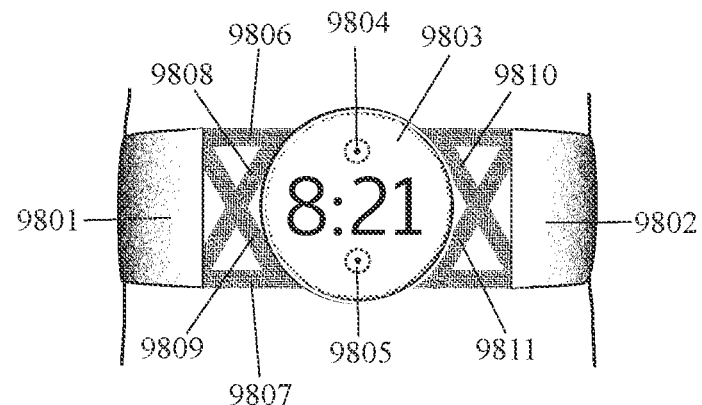

FIG. 98 shows a device with sensors on an enclosure connected to a strap by criss-crossed elastic members.

Figure 99:
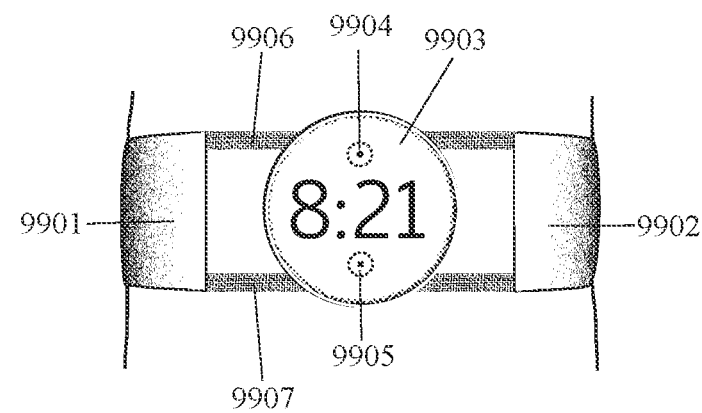

FIG. 99 shows a device with sensors on an enclosure connected to a strap by two parallel elastic members.

Figure 100:
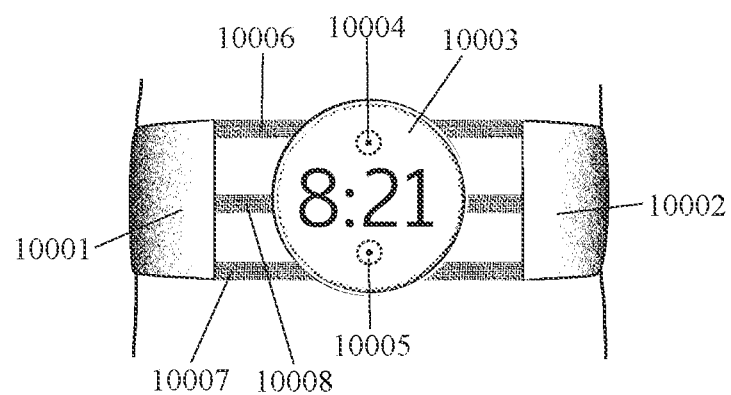

FIG. 100 shows a device with sensors on an enclosure connected to a strap by three parallel elastic members.

Figure 101:
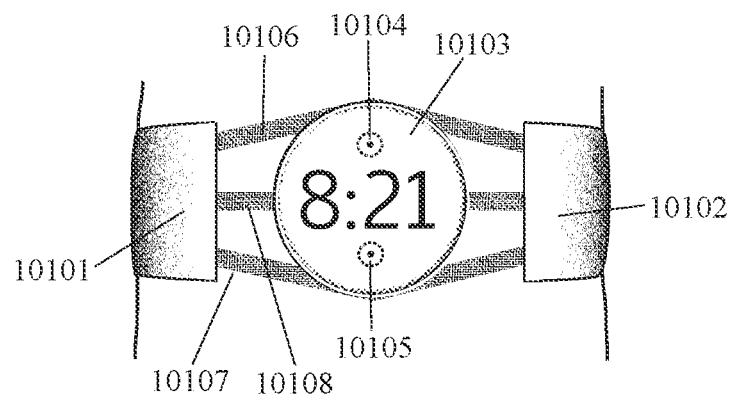

FIG. 101 shows a device with sensors on an enclosure connected to a strap by three non-parallel elastic members.

Figure 102:
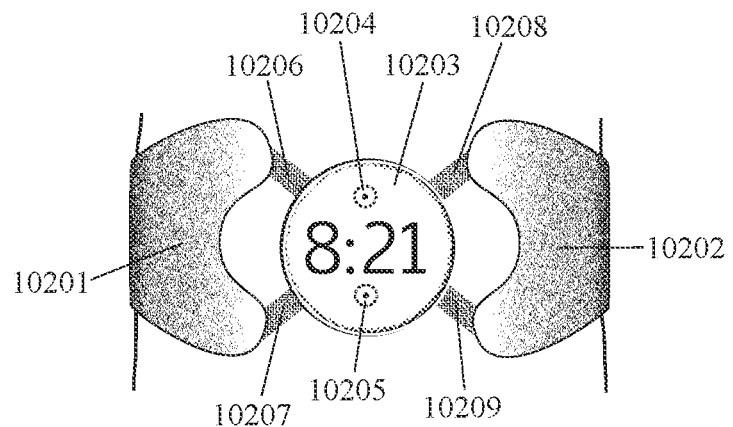

FIG. 102 shows a device with sensors on an enclosure connected to a strap by two generally-perpendicular elastic members.

Figure 103:
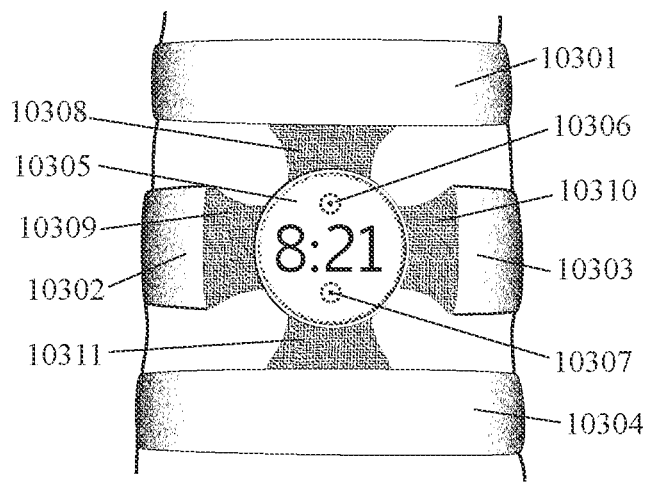

FIG. 103 shows a device with sensors and three circumferential bands.

Figure 104:
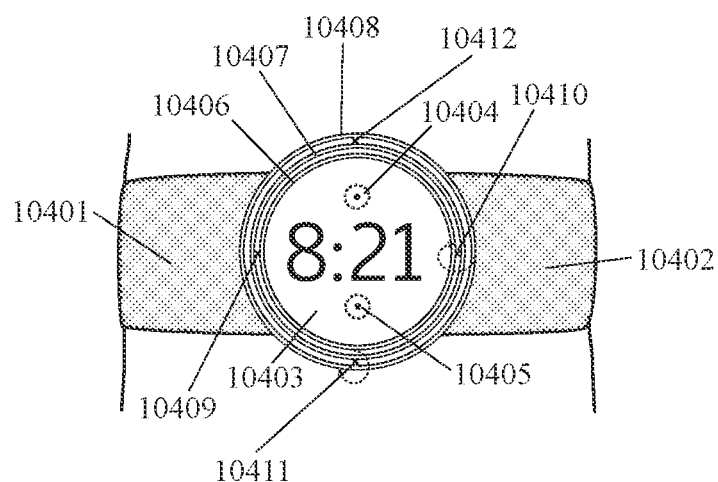

FIG. 104 shows a device with sensors on a gimbaled enclosure.

Figure 105:
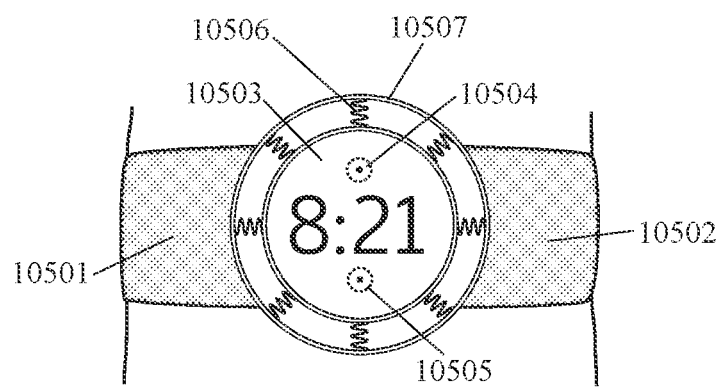

FIG. 105 shows a device with sensors on a radially-suspended enclosure.

Figure 106:
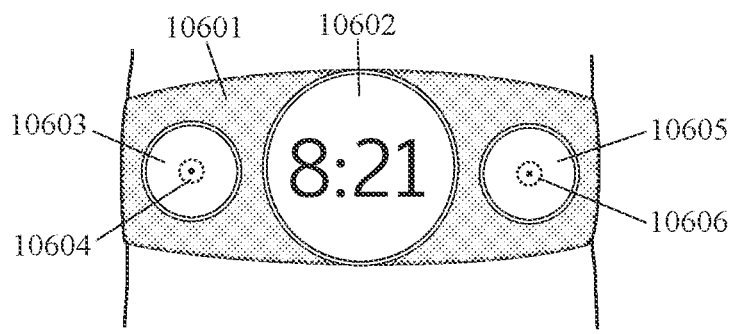

FIG. 106 shows a device with sensors on two arcuate enclosures.

Figure 107:
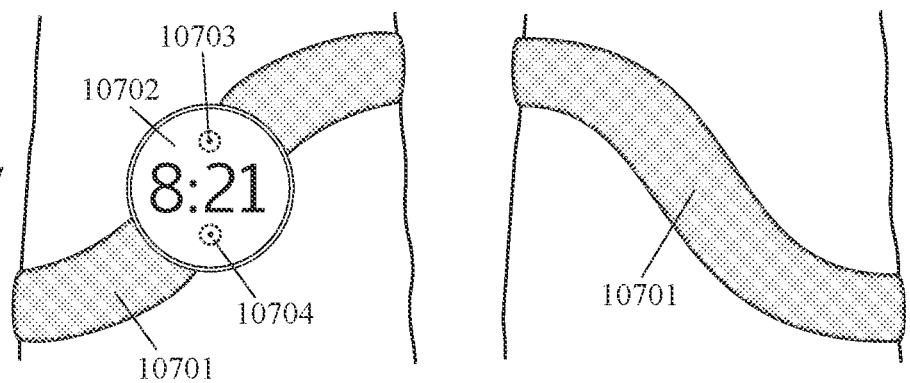

FIG. 107 shows a device with sensors on an enclosure which is diagonally connected to a strap.

Figure 108:
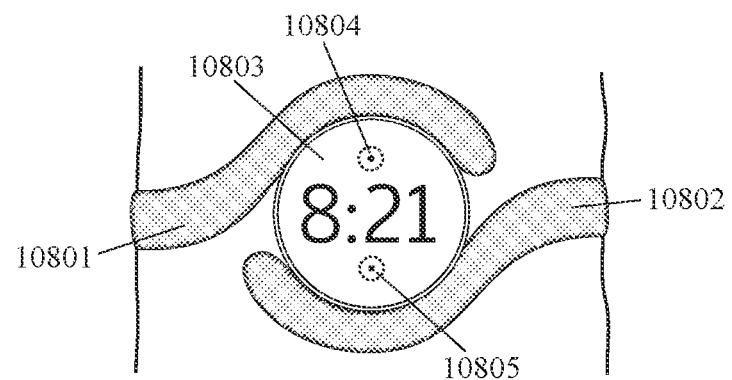

FIG. 108 shows a device with sensors and a "two gummi worm" design.

Figure 109:
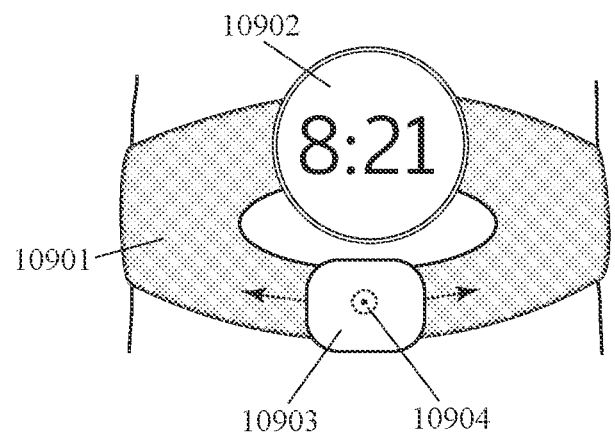

FIG. 109 shows a device with sensors on one arm of a bifurcating band.

Figure 110:
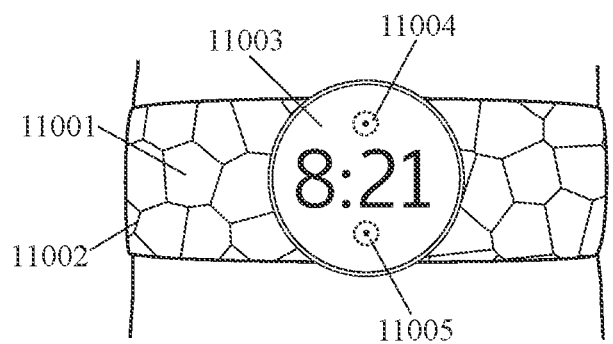

FIG. 110 shows a device with sensors and various-shaped polygons connected by flexible strips or joints.

Figure 111:
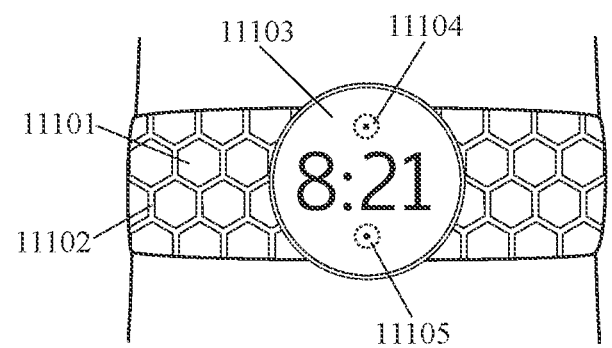

FIG. 111 shows a device with sensors and hexagons connected by flexible strips or joints.

Figure 112:
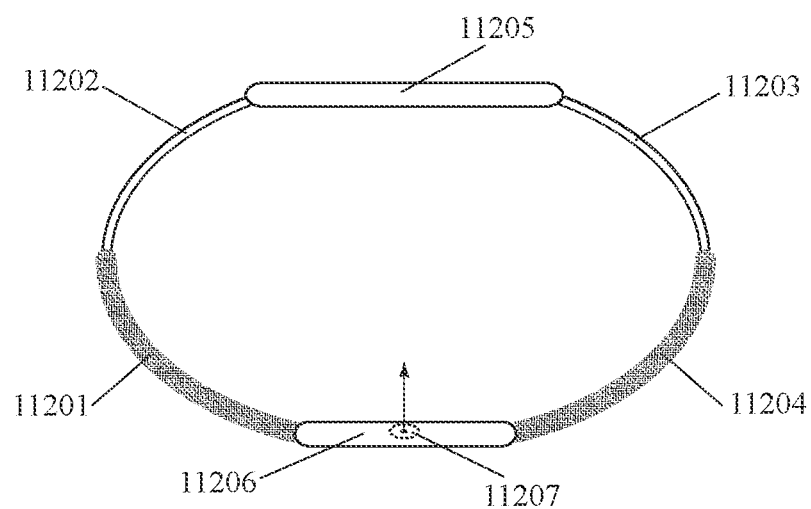

FIG. 112 shows a device with sensors and a band with two elastic quadrants.

Figure 113:
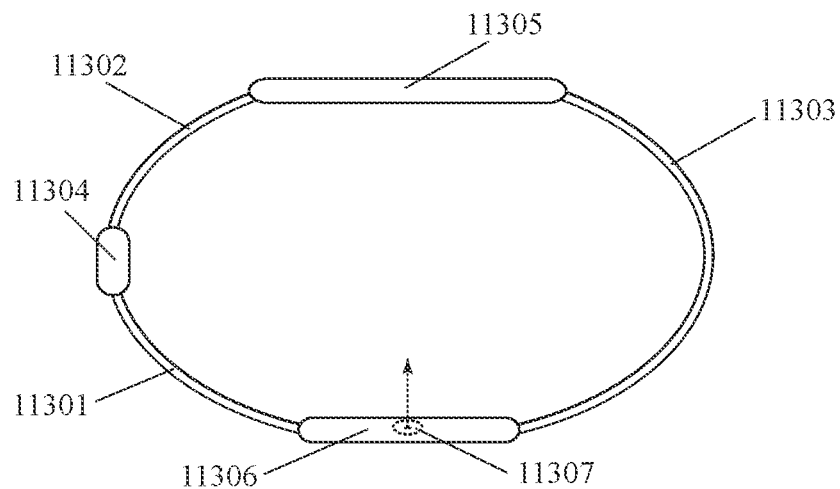

FIG. 113 shows a device with sensors and a band with a side buckle or clasp.

Figure 114:
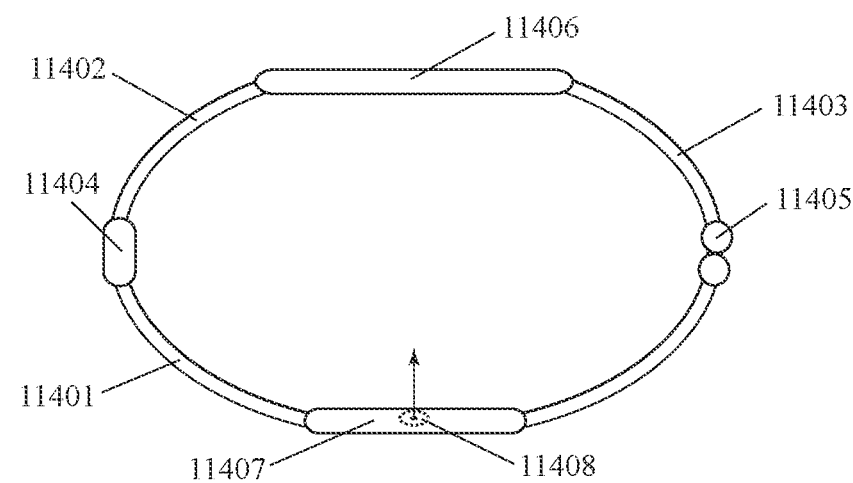

FIG. 114 shows a device with sensors and a "clam-shell" band.

Figure 115:
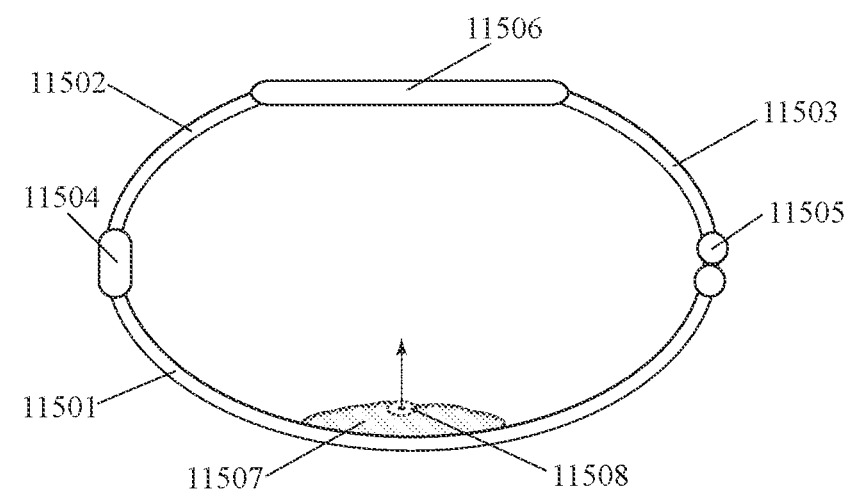

FIG. 115 shows a device with sensors, a "clam-shell" band, and a compressible member.

Figure 116:
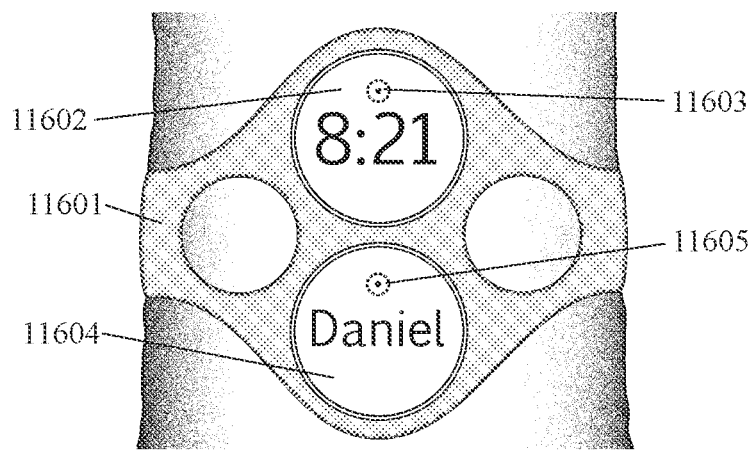

FIG. 116 shows a first device with sensors and a bulging band with two display screens.

Figure 117:
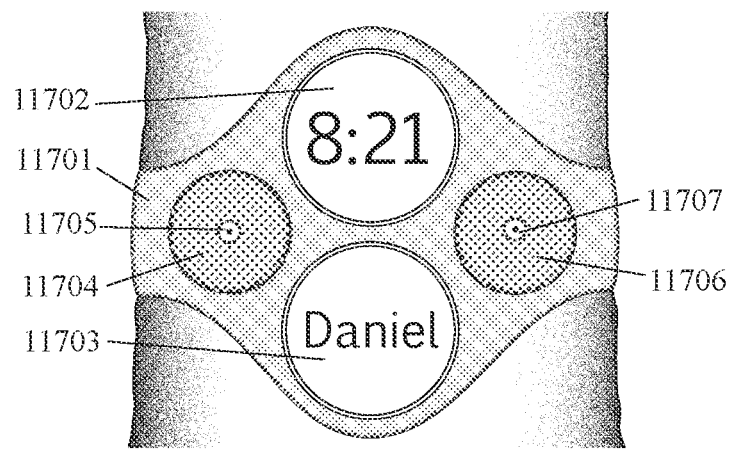

FIG. 117 shows a second device with sensors and a bulging band with two display screens.

Figure 118:
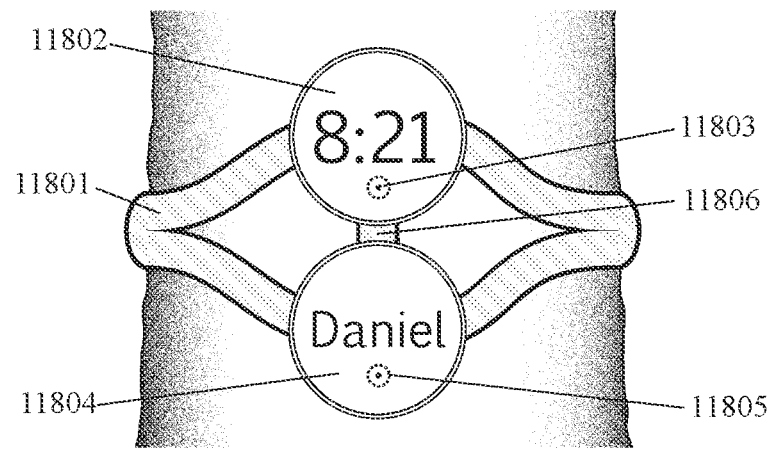

FIG. 118 shows a device with sensors and a bifurcating band with two display screens.

Figure 119:
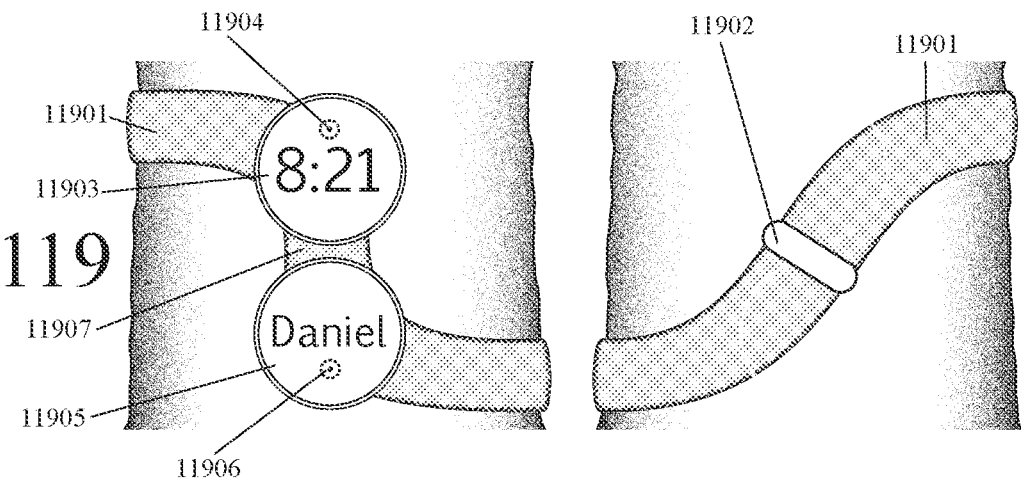

FIG. 119 shows a device with sensors and a serpentine band with two display screens.

Figure 120:
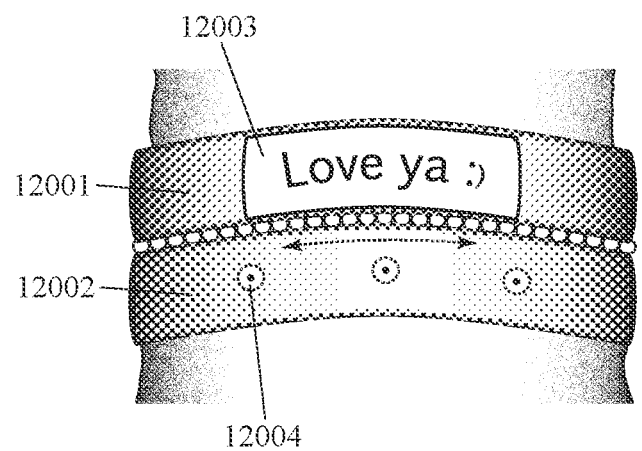

FIG. 120 shows a device with sensors and two separately-rotatable bands.

Figure 121:
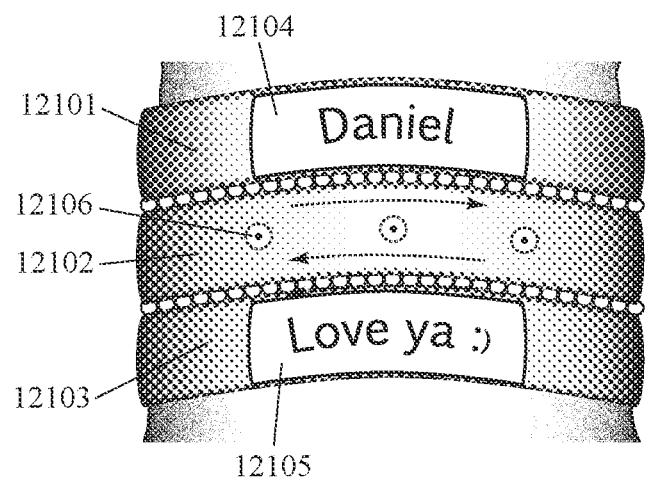

FIG. 121 shows a device with sensors and three bands.

Figure 122:
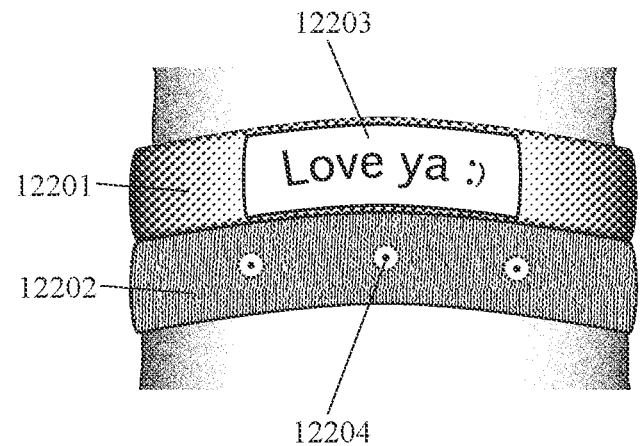

FIG. 122 shows a device with sensors, a rigid band, and an elastic band.

Figure 123:
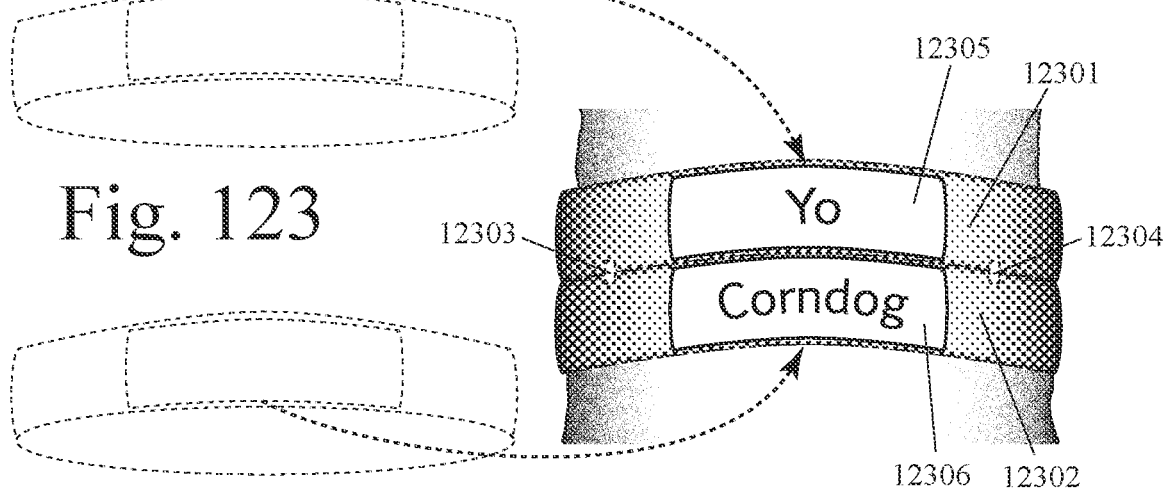

FIG. 123 shows a device with sensors and two connectable bands.

Figure 124:
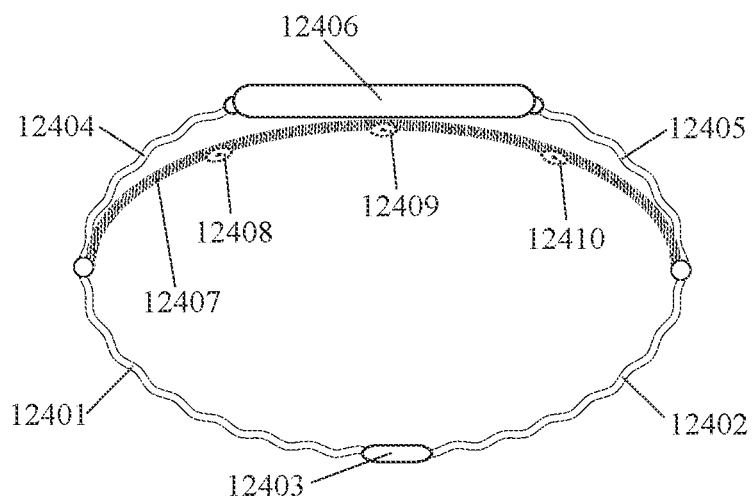

FIG. 124 shows a device with sensors, an outer rigid band, and an inner elastic half-band.

Figure 125:
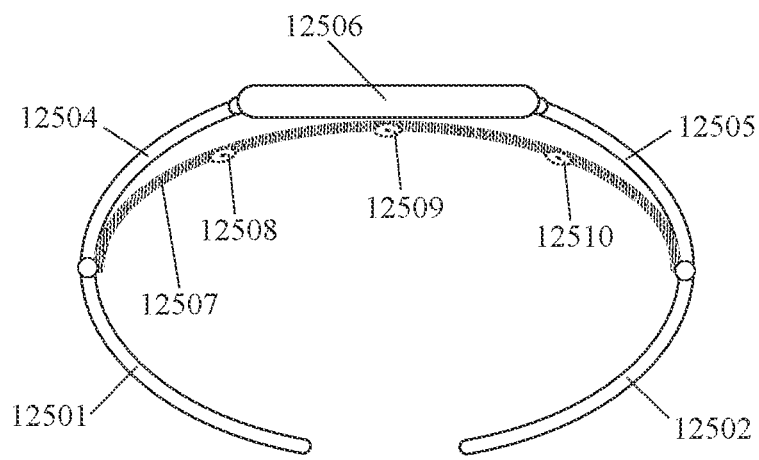

FIG. 125 shows a device with sensors, an outer rigid bracelet, and an inner elastic half-band.

Figure 126:
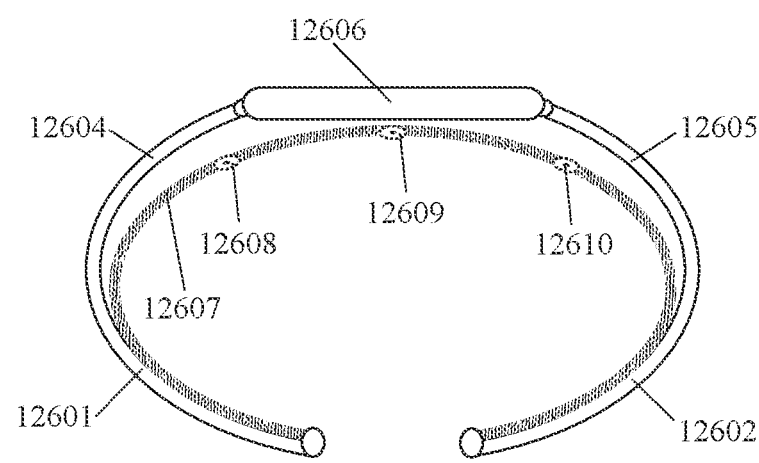

FIG. 126 shows a device with sensors, an outer rigid bracelet, and an inner elastic band.

Figure 127:
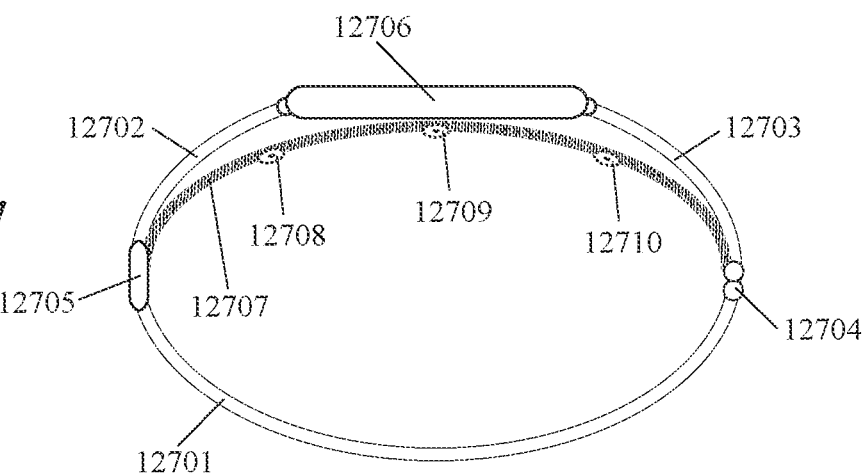

FIG. 127 shows a device with sensors, a clam-shell outer band, and an upper inner elastic half-band.

Figure 128:
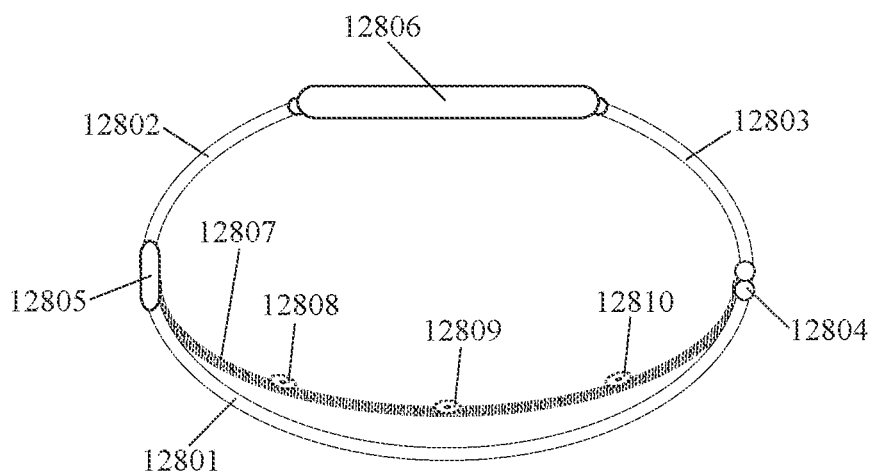

FIG. 128 shows a device with sensors, a clam-shell outer band, and a lower inner elastic half-band.

Figure 129:
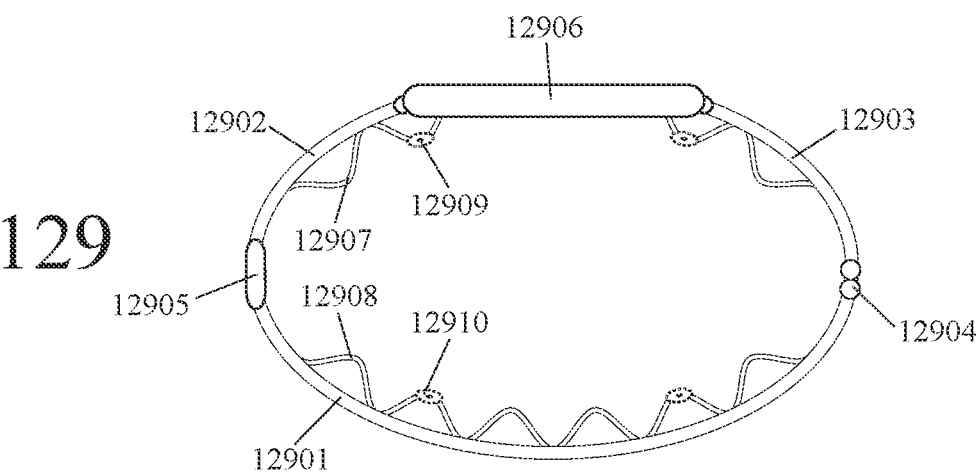

FIG. 129 shows a device with sensors, a clam-shell outer band, and an undulating inner flexible band.

Figure 130:
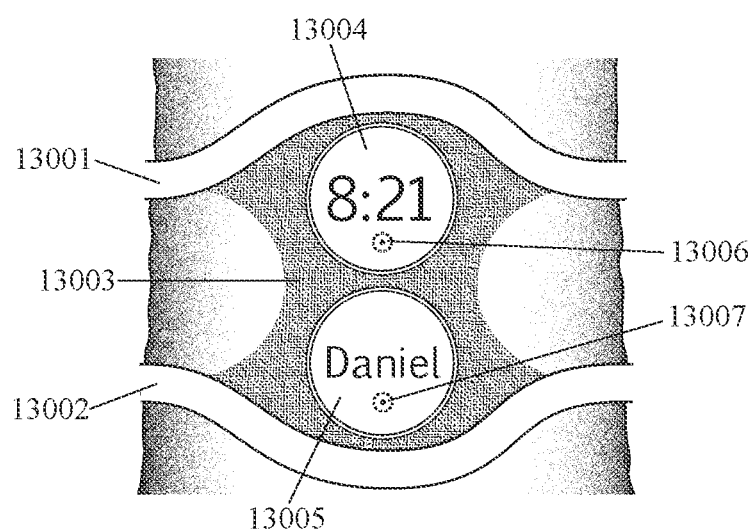

FIG. 130 shows a device with sensors and two bands connected by an hour-glass-shaped elastic member.

Figure 131:
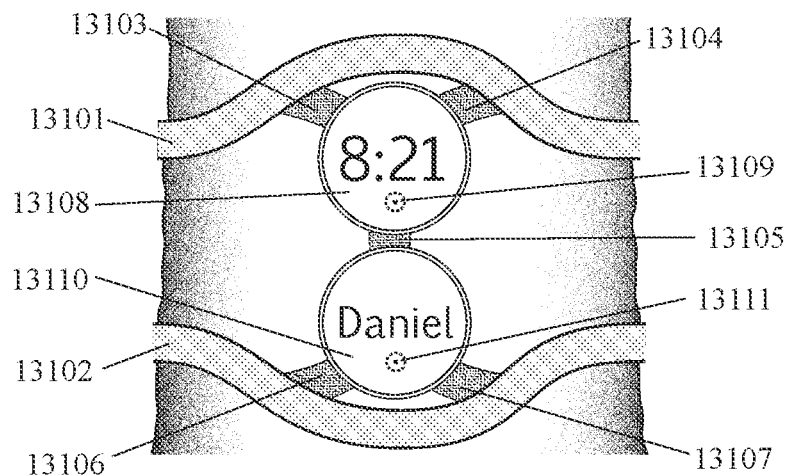

FIG. 131 shows a device with sensors and two bands connected by two elastic members.

Figure 132:
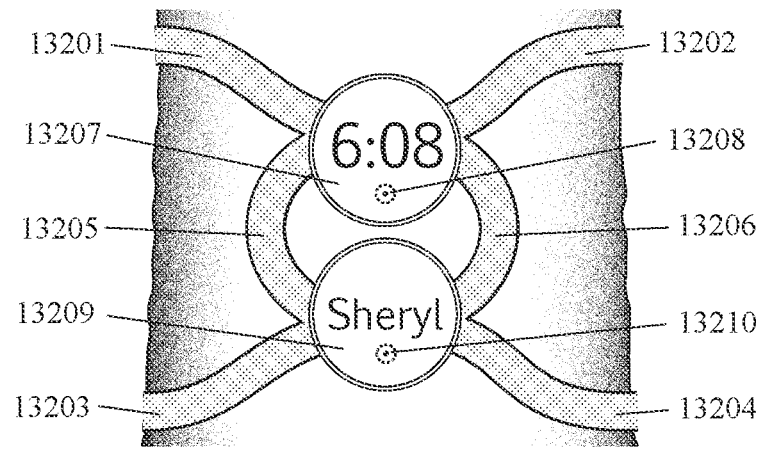

FIG. 132 shows a device with sensors and two undulating bands.

Figure 133:
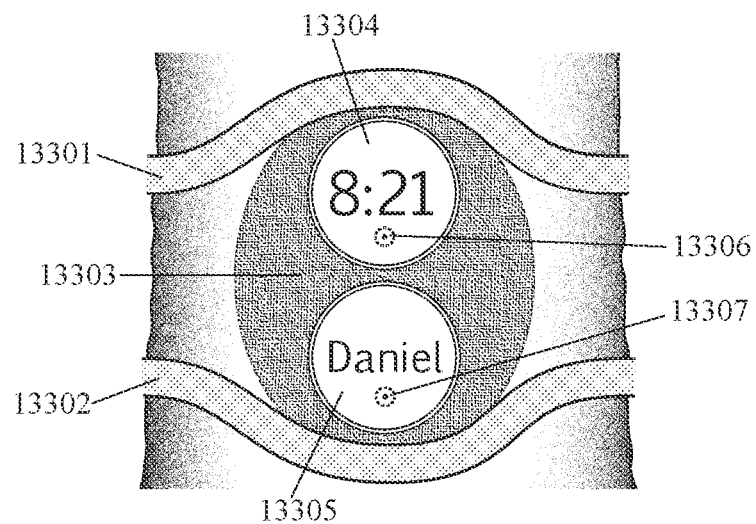

FIG. 133 shows a device with sensors and two bands connected by an oval-shaped elastic member.

DETAILED DESCRIPTION OF THE FIGURES

Figure 1:
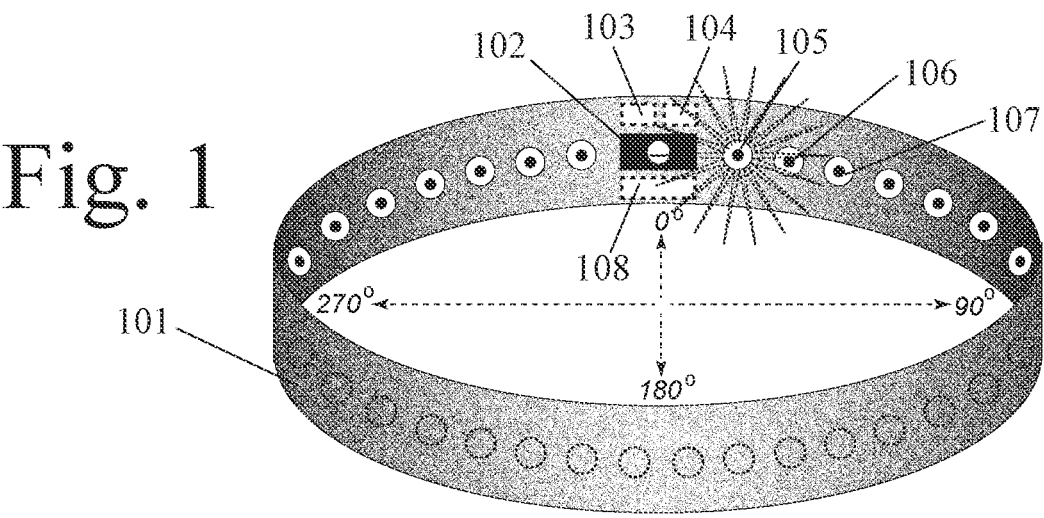
FIGS. 1 through 3 show three sequential views of a device with a circumferential emitter array and a single receiver.

FIGS. 1 through 133 of this disclosure show examples of how this invention can be embodied in an arcuate wearable device with a circumferential or annular array of spectroscopic sensors for measuring body hydration level. In an example, this invention can be embodied in a smart watch band, a specialized hydration-monitoring band, or a finger ring. Before discussing these figures specifically, however, it is useful to provide an introductory section which provides an overview of key concepts and variations for such a hydration monitoring device. The key concepts and variations discussed in the introductory section can be applied, where appropriate, to the specific examples shown in the following figures. Providing these concepts and variations once in a single introductory section helps to avoid the duplication and redundancy which would occur if these concepts and variations were repeated in the narrative sections accompanying each figure. (This disclosure is already large enough!) After the introductory section, the examples in FIGS. 1 through 133 are discussed in detail.

In an example, an arcuate wearable device for measuring a person's hydration level can include a circumferential or annular array of spectroscopic (or, using a noun as an adjective, "spectroscopy") sensors. In an example, a spectroscopic sensor can comprise a light energy emitter and a light energy receiver. The light energy emitter emits light energy toward a person's body tissue. The light energy receiver receives this light energy after this light energy has interacted with the person's body tissue. This interaction can include reflection of light energy from body tissue, transmission of light energy through body tissue, and/or absorption of light energy by body tissue. Changes in the spectrum of light energy due to this interaction with the person's body tissue are analyzed in order to measure changes in the person's hydration level. In an example, a wrist-worn or finger-worn device for measuring a person's hydration level can collect data concerning light energy that is reflected from and/or absorbed by the person's wrist or finger.

In an example, changes in a person's body hydration level can cause changes in the volume and flow of blood through the person's wrist, arm, and/or finger. In an example, an arcuate wearable device for measuring a person's hydration level can collect data from a two-dimensional circumferential or annular array of spectroscopic sensors (e.g. light emitters and light receivers) concerning changes in the volume and/or flow of the person's blood which can, in turn, be used to estimate changes in the person's body hydration level. In an example, this device can comprise a photoplethysmography (PPG) sensor. In an example, changes in a person's hydration level can also cause changes in the volume of interstitial fluid in the person's wrist, arm, and/or finger. In an example, an arcuate wearable device for measuring a person's hydration level can collect data from a two-dimensional circumferential or annular array of spectroscopic sensors (e.g. light emitters and light receivers) concerning changes in the volume of the person's interstitial fluid which can, in turn, be used to estimate changes in the person's body hydration level.

In an example, an arcuate wearable device for measuring a person's hydration level can comprise one or more near-infrared light spectroscopic sensors. In an example, an arcuate wearable device for measuring a person's hydration level can comprise one or more ultraviolet light spectroscopic sensors. In an example, an arcuate wearable device for measuring a person's hydration level can have an array of spectroscopic sensors which are distributed around the radially-inward-facing circumference of the device. In an example, spectroscopic sensors can be evenly distributed along different locations around the circumference of a wearable device. In an example, spectroscopic sensors can be clustered on ventral and/or dorsal portions of the circumference of a wearable device. In another example, an array of spectroscopic sensors can be distributed around the radially-inward-facing side of a modular smart watch strap, a specialized wrist-worn band, or a finger ring.

In an example, an arcuate wearable device for measuring a person's hydration level can have a two-dimensional array of spectroscopic sensors. Spectroscopic sensors in a two-dimensional array can differ in location circumferentially or annularly (e.g. be at different locations around the circumference of a wearable device) and laterally (e.g. be at different locations along axes which are perpendicular to the circumference of the device). In an example, spectroscopic sensors in a two-dimensional sensor array can each be configured to measure the spectrum of light energy reflected from (and/or absorbed by) the tissue of a person's wrist, arm, or finger. In an example, a light emitter and a light receiver together can comprise a near-infrared spectroscopic sensor. In an example, one or more near-infrared spectroscopic sensors can be used to monitor a person's water consumption.

In an example, an arcuate wearable device for measuring a person's hydration level can comprise: an arcuate band which is configured to be worn around at least half of the circumference of a person's wrist, arm, or finger; a circumferential or annular array of light emitters on the arcuate band located along a first circumferential line of the arcuate band, wherein the light emitters are configured to emit light toward the person's body; and a circumferential or annular array of light receivers on the arcuate band located along a second circumferential line of the arcuate band, and wherein the spectra of light rays which have interacted with the person's body tissue and are received by the one or more light receivers are analyzed in order to measure the person's hydration level. In an example, the second circumferential line can be different than the first circumferential line. In an example, a circumferential or annular array of light emitters can be configured to span at least half of the circumference of a person's wrist, arm, or finger. In an example, a circumferential or annular array of light receivers can be configured to span at least half of the circumference of a person's wrist, arm, or finger.

In an example, a first subset of one or more light emitters selected from an array of light emitters can have a first average polar coordinate and emit light at a first point in time and a second subset of one or more light emitters selected from an array of light emitters can have a second average polar coordinate and emit light at a second point in time. The second average coordinate can differ from the first average coordinate by at least 5 degrees. The light receivers can be configured to receive light from the first subset of light emitters at a first point in time after light from this subset has interacted with the person's body tissue and the light receivers can be configured to receive light from the second subset of light emitters at a second point in time after light from this subset has interacted with the person's body tissue.

In an example, an arcuate wearable device for measuring a person's hydration level can comprise: a rigid electronics housing which includes a display; a flexible band; a circumferential or annular array of light emitters on the flexible band, wherein the light emitters are configured to emit light toward the person's body; and a circumferential or annular array of light receivers on the flexible band, wherein the spectra of light rays received by the light receivers are analyzed in order to measure the person's hydration level. In an example, a light emitter and a light receiver together can comprise a near-infrared spectroscopic sensor. In an example, a near-infrared spectroscopic sensor can be used to monitor a person's water consumption. In an example, a circumferential or annular array of light emitters can be configured to span at least half of the circumference of a person's wrist, arm, or finger. In an example, a circumferential or annular array of light receivers can be configured to span at least half of the circumference of a person's wrist, arm, or finger.

In an example, an arcuate wearable device for measuring a person's hydration level can comprise: a primary electronics housing which is configured to be worn on the dorsal surface of a person's wrist, arm, or finger; a circumferential or annular series of secondary electronics housings, wherein at least one secondary electronics housing has both a light emitter and a light receiver, wherein the light emitter emits light toward the surface of the person's wrist, arm, or finger, wherein the light receiver receives light from the light emitter after this light has interacted with the person's body, and wherein the spectrum of light received by a light receiver is analyzed in order to measure a person's hydration level; and a circumferential or annular series of flexible members; wherein the flexible members are selected from the group consisting of bands, straps, strips, swatches, wires, cords, threads, joints, and chain links; wherein the flexible members connect the primary electronics housing and the secondary electronics housings into an arcuate wearable band which spans at least half of the circumference of a person's wrist, arm, or finger. In an example, each of the secondary electronics housings can have both a light emitter and a light receiver.

In an example, a primary electronics housing can include a display. In an example, this display can be a smart watch face. In an example, secondary electronics housings can be modular and reversibly connected to each other, a strap, or the primary electronics housing. In an example, a device for measuring a person's hydration level can have between two and six secondary electronics housings. In an example, a device for measuring a person's hydration level can have more than six secondary electronics housings. In an example, at least one secondary electronics housing can include a circular and/or polygonal array of light emitters around a central light receiver. In an example, each of the secondary electronics housings can include a circular and/or polygonal array of light emitters around a central light receiver. In an example, secondary electronics housings can be (disproportionately) located and/or clustered on dorsal and/or ventral portions of a device.

In an example, a circumferential or annular spectroscopic sensor array can include at least one light emitter (which is configured to emit light energy toward the person's body) and at least one light receiver (which is configured to receive light energy that has passed through and/or been reflected from the person's body). In an example, a first light emitter can emit light with a first frequency and/or spectrum and a second light emitter can emit light with a second frequency and/or spectrum. In an example, a first light emitter can emit light at a first angle and a second light emitter can emit light at a second angle.

In an example, an arcuate wearable device for measuring a person's hydration level can comprise: an attachment member which spans at least a portion of the circumference of a person's wrist, arm, or finger; an enclosure which is part of and/or attached to the attachment member; a first spectroscopic sensor in the enclosure which projects a beam of light onto the arm surface at a first angle relative to the enclosure; and a second spectroscopic sensor in the enclosure which projects a beam of light onto the arm surface at a second angle relative to the enclosure, wherein the first angle differs from the second angle by at least 10 degrees.

In an example, an arcuate wearable device for measuring a person's hydration level can comprise: an attachment member which spans at least a portion of the circumference of a person's wrist, arm, or finger; an enclosure which is part of and/or attached to the attachment member; an elastic member filled with a fluid, gel, or gas which is attached to and/or part of the enclosure; and one or more spectroscopic sensors which collect data concerning light which has interacted with the person's tissue, wherein these one or more spectroscopic sensors are attached to a circumference-center-facing wall of the elastic member.

In an example, an arcuate wearable device for measuring a person's hydration level can comprise: a circumferentially or annularly-undulating attachment member which spans at least a portion of the circumference of a person's wrist, arm, or finger; and a plurality of spectroscopic sensors which collect data concerning light which has interacted with wrist, arm, or finger tissue, wherein each spectroscopic sensor is located at the proximal portion of an undulation, and wherein the proximal portion of an undulation is the portion of an undulating wave which is closest to the circumferential center of the device.

In an example, an attachment member can be selected from the group consisting of: strap, band, bracelet, ring, armlet, cuff, and sleeve. In an example, an attachment member can be configured to be attached to the person's arm by connecting two ends of the attachment member with a clasp, clip, buckle, hook, pin, plug, or hook-and-eye mechanism. In an example, an attachment member can be configured to be attached to a person's arm by stretching and sliding it over the person's hand onto the arm. In an example, an attachment member can be configured to be attached to a person's finger by sliding it over the person's finger.

In an example, an arcuate wearable device for measuring a person's hydration level can comprise: an arcuate band which is configured to span (some or all of) the circumferential perimeter of a part of a person's body (such as a wrist, arm, or finger); a light energy emitter which is configured to emit energy toward the part of the person's body; a light energy receiver which is configured to receive energy from the light energy emitter after that energy has passed through and/or been reflected from the part of the person's body; a data processor which receives data from the light energy receiver which is analyzed in order to measure the person's hydration level; and an energy source which provides energy to the light energy emitter and/or to the data processor.

In an example, an arcuate wearable device for measuring a person's hydration level can comprise: an arcuate band which is configured to span (some or all of) the circumferential perimeter of a part of a person's body (such as a wrist, arm, or finger); a light energy emitter which is configured to emit energy toward the part of the person's body; a light energy receiver which is configured to receive energy from the light energy emitter after that energy has passed through and/or been reflected from the part of the person's body; a data processor which receives data from the light energy receiver which is analyzed in order to measure the person's hydration level; an energy source which provides energy to the light energy emitter and/or to the data processor; a data transmitter which transmits data from the data processor to a remote device and/or remote location; and an energy barrier between the light energy emitter and the light energy receiver which reduces transmission of energy from the light energy emitter to the light energy receiver.

In an example, an arcuate wearable device for measuring a person's hydration level can comprise: an arcuate band which is configured to span (some or all of) the circumferential perimeter of a part of a person's body (such as a wrist, arm, or finger); a light energy emitter which is configured to emit energy toward the part of the person's body; a light energy receiver which is configured to receive energy from the light energy emitter after that energy has passed through and/or been reflected from the part of the person's body; a data processor which receives data from the light energy receiver which is analyzed in order to measure the person's hydration level; an energy source which provides energy to the light energy emitter and/or to the data processor; a data transmitter which transmits data from the data processor to a remote device and/or remote location; and an energy conductor between the light energy emitter and the light energy receiver which increases transmission of energy from the light energy emitter to the light energy receiver.

In an example, an arcuate wearable device for measuring a person's hydration level can comprise: an arcuate band which is configured to span (some or all of) the circumferential perimeter of a part of a person's body (such as a wrist, arm, or finger); a light energy emitter which is configured to emit energy toward the part of the person's body; a light energy receiver which is configured to receive energy from the light energy emitter after that energy has passed through and/or been reflected from the part of the person's body; a data processor which receives data from the light energy receiver which is analyzed in order to measure the person's hydration level; an energy source which provides energy to the light energy emitter and/or to the data processor; a data transmitter which transmits data from the data processor to a remote device and/or remote location; and a housing which is held on the person's body by the arcuate band, wherein the light energy emitter and the light energy receiver are part of the housing.

In an example, a band can be flexible. In an example, a band can be rigid. In an example, portions of a band can be flexible and portions can be rigid. In an example, a band can be elastic or stretchable. In an example, a band can be made from a metal, a polymer, a fabric, or a combination thereof. In an example, a band can be a bracelet, bangle, armlet, or arm band. In an example, a band can be a fitness band or smart watch. In an example, a band can be the strap portion of a fitness monitor or smart watch. In an example, a band can be a finger ring. In an example, a band can include electronic components such as spectroscopic sensors and a display. In an example, a band can further comprise a housing which includes electronic components such as spectroscopic sensors and a display. In an example, a band can be selected from the group consisting of: arm band, armlet, bangle, bracelet, finger ring, finger sleeve, fitness band, shirt cuff, and smart watch. In an example, an arcuate wearable device for measuring a person's hydration level can be incorporated into the cuff of a shirt or pair of pants.

In an example, a band can span the full circumference of the cross-sectional perimeter of a part of a person's body. In an example, a band can fully encircle a person's wrist, arm, or finger. In an example, a band can span between 50% and 95% of the cross-sectional perimeter of a part of a person's body. In an example, a band can span between 50% and 95% of the cross-sectional perimeter of a part of a person's wrist, arm, or finger. In an example, a band can span between 75% and 95% of the cross-sectional perimeter of a part of a person's wrist, arm, or finger. In an example, a band can comprise a single, continuous piece of material. In an example, a band can comprise two or more pieces and/or segments. In an example, a band can comprise a (partially) circumferential or annular series of flexibly-connected segments.

In an example, the term "proximal" when applied to a person's wrist, arm, or finger can mean "closer to the person's shoulder when the arm is extended" and the term "distal" can mean "farther from the person's shoulder when the arm is extended." In an example, a proximal-to-distal axis can be defined for a band worn on the wrist, arm, or finger using this shoulder-based definition of proximal and distal. In an example, the cross-sectional perimeter and/or circumference of an arm can be perpendicular to the central proximal-to-distal axis of that arm. In an example, the cross-sectional perimeter and/or circumference of a forearm can be perpendicular to the central proximal-to-distal axis of that forearm.

In an example, a band can have two ends which can be connected to each other around a part of a person's body by a mechanism selected from the group consisting of: buckle, clasp, hook, pin, knob, button, zipper, magnet, adhesive, and hook-and-eye fabric. In an example, a band can be stretched or expanded so as to slip over a person's hand onto their wrist, arm, or finger or over a person's foot onto their ankle and/or leg. In an example, a band can have two moveable portions connected by a hinge or joint, wherein these two moveable portions can be locked into position around a person's wrist, arm, or finger. In an example, a band can have two ends which can be pulled apart from each other by application of an external force to slip the band around a person's wrist, arm, or finger and then these two ends move back together when the force is removed so as to hold the band around the person's wrist, arm, or finger.

In an example, a light energy emitter can be located on the radially-inward (i.e. body-facing) side of a band. In an example, a light energy receiver can also be located on the radially-inward (i.e. body-facing) side of a band. In an example, a light energy emitter and a light energy receiver can emit and receive light energy, respectively. In an example, a light energy emitter can emit light energy toward body tissue and a light energy receiver can receive a portion of that light energy, after the light energy has passed through and/or been reflected from the body tissue.

In an example, a light energy emitter and a light energy receiver together can comprise a spectroscopic (or "spectroscopy") sensor. In an example, the spectrum of light energy is changed when the light energy passes through body tissue and/or is reflected from body tissue. In an example, changes in the spectrum of light energy which has passed through and/or been reflected from body tissue can be analyzed to detect the composition and/or configuration of body tissue. In an example, a light energy emitter and a light energy receiver together can comprise a photoplethysmography (PPG) sensor.

In an example, changes in the spectrum of light energy caused by interaction with body tissue can be analyzed to provide information on the composition and/or configuration of body tissue which, in turn, enables measurement of body hydration level. In an example, a light energy emitter and a light energy receiver together can comprise a sensor selected from the group consisting of: backscattering spectrometry sensor, infrared spectroscopic sensor, ion mobility spectroscopic sensor, mass spectrometry sensor, near infrared spectroscopic sensor (NIS), photodetector, photoplethysmography (PPG) sensor, Raman spectroscopic sensor, spectrometry sensor, spectrophotometer, spectroscopic sensor, ultraviolet spectroscopic sensor, and white light spectroscopic sensor.

In an example, a light energy emitter can emit coherent light. In an example, a light energy emitter can be a laser. In an example, a light energy emitter can be a Light Emitting Diode (LED). In an example, a light energy emitter can emit infrared or near-infrared light. In an example, a light energy emitter can emit ultraviolet light. In an example, a light energy emitter emit red light and/or be a red-light laser. In an example, a light energy emitter emit green light and/or be a green-light laser. In an example, a light energy emitter can emit white light and/or be a white-light laser. In an example, a light energy emitter can emit light with frequency and/or spectrum changes over time. In an example, a light energy emitter can emit a sequence of light pulses at different selected frequencies. In an example, a light energy emitter can emit polarized light. In an example, the polarization of light can change after the light passes through and/or is reflected from body tissue and these changes can be used to measure body hydration level.

In an example, the depth, breadth, location, and/or type of body tissue or fluid from which light from a light energy emitter is reflected can be changed by adjusting the frequency, color, and/or spectrum of light emitted from the light energy emitter. In an example, the frequency, color, and/or spectrum of light emitted from the light energy emitter can be adjusted in order to more accurately measure body hydration level. In an example, the frequency, color, and/or spectrum of light emitted from the light energy emitter can be adjusted automatically (in an iterative manner) by a device in order to more accurately measure body hydration level for a specific person, for a specific type of activity, or for a specific configuration of the device relative to the person's body surface. In an example, the frequency, color, and/or spectrum of light emitted from the light energy emitter can be adjusted automatically to maintain accurate measurement of body hydration level even if the device shifts and/or moves relative to the person's body surface. In an example, a device can automatically vary the frequency, color, and/or spectrum of light from a light emitter to scan through a range of tissue depths, locations, and/or types in order to obtain more accurate measurement of body hydration level. In an example, an arcuate wearable device for measuring a person's hydration level can further comprise one or more optical filters or lenses which change the frequency, color, and/or spectrum of light emitted by a light energy emitter.

In an example, the depth, breadth, location, and/or type of body tissue or fluid from which light from a light energy emitter is reflected can be changed by adjusting the power and/or intensity of light emitted from the light energy emitter. In an example, the power and/or intensity of light emitted from the light energy emitter can be adjusted in order to more accurately measure body hydration level. In an example, the power and/or intensity of light emitted from the light energy emitter can be adjusted automatically (in an iterative manner) by a device in order to more accurately measure body hydration level for a specific person, for a specific type of activity, or for a specific configuration of the device relative to the person's body surface. In an example, the power and/or intensity of light emitted from the light energy emitter can be adjusted automatically to maintain accurate measurement of body hydration level even if the device shifts and/or moves relative to the person's body surface. In an example, a device can automatically vary the power and/or intensity of light from a light emitter to scan through a range of tissue depths, locations, and/or types in order to obtain more accurate measurement of body hydration level.

In an example, the depth, breadth, location, and/or type of body tissue or fluid from which light from a light energy emitter is reflected can be changed by adjusting the angle of light emitted from the light energy emitter. In an example, the angle of light emitted from the light energy emitter can be adjusted in order to more accurately measure body hydration level. In an example, the angle of light emitted from the light energy emitter can be adjusted automatically (in an iterative manner) by a device in order to more accurately measure body hydration level for a specific person, for a specific type of activity, or for a specific configuration of the device relative to the person's body surface. In an example, the angle of light emitted from the light energy emitter can be adjusted automatically to maintain accurate measurement of body hydration level even if the device shifts and/or moves relative to the person's body surface. In an example, a device can automatically vary the angle of light from a light emitter to scan through a range of tissue depths, locations, and/or types in order to obtain more accurate measurement of body hydration level. In an example, an arcuate wearable device for measuring a person's hydration level can further comprise one or more optical filters or lenses which change the projection and/or body incidence angle of a light beam emitted by a light energy emitter.

In an example, the depth, breadth, location, and/or type of body tissue or fluid from which light from a light energy emitter is reflected can be changed by adjusting the coherence, polarization, and/or phase of light emitted from the light energy emitter. In an example, the coherence, polarization, and/or phase of light emitted from the light energy emitter can be adjusted in order to more accurately measure body hydration level. In an example, the coherence, polarization, and/or phase of light emitted from the light energy emitter can be adjusted automatically (in an iterative manner) by a device in order to more accurately measure body hydration level for a specific person, for a specific type of activity, or for a specific configuration of the device relative to the person's body surface. In an example, the coherence, polarization, and/or phase of light emitted from the light energy emitter can be adjusted automatically to maintain accurate measurement of body hydration level even if the device shifts and/or moves relative to the person's body surface. In an example, a device can automatically vary the coherence, polarization, and/or phase of light from a light emitter to scan through a range of tissue depths, locations, and/or types in order to obtain more accurate measurement of body hydration level. In an example, an arcuate wearable device for measuring a person's hydration level can further comprise one or more optical filters or lenses which change the coherence, polarization, and/or phase of light emitted by a light energy emitter.

In an example, an arcuate wearable device for measuring a person's hydration level can comprise a first light energy emitter and a second light energy emitter. In an example, the first light energy emitter can emit light with a first light frequency, color, and/or spectrum and the second light energy emitter can emit light with a second light frequency, color, and/or spectrum. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, an arcuate wearable device for measuring a person's hydration level can comprise a first light energy emitter and a second light energy emitter. In an example, the first light energy emitter can emit light with a first light power and/or intensity and the second light energy emitter can emit light with a second light power and/or intensity. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously.

In an example, first and second light energy emitters can emit light in a selected chronological sequence and/or timing pattern.

In an example, an arcuate wearable device for measuring a person's hydration level can comprise a first light energy emitter and a second light energy emitter. In an example, the first light energy emitter can emit light with a first light projection and/or body incidence angle and the second light energy emitter can emit light with a second light projection and/or body incidence angle. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, an arcuate wearable device for measuring a person's hydration level can comprise a first light energy emitter and a second light energy emitter. In an example, the first light energy emitter can emit light with a first light coherence, polarization, and/or phase and the second light energy emitter can emit light with a second light coherence, polarization, and/or phase. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, the depth, breadth, location, and/or type of body tissue or fluid from which light from a light energy emitter is reflected and received by a light energy receiver can be changed by adjusting the distance between a light energy emitter and a light energy receiver. In an example, the distance between a light energy emitter and a light energy receiver can be adjusted in order to more accurately measure body hydration level. In an example, the distance between a light energy emitter and a light energy receiver can be adjusted automatically (in an iterative manner) by a device in order to more accurately measure body hydration level for a specific person, for a specific type of activity, or for a specific configuration of the device relative to the person's body surface. In an example, the distance between a light energy emitter and a light energy receiver can be adjusted automatically to maintain accurate measurement of body hydration level even if the device shifts and/or moves relative to the person's body surface. In an example, a device can automatically vary the distance between a light energy emitter and a light energy receiver to scan through a range of tissue depths, locations, and/or types in order to obtain more accurate measurement of body hydration level.

In an example, the depths, breadths, locations, and/or types of body tissue or fluid from which light beams from a plurality of light energy emitters are reflected can be determined by a selected geometric configuration of the plurality of light energy emitters and a light energy receiver. In an example, a selected geometric configuration of a plurality of light energy emitters and a light energy receiver can be designed to most accurately measure body hydration level. In an example, the geometric configuration of a plurality of light energy emitters and a light energy receiver can be adjusted automatically (in an iterative manner) by a device in order to more accurately measure body hydration level for a specific person, for a specific type of activity, or for a specific configuration of the device relative to the person's body surface. In an example, the geometric configuration of a plurality of light energy emitters and a light energy receiver can be adjusted automatically to maintain accurate measurement of body hydration level even if the device shifts and/or moves relative to the person's body surface. In an example, a device can automatically vary the geometric configuration of a plurality of light energy emitters and a light energy receiver in order to scan through a range of tissue depths, locations, and/or types in order to measure body hydration level more accurately. In an example, a plurality of light energy emitters can emit light simultaneously. In an example, a plurality of light energy emitters can emit light in a selected chronological sequence and/or timing pattern.

In an example, a plurality of light energy emitters can be configured in a linear array in proximity to a light energy receiver. In an example, a plurality of light energy emitters can be configured in a linear array including a light energy receiver. In an example, a plurality of light energy emitters can be configured in a polygonal array in proximity to a light energy receiver. In an example, a plurality of light energy emitters can be configured in a polygonal array including a light energy receiver. In an example, a plurality of light energy emitters can be configured in a polygonal array around a light energy receiver. In an example, a plurality of light energy emitters can be configured in a circular or other arcuate array in proximity to a light energy receiver. In an example, a plurality of light energy emitters can be configured in a circular or other arcuate array including a light energy receiver. In an example, a plurality of light energy emitters can be configured in a circular or other arcuate array around a light energy receiver. In an example, a plurality of light energy emitters can emit light in a circular sequence around a central light energy receiver.

In an example, the depths, breadths, locations, and/or types of body tissue or fluid from which light beams are reflected and received by a plurality of light energy receivers can be determined by a selected geometric configuration of a light energy emitter and the plurality of light energy receivers. In an example, a selected geometric configuration of a light energy emitter and a plurality of light energy receivers can be designed to most accurately measure body hydration level. In an example, the geometric configuration of a light energy emitter and a plurality of light energy receivers can be adjusted automatically (in an iterative manner) by a device in order to more accurately measure body hydration level for a specific person, for a specific type of activity, or for a specific configuration of the device relative to the person's body surface. In an example, the geometric configuration of a light energy emitter and a plurality of light energy receivers can be adjusted automatically to maintain accurate measurement of body hydration level even if the device shifts and/or moves relative to the person's body surface. In an example, a device can automatically vary the geometric configuration of a light energy emitter and a plurality of light energy receivers in order to scan through a range of tissue depths, locations, and/or types in order to measure body hydration level more accurately.

In an example, a plurality of light energy receivers can be configured in a linear array in proximity to a light energy emitter. In an example, a plurality of light energy receivers can be configured in a linear array including a light energy emitter. In an example, a plurality of light energy receivers can be configured in a polygonal array in proximity to a light energy emitter. In an example, a plurality of light energy receivers can be configured in a polygonal array including a light energy emitter. In an example, a plurality of light energy receivers can be configured in a polygonal array around a light energy emitter. In an example, a plurality of light energy receivers can be configured in a circular or other arcuate array in proximity to a light energy emitter. In an example, a plurality of light energy receivers can be configured in a circular or other arcuate array including a light energy emitter. In an example, a plurality of light energy receivers can be configured in a circular or other arcuate array around a light energy emitter.

In an example, a light energy emitter can be part of an arcuate band. In an example, a light energy emitter can be part of a housing which is held on a person's body by an arcuate band. In an example, an arcuate wearable device for measuring a person's hydration level can comprise an array, grid, and/or matrix of two or more light energy emitters with a proximal-to-distal orientation. In an example, an arcuate wearable device for measuring a person's hydration level can comprise an array, grid, and/or matrix of two or more light energy emitters along a proximal-to-distal axis. In an example, an arcuate wearable device for measuring a person's hydration level can comprise an array, grid, and/or matrix of two or more light energy emitters with a circumferential orientation. In an example, an arcuate wearable device for measuring a person's hydration level can comprise an array, grid, and/or matrix of two or more light energy emitters along a circumferential axis.

In an example, an arcuate wearable device for measuring a person's hydration level can comprise a linear array, grid, and/or matrix of light energy emitters. In an example, an arcuate wearable device for measuring a person's hydration level can comprise a rectangular array, grid, and/or matrix of light energy emitters. In an example, an arcuate wearable device for measuring a person's hydration level can comprise a circular or elliptical array, grid, and/or matrix of light energy emitters. In an example, an arcuate wearable device for measuring a person's hydration level can comprise a checkerboard array, grid, and/or matrix of light energy emitters. In an example, an arcuate wearable device for measuring a person's hydration level can comprise a three-dimensional stacked array, grid, and/or matrix of light energy emitters. In an example, an arcuate wearable device for measuring a person's hydration level can comprise a sunburst and/or radial-spoke array, grid, and/or matrix of light energy emitters. In an example, an arcuate wearable device for measuring a person's hydration level can comprise a sinusoidal array, grid, and/or matrix of light energy emitters.

In an example, an array, grid, and/or matrix of two or more light energy emitters can span up to 10% of the cross-sectional circumference of a part of a person's body such as a wrist, arm, or finger. In an example, an array, grid, and/or matrix of two or more light energy emitters can span between 10% and 25% of the cross-sectional circumference of a part of a person's body such as a wrist, arm, or finger. In an example, an array, grid, and/or matrix of two or more light energy emitters can span between 25% and 50% of the cross-sectional circumference of a part of a person's body such as a wrist, arm, or finger. In an example, an array, grid, and/or matrix of two or more light energy emitters can span between 50% and 100% of the cross-sectional circumference of a part of a person's body such as a wrist, arm, or finger.

In an example, a light energy receiver can be part of an arcuate band. In an example, a light energy receiver can be part of a housing which is held on a person's body by an arcuate band. In an example, an arcuate wearable device for measuring a person's hydration level can comprise an array, grid, and/or matrix of two or more light energy receivers with a proximal-to-distal orientation. In an example, an arcuate wearable device for measuring a person's hydration level can comprise an array, grid, and/or matrix of two or more light energy receivers along a proximal-to-distal axis. In an example, an arcuate wearable device for measuring a person's hydration level can comprise an array, grid, and/or matrix of two or more light energy receivers with a circumferential orientation. In an example, an arcuate wearable device for measuring a person's hydration level can comprise an array, grid, and/or matrix of two or more light energy receivers along a circumferential axis.

In an example, an arcuate wearable device for measuring a person's hydration level can comprise a linear array, grid, and/or matrix of light energy receivers. In an example, an arcuate wearable device for measuring a person's hydration level can comprise a rectangular array, grid, and/or matrix of light energy receivers. In an example, an arcuate wearable device for measuring a person's hydration level can comprise a circular or elliptical array, grid, and/or matrix of light energy receivers. In an example, an arcuate wearable device for measuring a person's hydration level can comprise a checkerboard array, grid, and/or matrix of light energy receivers. In an example, an arcuate wearable device for measuring a person's hydration level can comprise a three-dimensional stacked array, grid, and/or matrix of light energy receivers. In an example, an arcuate wearable device for measuring a person's hydration level can comprise a sunburst and/or radial-spoke array, grid, and/or matrix of light energy receivers. In an example, an arcuate wearable device for measuring a person's hydration level can comprise a sinusoidal array, grid, and/or matrix of light energy receivers.

In an example, an array, grid, and/or matrix of two or more light energy receivers can span up to 10% of the cross-sectional circumference of a part of a person's body such as a wrist, arm, or finger. In an example, an array, grid, and/or matrix of two or more light energy receivers can span between 10% and 25% of the cross-sectional circumference of a part of a person's body such as a wrist, arm, or finger. In an example, an array, grid, and/or matrix of two or more light energy receivers can span between 25% and 50% of the cross-sectional circumference of a part of a person's body such as a wrist, arm, or finger. In an example, an array, grid, and/or matrix of two or more light energy receivers can span between 50% and 100% of the cross-sectional circumference of a part of a person's body such as a wrist, arm, or finger.

In an example, a light energy emitter and a light energy receiver can be part of an arcuate band. In an example, a light energy emitter and a light energy receiver can be part of a housing which is held on a person's body by an arcuate band. In an example, an arcuate wearable device for measuring a person's hydration level can comprise an array, grid, and/or matrix of (alternating) light energy emitters and receivers with a proximal-to-distal orientation. In an example, an arcuate wearable device for measuring a person's hydration level can comprise an array, grid, and/or matrix of (alternating) light energy emitters and receivers along a proximal-to-distal axis. In an example, an arcuate wearable device for measuring a person's hydration level can comprise an array, grid, and/or matrix of (alternating) light energy emitters and receivers with a circumferential orientation. In an example, an arcuate wearable device for measuring a person's hydration level can comprise an array, grid, and/or matrix of (alternating) light energy emitters and receivers along a circumferential axis.

In an example, an arcuate wearable device for measuring a person's hydration level can comprise a linear array, grid, and/or matrix of (alternating) light energy emitters and receivers. In an example, an arcuate wearable device for measuring a person's hydration level can comprise a rectangular array, grid, and/or matrix of (alternating) light energy emitters and receivers. In an example, an arcuate wearable device for measuring a person's hydration level can comprise a circular or elliptical array, grid, and/or matrix of (alternating) light energy emitters and receivers. In an example, an arcuate wearable device for measuring a person's hydration level can comprise a checkerboard array, grid, and/or matrix of (alternating) light energy emitters and receivers. In an example, an arcuate wearable device for measuring a person's hydration level can comprise a three-dimensional stacked array, grid, and/or matrix of (alternating) light energy emitters and receivers. In an example, an arcuate wearable device for measuring a person's hydration level can comprise a sunburst and/or radial-spoke array, grid, and/or matrix of (alternating) light energy emitters and receivers. In an example, an arcuate wearable device for measuring a person's hydration level can comprise a sinusoidal array, grid, and/or matrix of (alternating) light energy emitters and receivers.

In an example, an array, grid, and/or matrix of (alternating) light energy emitters and receivers can span up to 10% of the circumference of a part of a person's body such as a wrist, arm, or finger. In an example, an array, grid, and/or matrix of (alternating) light energy emitters and receivers can span between 10% and 25% of the circumference of a part of a person's body such as a wrist, arm, or finger. In an example, an array, grid, and/or matrix of (alternating) light energy emitters and receivers can span between 25% and 50% of the circumference of a part of a person's body such as a wrist, arm, or finger. In an example, an array, grid, and/or matrix of (alternating) light energy emitters and receivers can span between 50% and 100% of the circumference of a part of a person's body such as a wrist, arm, or finger.

In an example, an arcuate wearable device for measuring a person's hydration level can comprise an array, grid, and/or matrix of light energy emitters which differ in one or more parameters selected from the group consisting of: location and/or distance from a light energy receiver; distance to body surface; light beam frequency, color, and/or spectrum; light beam coherence, polarity, and/or phase; light beam power and/or intensity; light beam projection and/or body incidence angle; light beam duration; light beam size; and light beam focal distance. In an example, an arcuate wearable device for measuring a person's hydration level can comprise an array, grid, and/or matrix of light energy receivers which differ in: location and/or distance from a light energy emitter; and/or distance to body surface.

In an example, the frequency, color, and/or spectrum of a beam of light emitted from a light energy emitter can be changed over time to create a chronological sequence of beams of light with different frequencies, colors, and/or spectrums. In an example, the angle of a beam of light emitted from a light energy emitter can be changed over time to create a chronological sequence of beams of light with different projection and/or body incidence angles. In an example, the power or intensity of a beam of light emitted from a light energy emitter can be changed over time to create a chronological sequence of beams of light with different power or intensity levels. Such sequences can help to more accurately measure body hydration level.

In an example, the frequency, color, and/or spectrum of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level. In an example, the projection angle of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level. In an example, the power and/or intensity of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level.

In an example, a light energy emitter can be separated from a light energy receiver by a selected distance. In an example, there can be a selected distance between a light energy emitter and a light energy receiver. In an example, (an orthogonal component of) this distance can be measured along a circumferential axis. In an example, a light energy emitter and a light energy receiver can both be along the same circumferential line. In an example, (an orthogonal component of) this distance can be measured along a proximal-to-distal axis. In an example, a light energy emitter and a light energy receiver can both be along the same proximal-to-distal line. In an example, this selected distance can be expressed in inches and be within the range of $\frac{1}{16}$" to 2". In an example, this selected distance can be expressed in metric units and be within the range of 2 mm to 5 cm. In an example, if this selected distance is along a circumferential axis, this distance can be expressed in (compass or polar coordinate) degrees and be within the range of 2 degrees to 60 degrees.

In an example, an arcuate wearable device for measuring a person's hydration level can have two (or more) light energy emitters. In an example, two (or more) energy emitters can emit energy in a non-simultaneous (e.g. sequential) manner. In an example, a first energy emitter can be separated from a second energy emitter by a selected distance. In an example, there can be a selected distance between a first energy emitter and a second energy receiver. In an example, (an orthogonal component of) this distance can be measured along a circumferential axis. In an example, a first energy emitter and a second energy emitter can both be along the same circumferential line. In an example, (an orthogonal component of) this distance can be measured along a proximal-to-distal axis. In an example, a first energy emitter and a second energy emitter can both be along the same proximal-to-distal line. In an example, this selected distance can be expressed in inches and be within the range of $\frac{1}{16}$" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, an arcuate wearable device for measuring a person's hydration level can have a circumferential or annular array, matrix, or grid of four or more light energy emitters, each of which is separated from the nearest other energy emitter by a distance within the range of 1/16" to 2". In an example, an arcuate wearable device for measuring a person's hydration level can have a circumferential or annular array, matrix, or grid of four or more energy emitters, each of which is separated from the nearest other energy emitter by a distance within the range of 2 mm to 5 cm. In an example, an arcuate wearable device for measuring a person's hydration level can have a circumferential or annular array, matrix, or grid of four or more energy emitters, each of which is separated from the nearest other energy emitter by a distance within the range of 2 degrees to 60 degrees. In an example, an arcuate wearable device for measuring a person's hydration level can have a circumferential or annular array of energy emitters which spans between 25% and 100% of the cross-sectional perimeter circumference of a part of the body (e.g. wrist, arm, or finger) to which the device is attached. In an example, this circumferential or annular array of energy emitters can be even spaced or distributed, with the same pair-wise distance or number of degrees between adjacent energy emitters.

In an example, an arcuate wearable device for measuring a person's hydration level can have two (or more) light energy receivers. In an example, a first energy receiver can be separated from a second energy receiver by a selected distance. In an example, there can be a selected distance between a first energy receiver and a second energy receiver. In an example, (an orthogonal component of) this distance can be measured along a circumferential axis. In an example, a first energy receiver and a second energy receiver can both be along the same circumferential line. In an example, (an orthogonal component of) this distance can be measured along a proximal-to-distal axis. In an example, a first energy receiver and a second energy receiver can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, an arcuate wearable device for measuring a person's hydration level can have a circumferential or annular array, matrix, or grid of four or more light energy receivers, each of which is separated from the nearest other energy receiver by a distance within the range of 1/16" to 2". In an example, an arcuate wearable device for measuring a person's hydration level can have a circumferential or annular array, matrix, or grid of four or more energy receivers, each of which is separated from the nearest other energy receiver by a distance within the range of 2 mm to 5 cm. In an example, an arcuate wearable device for measuring a person's hydration level can have a circumferential or annular array, matrix, or grid of four or more energy receivers, each of which is separated from the nearest other energy receiver by a distance within the range of 2 degrees to 60 degrees. In an example, an arcuate wearable device for measuring a person's hydration level can have a circumferential or annular array of energy receivers which spans between 25% and 100% of the cross-sectional perimeter circumference of a part of the body (e.g. wrist, arm, or finger) to which the device is attached. In an example, this circumferential or annular array of energy receivers can be even spaced or distributed, with the same pair-wise distance or number of degrees between adjacent energy receivers.

In an example, a light energy emitter can be within the circumferential section bounded by 330 degrees and 0 degrees and a light energy receiver can be within the circumferential section bounded by 0 degrees and 30 degrees, or vice versa. In an example, a light energy emitter can be within the circumferential section bounded by 300 degrees and 0 degrees and a light energy receiver can be within the circumferential section bounded by 0 degrees and 60 degrees, or vice versa. In an example, a light energy emitter can be within the circumferential section bounded by 330 degrees and 30 degrees, a first energy receiver can be within the circumferential section bounded by 270 degrees and 330 degrees, and a second energy receiver can be within the circumferential section bounded by 30 degrees and 90 degrees. In an example, a light energy receiver can be within the circumferential section bounded by 330 degrees and 30 degrees, a first energy emitter can be within the circumferential section bounded by 270 degrees and 330 degrees, and a second energy emitter can be within the circumferential section bounded by 30 degrees and 90 degrees.

In an example, an arcuate wearable device for measuring a person's hydration level can comprise an array of light energy emitters and light energy receivers which is part of a wearable arcuate band or one or more segments (or housings) which are attached to a wearable arcuate band. In an example, an arcuate wearable device for measuring a person's hydration level can comprise a two-dimensional array of energy emitters and energy receivers which is part of a wearable arcuate band or one or more segments (or housings) which are attached to a wearable arcuate band. In an example, an arcuate wearable device for measuring a person's hydration level can comprise a three-dimensionally stacked array of energy emitters and energy receivers which is part of a wearable arcuate band or one or more segments (or housings) which are attached to a wearable arcuate band. In an example, data from this array can be analyzed to measure a person's body hydration level.

In an example, an array of light energy emitters and/or light energy receivers can have a circumferential axis and a proximal-to-distal axis. In an example, this array can have at least three energy emitters and/or energy receivers along a circumferential axis and at least two energy emitters and/or energy receivers along a proximal-to-distal axis. In an example, an array can be formed from a plurality of sets of energy emitters and energy receivers, wherein each set forms the vertexes of a square or rectangle. In an example, an array can be formed from a plurality of sets of energy emitters and energy receivers, wherein each set forms the vertexes of a hexagon. In an example, an array can be formed from a plurality of sets of energy emitters and energy receivers, wherein each set forms a circle.

In an example, an array of light energy emitters and light energy receivers can have a square or rectangular shape. In an example, an array of energy emitters and energy receivers can have a hexagonal shape. In an example, an array of energy emitters and energy receivers can have a circular shape. In an example, an array of energy emitters and energy receivers can have a sunburst (e.g. radial spoke) shape. In an example, an array of energy emitters and energy receivers can have a cylindrical and/or ring shape. In an example, an array of energy emitters and energy receivers can have a conic section shape. In an example, an array of energy emitters and energy receivers can have a saddle shape. In an example, an array of energy emitters and energy receivers can have a helical shape.

In an example, an arcuate wearable device for measuring a person's hydration level can further comprise a track, channel, or slot along which a light energy emitter, a light energy receiver, or both can be moved. In an example, this movement can be done manually. In an example, this movement can be done automatically by one or more actuators. In an example, this track, channel, or slot can have a circumferential orientation. In an example, this track, channel, or slot can have a proximal-to-distal orientation. In an example, the distance between a light energy emitter and a light energy receiver can be adjusted by moving the light energy emitter, the light energy receiver, or both along such a track, channel, or slot. In an example, the location of a light energy emitter and/or a light energy receiver relative to a person's body can be adjusted by moving the light energy emitter, the light energy receiver, or both along such a track, channel, or slot. In an example, movement of a light energy emitter, a light energy receiver, or both along a track, channel, or slot can enable more accurate measurement of body hydration level. In an example, movement of a light energy emitter, a light energy receiver, or both along a track, channel, or slot can enable customization of a device to the anatomy of a specific person for more accurate measurement of that person's body hydration level.

In an example, an arcuate wearable device for measuring a person's hydration level can further comprise a rotating member which holds a light energy emitter, a light energy receiver, or both. In an example, rotation of this member can be done manually. In an example, this rotation can be done automatically by one or more actuators. In an example, the distance between a light energy emitter and a light energy receiver can be adjusted by rotating the rotating member. In an example, the location of a light energy emitter and/or a light energy receiver relative to a person's body can be adjusted by rotating the rotating member. In an example, movement of a light energy emitter, a light energy receiver, or both by a rotating member can enable more accurate measurement of body hydration level. In an example, such movement of a light energy emitter, a light energy receiver, or both can enable customization of a device to the anatomy of a specific person for more accurate measurement of that person's body hydration level.

In an example, an arcuate wearable device for measuring a person's hydration level can include a charge coupled device (CCD). In an example, an arcuate wearable device for measuring a person's hydration level can include an energy source which powers a light energy emitter, a light energy receiver, a data processor, a data transmitter, and/or a charge coupled device. In an example, an energy source can be a battery. In an example, an energy source can transduce, harvest, and/or generate energy from body motion or kinetic energy. In an example, an energy source can transduce, harvest, and/or generate energy from ambient light energy. In an example, an energy source can transduce, harvest, and/or generate energy from body thermal energy. In an example, an energy source can transduce, harvest, and/or generate energy from ambient electromagnetic energy.

In an example, an arcuate wearable device for measuring a person's hydration level can further include a wireless data transmitter and/or data receiver. In various examples, this device can be in wireless communication with an external device selected from the group consisting of: a cell phone, an electronic tablet, electronically-functional eyewear, a home electronics portal, an implanted medical device, an internet portal, a laptop computer, a mobile computer, a mobile phone, a remote computer, a remote control unit, a smart phone, a smart utensil, a television set, and a wearable data processing hub. In an example, additional data processing and analysis can be done within an external device.

In an example, an arcuate wearable device for measuring a person's hydration level can include a electronics housing which is held on a person's body by an arcuate band. In an example, this electronics housing can be more rigid (less flexible) than the band. In an example, this electronics housing can hold a light energy emitter and a light energy receiver. In an example, an electronics housing can include the display (and/or primary processing) component of a smart watch, fitness band, or specialized wearable body hydration monitor.

In an example, an arcuate wearable device for measuring a person's hydration level can further comprise one or more other types of biometric or environmental sensors in addition to the primary energy emitters and receivers discussed above. In an example, the primary energy emitter and the primary energy receiver of this device, discussed above, can be a light energy emitter and a light energy receiver, but an arcuate wearable device for measuring a person's hydration level can also include a (non-light-spectrum) electromagnetic energy emitter and a (non-light-spectrum) electromagnetic energy receiver. In an example, the primary energy emitter and the primary energy receiver of this device, discussed above, can be a (non-light-spectrum) electromagnetic energy emitter and a (non-light-spectrum) electromagnetic energy receiver, but an arcuate wearable device for measuring a person's hydration level can also include a light energy emitter and a light energy receiver.

In various examples, an arcuate wearable device for measuring a person's hydration level can include one or more sensors selected from the group consisting of: optical sensor, infrared sensor, optoelectronic sensor, spectral analysis sensor, and spectrophotometer. In an example, an arcuate wearable device for measuring a person's hydration level can further comprise an electromagnetic sensor or skin galvanic response (Galvanic Skin Response) sensor. In an example, an arcuate wearable device for measuring a person's hydration level can detect if it loses close contact with a person's body by monitoring skin electromagnetism. In an example, a wearable device can detect if it loses close contact with a person's body by detecting a lack electromagnetic response from skin. In various examples, a wearable device can continually monitor electromagnetic signals that indicate whether the device is properly worn by a person.

In an example, an arcuate wearable device for measuring a person's hydration level can be worn directly on a person's body. In an example an arcuate wearable device for measuring a person's hydration level can be worn on, or incorporated into, a person's clothing. In various examples, a wearable sensor can be worn on a person in a manner like a clothing accessory or piece of jewelry selected from the group consisting of: wristwatch, wristphone, wristband, bracelet, cufflink, armband, armlet, and finger ring. In an example, an arcuate wearable device for measuring a person's hydration level can be worn in a manner similar to a piece of jewelry or accessory. In various examples, an arcuate wearable device for measuring a person's hydration level can be worn in a manner similar to a piece of jewelry or accessory selected from the group consisting of: smart watch, wrist band, wrist phone, wrist watch, fitness watch, or other wrist-worn device; and arm band, arm bracelet, charm bracelet, or smart bracelet. In an example, an arcuate wearable device for measuring a person's hydration level can be incorporated into the cuff of a shirt or pair of pants.

In an example, an arcuate wearable device for measuring a person's hydration level can be entirely wearable or can include a wearable component. In an example, a wearable device or component can be worn directly on a person's body, can be worn on a person's clothing, or can be integrated into a specific article of clothing. In an example, an arcuate wearable device for measuring a person's hydration level can be in wireless communication with an external device. In various examples, an arcuate wearable device for measuring a person's hydration level can be in wireless communication with an external device selected from the group consisting of: a cell phone, an electronic tablet, electronically-functional eyewear, a home electronics portal, an internet portal, a laptop computer, a mobile phone, a remote computer, a remote control unit, a smart phone, a smart utensil, a television set, and a virtual menu system.

In an example, an arcuate wearable device for measuring a person's hydration level can further comprise multiple components selected from the group consisting of: Central Processing Unit (CPU) or microprocessor; food-consumption monitoring component (motion sensor, electromagnetic sensor, optical sensor, and/or chemical sensor); graphic display component (display screen and/or coherent light projection); human-to-computer communication component (speech recognition, touch screen, keypad or buttons, and/or gesture recognition); memory component (flash, RAM, or ROM); photoplethysmography (PPG) sensor; power source and/or power-transducing component; time keeping and display component; wireless data transmission and reception component; and strap or band.

In an example, an arcuate wearable device for measuring a person's hydration level can include a hand-held component in addition to a wearable component. In an example, the combination and integration of a wearable member and a hand-held member can provide advantages that are not possible with either a wearable member alone or a hand-held member alone. In an example, an arcuate wearable device for measuring a person's hydration level can include a hand-held component that is selected from the group consisting of: smart phone, mobile phone, cell phone, holophone, or application of such a phone; electronic tablet, other flat-surface mobile electronic device, personal Digital Assistant (PDA), or laptop; digital camera; and smart eyewear, electronically-functional eyewear, or augmented reality eyewear. In an example, such a hand-held component can be in wireless communication with a wearable component of such a system. In an example, an arcuate wearable device for measuring a person's hydration level can include integration with a general-purpose mobile device that is used to collect data concerning food consumption. In an example, the hand-held component can be a general purpose device, of which collecting data for food identification is only one among many functions that it performs.

In various examples, an arcuate wearable device for measuring a person's hydration level can provide feedback to the person that is selected from the group consisting of: auditory feedback (such as a voice message, alarm, buzzer, ring tone, or song); feedback via computer-generated speech; mild external electric charge or neural stimulation; periodic feedback at a selected time of the day or week; phantom taste or smell; phone call; pre-recorded audio or video message by the person from an earlier time; television-based messages; and tactile, vibratory, or pressure-based feedback.

In various examples, an arcuate wearable device for measuring a person's hydration level can be in wireless communication with an external device or system selected from the group consisting of: internet portal; smart phone, mobile phone, cell phone, holophone, or application of such a phone; electronic tablet, other flat-surface mobile electronic device, personal Digital Assistant (PDA), remote control unit, or laptop; smart eyewear, electronically-functional eyewear, or augmented reality eyewear; electronic store display, electronic restaurant menu, or vending machine; and desktop computer, television, or mainframe computer. In an example, a wearable device for measuring a person's hydration can prompt them to drink more. In an example, a wearable device for measuring a person's hydration level can be in electromagnetic communication with a self-driving vehicle. In an example, such a device can drive someone to drink.

In an example, a spectroscopic sensor can be selected from the group consisting of: spectroscopic sensor, spectrometry sensor, white light spectroscopic sensor, infrared spectroscopic sensor, near-infrared spectroscopic sensor, ultraviolet spectroscopic sensor, ion mobility spectroscopic sensor, mass spectrometry sensor, backscattering spectrometry sensor, and spectrophotometer. In an example, a spectroscopic sensor can be selected from the group consisting of: ambient light spectroscopic sensor, analytical chromatographic sensor, backscattering spectrometry sensor, spectroscopic camera, chemiluminescence sensor, chromatographic sensor, coherent light spectroscopic sensor, colorimetric sensor, fiber optic spectroscopic sensor, fluorescence sensor, gas chromatography sensor, infrared light energy sensor, infrared spectroscopic sensor, ion mobility spectroscopic sensor, laser spectroscopic sensor, liquid chromatography sensor, mass spectrometry sensor, near infrared spectroscopic sensor, optoelectronic sensor, photocell, photochemical sensor, photodetector, photoplethysmography (PPG) sensor, Raman spectroscopic sensor, spectral analysis sensor, spectrographic sensor, spectrometric sensor, spectrometry sensor, spectrophotometer, spectroscopic body hydration sensor, spectroscopic oximeter, ultraviolet light energy sensor, ultraviolet spectroscopic sensor, visible light spectroscopic sensor, and white light spectroscopic sensor.

In an example, a spectroscopic sensor can operate on ambient light alone. In an example, a spectroscopic sensor can comprise a light receiver alone (no light emitter) if it operates on ambient light alone after that ambient light has been reflected from (or has passed through) body tissue, organs, and/or fluid. In an example, a light (energy) sensor can be a photodetector. In an example, a spectroscopic sensor can comprise both a light emitter and a light receiver if it the light receiver receives light which has been emitted by the light emitter and then reflected from (or passed through) body tissue, organs, and/or fluid. In an example, a light emitter and light receiver can be paired together. In an example, a light emitter and light receiver together can be referred to as a spectroscopic sensor.

In an example, a light energy sensor of a wearable device for measuring a person's body hydration can be a spectroscopic sensor, including a light emitter and light receiver, which collects light energy data which then is analyzed using spectroscopic analysis in order to measure the chemical composition of body tissue, organs, and/or fluid. In an example, a light energy sensor of a wearable device for measuring a person's body hydration can be a spectroscopic sensor, including a light emitter and light receiver, which collects light energy data which then is analyzed using spectroscopic analysis in order to monitor changes in the chemical composition of body tissue, organs, and/or fluid. In an example, changes, gaps, and/or shifts in selected frequencies in the spectrum of ambient light due to interaction with a person's body tissue and/or fluid can be analyzed to monitor changes in the chemical composition of the person's body tissue and/or fluid. In an example, data from a spectroscopic sensor can be analyzed to determine how the spectrum of ambient light has been changed by reflection from, or passage through, body tissue, organs, and/or fluid.

In an example, a spectroscopic sensor can include one or more light (energy) emitters. In an example, a light (energy) emitter can be selected from the group consisting of: coherent light source, incandescent light, infrared light emitter, low-power laser, Laser Diode (LD), Light Emitting Diode (LED), microplasma light emitter, multi-wavelength source, Organic Light Emitting Diode (OLED), Resonant Cavity Light Emitting Diode (RCLED), Quasi Monochromatic (QM) light, Superluminescent Light Emitting Diode (SLED), and UltraViolet (UV) light emitter. In an example, a spectroscopic sensor can include one or more light (energy) receivers.

In an example, a spectroscopic sensor of wearable device for measuring a person's body hydration can include one or more light emitters which emit light energy toward a person's skin and/or body surface. In an example, one or more light emitters can emit light energy toward a person's body tissue, organs, and/or fluid. In an example, one or more light emitters can deliver light energy to a person's body tissue, organs, and/or fluid. In an example, one or more light emitters can deliver light energy to body tissue, organs, and/or fluid directly via direct optical communication. In an example, one or more light emitters can deliver light energy to body tissue, organs, and/or fluid indirectly via one or more light guides. In an example, this light energy can be reflected from body tissue, organs, and/or fluid and then the reflected light energy can be received by a light receiver, which is also part of this device. In an example, this light energy can be transmitted through body tissue, organs, and/or fluid and then the transmitted light energy can be received by a light receiver, which is also part of this device. In an example, one or more light emitters can deliver light energy in one or more selected wavelengths (or wavelength ranges or spectra) to body tissue, organs, and/or fluid. In an example, one or more light emitters can deliver infrared light energy, near infrared light energy, ultraviolet light energy, and/or visible light energy to body tissue, organs, and/or fluid.

In an example, a wearable device for measuring a person's body hydration can include one or more light guides which direct light energy from a first location, angle, and/or transmission vector to a second location, angle, and/or transmission vector. In an example, a light guide can direct light from a light emitter toward body tissue, organs, and/or fluid. In an example, a light guide can collect and direct ambient light toward body tissue, organs, and/or fluid. In an example, a light guide can direct light reflected from, or having passed through, body tissue, organs, and/or fluid toward a light receiver. In an example, a light guide can be generally cylindrical and/or columnar. In an example, a light guide can be rigid. In an example, a light guide can be flexible. In an example, a light guide can be made from one or more materials selected from the group consisting of: acrylic, crystal, elastomeric light-transmissive material, glass, high-durometer plastic, low-durometer plastic, optical-pass material, polycarbonate, polyethylene, polymer, polyurethane, polywanacracur, resin, sapphire, and transparent polymer.

In an example, a spectroscopic sensor of a wearable device for measuring a person's body hydration can include an array of light (energy) emitters. In an example, different emitters in this array can be configured to have different locations relative to the person's body. In an example, different emitters in this array can emit light at different angles with respect to the surface of a person's body. In an example, different emitters in this array can emit light at different wavelengths and/or with different light spectral distributions. In an example, different emitters in this array can emit light with different levels of coherence.

In an example, a spectroscopic sensor of a wearable device for measuring a person's body hydration can include a first light emitter and a second light emitter. In an example, the first light emitter can have a first location relative to a person's body and the second light emitter can have a second location relative to the person's body. In an example, the first light emitter can emit light at a first angle with respect to the surface of a person's body and the second light emitter can emit light at a second angle with respect to the surface of a person's body. In an example, the first light emitter can emit light with a first wavelength (or spectral distribution) and the second light emitter can emit light with a second wavelength (or spectral distribution). In an example, the first light emitter can emit coherent light and the second light emitter can emit non-coherent light.

In an example, a first light emitter can emit light during a first time period and a second light emitter can emit light during a second time period. In an example, the first light emitter can emit light during a first environmental condition and the second light emitter can emit light during a second environmental condition. In an example, the first light emitter can emit light when the person is engaged in a first type of physical activity and the second light emitter can emit light when the person is engaged in a second type of physical activity.

In an example, different emitters in an array of light emitters can emit light at different times. In an example, different emitters in an array can emit light based on data from one or more light energy sensors detecting different biological or physiological parameters or conditions. In an example, different emitters in an array can emit light based on data from one or more light energy sensors when a person is engaged in different types of activities. In an example, different emitters in an array can emit light based on data from one or more environmental sensors in response to different environmental parameters or conditions.

In an example, different emitters in an array can emit light with different wavelengths or wavelength ranges. In an example, different emitters in an array can emit light with different wavelengths or wavelength ranges based on data from one or more light energy sensors detecting different biological or physiological parameters or conditions. In an example, different emitters in an array can emit light with different wavelengths or wavelength ranges based on data from one or more light energy sensors when a person is engaged in different types of activities. In an example, different emitters in an array can emit light with different wavelengths or wavelength ranges based on data from one or more environmental sensors in response to different environmental parameters or conditions.

In an example, different emitters in an array can emit light at different angles with respect to a body surface. In an example, different emitters in an array can emit light at different angles with respect to a body surface based on data from one or more light energy sensors detecting different biological or physiological parameters or conditions. In an example, different emitters in an array can emit light at different angles with respect to a body surface based on data from one or more light energy sensors when a person is engaged in different types of activities. In an example, different emitters in an array can emit light at different angles with respect to a body surface based on data from one or more environmental sensors in response to different environmental parameters or conditions.

In an example, a light emitter of a wearable device for measuring a person's body hydration can be automatically moved by an actuator relative to a wearable housing which holds it. In an example, a light emitter can be automatically tilted by an actuator. In an example, a light emitter can be automatically rotated by an actuator. In an example, a light emitter can be automatically raised or lowered by an actuator. In an example, a light emitter can be automatically tilted, rotated, raised, or lowered when the wearable housing which holds it moves relative to the body surface on which it is worn. In an example, a light emitter can be automatically tilted, rotated, raised, or lowered in order to maintain a selected distance (or distance range) from the surface of a person's body. In an example, a light emitter can be automatically tilted, rotated, raised, or lowered in order to maintain a selected angle (or angle range) with respect to the surface of a person's body.

In an example, a beam of light emitted by a light emitter can be automatically moved by using an actuator to automatically move a lens through which this beam is transmitted. In an example, a beam of light emitted by a light emitter can be automatically moved by using an actuator to automatically rotate, tilt, raise, or lower a lens through which this beam is transmitted. In an example, a beam of light emitted by a light emitter can be automatically moved by using an actuator to automatically change the focal distance of a lens through which this beam is transmitted. In an example, a beam of light emitted by a light emitter can be automatically moved by using an actuator to automatically move a light guide through which this beam is transmitted. In an example, a beam of light emitted by a light emitter can be automatically moved by using an actuator to automatically rotate, tilt, raise, or lower a light guide through which this beam is transmitted. In an example, a beam of light emitted by a light emitter can be automatically moved by using an actuator to automatically move a light reflector (such as a mirror) from which this beam is reflected. In an example, a beam of light emitted by a light emitter can be automatically moved by using an actuator to automatically rotate, tilt, raise, or lower a light reflector (such as a mirror) from which this beam is reflected.

In an example, a first light emitter can emit light energy with a first light wavelength (or wavelength range or spectral distribution) and a second light emitter can simultaneously emit light energy with a second light wavelength (or wavelength range or spectral distribution) during the same time period. In an example, a first light emitter can emit light energy with a first light wavelength (or wavelength range or spectral distribution) and a second light emitter can simultaneously emit light energy with a second light wavelength (or wavelength range or spectral distribution) during the same time period in order to measure different physiological parameters, analytes, or conditions.

In an example, a light emitter can emit light energy with a first light wavelength (or wavelength range or spectral distribution) during a first time period and can emit light energy with a second light wavelength (or wavelength range or spectral distribution) during a second time period. In an example, a light emitter can emit light energy with a first light wavelength (or wavelength range or spectral distribution) during a first time period and can emit light energy with a second light wavelength (or wavelength range or spectral distribution) during a second time period in order to measure different physiological parameters, analytes, or conditions. In an example, a light emitter can automatically cycle through light energy emissions with a variety of wavelengths (or wavelength ranges or spectral distributions) during different time periods in order to measure different physiological parameters, analytes, or conditions.

In an example, a light emitter can emit light energy with a first light wavelength (or wavelength range or spectral distribution) during a first time period and can emit light energy with a second light wavelength (or wavelength range or spectral distribution) during a second time period in response to changing environmental conditions. In an example, a light emitter can emit light energy with a first light wavelength (or wavelength range or spectral distribution) during a first time period and can emit light energy with a second light wavelength (or wavelength range or spectral distribution) during a second time period in response to changing biometric results. In an example, a light emitter can emit light energy with a first light wavelength (or wavelength range or spectral distribution) during a first time period and can emit light energy with a second light wavelength (or wavelength range or spectral distribution) during a second time period in response to changing physiological conditions.

In an example, an arcuate wearable device for measuring a person's hydration level can collect light energy data which is used to measure changes in the chemical composition and/or physical configuration of skin, blood, blood vessels, intercellular fluid, and/or muscles based on how the spectral distribution of light is changed by being reflected from, or passing through, the skin, blood, blood vessels, intercellular fluid, and/or muscles. In an example, such a device can comprise a photoplethysmography (PPG) sensor. In an example, such a device can direct, guide, focus, and/or concentrate light energy toward body tissue, organs, and/or fluid in order to measure changes in light after that light has been reflected from, or passed through, that body tissue, organs, and/or fluid.

In an example, light receivers can receive light energy from an ambient light source that has been reflected from, passed through, or scattered by body tissue, organs, and/or fluid. In an example, an ambient light source can be solar radiation. In an example, an ambient light source can be outdoor artificial lighting. In an example, ambient light source can be indoor artificial lighting. In an example, a wearable light receiver can be optically isolated from a wearable light emitter by means of a light blocking layer, coating, cladding, or component so that only ambient light reflected from, or having passed through, body tissue, organs, or fluid reaches the light receiver.

In an example, a light emitter can emit light along a first vector and a light receiver can receive light along a second vector. In an example, the second vector can be substantially reversed from and parallel to the first vector. In an example, a beam of light can: be emitted by the light emitter along a first vector; pass through the first (transmissive) side of an angled one-way mirror; hit body tissue; reflect back from the body tissue; reflect off the second (reflective) side of the angled one-way mirror; reflect off a second mirror; and enter the light receiver along a second vector which is reversed from and parallel to the first vector.

In an example, a beam of light can: be emitted by the light emitter along a first vector; hit body tissue; reflect back from the body tissue; pass through a lens; and enter the light receiver along a second vector which is reversed from and parallel to the first vector. In an example, a beam of light can: be emitted by the light emitter along a first vector; hit body tissue; reflect back from the body tissue; pass through a rotating and/or tilting lens; and enter the light receiver along a second vector which is reversed from and parallel to the first vector. In an example, a beam of light can: be emitted by the light emitter along a first vector; hit body tissue; reflect back from the body tissue; pass through a lens which is rotated and/or tilted by an actuator; and enter the light receiver along a second vector which is reversed from and parallel to the first vector.

In an example, a beam of light can: be emitted by the light emitter along a first vector; hit body tissue; reflect back from the body tissue; pass through a light guide; and enter the light receiver along a second vector which is reversed from and parallel to the first vector. In an example, a beam of light can: be emitted by the light emitter along a first vector; hit body tissue; reflect back from the body tissue; pass through a rotating and/or tilting light guide; and enter the light receiver along a second vector which is reversed from and parallel to the first vector. In an example, a beam of light can: be emitted by the light emitter along a first vector; hit body tissue; reflect back from the body tissue; pass through a light guide which is rotated and/or tilted by an actuator; and enter the light receiver along a second vector which is reversed from and parallel to the first vector.

In an example, a light emitter can emit light along a first vector and a light receiver can receive light along a second vector. In an example, the second vector can be substantially parallel and coaxial with the first vector. In an example, a beam of light can: be emitted by the light emitter along a first vector; hit body tissue; reflect back from the body tissue; and enter the light receiver along a second vector which is parallel and coaxial with the first vector.

In an example, a light emitter can emit light along a first vector and a light receiver can receive light along a second vector. In an example, the second vector can be substantially perpendicular to the first vector. In an example, a beam of light can: be emitted by the light emitter along a first vector; pass through the first (transmissive) side of an angled one-way mirror; hit body tissue; reflect back from the body tissue; reflect off the second (reflective) side of the angled one-way mirror; and enter the light receiver along a second vector which is perpendicular to the first vector.

In an example, a light emitter can emit light along a first vector and a light receiver can receive light along a second vector. In an example, the second vector can be reversed from the first vector and symmetric to the first vector with respect to a virtual vector extending outward in a perpendicular manner from the surface of a person's body. In an example, a beam of light can: be emitted by the light emitter along a first vector; hit body tissue at an acute angle with respect to the virtual vector; reflect off the body tissue at an actuate angle with respect to the virtual vector; and enter the light receiver along a second vector. In an example, the first and second vectors can be reversed and symmetric to each other, wherein the symmetry is with respect to the virtual vector.

In an example, a light receiver of a wearable device for measuring a person's body hydration can be automatically moved relative to a wearable housing which holds it. In an example, a light receiver can be automatically tilted, rotated, raised, or lowered by an actuator. In an example, a light receiver can be automatically tilted, rotated, raised, or lowered if the wearable housing which holds it moves relative to the body surface on which it is worn. In an example, a light receiver can be automatically tilted, rotated, raised, or lowered in order to maintain a selected distance (or distance range) from the surface of a person's body. In an example, a light receiver can be automatically tilted, rotated, raised, or lowered in order to maintain a selected angle (or angle range) with respect to the surface of a person's body.

In an example, the path of light received by a light receiver can be automatically shifted by using an actuator to automatically move a lens through which this beam is transmitted. In an example, the path of light received by a light receiver can be automatically shifted by using an actuator to automatically rotate, tilt, raise, or lower a lens through which this light travels. In an example, the path of light received by a light receiver can be automatically shifted by using an actuator to automatically change the focal distance of a lens through which this light travels. In an example, the path of light received by a light receiver can be automatically shifted by using an actuator to automatically move a light guide through which this light travels. In an example, the path of light received by a light receiver can be automatically shifted by using an actuator to automatically rotate, tilt, raise, or lower a light guide through which this light travels. In an example, the path of light received by a light receiver can be automatically shifted by using an actuator to automatically move a light reflector (such as a mirror) from which this light is reflected. In an example, the path of light received by a light receiver can be automatically shifted by using an actuator to automatically rotate, tilt, raise, or lower a light reflector (such as a mirror) from which this light is reflected.

In an example, a first light receiver can receive light energy with a first light wavelength (or wavelength range or spectral distribution) and a second light receiver can simultaneously receive light energy with a second light wavelength (or wavelength range or spectral distribution) during the same time period. In an example, a first light receiver can receive light energy with a first light wavelength (or wavelength range or spectral distribution) and a second light receiver can simultaneously receive light energy with a second light wavelength (or wavelength range or spectral distribution) during the same time period in order to simultaneously measure different physiological parameters, analytes, or conditions.

In an example, a light receiver can receive light energy with a first light wavelength (or wavelength range or spectral distribution) during a first time period and can receive light energy with a second light wavelength (or wavelength range or spectral distribution) during a second time period. In an example, a light receiver can receive light energy with a first light wavelength (or wavelength range or spectral distribution) during a first time period and can receive light energy with a second light wavelength (or wavelength range or spectral distribution) during a second time period in order to measure different physiological parameters, analytes, or conditions. In an example, a light receiver can automatically cycle through light energy emissions with a variety of wavelengths (or wavelength ranges or spectral distributions) during a different time periods in order to measure different physiological parameters, analytes, or conditions.

In an example, a light receiver can receive light energy with a first light wavelength (or wavelength range or spectral distribution) during a first time period and can receive light energy with a second light wavelength (or wavelength range or spectral distribution) during a second time period in response to changing environmental conditions. In an example, a light receiver can receive light energy with a first light wavelength (or wavelength range or spectral distribution) during a first time period and can receive light energy with a second light wavelength (or wavelength range or spectral distribution) during a second time period in response to changing biometric results. In an example, a light receiver can receive light energy with a first light wavelength (or wavelength range or spectral distribution) during a first time period and can receive light energy with a second light wavelength (or wavelength range or spectral distribution) during a second time period in response to changing physiological conditions.

In an example, this invention can be embodied in an arcuate wearable device for measuring a person's hydration level comprising: a smart watch band, a specialized hydration-monitoring band, or a finger ring which is configured to be worn by a person, wherein the finger ring, wrist band, or watch further can comprise; a circumferential or annular spectroscopic sensor array along a circumference of the smart watch band, specialized hydration-monitoring band, or finger ring, wherein the circumferential or annular spectroscopic sensor array includes at least one light emitter which is configured to emit light toward the person's body and at least one light receiver which is configured to receive light that has passed through and/or been reflected from the person's body; a power source; a data processor which receives data from the light receiver which is analyzed in order to measure the person's hydration level; and a data transmitter. In an example, the circumferential or annular spectroscopic sensor array spans at least 25% of the circumference of the smart watch band, specialized hydration-monitoring band, or finger ring.

In an example, a first light emitter emits light with a first frequency and/or spectrum, a second light emitter emits light with a second frequency and/or spectrum, and the second frequency and/or spectrum is different than the first frequency and/or spectrum. In an example, a first light emitter emits light at a first angle with respect to the smart watch band, specialized hydration-monitoring band, or finger ring, a second light emitter emits light at a second angle with respect to the smart watch band, specialized hydration-monitoring band, or finger ring, and the second angle is different than the first angle. In an example, the frequency and/or spectrum of light emitted by a light emitter is changed over time. In an example, the angle at which light is emitted from a light emitter is changed over time.

In an example, the circumferential or annular spectroscopic sensor array can comprise at least two spectroscopic sensor pairs along a circumference of the smart watch band, specialized hydration-monitoring band, or finger ring, wherein each sensor pair can comprise a light emitter and a light receiver. In an example, the circumferential or annular spectroscopic sensor array can comprise an alternating sequence of light emitters and light receivers along a circumference of the smart watch band, specialized hydration-monitoring band, or finger ring.

In an example, this invention can be embodied in a wearable band with a circumferential or annular array of sequentially-activated light emitters for measuring a person's hydration level. In an example, a wearable band for measuring body hydration level can comprise: an arcuate band which is configured to be worn around at least half of the circumference of a person's finger, wrist, and/or arm, wherein a selected location on circumference of the arcuate band is defined as having a polar coordinate of 0 degrees and wherein other locations around the circumference of the arcuate band have other polar coordinates between 0 and 360 degrees; a circumferential or annular array of light emitters held by the arcuate band, wherein the light emitters are configured to emit light toward the person's body, wherein a polar coordinate of each of light emitter in the array is identified using the above-defined polar coordinates, wherein a first subset of one or more light emitters from the array with a first average polar coordinate emits light at a first point in time, wherein a second subset of one or more light emitters from the array with a second average polar coordinate emits light at a second point in time, and wherein the second average coordinate differs from the first average coordinate by at least 10 degrees; one or more light receivers, wherein the one or more light receivers are configured to receive light from the first subset of light emitters after the light has interacted with the person's body tissue at a first point in time and to receive light from the second subset of light emitters after the light has interacted with the person's body tissue at a second point in time; and a data processor which analyzes light received by the one or more light receivers in order to measure the person's hydration level.

In an example, a wearable band can further comprise an energy source (e.g. battery) and a data transceiver (e.g. data transmitter and data receiver). In an example, a wearable band can further comprise a housing which contains electronics and a display (such as a smart watch face). In an example, a wearable band can comprise two segments whose first ends are connected to the housing and whose second ends are connected to each other by a buckle, clasp, pin, clip, prong, hook-and-eye textile, or magnet. In an example, each of the two segments can comprise a circumferential or annular array of light emitters which spans a portion of the circumference of the person's finger, wrist, and/or arm.

In an example, this invention can be embodied in a smart watch for measuring body hydration level. In an example, a smart watch for measuring body hydration level can comprise: a watch housing (which houses electronics and a display); a watch band connected to the watch housing, wherein a selected location on circumference of the watch band is defined as having a polar coordinate of 0 degrees and wherein other locations around the circumference of the watch band have other polar coordinates between 0 and 360 degrees; a circumferential or annular array of light emitters held by the watch band, wherein the light emitters are configured to emit light toward the person's body, wherein a polar coordinate of each of light emitter in the array is identified using the above-defined polar coordinates, wherein a first subset of one or more light emitters from the array with a first average polar coordinate emits light at a first point in time, wherein a second subset of one or more light emitters from the array with a second average polar coordinate emits light at a second point in time, and wherein the second average coordinate differs from the first average coordinate by at least 10 degrees; one or more light receivers, wherein the one or more light receivers are configured to receive light from the first subset of light emitters after the light has interacted with the person's body tissue at a first point in time and to receive light from the second subset of light emitters after the light has interacted with the person's body tissue at a second point in time; and a data processor which analyzes light received by the one or more light receivers in order to measure the person's hydration level.

In an example, a smart watch can further comprise an energy source (e.g. battery) and a data transceiver (e.g. data transmitter and data receiver). In an example, a smart watch can comprise two band segments whose first ends are connected to the watch housing and whose second ends are connected to each other by a buckle, clasp, pin, clip, prong, hook-and-eye textile, or magnet. In an example, each of the two segments can comprise a circumferential or annular array of light emitters which spans a portion of the circumference of the person's finger, wrist, and/or arm. In an example, there can be electromagnetic plugs, pins, or other electromagnetic connectors which create electromagnetic communication between the band segments and the watch housing.

In an example, this invention can be embodied in a finger ring for measuring body hydration level. In an example, a finger ring for measuring body hydration level can comprise: a finger ring, wherein a selected location on circumference of the arcuate band is defined as having a polar coordinate of 0 degrees and wherein other locations around the circumference of the finger ring have other polar coordinates between 0 and 360 degrees; a circumferential or annular array of light emitters held by the finger ring, wherein the light emitters are configured to emit light toward the person's body, wherein a polar coordinate of each of light emitter in the array is identified using the above-defined polar coordinates, wherein a first subset of one or more light emitters from the array with a first average polar coordinate emits light at a first point in time, wherein a second subset of one or more light emitters from the array with a second average polar coordinate emits light at a second point in time, and wherein the second average coordinate differs from the first average coordinate by at least 10 degrees; one or more light receivers, wherein the one or more light receivers are configured to receive light from the first subset of light emitters after the light has interacted with the person's body tissue at a first point in time and to receive light from the second subset of light emitters after the light has interacted with the person's body tissue at a second point in time; and a data processor which analyzes light received by the one or more light receivers in order to measure the person's hydration level.

In an example, a finger ring can further comprise an energy source (e.g. battery) and a data transceiver (e.g. data transmitter and data receiver). In an example, a finger ring can further comprise a lighted crystal or gem. In an example, the color of the lighted crystal or gem can be changed to reflect the level of body hydration which is measured by the data processor.

In an example, this invention can be embodied in a forearm display device for measuring body hydration level. In an example, a forearm display device for measuring body hydration level can comprise: a display housing (which houses electronics and a display) which is configured to be worn on a person's forearm; a first arcuate band which is connected to the distal half of the display housing, wherein this first arcuate band spans at least half of the circumference of the person's forearm; a first circumferential or annular array of light emitters held by the first arcuate band, wherein light emitters in the first array are configured to emit light toward the person's body; a first light receiver which is configured to receive light from the light emitters in the first circumferential or annular array of light emitters; a second arcuate band which is connected to the proximal half of the display housing, wherein this second arcuate band spans at least half of the circumference of the person's forearm; a second circumferential or annular array of light emitters held by the second arcuate band, wherein light emitters in the second array are configured to emit light toward the person's body; a second light receiver which is configured to receive light from the light emitters in the second circumferential or annular array of light emitters; and a data processor which analyzes light received by the first light receiver and light received by the second light receiver in order to measure the person's hydration level.

In an example, a forearm display device can further comprise an energy source (e.g. battery) and a data transceiver (e.g. data transmitter and data receiver. In an example, there can be electromagnetic plugs, pins, or other electromagnetic connectors which create electromagnetic communication between the display housing and the first and second arcuate bands. In an example, the housing (and display) can be flat. In an example, the housing (and display) can have a circular, oval, egg, or rounded-quadrilateral shape. In an example, the housing (and display) can be curved. In an example, the housing (and display) can have a shape which is a cylindrical section, conic section, paraboloid section, or hyperboloid section. In an example, the housing (and display) can have a proximal-to-distal dimension in the range of 2 to 6 inches. In an example, the housing (and display) can have a lateral or circumferential dimension in the range of 1 to 4 inches.

In an example, an arcuate band can span the entire 360-degree circumference of a person's finger, wrist, and/or arm. In an example, an arcuate band can span at least three-quarters of the circumference of a person's finger, wrist, and/or arm, but not the entire circumference. In an example, an arcuate band can span at least half of the circumference of a person's finger, wrist, and/or arm, but not the entire circumference. In an example, an arcuate band can have a circumferential axis which encircles (at least a portion of) the circumference of a person's finger, wrist, and/or arm and lateral axes which are perpendicular to the circumferential axis manner. In an example, a lateral axis can span in a distal-to-proximal or proximal-to-distal direction, wherein proximal is closer to the person's elbow and distal is further from the person's elbow. In an example, the width of an arcuate band can be measured along a lateral axis. In an example, an arcuate band can have a constant width as measured from any point on its circumferential axis. In an example, the width of an arcuate band can be between ¼" and 3". In an example, the portion of an arcuate band which spans the dorsal surface of a finger, wrist, and/or arm can be wider than the portion of the arcuate band which spans the ventral surface of the finger, wrist, and/or arm, or vice versa.

In an example, an arcuate band can be a single continuous piece. In an example, an arcuate band can comprise two segments whose ends are connected to each other by a buckle, clip, pin, hook, clasp, snap, hook-and-eye textile, or magnet. In an example, an arcuate band can comprise a series of relatively rigid segments which are flexibly connected by joints, chains, fabric, or other flexible members. In an example, an arcuate band can be a series of flexibly-connected links. In an example, an arcuate band can be flexible, elastic, stretchable, and/or expandable. In an example, an arcuate band can woven or otherwise made from a textile. In an example, an arcuate band can be made with electromagnetically-conductive fabric. In an example, an arcuate band can be expanded and slid onto a finger, wrist, and/or arm. In an example, an arcuate band can be made from a metal or polymer. In an example, an arcuate band can be rigid and slid onto a finger.

In an example, an arcuate band can comprise a single continuous band which encircles a person's finger, wrist, and/or arm. In an example, an arcuate band can comprise: a housing which contains electronics; and one or more band segments attached to the housing. In an example, the housing can further comprise a display, a power source, and a data transceiver (e.g. data transmitter and data receiver). In an example, an arcuate band can comprise a smart watch with a rigid watch housing connected to a flexible watch band or strap. In an example, a light receiver can be located on the watch housing. In an example, a plurality of light receivers can be located on the one or more band segments along with the array of light emitters. In an example, an arcuate band can be selected from the group consisting of: single continuous band; smart watch with a rigid housing attached to one or more flexible band segments; rigid finger ring; fitness band; wrist bracelet or bangle; clothing sleeve or stand-alone arm sleeve or gauntlet; and arm band.

In an example, this invention can be embodied in a wearable device with two arcuate bands, each of which spans (a portion of) the circumference of a person's finger, wrist, and/or arm. In an example, these two arcuate bands can each be connected to a housing on the dorsal or ventral surface of a person's finger, wrist, and/or arm. In an example, these two arcuate bands can be directly connected to each other on the dorsal or ventral surface of a person's finger, wrist, and/or arm. In an example, this invention can be embodied in a wearable forearm display which is attached to a person's forearm by two arcuate bands—a proximal arcuate band and a distal arcuate band.

In an example, a light emitter can be a Light Emitting Diode (LED). In an example, a light emitter can emit light in the near infrared spectrum. In an example, a light emitter can emit red light. In an example, light emitter can emit green light. In an example, a light emitter can emit coherent light. In an example, a subset of light emitters in a circumferential or annular array of light emitters can be a single light. In an example, light emitters in a circumferential or annular array can be activated to shine, one light at a time, around the circumference of a finger, wrist, and/or arm in a clockwise (or counter clockwise) direction. This can create the appearance of a light which is moving around in circles—like the apparently-moving sequentially-lit light bulbs in a theater marquee.

In an example, a subset of light emitters in a circumferential or annular array of light emitters can be two or more light emitters. In an example, a subset of light emitters in a circumferential or annular array of light emitters can be two or more laterally-proximal light emitters which share the same polar coordinates. In an example, a subset of light emitters in a circumferential or annular array of light emitters can be two or more circumferentially or annularly-proximal light emitters with different polar coordinates. In an example, a subset of light emitters can be two light emitters which are diametrically opposite each other with respect to the circumference of a person's finger, wrist, and/or arm.

In an example, a circumferential or annular array of light emitters can span the entire 360-degree circumference of an arcuate band. In an example, a circumferential or annular array of light emitters can span at least three-quarters of an arcuate band, but not the entire circumference of the band. In an example, a circumferential or annular array of light emitters can span at least half of the circumference of an arcuate band. In an example, a circumferential or annular array of light emitters can span the entire 360-degree circumference of a person's finger, wrist, and/or arm. In an example, a circumferential or annular array of light emitters can span at least three-quarters of a person's finger, wrist, and/or arm, but not the entire circumference of the band. In an example, a circumferential or annular array of light emitters can span at least half of the circumference of a person's finger, wrist, and/or arm.

In an example, a circumferential or annular array of light emitters can be aligned around a common circumferential axis (e.g. circumference line) of an arcuate band. It is to be understood that a circumferential axis (or line) does not have to be a perfect circle. Even if it the cross-sectional perimeter of an arcuate band is an oval, other convex shape, or undulating shape—its centroid can still be determined for the purposes of identifying polar coordinates around the circumference and an array of light emitters can still be distributed around its cross-sectional perimeter. Thus, in this disclosure, the term "circumference" is not restricted to the perimeter of a perfect circle.

In an example, an arcuate band can have a single circumferential or annular array of light emitters along a single circumferential axis (e.g. circumferential line). In an example, an arcuate band can have a first circumferential or annular array of light emitters around a first circumferential axis and a second circumferential or annular array of light emitters around a second circumferential axis, wherein the first and second circumferential axes are parallel to each other. In an example, an arcuate band can have two or more circumferential or annular arrays of light emitters around circumferential axes which are parallel to each other. In an example, light emitters in different circumferential or annular arrays which share the same polar coordinate but have different lateral (distal to proximal) positions can be activated simultaneously. In an example, light emitters in different circumferential or annular arrays which share the same polar coordinate but have different lateral (distal to proximal) positions can be activated at different times.

In an example, an arcuate band can have a single light receiver at a single polar coordinate. In an example, an arcuate band can have a circumferential or annular array of light receivers along a single circumferential axis (e.g. circumferential line). In an example, an arcuate band can have a first circumferential or annular array of light receivers around a first circumferential axis and a second circumferential or annular array of light receivers around a second circumferential axis, wherein the first and second circumferential axes are parallel to each other. In an example, an arcuate band can have two or more circumferential or annular arrays of light receivers around circumferential axes which are parallel to each other. In an example, an arcuate band can have a (single) light receiver which is part of a housing to which one or more actuate bands are connected.

In an example, an arcuate band can comprise pairs of light emitters and light receivers. In an example, a paired light emitter and light receiver can share the same polar coordinate, but be on different lateral (distal to proximal) axes. In an example, a paired light emitter and light receiver can have different polar coordinates, but share the same lateral (distal to proximal) axis. In an example, an arcuate band can have a circumferential or annular array with both light emitters and light receivers. In an example, an arcuate band can have a circumferential or annular array with alternating light emitters and light receivers. In an example, data from a sequentially-activated circumferential or annular array of light emitters and light receivers can be used to create a two-dimensional image showing variation in analyte levels within a virtual cross-section of a person's finger, wrist, and/or arm.

In an example, there can be differences in the lateral locations of light emitters at different points around the circumference of an arcuate band. In an example, some light emitters in a circumferential or annular array can on one side of a circumferential line and other light emitters can be on the other side of the circumferential line. In an example, there can be a plurality of light emitters (at different lateral locations) at the same polar coordinate of an arcuate band. In an example, there can be two or more parallel circumferential or annular arrays of light emitters on an arcuate band. In an example, there can be a first circumferential or annular array of light emitters on an arcuate band and a second circumferential or annular array of light emitters on the arcuate band, wherein the central circumferential line of the first array is parallel to the central circumferential line of the second array.

In an example, light emitters in a circumferential or annular array can be equally spaced and/or distributed around (a portion of) the circumference of an arcuate band. In an example, proximal pairs of light emitters in a circumferential or annular array on an arcuate band can be separated by the same number of polar degrees and/or the same distance. In an example, a circumferential or annular array of light emitters can comprise 24, 12, 6, or 4 emitters. In an example, proximal pairs of light emitters in a circumferential or annular array can have polar coordinates which differ by 15, 30, 60, or 90 degrees. In an example, proximal pairs of light emitters in a circumferential or annular array can be separated by 15, 30, 60, or 90 degrees. In an example, proximal pairs of light emitters in a circumferential or annular array can have polar coordinates which differ by 1 to 15 degrees. In an example, light emitters in a circumferential or annular array can have polar coordinates which differ by 15, 30, 60, or 90 degrees. In an example, light emitters in a circumferential or annular array can be separated by 15, 30, 60, or 90 degrees. In an example, light emitters in a circumferential or annular array can have polar coordinates which differ by a number of degrees in the range of 1 to 15.

In an example, an arcuate band can have a single light receiver. In an example, an arcuate band can have a plurality of light receivers. In an example, light receivers in a circumferential or annular array can be equally spaced and/or distributed around (a portion of) the circumference of an arcuate band. In an example, proximal pairs of light receivers in a circumferential or annular array on an arcuate band can be separated by the same number of polar degrees and/or the same distance. In an example, a circumferential or annular array of light receivers can comprise 24, 12, 6, or 4 receivers. In an example, proximal pairs of light receivers in a circumferential or annular array can have polar coordinates which differ by 15, 30, 60, or 90 degrees. In an example, proximal pairs of light receivers in a circumferential or annular array can be separated by 15, 30, 60, or 90 degrees. In an example, proximal pairs of light receivers in a circumferential or annular array can have polar coordinates which differ by 1 to 15 degrees. In an example, light receivers in a circumferential or annular array can have polar coordinates which differ by 15, 30, 60, or 90 degrees. In an example, light receivers in a circumferential or annular array can be separated by 15, 30, 60, or 90 degrees. In an example, light receivers in a circumferential or annular array can have polar coordinates which differ by a number of degrees in the range of 1 to 15.

In an example, light emitters in a circumferential or annular array can be located on inward-curving portions of an undulating arcuate band. In an example, light emitters in a circumferential or annular array can be located on soft and compressible inward-facing protrusions on an arcuate band. In an example, light emitters in a circumferential or annular array can be recessed within the inward-facing concave side of an arcuate band. In an example, light emitters in a circumferential or annular array can each be surrounded by soft and compressible inward-facing protrusions on an arcuate band. In an example, light emitters in a circumferential or annular array can each be surrounded by a light-blocking structure, such as a circular light barrier or a polygonal light barrier. In an example, a light-blocking structure can be soft and compressible.

In an example, light emitters in a circumferential or annular array can be activated in a sequence like "moving" lights on a theater marquee. In an example, light emitters in a circumferential or annular array can be activated in a clockwise (or counter-clockwise) sequence. In an example, a first light at a first polar coordinate can be activated to emit light at a first time and second light at a second polar coordinate can be activated to emit light at a second time. In an example, a first light at a first polar coordinate can be activated to emit light at a first time and second light at a second polar coordinate can be activated to emit light at a second time, wherein the second light is the light in the array which is clockwise (or counter-clockwise) most proximal to the first light. In an example, a clockwise (or counter-clockwise) sequence of light can be activated to cause a series of light emissions which encircle the circumference of the arcuate band and/or the finger, wrist, or arm.

In an example, light emitters in a circumferential or annular array can be activated in a (relatively) random manner. In an example, light emitters in a circumferential or annular array can initially be activated in a (relatively) random manner and then light emitters in a particular area which provide the most accurate analyte readings can be selected for further activation. In an example, larger subsets of light emitters can be activated at first and then smaller subsets of light emitters can be activated, wherein initial readings from the larger subsets are used to identify promising smaller subsets of light emitters which are likely to provide more accurate data. In an example, the most accurate locations for measuring an analyte can be identified depending on the current configuration of a band on the person's finger, wrist, and/or arm. This can help to control for shifting and/or rotation of a band with respect to a person's finger, wrist, and/or arm. For example, if a particular area of a person's finger, wrist, or arm is best for measuring analyte concentration, but the band shifts over time, then pattern recognition can be done to identify which subset of light emitters are over that particular area at a given time and sequential light activation can be concentrated on that area.

Activating different subsets of light emitters at different times enables a light receiver to separately analyze light beams which have been reflected from, or transmitted through, body tissue along different pathways. In an example, there can be pauses between the times when different subsets of light emitters are activated in a circumferential or annular array. In an example, there can be overlap in the times that different subsets of light emitters are activated in a circumferential or annular array. In an example, the lengths of time wherein light emitters are activated can be changed and/or adjusted to refine measurement of analyte levels. In an example, the color and/or spectrum of light from light emitters can be changed and/or adjusted to refine measurement of analyte levels. In an example, the duration of activation of different subsets of light emitters in a circumferential or annular array can be adjusted based on analysis of light spectra. In an example, the speed with which light emitters in a circle around a finger, wrist, or arm are sequentially activated in a clockwise (or counter-clockwise) manner can be increased or decreased based on analysis of light spectra.

In an example, varying the distance between a light receiver and different light emitters in a circumferential or annular array of light emitters at different times can measure analyte concentration at different tissue levels and locations in a person's finger, wrist, and/or arm. In an example, a circumferential or annular array of light emitters can also enable analysis of variation in analyte levels by tissue depth and location. This provides richer information on analyte levels within body tissue than is possible, for example, with a single light emitter and receiver pair on the inward-surface of the enclosure of a smart watch display. Incorporating multiple light emitters around the circumference of a band provides data on analyte levels at different locations and tissue depths. It can also help to control for shifts of the device on (or around) a person's finger, wrist, and/or arm.

In an example, as different light emitters are activated in a circle around a person's finger, wrist, and/or arm, this enables a cross-sectional (and/or volumetric) scan of analyte levels in the person's finger, wrist, and/or arm. In an example, different combinations of light emitters in a circumferential or annular array can be activated in order to measure combined effects of light reflected from, or having passed through, the body along different pathways. Activating light emitters in different locations around the circumferential or annular array may even enable light beam triangulation to measure analyte levels in specific (cross-sectional) areas of a person's finger, wrist, and/or arm.

In an example, there can be a first circumferential or annular array of light emitters of a first type and a second circumferential or annular array of light emitters of a second type, wherein the first and second types of light emitters differ from each other by one or more characteristics selected from the group consisting of: light beam color and/or spectral frequency; light beam intensity and/or power; size and/or shape; angle of light beam projection; light coherence; and light polarity.

In an example, a wearable band can have different rings or layers. In an example, an outer ring or layer (facing away from the surface of a person's finger, wrist, and/or arm) can have a first elasticity level, an inner ring or layer (facing towards the surface of a person's finger, wrist, and/or arm) can have a second elasticity level, and the second elasticity level can be greater than the first elasticity level. In an example, an outer ring or layer can have a first hardness level, an inner ring or layer can have a second hardness level, and the second hardness level can be less than the first hardness level. In an example, an outer ring or layer can have a first shore value, an inner ring or layer can have a second shore value, and the second shore value can be less than the first shore value. In an example, an inner ring or layer can comprise compressible foam. In an example, an inner ring or layer can be inflatable.

In an example, a wearable band can have undulating rings or layers. In an example, a wearable band can have lateral undulations in width around its circumference. In an example, a wearable band can have radial undulations in depth around its circumference. In an example, these undulations can be sinusoidal. In an example, a circumferential or annular array of light emitters can be located at selected locations on these undulations. In an example, a circumferential or annular array of light emitters can be located on wider portions of a band with lateral undulations. In an example, a circumferential or annular array of light emitters can be located on inward-extending portions of a band with radial undulations.

In an example, this invention can be embodied in an arcuate wearable device for measuring body hydration level comprising: an arcuate band which is configured to span (some or all of) the circumferential perimeter of a part of a person's body (such as a wrist, arm, finger, ankle, and/or leg); an energy emitter which is configured to emit energy toward the part of the person's body; an energy receiver which is configured to receive energy from the energy emitter after that energy has passed through and/or been reflected from the part of the person's body; a data processor which receives data from the energy receiver which is analyzed in order to measure the person's body hydration level; and an energy source which provides energy to the energy emitter and/or to the data processor.

In an example, this invention can be embodied in an arcuate wearable device for measuring body hydration level comprising: an arcuate band which is configured to span (some or all of) the circumferential perimeter of a part of a person's body (such as a wrist, arm, finger, ankle, and/or leg); an energy emitter which is configured to emit energy toward the part of the person's body; an energy receiver which is configured to receive energy from the energy emitter after that energy has passed through and/or been reflected from the part of the person's body; a data processor which receives data from the energy receiver which is analyzed in order to measure the person's body hydration level; an energy source which provides energy to the energy emitter and/or to the data processor; a data transmitter which transmits data from the data processor to a remote device and/or remote location; and an energy barrier between the energy emitter and the energy receiver which reduces transmission of energy from the energy emitter to the energy receiver.

In an example, this invention can be embodied in an arcuate wearable device for measuring body hydration level comprising: an arcuate band which is configured to span (some or all of) the circumferential perimeter of a part of a person's body (such as a wrist, arm, finger, ankle, and/or leg); an energy emitter which is configured to emit energy toward the part of the person's body; an energy receiver which is configured to receive energy from the energy emitter after that energy has passed through and/or been reflected from the part of the person's body; a data processor which receives data from the energy receiver which is analyzed in order to measure the person's body hydration level; an energy source which provides energy to the energy emitter and/or to the data processor; a data transmitter which transmits data from the data processor to a remote device and/or remote location; and an energy conductor between the energy emitter and the energy receiver which increases transmission of energy from the energy emitter to the energy receiver.

In an example, this invention can be embodied in an arcuate wearable device for measuring body hydration level comprising: an arcuate band which is configured to span (some or all of) the circumferential perimeter of a part of a person's body (such as a wrist, arm, finger, ankle, and/or leg); an energy emitter which is configured to emit energy toward the part of the person's body; an energy receiver which is configured to receive energy from the energy emitter after that energy has passed through and/or been reflected from the part of the person's body; a data processor which receives data from the energy receiver which is analyzed in order to measure the person's body hydration level; an energy source which provides energy to the energy emitter and/or to the data processor; a data transmitter which transmits data from the data processor to a remote device and/or remote location; and a housing which is held on the person's body by the arcuate band, wherein the energy emitter and the energy receiver are part of the housing.

In an example, a band can be flexible. In an example, a band can be rigid. In an example, portions of a band can be flexible and portions can be rigid. In an example, a band can be elastic or stretchable. In an example, a band can be made from a metal, a polymer, a fabric, or a combination thereof. In an example, a band can be a bracelet, bangle, armlet, or arm band. In an example, a band can be a fitness band or smart watch. In an example, a band can be the strap portion of a fitness monitor or smart watch. In an example, a band can be a finger ring. In an example, a band can be a finger sleeve. In an example, a band can be the cuff of a shirt, pants, shorts, or sock. In an example, an arcuate wearable device for measuring a person's hydration level can be incorporated into the cuff of a shirt or pair of pants. In an example, a band can include electronic components such as biometric sensors and a display. In an example, a band can further comprise a housing which includes electronic components such as biometric sensors and a display. In an example, a band can be selected from the group consisting of: arm band, armlet, bangle, bracelet, finger ring, finger sleeve, fitness band, pants cuff, shirt cuff, smart watch, and sock cuff. In an example, an arcuate wearable device for measuring a person's hydration level can be incorporated into the cuff of a shirt or pair of pants.

In an example, a band can span the full circumference of the cross-sectional perimeter of a part of a person's body. In an example, a band can fully encircle a person's wrist, arm, finger, ankle, and/or leg. In an example, a band can span between 50% and 95% of the cross-sectional perimeter of a part of a person's body. In an example, a band can span between 50% and 95% of the cross-sectional perimeter of a part of a person's wrist, arm, finger, ankle, and/or leg. In an example, a band can span between 75% and 95% of the cross-sectional perimeter of a part of a person's wrist, arm, finger, ankle, and/or leg. In an example, a band can comprise a single, continuous piece of material. In an example, a band can comprise two or more pieces and/or segments. In an example, a band can comprise a (partially) circumferential or annular series of flexibly-connected segments.

In an example, the term "proximal" when applied to a person's wrist, arm, or finger means "closer to the person's shoulder when the arm is extended" and the term "distal" means "farther from the person's shoulder when the arm is extended." In an example, a proximal-to-distal axis can be defined for a band worn on the wrist, arm, or finger using this shoulder-based definition of proximal and distal. In an example, the term "proximal" when applied to a person's ankle or leg means "closer to the person's hip when the leg is extended" and the term "distal" means "farther from the person's hip when the leg is extended." In an example, a proximal-to-distal axis can be defined for a band worn on the ankle and/or leg using this hip-based definition of proximal and distal. In an example, the cross-sectional perimeter and/or circumference of an arm or leg can be perpendicular to the central proximal-to-distal axis of that arm or leg, respectively. In an example, the cross-sectional perimeter and/or circumference of a forearm or lower leg can be perpendicular to the central proximal-to-distal axis of that forearm or lower leg, respectively.

In an example, a band can have two ends which can be connected to each other around a part of a person's body by a mechanism selected from the group consisting of: buckle, clasp, hook, pin, knob, button, zipper, magnet, adhesive, and hook-and-eye fabric. In an example, a band can be stretched or expanded so as to slip over a person's hand onto their wrist, arm, or finger or over a person's foot onto their ankle and/or leg. In an example, a band can have two moveable portions connected by a hinge or joint, wherein these two moveable portions can be locked into position around a person's wrist, arm, ankle, or leg. In an example, a band can have two ends which can be pulled apart from each other by application of an external force to slip the band around a person's wrist, arm, ankle, or leg and then these two ends move back together when the force is removed so as to hold the band around the person's wrist, arm, ankle, or leg.

In an example, an energy emitter can be located on the radially-inward (i.e. body-facing) side of a band. In an example, an energy receiver can also be located on the radially-inward (i.e. body-facing) side of a band. In an example, an energy emitter and an energy receiver can emit and receive light energy, respectively. In an example, a light energy emitter can emit light energy toward body tissue and an energy receiver can receive a portion of that light energy, after the light energy has passed through and/or been reflected from the body tissue.

In an example, a light energy emitter and a light energy receiver together can comprise a spectroscopic (or "spectroscopy") sensor. In an example, the spectrum of light energy is changed when the light energy passes through body tissue and/or is reflected from body tissue. In an example, changes in the spectrum of light energy which has passed through and/or been reflected from body tissue can be analyzed to detect the composition and/or configuration of body tissue. In an example, these changes in the spectrum of light energy can be analyzed to provide information on the composition and/or configuration of body tissue which, in turn, enables measurement of body hydration level. In an example, a light energy emitter and a light energy receiver together can comprise a sensor selected from the group consisting of: backscattering spectrometry sensor, infrared spectroscopic sensor, ion mobility spectroscopic sensor, mass spectrometry sensor, near infrared spectroscopic sensor (NIS), Raman spectroscopic sensor, spectrometry sensor, spectrophotometer, spectroscopic sensor, ultraviolet spectroscopic sensor, and white light spectroscopic sensor.

In an example, a light energy emitter can emit coherent light. In an example, a light energy emitter can be a laser. In an example, a light energy emitter can be a Light Emitting Diode (LED). In an example, a light energy emitter can emit infrared or near-infrared light. In an example, a light energy emitter can emit ultraviolet light. In an example, a light energy emitter emit red light and/or be a red-light laser. In an example, a light energy emitter emit green light and/or be a green-light laser. In an example, a light energy emitter can emit white light and/or be a white-light laser. In an example, a light energy emitter can emit light with frequency and/or spectrum changes over time. In an example, a light energy emitter can emit a sequence of light pulses at different selected frequencies. In an example, a light energy emitter can emit polarized light. In an example, the polarization of light can change after the light passes through and/or is reflected from body tissue and these changes can be used to measure body hydration level.

In an example, portions of the spectrum of light emitted by a light energy emitter can be absorbed by body tissue and spectral analysis of these absorbed portions can enable measurement of body hydration level. In an example, portions of the spectrum of light emitted by a light energy emitter can be amplified by body tissue and spectral analysis of these amplified portions can enable measurement of body hydration level. In an example, portions of the spectrum of light emitted by a light energy emitter can be shifted by interaction with body tissue and spectral analysis of these shifted portions can enable measurement of body hydration level.

In an example, the depth, breadth, location, and/or type of body tissue or fluid from which light from a light energy emitter is reflected can be changed by adjusting the frequency, color, and/or spectrum of light emitted from the light energy emitter. In an example, the frequency, color, and/or spectrum of light emitted from the light energy emitter can be adjusted in order to more accurately measure body hydration level. In an example, the frequency, color, and/or spectrum of light emitted from the light energy emitter can be adjusted automatically (in an iterative manner) by a device in order to more accurately measure body hydration level for a specific person, for a specific type of activity, or for a specific configuration of the device relative to the person's body surface. In an example, the frequency, color, and/or spectrum of light emitted from the light energy emitter can be adjusted automatically to maintain accurate measurement of body hydration level even if the device shifts and/or moves relative to the person's body surface. In an example, a device can automatically vary the frequency, color, and/or spectrum of light from a light emitter to scan through a range of tissue depths, locations, and/or types in order to obtain more accurate measurement of body hydration level. In an example, this device can further comprise one or more optical filters or lenses which change the frequency, color, and/or spectrum of light emitted by a light energy emitter.

In an example, the depth, breadth, location, and/or type of body tissue or fluid from which light from a light energy emitter is reflected can be changed by adjusting the power and/or intensity of light emitted from the light energy emitter. In an example, the power and/or intensity of light emitted from the light energy emitter can be adjusted in order to more accurately measure body hydration level. In an example, the power and/or intensity of light emitted from the light energy emitter can be adjusted automatically (in an iterative manner) by a device in order to more accurately measure body hydration level for a specific person, for a specific type of activity, or for a specific configuration of the device relative to the person's body surface. In an example, the power and/or intensity of light emitted from the light energy emitter can be adjusted automatically to maintain accurate measurement of body hydration level even if the device shifts and/or moves relative to the person's body surface. In an example, a device can automatically vary the power and/or intensity of light from a light emitter to scan through a range of tissue depths, locations, and/or types in order to obtain more accurate measurement of body hydration level.

In an example, the depth, breadth, location, and/or type of body tissue or fluid from which light from a light energy emitter is reflected can be changed by adjusting the angle of light emitted from the light energy emitter. In an example, the angle of light emitted from the light energy emitter can be adjusted in order to more accurately measure body hydration level. In an example, the angle of light emitted from the light energy emitter can be adjusted automatically (in an iterative manner) by a device in order to more accurately measure body hydration level for a specific person, for a specific type of activity, or for a specific configuration of the device relative to the person's body surface. In an example, the angle of light emitted from the light energy emitter can be adjusted automatically to maintain accurate measurement of body hydration level even if the device shifts and/or moves relative to the person's body surface. In an example, a device can automatically vary the angle of light from a light emitter to scan through a range of tissue depths, locations, and/or types in order to obtain more accurate measurement of body hydration level. In an example, this device can further comprise one or more optical filters or lenses which change the projection and/or body incidence angle of a light beam emitted by a light energy emitter.

In an example, the depth, breadth, location, and/or type of body tissue or fluid from which light from a light energy emitter is reflected can be changed by adjusting the coherence, polarization, and/or phase of light emitted from the light energy emitter. In an example, the coherence, polarization, and/or phase of light emitted from the light energy emitter can be adjusted in order to more accurately measure body hydration level. In an example, the coherence, polarization, and/or phase of light emitted from the light energy emitter can be adjusted automatically (in an iterative manner) by a device in order to more accurately measure body hydration level for a specific person, for a specific type of activity, or for a specific configuration of the device relative to the person's body surface. In an example, the coherence, polarization, and/or phase of light emitted from the light energy emitter can be adjusted automatically to maintain accurate measurement of body hydration level even if the device shifts and/or moves relative to the person's body surface. In an example, a device can automatically vary the coherence, polarization, and/or phase of light from a light emitter to scan through a range of tissue depths, locations, and/or types in order to obtain more accurate measurement of body hydration level. In an example, this device can further comprise one or more optical filters or lenses which change the coherence, polarization, and/or phase of light emitted by a light energy emitter.

In an example, a device can comprise a first light energy emitter and a second light energy emitter. In an example, the first light energy emitter can emit light with a first light frequency, color, and/or spectrum and the second light energy emitter can emit light with a second light frequency, color, and/or spectrum. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, a device can comprise a first light energy emitter and a second light energy emitter. In an example, the first light energy emitter can emit light with a first light power and/or intensity and the second light energy emitter can emit light with a second light power and/or intensity. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, a device can comprise a first light energy emitter and a second light energy emitter. In an example, the first light energy emitter can emit light with a first light projection and/or body incidence angle and the second light energy emitter can emit light with a second light projection and/or body incidence angle. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, a device can comprise a first light energy emitter and a second light energy emitter. In an example, the first light energy emitter can emit light with a first light coherence, polarization, and/or phase and the second light energy emitter can emit light with a second light coherence, polarization, and/or phase. In an example, light from the first light energy emitter can reflect primarily from a first depth, breadth, location, and/or type of body tissue and light from the second light energy emitter can reflect primarily from a first depth, breadth, location, and/or type of body tissue. In an example, first and second light energy emitters can emit light simultaneously. In an example, first and second light energy emitters can emit light in a selected chronological sequence and/or timing pattern.

In an example, the depth, breadth, location, and/or type of body tissue or fluid from which light from a light energy emitter is reflected and received by a light energy receiver can be changed by adjusting the distance between a light energy emitter and a light energy receiver. In an example, the distance between a light energy emitter and a light energy receiver can be adjusted in order to more accurately measure body hydration level. In an example, the distance between a light energy emitter and a light energy receiver can be adjusted automatically (in an iterative manner) by a device in order to more accurately measure body hydration level for a specific person, for a specific type of activity, or for a specific configuration of the device relative to the person's body surface. In an example, the distance between a light energy emitter and a light energy receiver can be adjusted automatically to maintain accurate measurement of body hydration level even if the device shifts and/or moves relative to the person's body surface. In an example, a device can automatically vary the distance between a light energy emitter and a light energy receiver to scan through a range of tissue depths, locations, and/or types in order to obtain more accurate measurement of body hydration level.

In an example, the depths, breadths, locations, and/or types of body tissue or fluid from which light beams from a plurality of light energy emitters are reflected can be determined by a selected geometric configuration of the plurality of light energy emitters and a light energy receiver. In an example, a selected geometric configuration of a plurality of light energy emitters and a light energy receiver can be designed to most accurately measure body hydration level. In an example, the geometric configuration of a plurality of light energy emitters and a light energy receiver can be adjusted automatically (in an iterative manner) by a device in order to more accurately measure body hydration level for a specific person, for a specific type of activity, or for a specific configuration of the device relative to the person's body surface. In an example, the geometric configuration of a plurality of light energy emitters and a light energy receiver can be adjusted automatically to maintain accurate measurement of body hydration level even if the device shifts and/or moves relative to the person's body surface. In an example, a device can automatically vary the geometric configuration of a plurality of light energy emitters and a light energy receiver in order to scan through a range of tissue depths, locations, and/or types in order to measure body hydration level more accurately. In an example, a plurality of light energy emitters can emit light simultaneously. In an example, a plurality of light energy emitters can emit light in a selected chronological sequence and/or timing pattern.

In an example, a plurality of light energy emitters can be configured in a linear array in proximity to a light energy receiver. In an example, a plurality of light energy emitters can be configured in a linear array including a light energy receiver. In an example, a plurality of light energy emitters can be configured in a polygonal array in proximity to a light energy receiver. In an example, a plurality of light energy emitters can be configured in a polygonal array including a light energy receiver. In an example, a plurality of light energy emitters can be configured in a polygonal array around a light energy receiver. In an example, a plurality of light energy emitters can be configured in a circular or other arcuate array in proximity to a light energy receiver. In an example, a plurality of light energy emitters can be configured in a circular or other arcuate array including a light energy receiver. In an example, a plurality of light energy emitters can be configured in a circular or other arcuate array around a light energy receiver. In an example, a plurality of light energy emitters can emit light in a circular sequence around a central light energy receiver.

In an example, the depths, breadths, locations, and/or types of body tissue or fluid from which light beams are reflected and received by a plurality of light energy receivers can be determined by a selected geometric configuration of a light energy emitter and the plurality of light energy receivers. In an example, a selected geometric configuration of a light energy emitter and a plurality of light energy receivers can be designed to most accurately measure body hydration level. In an example, the geometric configuration of a light energy emitter and a plurality of light energy receivers can be adjusted automatically (in an iterative manner) by a device in order to more accurately measure body hydration level for a specific person, for a specific type of activity, or for a specific configuration of the device relative to the person's body surface. In an example, the geometric configuration of a light energy emitter and a plurality of light energy receivers can be adjusted automatically to maintain accurate measurement of body hydration level even if the device shifts and/or moves relative to the person's body surface. In an example, a device can automatically vary the geometric configuration of a light energy emitter and a plurality of light energy receivers in order to scan through a range of tissue depths, locations, and/or types in order to measure body hydration level more accurately.

In an example, a plurality of light energy receivers can be configured in a linear array in proximity to a light energy emitter. In an example, a plurality of light energy receivers can be configured in a linear array including a light energy emitter. In an example, a plurality of light energy receivers can be configured in a polygonal array in proximity to a light energy emitter. In an example, a plurality of light energy receivers can be configured in a polygonal array including a light energy emitter. In an example, a plurality of light energy receivers can be configured in a polygonal array around a light energy emitter. In an example, a plurality of light energy receivers can be configured in a circular or other arcuate array in proximity to a light energy emitter. In an example, a plurality of light energy receivers can be configured in a circular or other arcuate array including a light energy emitter. In an example, a plurality of light energy receivers can be configured in a circular or other arcuate array around a light energy emitter.

In an example, a light energy emitter can be part of an arcuate band. In an example, a light energy emitter can be part of a housing which is held on a person's body by an arcuate band. In an example, this device can comprise an array, grid, and/or matrix of two or more light energy emitters with a proximal-to-distal orientation. In an example, this device can comprise an array, grid, and/or matrix of two or more light energy emitters along a proximal-to-distal axis. In an example, this device can comprise an array, grid, and/or matrix of two or more light energy emitters with a circumferential orientation. In an example, this device can comprise an array, grid, and/or matrix of two or more light energy emitters along a circumferential axis.

In an example, this device can comprise a linear array, grid, and/or matrix of light energy emitters. In an example, this device can comprise a rectangular array, grid, and/or matrix of light energy emitters. In an example, this device can comprise a circular or elliptical array, grid, and/or matrix of light energy emitters. In an example, this device can comprise a checkerboard array, grid, and/or matrix of light energy emitters. In an example, this device can comprise a three-dimensional stacked array, grid, and/or matrix of light energy emitters. In an example, this device can comprise a sunburst and/or radial-spoke array, grid, and/or matrix of light energy emitters. In an example, this device can comprise a sinusoidal array, grid, and/or matrix of light energy emitters.

In an example, an array, grid, and/or matrix of two or more light energy emitters can span up to 10% of the cross-sectional circumference of a part of a person's body such as a wrist, arm, finger, ankle, or leg. In an example, an array, grid, and/or matrix of two or more light energy emitters can span between 10% and 25% of the cross-sectional circumference of a part of a person's body such as a wrist, arm, finger, ankle, or leg. In an example, an array, grid, and/or matrix of two or more light energy emitters can span between 25% and 50% of the cross-sectional circumference of a part of a person's body such as a wrist, arm, finger, ankle, or leg. In an example, an array, grid, and/or matrix of two or more light energy emitters can span between 50% and 100% of the cross-sectional circumference of a part of a person's body such as a wrist, arm, finger, ankle, or leg.

In an example, a light energy receiver can be part of an arcuate band. In an example, a light energy receiver can be part of a housing which is held on a person's body by an arcuate band. In an example, this device can comprise an array, grid, and/or matrix of two or more light energy receivers with a proximal-to-distal orientation. In an example, this device can comprise an array, grid, and/or matrix of two or more light energy receivers along a proximal-to-distal axis. In an example, this device can comprise an array, grid, and/or matrix of two or more light energy receivers with a circumferential orientation. In an example, this device can comprise an array, grid, and/or matrix of two or more light energy receivers along a circumferential axis.

In an example, this device can comprise a linear array, grid, and/or matrix of light energy receivers. In an example, this device can comprise a rectangular array, grid, and/or matrix of light energy receivers. In an example, this device can comprise a circular or elliptical array, grid, and/or matrix of light energy receivers. In an example, this device can comprise a checkerboard array, grid, and/or matrix of light energy receivers. In an example, this device can comprise a three-dimensional stacked array, grid, and/or matrix of light energy receivers. In an example, this device can comprise a sunburst and/or radial-spoke array, grid, and/or matrix of light energy receivers. In an example, this device can comprise a sinusoidal array, grid, and/or matrix of light energy receivers.

In an example, an array, grid, and/or matrix of two or more light energy receivers can span up to 10% of the cross-sectional circumference of a part of a person's body such as a wrist, arm, finger, ankle, or leg. In an example, an array, grid, and/or matrix of two or more light energy receivers can span between 10% and 25% of the cross-sectional circumference of a part of a person's body such as a wrist, arm, finger, ankle, or leg. In an example, an array, grid, and/or matrix of two or more light energy receivers can span between 25% and 50% of the cross-sectional circumference of a part of a person's body such as a wrist, arm, finger, ankle, or leg. In an example, an array, grid, and/or matrix of two or more light energy receivers can span between 50% and 100% of the cross-sectional circumference of a part of a person's body such as a wrist, arm, finger, ankle, or leg.

In an example, a light energy emitter and a light energy receiver can be part of an arcuate band. In an example, a light energy emitter and a light energy receiver can be part of a housing which is held on a person's body by an arcuate band. In an example, this device can comprise an array, grid, and/or matrix of (alternating) light energy emitters and receivers with a proximal-to-distal orientation. In an example, this device can comprise an array, grid, and/or matrix of (alternating) light energy emitters and receivers along a proximal-to-distal axis. In an example, this device can comprise an array, grid, and/or matrix of (alternating) light energy emitters and receivers with a circumferential orientation. In an example, this device can comprise an array, grid, and/or matrix of (alternating) light energy emitters and receivers along a circumferential axis.

In an example, this device can comprise a linear array, grid, and/or matrix of (alternating) light energy emitters and receivers. In an example, this device can comprise a rectangular array, grid, and/or matrix of (alternating) light energy emitters and receivers. In an example, this device can comprise a circular or elliptical array, grid, and/or matrix of (alternating) light energy emitters and receivers. In an example, this device can comprise a checkerboard array, grid, and/or matrix of (alternating) light energy emitters and receivers. In an example, this device can comprise a three-dimensional stacked array, grid, and/or matrix of (alternating) light energy emitters and receivers. In an example, this device can comprise a sunburst and/or radial-spoke array, grid, and/or matrix of (alternating) light energy emitters and receivers. In an example, this device can comprise a sinusoidal array, grid, and/or matrix of (alternating) light energy emitters and receivers.

In an example, an array, grid, and/or matrix of (alternating) light energy emitters and receivers can span up to 10% of the circumference of a part of a person's body such as a wrist, arm, finger, ankle, or leg. In an example, an array, grid, and/or matrix of (alternating) light energy emitters and receivers can span between 10% and 25% of the circumference of a part of a person's body such as a wrist, arm, finger, ankle, or leg. In an example, an array, grid, and/or matrix of (alternating) light energy emitters and receivers can span between 25% and 50% of the circumference of a part of a person's body such as a wrist, arm, finger, ankle, or leg. In an example, an array, grid, and/or matrix of (alternating) light energy emitters and receivers can span between 50% and 100% of the circumference of a part of a person's body such as a wrist, arm, finger, ankle, or leg.

In an example, this device can comprise an array, grid, and/or matrix of light energy emitters which differ in one or more parameters selected from the group consisting of: location and/or distance from a light energy receiver; distance to body surface; light beam frequency, color, and/or spectrum; light beam coherence, polarity, and/or phase; light beam power and/or intensity; light beam projection and/or body incidence angle; light beam duration; light beam size; and light beam focal distance. In an example, this device can comprise an array, grid, and/or matrix of light energy receivers which differ in: location and/or distance from a light energy emitter; and/or distance to body surface.

In an example, the frequency, color, and/or spectrum of a beam of light emitted from a light energy emitter can be changed over time to create a chronological sequence of beams of light with different frequencies, colors, and/or spectrums. In an example, the angle of a beam of light emitted from a light energy emitter can be changed over time to create a chronological sequence of beams of light with different projection and/or body incidence angles. In an example, the power or intensity of a beam of light emitted from a light energy emitter can be changed over time to create a chronological sequence of beams of light with different power or intensity levels. Such sequences can help to more accurately measure body hydration level.

In an example, the frequency, color, and/or spectrum of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level. In an example, the projection angle of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level. In an example, the power and/or intensity of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level.

In an example, an energy emitter and an energy receiver can emit and receive electromagnetic energy, respectively. In an example, an electromagnetic energy emitter can be an antenna. In an example, an electromagnetic energy emitter can emit electricity. In an example, an electromagnetic energy emitter can emit microwaves. In an example, an electromagnetic energy emitter can emit radio waves. In an example, an electromagnetic energy receiver can be an electromagnetic energy sensor. In an example, an electromagnetic energy receiver can be an electromagnetic antenna. In an example, an electromagnetic energy emitter can emit electromagnetic energy into body tissue and an electromagnetic energy receiver can receive a portion of that electromagnetic energy after the electromagnetic energy has passed through the body tissue.

In an example, changes in electromagnetic energy received by an electromagnetic energy receiver can be analyzed to detect changes in the conductivity, resistance, capacitance, impedance, and/or permittivity of body tissue. In an example, changes in the conductivity, resistance, capacitance, impedance, and/or permittivity of body tissue can be analyzed to detect changes in the composition and/or configuration of the body tissue. In an example, changes in the conductivity, resistance, capacitance, impedance, and/or permittivity of body tissue can be analyzed to detect changes in body hydration level. In an example, changes in electromagnetic energy received by the electromagnetic energy receiver can be analyzed to detect changes in body hydration level.

In an example, the depth, breadth, location, and/or type of body tissue or fluid through which electromagnetic energy passes can be changed by adjusting the power, wavelength, and/or frequency of electromagnetic energy emitted from an electromagnetic energy emitter. In an example, the power, wavelength, and/or frequency of electromagnetic energy emitted from an electromagnetic energy emitter can be adjusted in order to more accurately measure body hydration level. In an example, the power, wavelength, and/or frequency of electromagnetic energy emitted from an electromagnetic energy emitter can be adjusted automatically (in an iterative manner) by a device in order to more accurately measure body hydration level for a specific person, for a specific type of activity, or for a specific configuration of the device relative to the person's body surface. In an example, the power, wavelength, and/or frequency of electromagnetic energy emitted from an electromagnetic energy emitter can be adjusted automatically to maintain accurate measurement of body hydration level even if the device shifts and/or moves relative to the person's body surface. In an example, a device can automatically vary the power, wavelength, and/or frequency of electromagnetic energy from an electromagnetic energy emitter to scan through a range of tissue depths, locations, and/or types in order to obtain more accurate measurement of body hydration level.

In an example, the depth, breadth, location, and/or type of body tissue or fluid through which electromagnetic energy passes can be changed by adjusting the location or shape of an electromagnetic energy emitter. In an example, the location or shape of an electromagnetic energy emitter can be adjusted in order to more accurately measure body hydration level. In an example, the location or shape of an electromagnetic energy emitter can be adjusted automatically (in an iterative manner) by a device in order to more accurately measure body hydration level for a specific person, for a specific type of activity, or for a specific configuration of the device relative to the person's body surface. In an example, the location or shape of an electromagnetic energy emitter can be adjusted automatically to maintain accurate measurement of body hydration level even if the device shifts and/or moves relative to the person's body surface. In an example, a device can automatically vary the location an electromagnetic energy emitter to scan through a range of tissue depths, locations, and/or types in order to obtain more accurate measurement of body hydration level.

In an example, a device can comprise a first electromagnetic energy emitter and a second electromagnetic energy emitter. In an example, the first electromagnetic energy emitter can emit electromagnetic energy with a first electromagnetic energy frequency and the second electromagnetic energy emitter can emit electromagnetic energy with a second electromagnetic energy frequency. In an example, electromagnetic energy from the first electromagnetic energy emitter can reflect primarily from a first depth, breadth, location, and/or type of body tissue and electromagnetic energy from the second electromagnetic energy emitter can reflect primarily from a first depth, breadth, location, and/or type of body tissue. In an example, first and second electromagnetic energy emitters can emit electromagnetic energy simultaneously. In an example, first and second electromagnetic energy emitters can emit electromagnetic energy in a selected chronological sequence and/or timing pattern.

In an example, a selected geometric configuration of a plurality of electromagnetic energy emitters and an electromagnetic energy receiver can be designed to most accurately measure body hydration level. In an example, the geometric configuration of a plurality of electromagnetic energy emitters and an electromagnetic energy receiver can be adjusted automatically (in an iterative manner) by a device in order to more accurately measure body hydration level for a specific person, for a specific type of activity, or for a specific configuration of the device relative to the person's body surface. In an example, the geometric configuration of a plurality of electromagnetic energy emitters and an electromagnetic energy receiver can be adjusted automatically to maintain accurate measurement of body hydration level even if the device shifts and/or moves relative to the person's body surface. In an example, a device can automatically vary the geometric configuration of a plurality of electromagnetic energy emitters and an electromagnetic energy receiver in order to scan through a range of tissue depths, locations, and/or types in order to measure body hydration level more accurately. In an example, a plurality of electromagnetic energy emitters can emit electromagnetic energy simultaneously. In an example, a plurality of electromagnetic energy emitters can emit electromagnetic energy in a selected chronological sequence and/or timing pattern.

In an example, a selected geometric configuration of an electromagnetic energy emitter and a plurality of electromagnetic energy receivers can be designed to most accurately measure body hydration level. In an example, the geometric configuration of an electromagnetic energy emitter and a plurality of electromagnetic energy receivers can be adjusted automatically (in an iterative manner) by a device in order to more accurately measure body hydration level for a specific person, for a specific type of activity, or for a specific configuration of the device relative to the person's body surface. In an example, the geometric configuration of an electromagnetic energy emitter and a plurality of electromagnetic energy receivers can be adjusted automatically to maintain accurate measurement of body hydration level even if the device shifts and/or moves relative to the person's body surface. In an example, a device can automatically vary the geometric configuration of an electromagnetic energy emitter and a plurality of electromagnetic energy receivers in order to scan through a range of tissue depths, locations, and/or types in order to measure body hydration level more accurately.

In an example, an energy emitter and an energy receiver can emit and receive, respectively, microwave-level electromagnetic energy. In an example, there can be a resonator between a microwave energy emitter and a microwave energy receiver, wherein the resonant frequency of the resonator is changed by changes in body hydration levels of nearby tissue and/or fluid. In an example, a resonator can be a split ring resonator. In an example, changes in body hydration levels of nearby tissue and/or fluid change the permittivity of the tissue and/or fluid which, in turn, changes the resonant frequency of the resonator. In an example, this device can comprise a microwave energy emitter, a microwave energy receiver, and a resonator, wherein changes in microwave transmission from the microwave energy emitter to the microwave energy receiver are used to measure changes in body hydration levels of nearby tissue and/or fluid.

The permittivity of tissue and/or fluid is the ability of tissue and/or fluid to transmit an electromagnetic energy field. Permittivity depends on the amount of electrical energy that is stored within the tissue and/or fluid when the tissue and/or fluid is exposed to an electromagnetic energy field. In an example, this device can measure body hydration levels in nearby body fluid and/or tissue by measuring the permittivity of that body fluid and/or tissue. In an example, this device can measure changes body hydration levels in nearby body fluid and/or tissue by measuring changes in the permittivity of that body fluid and/or tissue. In an example, changes in body hydration levels of tissue and/or fluid can change the permittivity of that tissue and/or fluid, wherein these changes in turn can be measured by this device.

In an example, the permittivity of tissue and/or fluid can be different at different microwave energy frequencies. In an example, this device can emit microwave energy at varying frequencies to collect data on the electromagnetic energy interaction between that energy and tissue and/or fluid at different frequencies. In an example, this device can sweep through a selected range of microwave frequencies. In an example, this device can be an electromagnetic energy spectroscopic sensor which collects data on the permittivity of tissue and/or fluid across a selected (sub)spectrum of microwave frequencies. In an example, collecting data on the permittivity of tissue and/or fluid across a range of microwave frequencies can provide more accurate estimation of body hydration levels than collecting data on permittivity at a single microwave frequency.

In an example, this device can function as a dielectric constant sensor. A dielectric constant is the real part of permittivity. In an example, this device can measure body hydration levels in nearby body fluid and/or tissue by measuring the dielectric constant of that body fluid and/or tissue. In an example, this device can measure changes in body hydration levels in nearby body fluid and/or tissue by measuring changes in the dielectric constant of that body fluid and/or tissue.

In an example, this device can collect data concerning the amount and spectral distribution of microwave energy which is reflected from tissue and/or fluid. This can depend on the angle at which energy is reflected as well as the permittivity of the tissue and/or fluid. In an example, this device can measure changes in microwave energy that is reflected from tissue and/or fluid as well as microwave energy that is transmitted through tissue and/or fluid. In an example, changes in body hydration levels can change the reflection coefficient as measured by this device. In an example, changes in body hydration levels can change the resonant frequency of a resonator within this device. In an example, microwave energy emitted near tissue and/or fluid interacts with that tissue and/or fluid, dispersing energy into the transmitted energy and creating a measurable distorted output signal. This distorted output signal can be used to help estimate body hydration levels.

In an example, a microwave energy emitter which is part of this device can receive microwave energy as well as emit microwave energy. In an example, a microwave energy emitter can be configured to measure microwave energy which is reflected from tissue and/or fluid. In an example, changes in the amount and/or spectrum of microwave energy reflected from tissue and/or fluid can be used to measure changes in body hydration levels. In an example, this device can be a spectroscopic sensor which measures changes in the spectrum of electromagnetic energy caused by reflection of that energy from tissue and/or fluid.

In an example, this device can function as an impedance sensor. In an example, this device can estimate changes in body hydration levels in body fluid and/or tissue by measuring changes in the impedance of that body fluid and/or tissue. In an example, this device can be a resistance sensor. In an example, this device can estimate changes in body hydration levels in body fluid and/or tissue by measuring changes in the resistance of that body fluid and/or tissue. In an example, this device can be an inductance sensor. In an example, this device can estimate changes in body hydration levels in body fluid and/or tissue by measuring changes in the inductance of that body fluid and/or tissue.

In an example, this device can function as a capacitance sensor. In an example, this device can estimate changes in body hydration levels in body fluid and/or tissue by measuring changes in the capacitance of that body fluid and/or tissue. In an example, this device can be a conductance sensor. In an example, this device can estimate changes in body hydration levels in body fluid and/or tissue by measuring changes in the conductance of that body fluid and/or tissue. In an example, this device can be a conductivity sensor. In an example, this device can estimate changes in body hydration levels in body fluid and/or tissue by measuring changes in the conductivity of that body fluid and/or tissue.

In an example, this device can function as an impedance sensor. In an example, this device can collect data which is used to estimate changes in body hydration levels in body fluid and/or tissue by collecting data on changes in the impedance of that body fluid and/or tissue. In an example, this device can be a resistance sensor. In an example, this device can collect data which is used to estimate changes in body hydration levels in body fluid and/or tissue by collecting data on changes in the resistance of that body fluid and/or tissue. In an example, this device can be an inductance sensor. In an example, this device can collect data which is used to estimate changes in body hydration levels in body fluid and/or tissue by collecting data on changes in the inductance of that body fluid and/or tissue.

In an example, this device can function as a capacitance sensor. In an example, this device can collect data which is used to estimate changes in body hydration levels in body fluid and/or tissue by collecting data on changes in the capacitance of that body fluid and/or tissue. In an example, this device can be a conductance sensor. In an example, this device can collect data which is used to estimate changes in body hydration levels in body fluid and/or tissue by collecting data on changes in the conductance of that body fluid and/or tissue. In an example, this device can be a conductivity sensor. In an example, this device can collect data which is used to estimate changes in body hydration levels in body fluid and/or tissue by collecting data on changes in the conductivity of that body fluid and/or tissue.

In an example, an array, grid, and/or matrix of two or more electromagnetic energy emitters can span up to 10% of the circumference of a part of a person's body such as a wrist, arm, finger, ankle, or leg. In an example, an array, grid, and/or matrix of two or more electromagnetic energy emitters can span between 10% and 25% of the circumference of a part of a person's body such as a wrist, arm, finger, ankle, or leg. In an example, an array, grid, and/or matrix of two or more electromagnetic energy emitters can span between 25% and 50% of the circumference of a part of a person's body such as a wrist, arm, finger, ankle, or leg. In an example, an array, grid, and/or matrix of two or more electromagnetic energy emitters can span between 50% and 100% of the circumference of a part of a person's body such as a wrist, arm, finger, ankle, or leg.

In an example, an array, grid, and/or matrix of two or more electromagnetic energy receivers can span up to 10% of the circumference of a part of a person's body such as a wrist, arm, finger, ankle, or leg. In an example, an array, grid, and/or matrix of two or more electromagnetic energy receivers can span between 10% and 25% of the circumference of a part of a person's body such as a wrist, arm, finger, ankle, or leg. In an example, an array, grid, and/or matrix of two or more electromagnetic energy receivers can span between 25% and 50% of the circumference of a part of a person's body such as a wrist, arm, finger, ankle, or leg. In an example, an array, grid, and/or matrix of two or more electromagnetic energy receivers can span between 50% and 100% of the circumference of a part of a person's body such as a wrist, arm, finger, ankle, or leg.

In an example, an array, grid, and/or matrix of (alternating) electromagnetic energy emitters and receivers can span up to 10% of the circumference of a part of a person's body such as a wrist, arm, finger, ankle, or leg. In an example, an array, grid, and/or matrix of (alternating) electromagnetic energy emitters and receivers can span between 10% and 25% of the circumference of a part of a person's body such as a wrist, arm, finger, ankle, or leg. In an example, an array, grid, and/or matrix of (alternating) electromagnetic energy emitters and receivers can span between 25% and 50% of the circumference of a part of a person's body such as a wrist, arm, finger, ankle, or leg. In an example, an array, grid, and/or matrix of (alternating) electromagnetic energy emitters and receivers can span between 50% and 100% of the circumference of a part of a person's body such as a wrist, arm, finger, ankle, or leg.

In an example, the frequency and/or wavelength of electromagnetic energy emitted from an electromagnetic energy emitter can be changed over time to create a chronological sequence of electromagnetic energy with different frequencies and/or wavelengths. In an example, the power and/or current of electromagnetic energy emitted from an electromagnetic energy emitter can be changed over time to create a chronological sequence of electromagnetic energy with different power or current levels. Such sequences can help to more accurately measure body hydration level.

In an example, the frequency and/or wavelength of electromagnetic energy emitted from an electromagnetic energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level. In an example, the power and/or current of electromagnetic energy emitted from an electromagnetic energy emitter can be changed in response to specific environmental conditions (e.g. temperature or humidity) and/or specific activities in which the person wearing a device is engaged (e.g. high level of movement, eating, sleeping, etc.) in order to more accurately measure body hydration level.

In an example, an energy emitter can separated from an energy receiver by a selected distance. In an example, there can be a selected distance between an energy emitter and an energy receiver. In an example, (an orthogonal component of) this distance can be measured along a circumferential axis. In an example, an energy emitter and an energy receiver can both be along the same circumferential line. In an example, (an orthogonal component of) this distance can be measured along a proximal-to-distal axis. In an example, an energy emitter and an energy receiver can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this selected distance is along a circumferential axis, this distance can be expressed in (compass or polar coordinate) degrees and be within the range of 2 degrees to 60 degrees.

In an example, this device can have two (or more) energy emitters. In an example, two (or more) energy emitters can emit energy in a non-simultaneous (e.g. sequential) manner. In an example, a first energy emitter can be separated from a second energy emitter by a selected distance. In an example, there can be a selected distance between a first energy emitter and a second energy receiver. In an example, (an orthogonal component of) this distance can be measured along a circumferential axis. In an example, a first energy emitter and a second energy emitter can both be along the same circumferential line. In an example, (an orthogonal component of) this distance can be measured along a proximal-to-distal axis. In an example, a first energy emitter and a second energy emitter can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, this device can have a circumferential or annular array, matrix, or grid of four or more energy emitters, each of which is separated from the nearest other energy emitter by a distance within the range of 1/16" to 2". In an example, this device can have a circumferential or annular array, matrix, or grid of four or more energy emitters, each of which is separated from the nearest other energy emitter by a distance within the range of 2 mm to 5 cm. In an example, this device can have a circumferential or annular array, matrix, or grid of four or more energy emitters, each of which is separated from the nearest other energy emitter by a distance within the range of 2 degrees to 60 degrees. In an example, this device can have a circumferential or annular array of energy emitters which spans between 25% and 100% of the cross-sectional perimeter circumference of a part of the body (e.g. wrist, arm, finger, ankle, or leg) to which the device is attached. In an example, this circumferential or annular array of energy emitters can be even spaced or distributed, with the same pair-wise distance or number of degrees between adjacent energy emitters.

In an example, this device can have two (or more) energy receivers. In an example, a first energy receiver can be separated from a second energy receiver by a selected distance. In an example, there can be a selected distance between a first energy receiver and a second energy receiver. In an example, (an orthogonal component of) this distance can be measured along a circumferential axis. In an example, a first energy receiver and a second energy receiver can both be along the same circumferential line. In an example, (an orthogonal component of) this distance can be measured along a proximal-to-distal axis. In an example, a first energy receiver and a second energy receiver can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, this device can have a circumferential or annular array, matrix, or grid of four or more energy receivers, each of which is separated from the nearest other energy receiver by a distance within the range of 1/16" to 2". In an example, this device can have a circumferential or annular array, matrix, or grid of four or more energy receivers, each of which is separated from the nearest other energy receiver by a distance within the range of 2 mm to 5 cm. In an example, this device can have a circumferential or annular array, matrix, or grid of four or more energy receivers, each of which is separated from the nearest other energy receiver by a distance within the range of 2 degrees to 60 degrees. In an example, this device can have a circumferential or annular array of energy receivers which spans between 25% and 100% of the cross-sectional perimeter circumference of a part of the body (e.g. wrist, arm, finger, ankle, or leg) to which the device is attached. In an example, this circumferential or annular array of energy receivers can be even spaced or distributed, with the same pair-wise distance or number of degrees between adjacent energy receivers.

In an example, an energy emitter can be within the circumferential section bounded by 330 degrees and 0 degrees and an energy receiver can be within the circumferential section bounded by 0 degrees and 30 degrees, or vice versa. In an example, an energy emitter can be within the circumferential section bounded by 300 degrees and 0 degrees and an energy receiver can be within the circumferential section bounded by 0 degrees and 60 degrees, or vice versa. In an example, an energy emitter can be within the circumferential section bounded by 330 degrees and 30 degrees, a first energy receiver can be within the circumferential section bounded by 270 degrees and 330 degrees, and a second energy receiver can be within the circumferential section bounded by 30 degrees and 90 degrees. In an example, an energy receiver can be within the circumferential section bounded by 330 degrees and 30 degrees, a first energy emitter can be within the circumferential section bounded by 270 degrees and 330 degrees, and a second energy emitter can be within the circumferential section bounded by 30 degrees and 90 degrees.

In an example, this device can comprise an array of energy emitters and energy receivers which is part of a wearable arcuate band or one or more segments (or housings) which are attached to a wearable arcuate band. In an example, this device can comprise a two-dimensional array of energy emitters and energy receivers which is part of a wearable arcuate band or one or more segments (or housings) which are attached to a wearable arcuate band. In an example, this device can comprise a three-dimensionally stacked array of energy emitters and energy receivers which is part of a wearable arcuate band or one or more segments (or housings) which are attached to a wearable arcuate band. In an example, data from this array can be analyzed to measure a person's body hydration level.

In an example, the type of energy emitted by the energy emitters and received by the energy receivers can be light energy. In an example, the type of energy emitted by the energy emitters and received by the energy receivers can be (non-light-spectrum) electromagnetic energy. In an example, the type of energy emitted by the energy emitters and received by the energy receivers can be microwave energy.

In an example, an array of energy emitters and/or energy receivers can have a circumferential axis and a proximal-to-distal axis. In an example, this array can have at least three energy emitters and/or energy receivers along a circumferential axis and at least two energy emitters and/or energy receivers along a proximal-to-distal axis. In an example, an array can be formed from a plurality of sets of energy emitters and energy receivers, wherein each set forms the vertexes of a square or rectangle. In an example, an array can be formed from a plurality of sets of energy emitters and energy receivers, wherein each set forms the vertexes of a hexagon. In an example, an array can be formed from a plurality of sets of energy emitters and energy receivers, wherein each set forms a circle.

In an example, an array of energy emitters and energy receivers can have a square or rectangular shape. In an example, an array of energy emitters and energy receivers can have a hexagonal shape. In an example, an array of energy emitters and energy receivers can have a circular shape. In an example, an array of energy emitters and energy receivers can have a sunburst (e.g. radial spoke) shape. In an example, an array of energy emitters and energy receivers can have a cylindrical and/or ring shape. In an example, an array of energy emitters and energy receivers can have a conic section shape. In an example, an array of energy emitters and energy receivers can have a saddle shape. In an example, an array of energy emitters and energy receivers can have a helical shape.

In an example, a device can further comprise a track, channel, or slot along which an energy emitter, an energy receiver, or both can be moved. In an example, this movement can be done manually. In an example, this movement can be done automatically by one or more actuators. In an example, this track, channel, or slot can have a circumferential orientation. In an example, this track, channel, or slot can have a proximal-to-distal orientation. In an example, the distance between an energy emitter and an energy receiver can be adjusted by moving the energy emitter, the energy receiver, or both along such a track, channel, or slot. In an example, the location of an energy emitter and/or an energy receiver relative to a person's body can be adjusted by moving the energy emitter, the energy receiver, or both along such a track, channel, or slot. In an example, movement of an energy emitter, an energy receiver, or both along a track, channel, or slot can enable more accurate measurement of body hydration level. In an example, movement of an energy emitter, an energy receiver, or both along a track, channel, or slot can enable customization of a device to the anatomy of a specific person for more accurate measurement of that person's body hydration level.

In an example, a device can further comprise a rotating member which holds an energy emitter, an energy receiver, or both. In an example, rotation of this member can be done manually. In an example, this rotation can be done automatically by one or more actuators. In an example, the distance between an energy emitter and an energy receiver can be adjusted by rotating the rotating member. In an example, the location of an energy emitter and/or an energy receiver relative to a person's body can be adjusted by rotating the rotating member. In an example, movement of an energy emitter, an energy receiver, or both by a rotating member can enable more accurate measurement of body hydration level. In an example, such movement of an energy emitter, an energy receiver, or both can enable customization of a device to the anatomy of a specific person for more accurate measurement of that person's body hydration level.

In an example, this device can further comprise an energy source which powers an energy emitter, an energy receiver, a data processor, and/or a data transmitter. In an example, an energy source can be a battery. In an example, an energy source can transduce, harvest, and/or generate energy from body motion or kinetic energy. In an example, an energy source can transduce, harvest, and/or generate energy from ambient light energy. In an example, an energy source can transduce, harvest, and/or generate energy from body thermal energy. In an example, an energy source can transduce, harvest, and/or generate energy from ambient electromagnetic energy.

In an example, this device can further comprise a wireless data transmitter and/or data receiver. In various examples, this device can be in wireless communication with an external device selected from the group consisting of: a cell phone, an electronic tablet, electronically-functional eyewear, a home electronics portal, an implanted medical device, an internet portal, a laptop computer, a mobile computer, a mobile phone, a remote computer, a remote control unit, a smart phone, a smart utensil, a television set, and a wearable data processing hub. In an example, additional data processing and analysis can be done within an external device.

In an example, this device can further comprise an energy barrier between an energy emitter and an energy receiver which reduces the transmission of energy from the emitter to the receiver. In an example, an energy barrier between a light energy emitter and a light energy receiver can be opaque. In an example, an energy barrier between an electromagnetic energy emitter and an electromagnetic energy receiver can be non-conductive and/or radio-opaque. In an example, an energy barrier between a light energy emitter and a light energy receiver can be compressible, flexible, and/or elastic. In an example, an energy barrier can comprise compressible foam. In an example, an energy barrier can be an inflatable member (such as a balloon) which is filled with a gas or liquid. In an example, an energy barrier can have a linear shape. In an example, an energy barrier can have a circular, elliptical, sinusoidal, or other arcuate shape. In an example, an energy barrier can surround an energy receiver. In an example, an energy barrier can surround an energy emitter.

In an example, this device can further comprise an energy conductor between an energy emitter and an energy receiver which increases the transmission of energy from the emitter to the receiver. In an example, an energy conductor between a light energy emitter and a light energy receiver can be an optical lens and/or fiber optic conduit. In an example, an energy conductor between an electromagnetic energy emitter and an electromagnetic energy receiver can be a split-ring resonator. In an example, an energy conductor can be a circular split-ring resonator. In an example, an energy conductor can be a quadrilateral split-ring resonator. In an example, an energy conductor can comprise a plurality of split-ring resonators with a configuration selected from the group consisting of: nested or concentric; arrayed in series; arrayed in parallel; stacked three-dimensionally; symmetric; asymmetric; spiral and/or helical; and interdigitated or interlocking. In an example, an energy conductor between an electromagnetic energy emitter and an electromagnetic energy receiver can be a capacitor.

In an example, this device can further comprise a housing which is held on a person's body by an arcuate band. In an example, this housing can be more rigid (less flexible) than the band. In an example, this housing can hold an energy emitter and an energy receiver. In an example, a housing can be the display (and/or primary processing) component of a smart watch, fitness band, or wearable body hydration monitor.

In an example, this device can further comprise one or more other types of biometric or environmental sensors in addition to the primary energy emitters and receivers discussed above. In an example, the primary energy emitter and the primary energy receiver of this device, discussed above, can be a light energy emitter and a light energy receiver, but the device can also include a (non-light-spectrum) electromagnetic energy emitter and a (non-light-spectrum) electromagnetic energy receiver. In an example, the primary energy emitter and the primary energy receiver of this device, discussed above, can be a (non-light-spectrum) electromagnetic energy emitter and a (non-light-spectrum) electromagnetic energy receiver, but the device can also include a light energy emitter and a light energy receiver. In an example, this device can comprise both light energy and electromagnetic energy sensors for measuring body hydration levels. In an example, this device can comprise both spectroscopic and microwave energy sensors for measuring body hydration levels.

In an example, this device can further comprise one or more other types of biometric or environmental sensors selected from the group consisting of: accelerometer, action potential sensor, ballistocardiographic sensor, biochemical sensor, blood flow sensor, blood pressure sensor, camera, capacitance hygrometry sensor, chemiluminescence sensor, chemoreceptor sensor, chromatography sensor, conductivity sensor, electrical resistance sensor, electrocardiographic (ECG) sensor or other sensor measuring electromagnetic energy from (or transmitted through) a person's heart, electromagnetic resistance sensor, electromyographic (EMG) sensor or other sensor measuring electromagnetic energy from (or transmitted through) a person's muscles, electroporation sensor, galvanic skin response (GSR) sensor, glucose sensor, gyroscope, Hall-effect sensor, heart rate sensor, humidity sensor, impedance sensor, inertial sensor, infrared light sensor, infrared spectroscopic sensor, ion mobility spectroscopic sensor, laser sensor, light intensity sensor, light-spectrum-analyzing sensor, magnetic field sensor, magnetometer, and microphone or other sound sensor.

In an example, this device can further comprise one or more other types of biometric or environmental sensors selected from the group consisting of: motion sensor, muscle function monitor, near-infrared spectroscopic sensor, neural impulse monitor, neurosensor, optical sensor, optoelectronic sensor, oximetry sensor, pH level sensor, photochemical sensor, photodetector, photoelectric sensor, photoplethysmographic (PPG) sensor, piezocapacitive sensor, piezoelectric sensor, piezoresistive sensor, plethysmographic sensor, pressure sensor, pulse sensor, Raman spectroscopic sensor, respiratory or pulmonary function sensor, sensor measuring the quantity or spectrum of light absorbed by a person's body, sensor measuring the quantity or spectrum of light reflected from a person's body, skin conductance sensor, skin moisture sensor, sound sensor, spectral analysis sensor, spectrometry sensor, spectrophotometer sensor, spectroscopic sensor, strain gauge, stretch sensor, sweat sensor, sympathetic nerve activity sensor, systolic blood pressure sensor, thermal energy sensor, thermistor or other body temperature sensor, tissue impedance sensor, ultrasonic sensor, ultraviolet light sensor, ultraviolet spectroscopic sensor, variable impedance sensor, variable resistance sensor, variable translucence sensor, and voltmeter.

This invention can be embodied in a wearable device for measuring body hydration level with a plurality of close-fitting spectroscopic sensors comprising: an attachment member which spans at least a portion of the circumference of a person's arm; an enclosure which is part of and/or attached to the attachment member; a first spectroscopic sensor in the enclosure which projects a beam of light onto the arm surface at a first angle relative to the enclosure; and a second spectroscopic sensor in the enclosure which projects a beam of light onto the arm surface at a second angle relative to the enclosure, wherein the first angle differs from the second angle by at least 10 degrees. Data from the spectroscopic sensors is analyzed to measure a person's hydration level.

This invention can also be embodied in a wearable device for measuring body hydration level with one or more close-fitting spectroscopic sensors comprising: an attachment member which spans at least a portion of the circumference of a person's arm; an enclosure which is part of and/or attached to the attachment member; an elastic member filled with a fluid, gel, or gas which is attached to and/or part of the enclosure; and one or more spectroscopic sensors which record data concerning the person's arm tissue, wherein these one or more spectroscopic sensors are attached to a circumference-center-facing wall of the elastic member. A spectroscopic sensor can measure the spectrum of light energy reflected from and/or absorbed by tissue of the person's arm.

This invention can also be embodied in a wearable device for measuring body hydration level with a close-fitting spectroscopic sensor comprising: a circumferentially or annularly-undulating attachment member which spans at least a portion of the circumference of a person's arm; and a plurality of spectroscopic sensors which collect data concerning arm tissue, wherein each spectroscopic sensor is located at the proximal portion of an undulation, and wherein the proximal portion of an undulation is the portion of an undulating wave which is closest to the circumferential center of the device. Data from the one or more sensors are analyzed to measure a person's hydration level.

In an example, a wearable device for measuring body hydration level with a plurality of close-fitting spectroscopic sensors can comprise: an attachment member which is configured to span at least a portion of the circumference of a person's arm; an enclosure which is part of and/or attached to the attachment member; a first spectroscopic sensor in the enclosure which is configured to project a beam of light onto the arm surface at a first angle relative to the enclosure; and a second spectroscopic sensor in the enclosure which is configured to project a beam of light onto the arm surface at a second angle relative to the enclosure, wherein the first angle differs from the second angle by at least 10 degrees.

In an example, an attachment member can be selected from the group consisting of: strap, band, bracelet, ring, armlet, cuff, and sleeve. In an example, an attachment member can be configured to be attached to the person's arm by connecting two ends of the attachment member with a clasp, clip, buckle, hook, pin, plug, or hook-and-eye mechanism. In an example, an attachment member can be configured to be attached to the person's arm by stretching and sliding it over the person's hand onto the arm.

In an example, a wearable device for measuring body hydration level with one or more close-fitting spectroscopic sensors can comprise: an attachment member which is configured to span at least a portion of the circumference of a person's arm; an enclosure which is part of and/or attached to the attachment member; an elastic member filled with a fluid, gel, or gas which is attached to and/or part of the enclosure; and one or more spectroscopic sensors which are configured to record data concerning the person's arm tissue, wherein these one or more spectroscopic sensors are attached to a circumference-center-facing wall of the elastic member. In an example, a spectroscopic sensor can measure the spectrum of light energy reflected from and/or absorbed by tissue of the person's arm.

In an example, a wearable device for measuring body hydration level with a close-fitting spectroscopic sensor can comprise: a circumferentially or annularly-undulating attachment member which is configured to span at least a portion of the circumference of a person's arm; and a plurality of spectroscopic sensors which collect data concerning arm tissue, wherein each spectroscopic sensor is located at the proximal portion of an undulation, and wherein the proximal portion of an undulation is the portion of an undulating wave which is closest to the circumferential center of the device. In an example, a spectroscopic sensor can measure the spectrum of light energy reflected from and/or absorbed by tissue of the person's arm.

Key concepts and variations for wearable bands which have been discussed in the preceding introductory section can be applied where appropriate to the examples now shown in FIGS. 1 through 133, but are not repeated in the narrative accompanying each figure in order to avoid duplicative content. FIGS. 1 through 133 are now discussed in detail.

Figure 2:
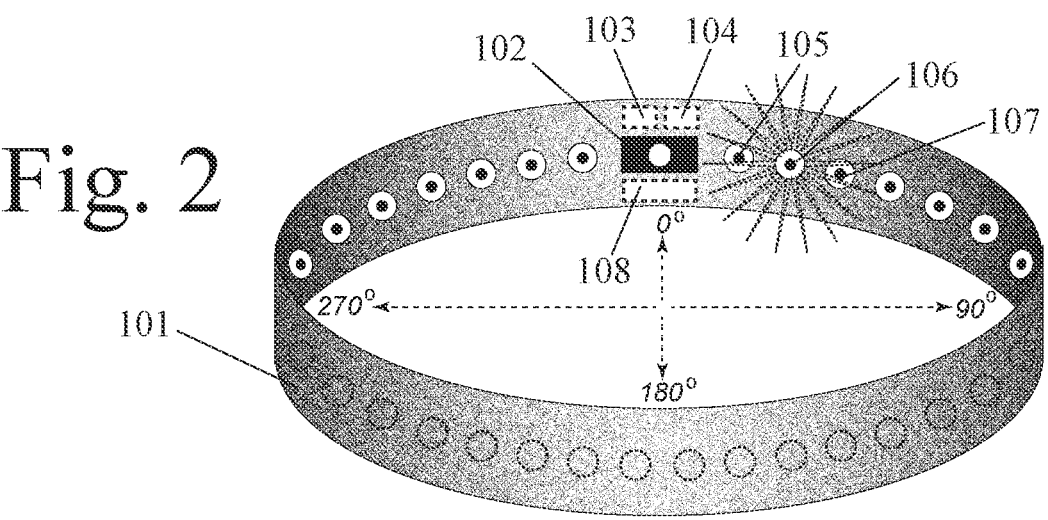
Figure 3:
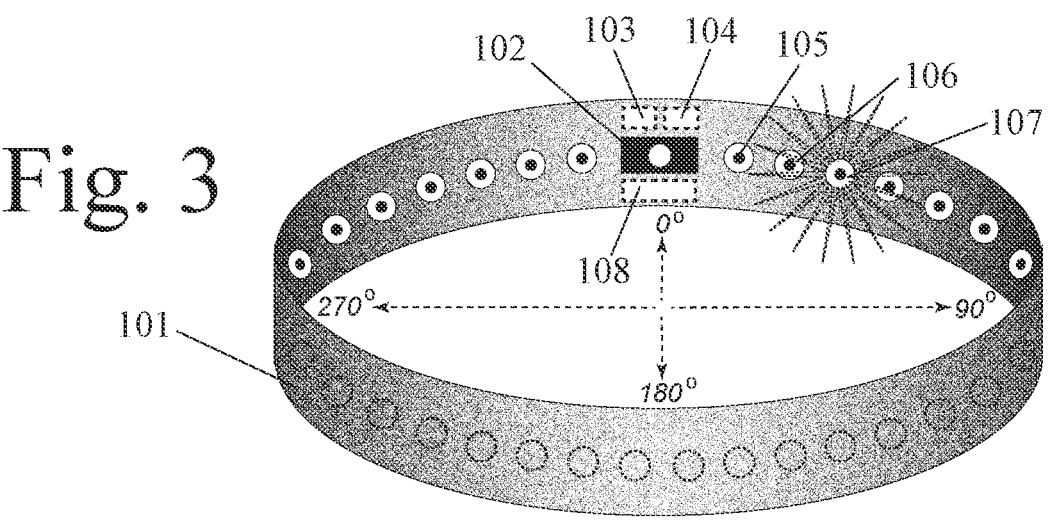

FIGS. 1 through 3 show three sequential views of an example of how this invention can be embodied in a wearable band for measuring a person's hydration level. This wearable band includes a series of sequentially-activated light emitters (such as LEDs) around at least a portion of the circumference of the band. Spectral changes in light which are caused by interactions with the person's body tissue at different cross-sectional locations and depths are analyzed in order to measure body hydration level more accurately than is possible without such a circumferential or annular array of light emitters.

FIGS. 1 through 3 show a wearable band for measuring a person's hydration level comprising: (a) an arcuate band which is configured to be worn around at least half of the circumference of a person's finger, wrist, and/or arm, wherein a selected location on the circumference of the arcuate band is defined as having a polar coordinate of 0 degrees and wherein other locations around the circumference of the arcuate band have other polar coordinates between 0 and 360 degrees; (b) a circumferential or annular array of light emitters held by the arcuate band, wherein the light emitters are configured to emit light toward the person's body, wherein the polar coordinate of each light emitter in the array is identified using the above-defined polar coordinates, wherein a first subset of one or more light emitters selected from the array of light emitters has a first average polar coordinate and emits light at a first point in time, wherein a second subset of one or more light emitters selected from the array of light emitters has a second average polar coordinate and emits light at a second point in time, and wherein the second average coordinate differs from the first average coordinate by at least 5 degrees; and (c) one or more light receivers, wherein the one or more light receivers are configured to receive light from the first subset of light emitters at a first point in time after light from this subset has interacted with the person's body tissue, wherein the one or more light receivers are configured to receive light from the second subset of light emitters at a second point in time after light from this subset has interacted with the person's body tissue, and wherein the spectra of light rays received by the one or more light receivers are analyzed in order to measure the person's hydration level.

A circumferential or annular array of light emitters can control for shifting and/or rotation of a wearable band relative to the surface of a person's finger, wrist, and/or arm which would otherwise interfere with accurate hydration measurement. For example, without a circumferential or annular array of light emitters, shifting and/or rotation of a wearable band can cause a gap between the band and the person's body at the location of a light emitter and/or receiver which interferes with hydration measurement. However, with a circumferential or annular array of light emitters, even if there is a gap between a band and the person's body at one circumferential location, the band (and thus light emitters and/or receivers) at another circumferential location will still be in close contact with the person's body. Accordingly, a wearable band with a circumferential or annular array of light emitters can provide good hydration measurement even when a band is shifting and/or rotating relative to a person's finger, wrist, and/or arm.

Also, if a particular tissue area or anatomic feature of a person's finger, wrist, and/or arm (such as a particular blood vessel) is especially useful for body hydration measurement, then a circumferential or annular array of light emitters can help to maintain analysis of this tissue area or feature even if the band shifts and/or rotates. Even if band shifting and/or rotation causes a first light emitter in the circumferential or annular array to move further away from the desired tissue area or anatomic feature, a second light emitter in the array will move closer to the desired tissue area or anatomic feature. This can help to ensure continuous measurement of hydration level of that tissue area or anatomic feature which would not be possible without a circumferential or annular array of light emitters.

Also, data from sequential activation of a circumferential or annular array of light emitters can enable the creation of a cross-sectional image of analyte levels in tissue in a cross-section of a person's finger, wrist, and/or arm. This is analogous to the way in which a CT or MRI scanner creates a cross-sectional image of tissue characteristics for part of a person's body. For example, a circumferential or annular array of light emitters can enable measurements of water concentrations at different tissue depths and locations within a cross-section of a person's finger, wrist, and/or arm. Measurements of water concentrations at different tissue depths and locations can be used to create a cross-sectional image of variation in water concentrations in this cross-section of a person's finger, wrist, and/or arm.

With respect to specific components, the wearable band in FIGS. 1 through 3 comprises: a wearable band 101; a circumferential or annular array of light emitters, including light emitters 105, 106, and 107; a light receiver 102; a data processor 103; a data transceiver 104; and a battery 108. In an example, light emitters in a circumferential or annular array can be activated (lit up) in a clockwise or counterclockwise sequential manner. A portion of such a sequence is shown in FIGS. 1 though 3. Light emitter 105 is activated (lit up) in FIG. 1, light emitter 106 is activated in FIG. 2, and light emitter 107 is activated in FIG. 3. This can continue in a clockwise manner around the entire circumferential or annular array of light emitters. In an alternative example, non-adjacent light emitters can be sequentially activated. In an alternative example, light emitters on opposite sides of a person's finger, wrist, and/or arm can be sequentially activated.

Sequentially activating different subsets of light emitters (and light receivers) around the circumference of a person's finger, wrist, and/or arm can change the relative proportion of light reflected from body tissue vs. light transmitted through body tissue. Activating light emitters closer to light receivers can provide more information on changes in light spectra caused by light reflection from tissue, while activating light emitters farther from light receivers can provide more information on changes in light spectra caused by light transmission through tissue. In this manner, using a circumferential or annular array of light emitters can provide much richer information on body hydration levels than is possible, for example, with light emitters which are limited to the back of a housing of a smart watch display.

In an example, this wearable band can further comprise one or more relatively-rigid housings with displays and other electronics. In an example, light spectra can be analyzed in a data processor on the band. In an example, data concerning light spectra can be transmitted to a remote data processor and analyzed in the remote data processor. In an example, a wearable band can further comprise a light shield around a light emitter and/or a light receiver. In an example, a light shield can comprise an opaque ring around a light emitter and/or a light receiver. In an example, a light shield around a light emitter and/or receiver can be soft and compressible. In an example, a light shield around a light emitter and/or receiver can be circular or polygonal.

In an example, a wearable band can function as a smart watch. In an example, a wearable band can further comprise a relatively-rigid primary housing with a display (and other electronics) on the dorsal or ventral portion of the band. In an example, a relatively-rigid primary housing can hold a light receiver and/or a subset of light emitters which are part of the circumferential or annular array of light emitters. In an example, (the rest of) a circumferential or annular array of light emitters can be on a watch band or strap. In an example, there can be electromagnetic communication between a relatively-rigid primary housing of a smart watch and a flexible watch band (or strap) containing a circumferential or annular array of light emitters. In an example, a wearable band can function as a fitness band, bracelet, arm band, or arm sleeve. In an example, a wearable band can function as a finger ring.

In an example, a wearable band can be made from a polymer, a natural textile, a metal, or a combination thereof. In an example, a wearable band can be elastic, stretchable, and/or expandable. In an example, a wearable band can be rigid. In this example, a wearable band is a single continuous band. In this example, a wearable band spans the entire circumference of a person's finger, wrist, and/or arm. In another example, a wearable band can span a portion of the circumference of a person's finger, wrist, and/or arm. In another example, a wearable band can span at least half, but not all, of the entire circumference of a person's finger, wrist, and/or arm.

In an example, a wearable band can be elastic, stretchable, and/or expandable so that it can be slid over a person's hand onto their person's wrist and/or arm. In an example, a wearable band can be rigid and slid onto a person's finger. In an example, a wearable band can have ends which are connected to each other by a buckle, clasp, pin, clip, prong, hook-and-eye textile, or magnet in order to fasten it around a person's wrist and/or arm. In an example, a wearable band can comprise a primary relatively-rigid housing and two flexible band (or strap) segments with first ends connected to the housing and second ends which are connected to each other by a buckle, clasp, pin, clip, prong, hook-and-eye textile, or magnet. In an example, a wearable can comprise two relatively-rigid segments whose first ends connect to each other by a hinge (or other flexible joint) and whose second ends connect to each other by a buckle, clasp, pin, clip, prong, hook-and-eye textile, or magnet.

In this example, the wearable band is a single continuous band. In an example, a wearable band can comprise a circumferential or annular series of relatively-rigid housings which are interconnected by relatively-flexible connecting members. In an example, a connecting member can be selected from the group consisting of: strap, band, strip, wire, thread, fabric swatch, elastic band, chain mail, and joint. In an example, a connecting member can contain wires or other electromagnetic pathways which enable electromagnetic communication between two (adjacent) relatively-rigid housings. In an example, relatively-rigid housings can be modular. In an example, relatively-rigid housings can be reversibly connected to a band and/or to each other. In an example, relatively-rigid housings with different electronic functions can be reversibly connected to a band and/or to each other.

In an example, a wearable band can comprise a smart watch with a primary relatively-rigid housing on the dorsal or ventral portion of the band and a circumferential or annular series of secondary relatively-rigid housings elsewhere around the band, wherein the primary housing further comprises a display and wherein the primary housing is larger than the secondary housings. In an example, a wearable band can comprise a smart watch with a primary housing with a display on the dorsal portion of the band and two secondary housings elsewhere around the circumference of the band. In an example, a wearable band can comprise a smart watch with a primary housing with a display on the dorsal portion of the band and four or five secondary housings elsewhere around the circumference of the band. In an example, (at least a portion of) a circumferential or annular series of light emitters can be located on a circumferential or annular series of secondary housings.

In this example, the wearable band is relatively flat. In an example, a wearable band can be toroidal. In an example, a wearable band can have an arcuate cross-sectional shape such as a circle, oval, ellipse, or rounded rectangle. In this example, the wearable band has a constant width. In an example, a wearable band can have a width which varies along its circumference. In an example, a wearable band can have an undulating width. In an example, a wearable band can have sinusoidal variation in width around its circumference.

In this example, the wearable band does not have radial undulations (i.e. variation in radial distance from the cross-sectional centroid of the finger, wrist, and/or arm). In an example, a wearable band can have radial undulations. In an example, a wearable band can have sinusoidal radial undulations. In an example, light emitters can be positioned on the inward-facing peaks of sinusoidal radial undulations. In an example, light emitters can be positioned on the outward-protruding troughs of sinusoidal radial undulations. In an example, a wearable band can have an even number of sinusoidal radial undulations. In an example, a wearable band can have six or eight sinusoidal radial undulations.

In this example, a wearable band has a single layer or ring. In an example, a wearable band can have multiple layers or rings. In an example, a wearable band can have an inner layer or ring which faces toward a person's body and an outer layer or ring which faces away from a person's body. In an example, light emitters and/or light receivers can be located on the inner layer or ring of a wearable band. In an example, an inner layer or ring can have a first durometer level, an outer layer or ring can have a second durometer level, and the second level is greater than the first level. This can help to hold light emitters and/or light receivers in close contact with a person's body without being uncomfortable, even when the person is moving vigorously. In an example, an inner layer or ring can have a first elasticity level, an outer layer or ring can have a second elasticity level, and the second level is less than the first level. In an example, an inner layer or ring can have a first elasticity level, an outer layer or ring can have a second elasticity level, and the second level is greater than the first level. In an example, an inner layer or ring can span less of the circumference of the band than an outer layer or ring. In an example, there can be a gap between (a portion of) an inner layer or ring and (a portion of) an outer layer or ring.

In an example, a light emitter can be a Light Emitting Diode (LED). In this example, the circumferential or annular array of light emitters spans virtually the entire circumference of the wearable band. In an example, an array of light emitters may span less than the circumference of the band, but at least two light emitters are separated by at least 5 degrees in polar coordinates around the circumference of the band. In this example, the array of light emitters is aligned along the same circumferential line (axis) of the band. In an example, an array of light emitters can be aligned along two (parallel) circumferential lines (axes) of a band. In an example, an array of light emitters can comprise a circumferential or annular series of pairs of light emitters, wherein each pair contains two light emitters with the same polar coordinate.

In an example, an array of light emitters can be located along three or more circumferential lines of a band. In an example, a cylindrical array of light emitters can comprise a matrix of light emitters with a circumferential dimension and a lateral dimension which is perpendicular to circumferential dimension. In an example, there can be two or three light emitters across a lateral dimension of such a matrix. In an example, light emitters can be distributed around a central light receiver in a circular manner. In an example, light emitters can be located on the vertexes of a polygon around a central light receiver. In an example, there can be four light emitters forming a square around a central light receiver. In an example, there can be six light emitters forming a hexagon around a central light receiver. In an example, there can be eight light emitters forming an octagon around a central light receiver. In an example, there can be two or more nested and/or concentric rings of light emitters around a central light receiver.

In this example, light emitters in an array are distributed relatively-evenly around the circumference of the band. In this example, pairs of adjacent light emitters in the array are relatively equidistant. In an example, light emitters can be unevenly distributed around a band. In an example, light emitters can be preferentially located or clustered over the ventral and dorsal surfaces of a person's finger, wrist, and/or arm. In this example, there are over a dozen light emitters in a circumferential or annular array. In an example, there can be an even number of light emitters in an array. In an example, there can be 2, 4, or 6 light emitters in a circumferential or annular array of light emitters. In an example, there can be 8 or 10 light emitters in a circumferential or annular array of light emitters.

In this example, there is a single light receiver. In an example, there can be a plurality of light receivers. In an example, there can be a circumferential or annular array of pairs of light emitters and light receivers around the circumference of a wearable band. In an example, a light emitter and a light receiver in each pair can have the same polar coordinate. In an example, a light emitter and a light receiver can be proximal to each other (with different polar coordinates) along the same circumferential line (axis) of a band. In an example, a wearable band can have a circumferential or annular array comprised of alternating light emitters and light receivers along the same circumferential line (axis).

In an example, light transmission between adjacent pairs of light emitters and receivers (after interaction with body tissue) can be analyzed to evaluate water concentrations of different areas of tissue around the circumference of a person's finger, wrist, and/or arm. In an example, light transmission between opposite-side light emitters and receivers (after interaction with body tissue) can be analyzed to evaluate water concentrations of different cross-sections of tissue through a person's finger, wrist, and/or arm. Transmission of light between different pairs of light emitters and receivers around the circumference of a person's finger, wrist, and/or arm can be analyzed, wherein the relative amounts of light reflected from tissue versus light transmitted through tissue are different for different pairs. Using different emitters and receivers in a circumferential or annular array in a band around a person's finger, wrist, and/or arm can provide richer information concerning analyte levels than is possible with such components located only on the back of the housing of a smart watch display.

In an example, changes in the spectra of light rays from different light emitters in a circumferential or annular array, having interacted with body tissue at different times, can be collectively analyzed in order to measure body hydration level. In an example, changes in the spectra of light rays from different light emitters in a circumferential or annular array, having interacted with body tissue at different times, can be analyzed in order to create a cross-sectional image of water concentration levels in cross-section of a person's finger, wrist, and/or arm. This can be compared to the way in which rotating imaging elements in a CT or MRI scanner create a cross-sectional image of tissue composition in a body part. A wearable band with a circumferential or annular array of light emitters can scan a person's finger, wrist, and/arm to create a cross-sectional image of analyte levels in finger, wrist, and/or arm tissue. Relevant example variations discussed in other places in this disclosure or in priority-linked disclosures can also be applied to the example shown in these figures.

Figure 4:
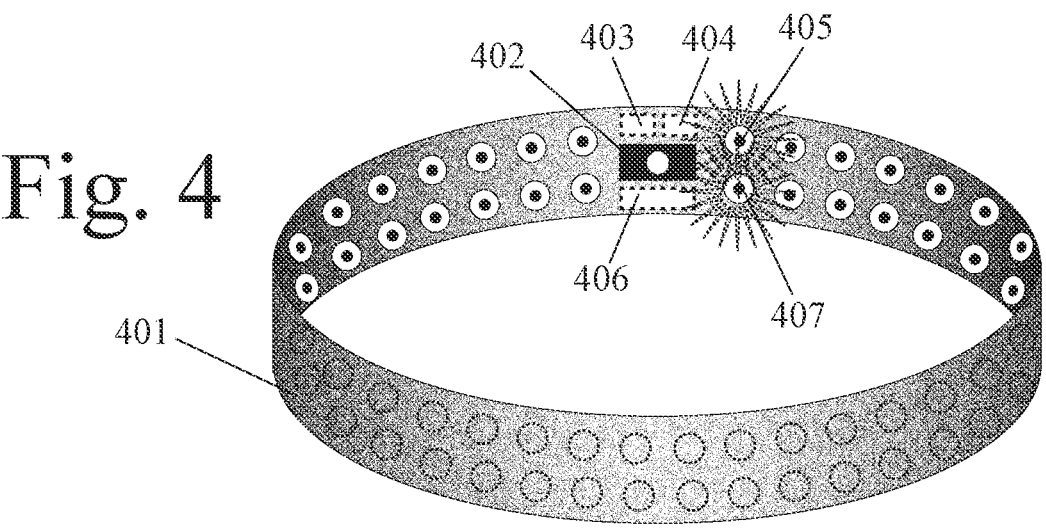
FIG. 4 shows a device with two circumferential emitter arrays and a single receiver.

FIG. 4 shows another example of how this invention can be embodied in a wearable band for measuring a person's hydration level. This example is similar to the one shown in FIGS. 1 through 3 except that the array of light emitters is aligned along two parallel circumferential lines (axes) of the wearable band. In this example, the array of light emitters comprises a circumferential or annular series of pairs of light emitters, wherein each pair contains two light emitters with the same polar coordinate. With respect to specific components, the wearable band in FIG. 4 comprises: a wearable band 401; a circumferential or annular array of light emitter pairs, including light emitter pair 405 and 407, wherein light emitters in a pair have the same polar coordinate; a light receiver 402; a data processor 403; a data transceiver 404; and a battery 406. Relevant example variations discussed in other places in this disclosure or in priority-linked disclosures can also be applied to this example.

Figure 5:
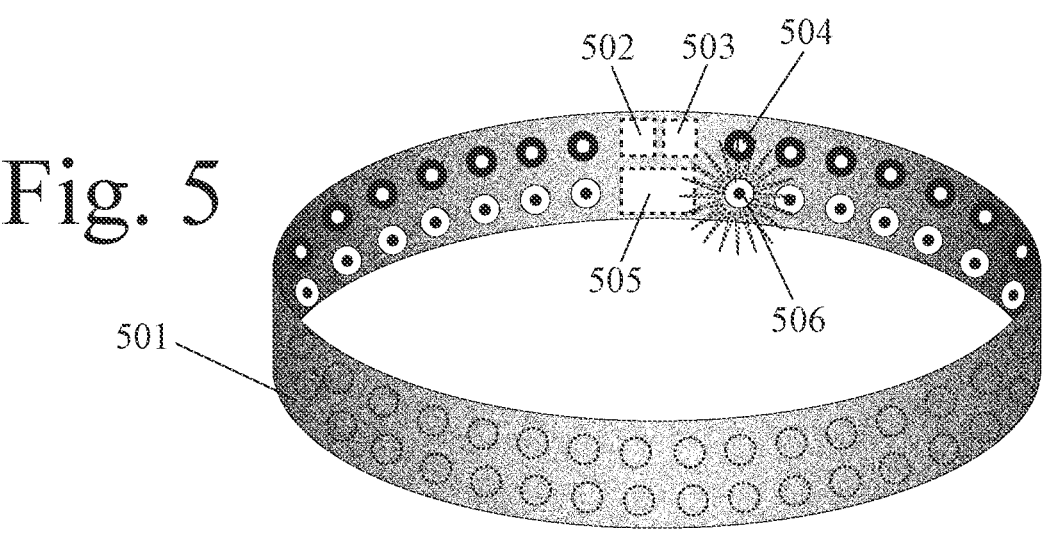
FIG. 5 shows a device with circumferential emitter and receiver arrays on different circumferential lines.

FIG. 5 shows another example of how this invention can be embodied in a wearable band for measuring a person's hydration level. This example is similar to the one shown in FIGS. 1 through 3, except that there is a circumferential or annular array of light receivers instead of just a single light receiver. This band includes a circumferential or annular array of light emitters along a first circumferential line (axis) of the band and a circumferential or annular array of light receivers along a second circumferential line (axis) of the band, wherein the first and second circumferential lines (axes) are parallel to each other. Expressing this in another way, this band has a circumferential or annular series of pairs of light emitters and receivers, wherein a light emitter and a light receiver in a pair have the same polar coordinate.

FIG. 5 shows a wearable band for measuring a person's hydration level comprising: (a) an arcuate band which is configured to be worn around at least half of the circumference of a person's finger, wrist, and/or arm, wherein a selected location on the circumference of the arcuate band is defined as having a polar coordinate of 0 degrees and wherein other locations around the circumference of the arcuate band have other polar coordinates between 0 and 360 degrees; (b) a circumferential or annular array of light emitters held by the arcuate band along a first circumferential line (axis) of the band, wherein the light emitters are configured to emit light toward the person's body, wherein the polar coordinate of each light emitter in the array is identified using the above-defined polar coordinates, wherein a first subset of one or more light emitters selected from the array of light emitters has a first average polar coordinate and emits light at a first point in time, wherein a second subset of one or more light emitters selected from the array of light emitters has a second average polar coordinate and emits light at a second point in time, and wherein the second average coordinate differs from the first average coordinate by at least 5 degrees; and (c) a circumferential or annular array of light receivers held by the arcuate band along a second circumferential line (axis) of the band, wherein the second circumferential line (axis) is parallel to the first circumferential line (axis), wherein one or more light receivers are configured to receive light from the first subset of light emitters at a first point in time after light from this subset has interacted with the person's body tissue, wherein the one or more light receivers are configured to receive light from the second subset of light emitters at a second point in time after light from this subset has interacted with the person's body tissue, and wherein the spectra of light rays received by the one or more light receivers are analyzed in order to measure the person's hydration level.

With respect to specific components, the wearable band in FIG. 5 comprises: a wearable band 501; a circumferential or annular array of light emitters including light emitter 506; a circumferential or annular array of light receivers including light receiver 504; a data processor 502; a data transceiver 503; and a battery 505. Relevant example variations discussed in other places in this disclosure or in priority-linked disclosures can also be applied to this example.

Figure 6:
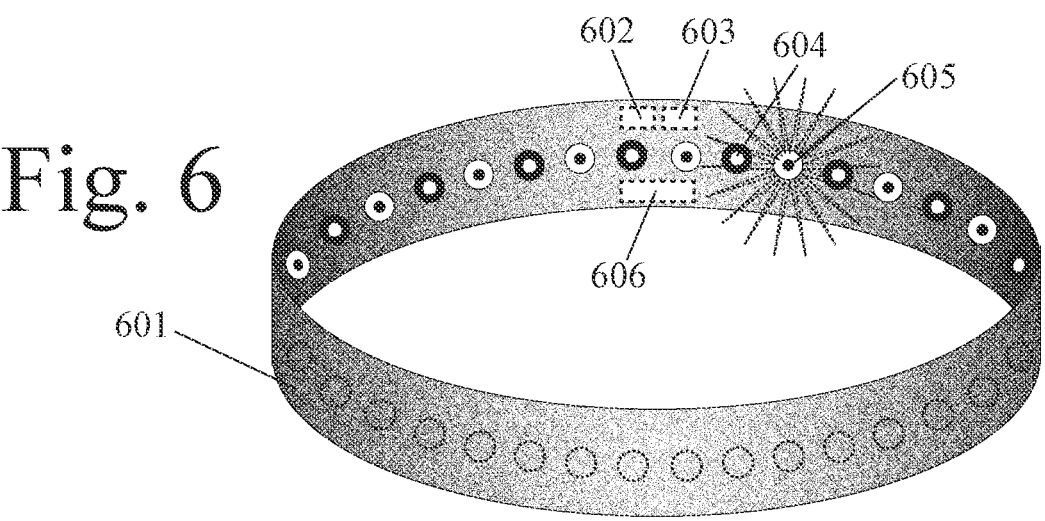
FIG. 6 shows a device with circumferential emitter and receiver arrays on the same circumferential line.

FIG. 6 shows another example of how this invention can be embodied in a wearable band for measuring a person's hydration level. This example is similar to the one shown in FIGS. 1 through 3, except that there is a circumferential or annular array of light emitters and light receivers along the same circumferential line (axis), with an alternating sequence of light emitters and receivers around the circumference.

FIG. 6 shows a wearable band for measuring a person's hydration level comprising: (a) an arcuate band which is configured to be worn around at least half of the circumference of a person's finger, wrist, and/or arm, wherein a selected location on the circumference of the arcuate band is defined as having a polar coordinate of 0 degrees and wherein other locations around the circumference of the arcuate band have other polar coordinates between 0 and 360 degrees; (b) a circumferential or annular array of light emitters held by the arcuate band along a circumferential line (axis) of the band, wherein the light emitters are configured to emit light toward the person's body, wherein the polar coordinate of each light emitter in the array is identified using the above-defined polar coordinates, wherein a first subset of one or more light emitters selected from the array of light emitters has a first average polar coordinate and emits light at a first point in time, wherein a second subset of one or more light emitters selected from the array of light emitters has a second average polar coordinate and emits light at a second point in time, and wherein the second average coordinate differs from the first average coordinate by at least 5 degrees; and (c) a circumferential or annular array of light receivers held by the arcuate band along the circumferential line (axis) of the band, wherein one or more light receivers are configured to receive light from the first subset of light emitters at a first point in time after light from this subset has interacted with the person's body tissue, wherein the one or more light receivers are configured to receive light from the second subset of light emitters at a second point in time after light from this subset has interacted with the person's body tissue, and wherein the spectra of light rays received by the one or more light receivers are analyzed in order to measure the person's hydration level.

With respect to specific components, the wearable band in FIG. 6 comprises: a wearable band 601; a circumferential or annular array of light emitters including light emitter 605; a circumferential or annular array of light receivers including light receiver 604; a data processor 602; a data transceiver 603; and a battery 606.

Food includes liquid beverages such as water. In an example, a food-consumption sensor can monitor a person's consumption of water, which can be useful for maintaining proper body hydration. In an example, a wearable food-consumption sensor can be a near-infrared spectroscopic sensor. In an example, a wearable food-consumption sensor can collect data concerning light energy that is reflected from a person's body and/or absorbed by the person's body.

In an example, an arcuate wrist-worn or finger-worn device can have a circumferentially or annularly distributed array of near-infrared spectroscopic sensors. In an example, near-infrared spectroscopic sensors can be distributed along different locations on the circumference of the device. In another example, an array of near-infrared spectroscopic sensors can be distributed along the circumference of an arcuate smart watch band or finger ring. In an example, an arcuate wrist-worn or finger-worn device can have a two-dimensional array of spectroscopic sensors. Sensors in a two-dimensional array can differ in location circumferentially or annularly (e.g. they are at different locations around the circumference of a wearable device) and laterally (e.g. they are at different locations along axes which are perpendicular to the circumference of the device). In an example, sensors in a two-dimensional sensor array can be spectroscopic sensors which are each configured to measure the spectrum of light energy reflected from (and/or absorbed by) tissue of a person's arm.

In an example, a wearable band for measuring a person's hydration level can comprise: an arcuate band which is configured to be worn around at least half of the circumference of a person's wrist and/or arm; a circumferential or annular array of light emitters on the arcuate band located along a first circumferential line of the arcuate band, wherein the light emitters are configured to emit light toward the person's body; and a circumferential or annular array of light receivers on the arcuate band located along a second circumferential line of the arcuate band, and wherein the spectra of light rays which have interacted with the person's body tissue and are received by the one or more light receivers are analyzed in order to measure the person's hydration level.

In an example, a light emitter and a light receiver together can comprise a near-infrared spectroscopic sensor. In an example, a near-infrared spectroscopic sensor can be used to monitor a person's water consumption. In an example, the second circumferential line can be different than the first circumferential line. In an example, a circumferential or annular array of light emitters can be configured to span at least half of the circumference of a person's wrist and/or arm. In an example, a circumferential or annular array of light receivers can be configured to span at least half of the circumference of a person's wrist and/or arm.

In an example: a first subset of one or more light emitters selected from the array can have a first average polar coordinate and emits light at a first point in time, wherein a second subset of one or more light emitters selected from the array can have a second average polar coordinate and emit light at a second point in time, and wherein the second average coordinate can differ from the first average coordinate by at least 5 degrees; and wherein the light receivers can be configured to receive light from the first subset of light emitters at a first point in time after light from this subset has interacted with the person's body tissue, wherein the light receivers can be configured to receive light from the second subset of light emitters at a second point in time after light from this subset has interacted with the person's body tissue. Relevant example variations discussed in other places in this disclosure or in priority-linked disclosures can also be applied to this example.

Figure 7:
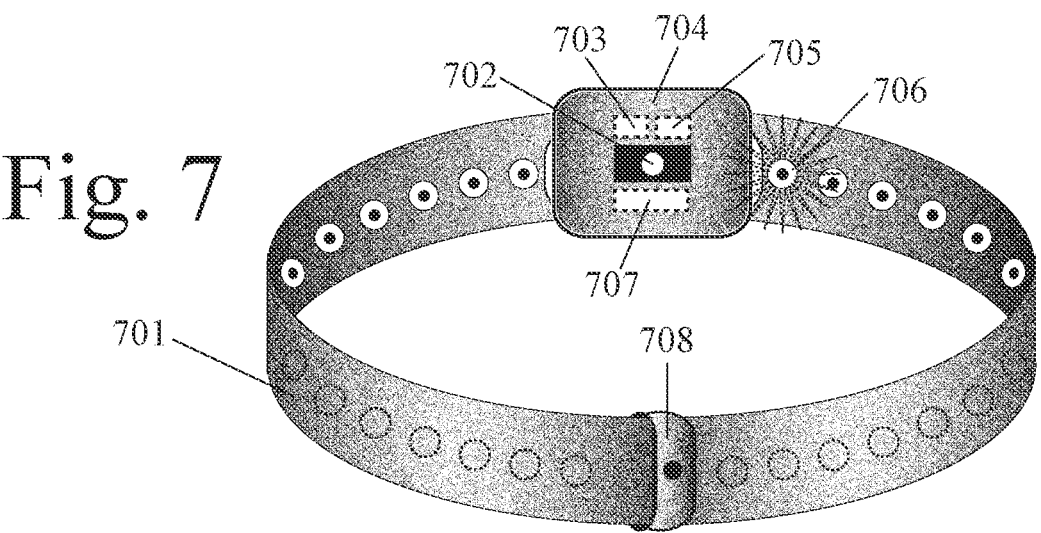
FIG. 7 shows a smart watch with a circumferential emitter array on the watch band and a receiver on the back of the watch display.

FIG. 7 shows an example of how this invention can be embodied in a smart watch for measuring a person's hydration level. This example is similar to the one shown in FIGS. 1 through 3, except that it includes a primary smart watch housing (which can include an electronic display on its outer side and a light receiver on its inner side) and a circumferential or annular array of light emitters on a flexible watch band. The outer side faces away from the surface of the person's wrist and the inner side faces toward the surface of the person's wrist.

FIG. 7 shows a smart watch for measuring a person's hydration level comprising: (a) a rigid electronics housing which can include a watch display; (b) a light receiver on the inner side of the electronics housing; (c) a flexible watch band; and (d) a circumferential or annular array of light emitters on the flexible watch band, wherein the light emitters are configured to emit light toward the person's body, wherein a first subset of one or more light emitters selected from the array of light emitters has a first average polar coordinate and emits light at a first point in time, wherein a second subset of one or more light emitters selected from the array of light emitters has a second average polar coordinate and emits light at a second point in time, and wherein the second average coordinate differs from the first average coordinate by at least 5 degrees; wherein the light receiver receives light from the first subset of light emitters at a first point in time after light from this subset has interacted with the person's body tissue, wherein the light receiver receives light from the second subset of light emitters at a second point in time after light from this subset has interacted with the person's body tissue, and wherein the spectra of light rays received by the light receiver are analyzed in order to measure the person's hydration level.

With respect to specific components, the smart watch in FIG. 7 comprises: a rigid electronics housing 704 which can include a display on the side not shown here; a flexible watch band 701; a band connector 708 (such as a buckle, snap, clip, clasp, pin, or magnet); a circumferential or annular array of light emitters including light emitter 706 on the watch band; a light receiver 702 on the electronics housing; a data processor 703; a data transceiver 705; and a battery 707. Relevant example variations discussed in other places in this disclosure or in priority-linked disclosures can also be applied to this example.

Figure 8:
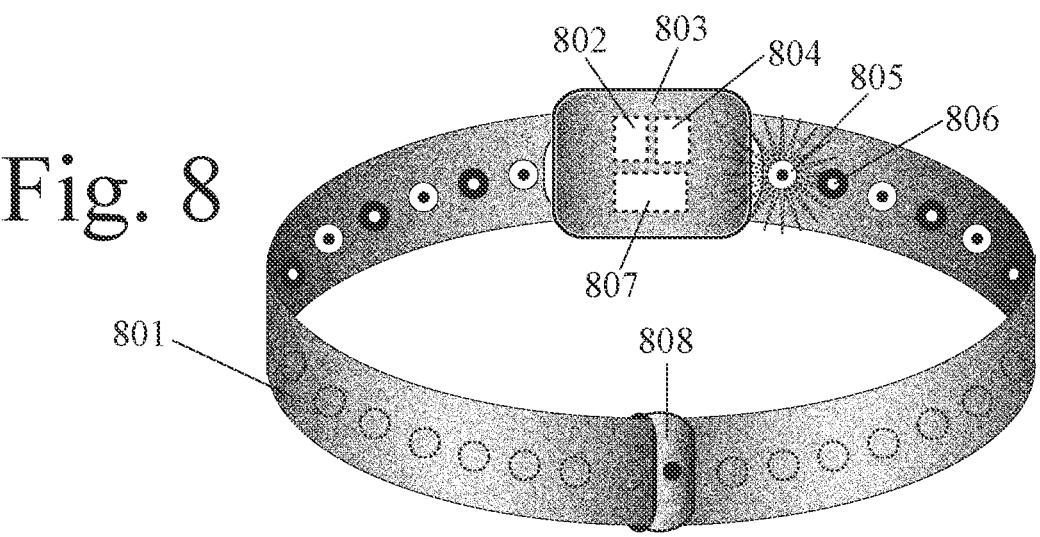
FIG. 8 shows a smart watch with circumferential emitter and receiver arrays on the watch band.

FIG. 8 shows another example of how this invention can be embodied in a smart watch for measuring a person's hydration level. This example is similar to the one shown in FIG. 7, except that there is a circumferential or annular array of light emitters and light receivers along the watch band, with an alternating sequence of light emitters and receivers.

FIG. 8 shows a smart watch for measuring a person's hydration level comprising: (a) a rigid electronics housing which can include a watch display; (b) a flexible watch band; (c) a circumferential or annular array of light emitters on the flexible watch band, wherein the light emitters are configured to emit light toward the person's body, wherein a first subset of one or more light emitters selected from the array of light emitters has a first average polar coordinate and emits light at a first point in time, wherein a second subset of one or more light emitters selected from the array of light emitters has a second average polar coordinate and emits light at a second point in time, and wherein the second average coordinate differs from the first average coordinate by at least 5 degrees; and (d) a circumferential or annular array of light receivers held by the flexible watch band, wherein the light receivers are configured to receive light from the first subset of light emitters at a first point in time after light from this subset has interacted with the person's body tissue, wherein the light receivers are configured to receive light from the second subset of light emitters at a second point in time after light from this subset has interacted with the person's body tissue, and wherein the spectra of light rays received by the light receivers are analyzed in order to measure the person's hydration level.

With respect to specific components, the smart watch in FIG. 8 comprises: a rigid electronics housing 803 which can include a display on the side not shown here; a flexible watch band 801; a band connector 808 (such as a buckle, snap, clip, clasp, pin, or magnet); a circumferential or annular array of light emitters including light emitter 805 on the watch band; a circumferential or annular array of light receivers including light receiver 806 on the watch band; a data processor 802; a data transceiver 804; and a battery 807.

Food consumption includes consumption of liquid beverages. In an example, a food-consumption sensor can detect a person's consumption of water. In an example, a wearable food-consumption sensor can be a near-infrared spectroscopic sensor. In an example, a wearable food-consumption sensor can collect data concerning light energy that is reflected from a person's body and/or absorbed by the person's body. In an example, an arcuate wrist-worn device can have a circumferentially or annularly distributed array of near-infrared spectroscopic sensors. In an example, near-infrared spectroscopic sensors can be distributed along different locations on the circumference of the device. In another example, an array of near-infrared spectroscopic sensors can be distributed along the circumference of an arcuate wrist-worn band or strap. In an example, an arcuate wrist-worn device can have a two-dimensional array of spectroscopic sensors. Sensors in a two-dimensional array can differ in location circumferentially or annularly (they are at different locations around the circumference of a wearable device) and laterally (they are at different locations along axes which are perpendicular to the circumference of the device). In an example, sensors in a two-dimensional sensor array can be spectroscopic sensors which are each configured to measure the spectrum of light energy reflected from (and/or absorbed by) tissue of a person's arm.

In an example, a smart watch for measuring a person's hydration level can comprise: a rigid electronics housing which includes a display; a flexible band; a circumferential or annular array of light emitters on the flexible band, wherein the light emitters are configured to emit light toward the person's body; and a circumferential or annular array of light receivers on the flexible band, wherein the spectra of light rays received by the light receivers are analyzed in order to measure the person's hydration level. In an example, a light emitter and a light receiver together can comprise a near-infrared spectroscopic sensor. In an example, a near-infrared spectroscopic sensor can be used to monitor a person's water consumption. In an example, a circumferential or annular array of light emitters can be configured to span at least half of the circumference of a person's wrist and/or arm. In an example, a circumferential or annular array of light receivers can be configured to span at least half of the circumference of a person's wrist and/or arm.

In an example: a first subset of one or more light emitters selected from the array can have a first average polar coordinate and emits light at a first point in time, wherein a second subset of one or more light emitters selected from the array can have a second average polar coordinate and emit light at a second point in time, and wherein the second average coordinate can differ from the first average coordinate by at least 5 degrees; and wherein the light receivers can be configured to receive light from the first subset of light emitters at a first point in time after light from this subset has interacted with the person's body tissue, wherein the light receivers can be configured to receive light from the second subset of light emitters at a second point in time after light from this subset has interacted with the person's body tissue. Relevant example variations discussed in other places in this disclosure or in priority-linked disclosures can also be applied to this example.

Figure 9:
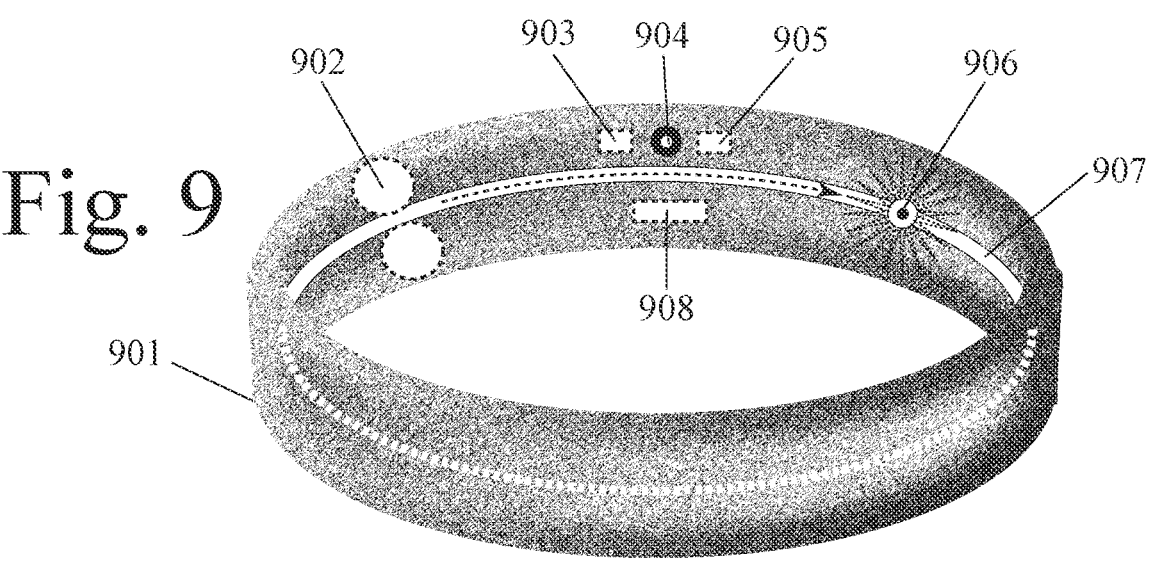
FIG. 9 shows a smart ring with a circumferential track along which an emitter is moved.

FIG. 9 shows another example of how this invention can be embodied in an arcuate band for measuring a person's hydration level. In an example, this arcuate band can function as a finger ring. In this example, a light emitter is moved along the circumference of the band by an actuator.

FIG. 9 shows a smart finger ring for measuring a person's hydration level comprising: (a) a finger ring; (b) an actuator; (c) a light emitter which is configured to emit light toward the person's body, wherein the light emitter is moved along the circumference of the finger ring by the actuator; (d) a light receiver which is configured to receive light from the light emitter after light from the light emitter has interacted with the person's body tissue, and wherein the spectra of light rays received by the light receiver are analyzed in order to measure the person's hydration level; (e) a data processor; (f) a data transceiver; and (g) a battery.

In an example, this finger ring can further comprise a circumferential or annular array along which the light emitter is moved by the actuator. In an example, this finger ring can further comprise a central ring or band to which the light emitter is attached, wherein this ring or band is rotated by the actuator. In an example, the actuator can be a small-scale electromagnetic motor. With respect to specific components, the smart finger ring in FIG. 9 comprises: finger ring 901; actuator 902; light emitter 906; circumferential or annular array 907; light receiver 904; data processor 903; data transceiver 905; and battery 908. Relevant example variations discussed in other places in this disclosure or in priority-linked disclosures can also be applied to this example.

Figure 10:
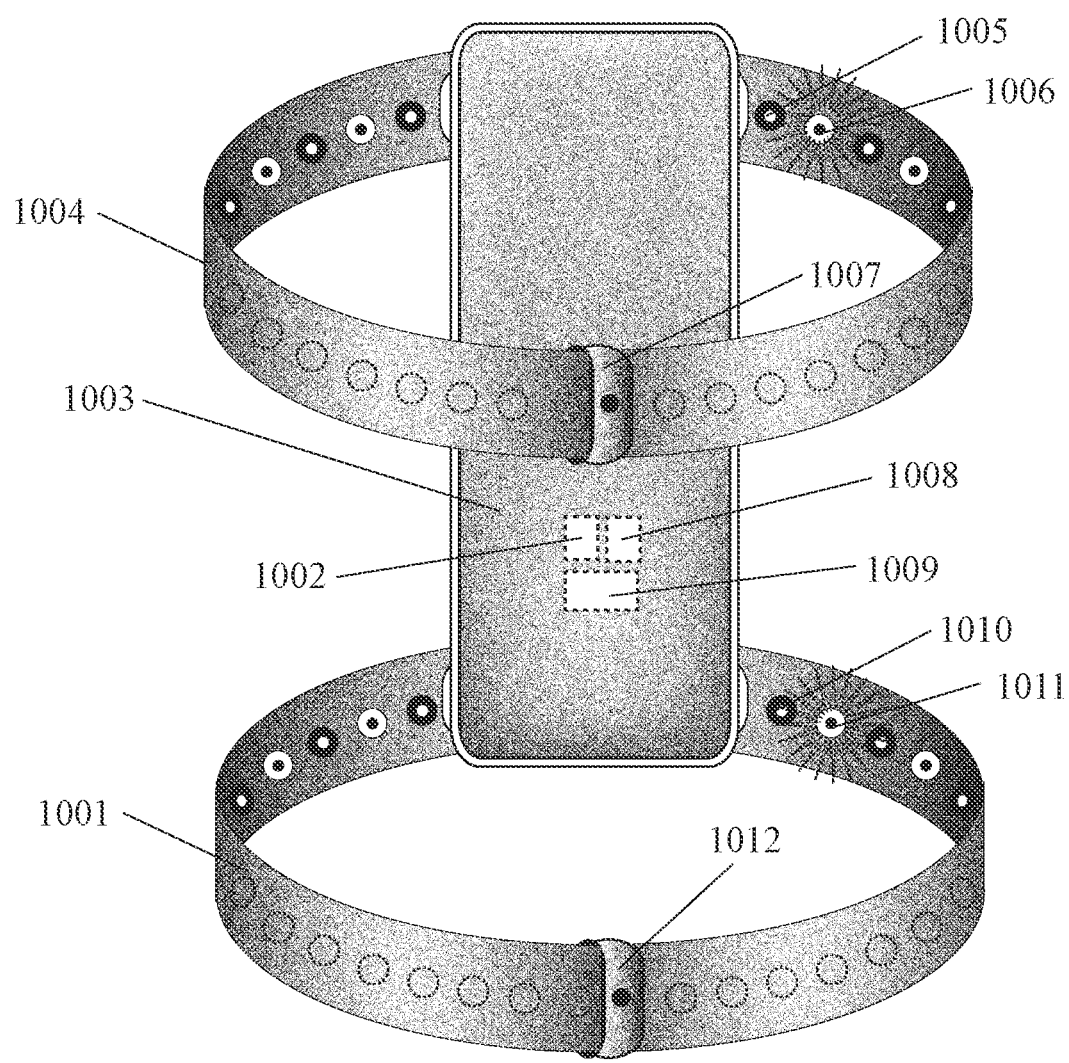
FIG. 10 shows a device with a rounded rectangular display and emitters and receivers on two separate bands.

FIG. 10 shows another example of how this invention can be embodied in a wrist and/or arm worn device for measuring a person's hydration level. The device in this example has rounded rectangular (display) housing with two arcuate bands which connect the housing to a person's wrist and/or arm. In this example, each of the arcuate bands has a circumferential or annular array of light emitters and light receivers.

FIG. 10 shows an arcuate wearable device for measuring a person's hydration level comprising: (a) a rounded rectangular housing for an electronic display; (b) a proximal arcuate band which is configured to attach a proximal portion of the housing to the person's wrist and/or arm; (c) a distal arcuate band which is configured to attach a distal portion of the housing to the person's wrist and/or arm; (d) a first array of light emitters and light receivers on the proximal arcuate band, wherein light emitters in the first array are configured to emit light toward the person's body, and wherein the light receivers in the first array are configured to receive light from light emitters in the first array after this light has interacted with the person's body tissue; (e) a second array of light emitters and light receivers on the distal arcuate band, wherein light emitters in the second array are configured to emit light toward the person's body, wherein the light receivers in the second array are configured to receive light from light emitters in the second array after this light has interacted with the person's body tissue, and wherein the spectra of light rays received by light receivers in the first and second arrays are analyzed in order to measure the person's hydration level; (f) a data processor; (g) a data transceiver; and (h) a battery.

With respect to specific components, the wearable device in FIG. 10 comprises: rounded rectangular housing 1003; proximal arcuate band 1004; distal arcuate band 1001; a first array of light emitters (including 1006) and light receivers (including 1005) on the proximal arcuate band; a second array of light emitters (including 1011) and light receivers (including 1010) on the distal arcuate band; data processor 1002; data transceiver 1008; battery 1009; and buckles (or clasp, clip, pin, or snap) 1007 and 1012. Relevant example variations discussed in other places in this disclosure or in priority-linked disclosures can also be applied to this example.

Figure 11:
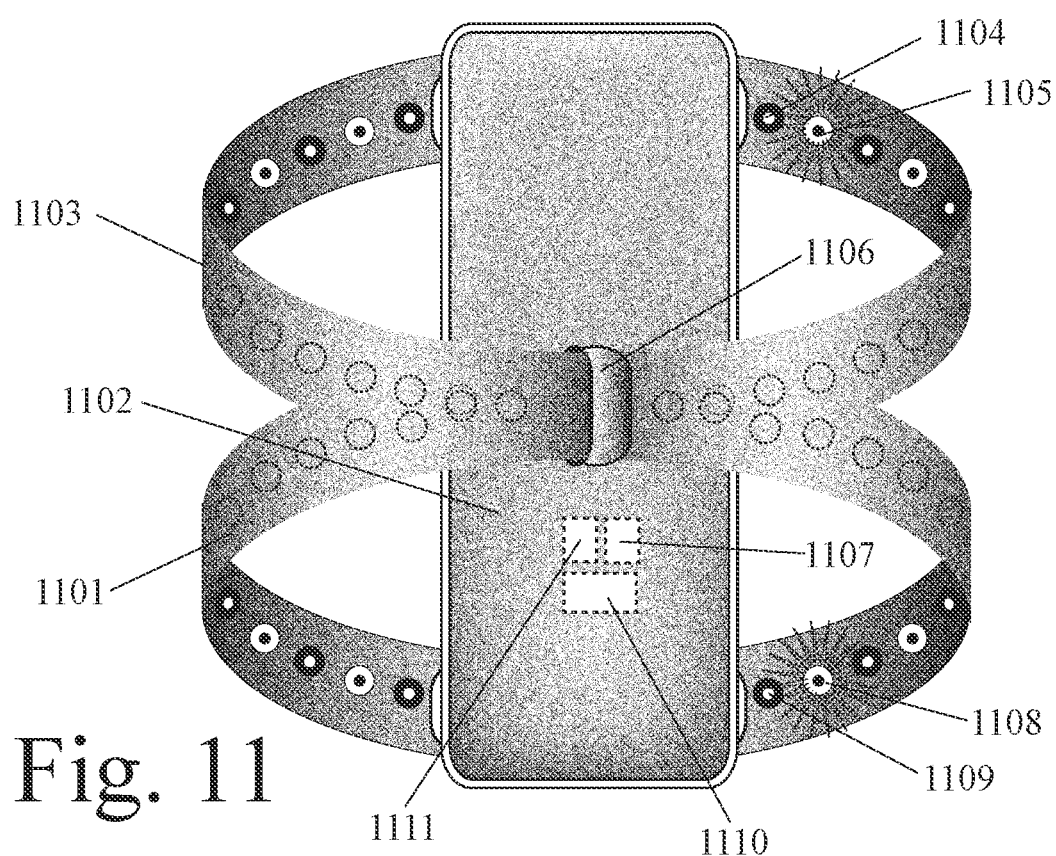
FIG. 11 shows a device with a rounded rectangular display and emitters and receivers on two converging bands.

FIG. 11 shows another example of a wrist and/or arm worn device that is similar to the one shown in FIG. 10 except that the two arcuate bands converge on the ventral surface of the person's wrist and/or arm. FIG. 11 shows an arcuate wearable device for measuring a person's hydration level comprising: (a) a rounded rectangular housing for an electronic display on the dorsal side of a person's wrist and/or arm; (b) a proximal arcuate band which is configured to attach a proximal portion of the housing to the person's wrist and/or arm; (c) a distal arcuate band which is configured to attach a distal portion of the housing to the person's wrist and/or arm, wherein the proximal arcuate band and the distal arcuate band are configured to converge on the ventral side of the person's wrist and/or arm; (d) a first array of light emitters and light receivers on the proximal arcuate band, wherein light emitters in the first array are configured to emit light toward the person's body, and wherein the light receivers in the first array are configured to receive light from light emitters in the first array after this light has interacted with the person's body tissue; (e) a second array of light emitters and light receivers on the distal arcuate band, wherein light emitters in the second array are configured to emit light toward the person's body, wherein the light receivers in the second array are configured to receive light from light emitters in the second array after this light has interacted with the person's body tissue, and wherein the spectra of light rays received by light receivers in the first and second arrays are analyzed in order to measure the person's hydration level; (f) a data processor; (g) a data transceiver; and (h) a battery.

With respect to specific components, the wearable device in FIG. 11 comprises: rounded rectangular housing 1102; proximal arcuate band 1103; distal arcuate band 1101; a first array of light emitters (including 1105) and light receivers (including 1104) on the proximal arcuate band; a second array of light emitters (including 1108) and light receivers (including 1109) on the distal arcuate band; data processor 1111; data transceiver 1107; battery 1110; and a buckle (or clasp, clip, pin, or snap) 1106. Relevant example variations discussed in other places in this disclosure or in priority-linked disclosures can also be applied to this example.

Figure 12:
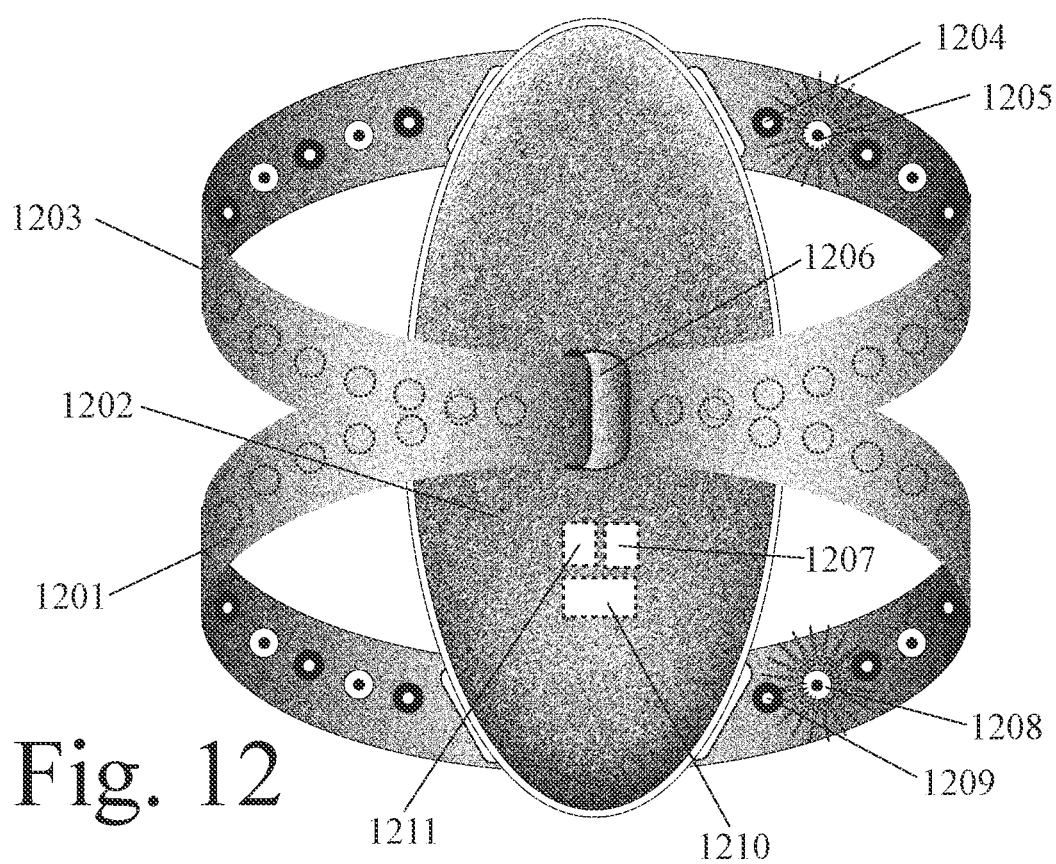
FIG. 12 shows a device with an elliptical or oval display and emitters and receivers on two converging bands.

FIG. 12 shows another example of a wrist and/or arm worn device that is similar to the one shown in FIG. 11 except that the housing has an oval (or elliptical) shape instead of a rounded rectangular shape. FIG. 12 shows an arcuate wearable device for measuring a person's hydration level comprising: (a) an oval or elliptical housing for an electronic display on the dorsal side of a person's wrist and/or arm; (b) a proximal arcuate band which is configured to attach a proximal portion of the housing to the person's wrist and/or arm; (c) a distal arcuate band which is configured to attach a distal portion of the housing to the person's wrist and/or arm, wherein the proximal arcuate band and the distal arcuate band are configured to converge on the ventral side of the person's wrist and/or arm; (d) a first array of light emitters and light receivers on the proximal arcuate band, wherein light emitters in the first array are configured to emit light toward the person's body, and wherein the light receivers in the first array are configured to receive light from light emitters in the first array after this light has interacted with the person's body tissue; (e) a second array of light emitters and light receivers on the distal arcuate band, wherein light emitters in the second array are configured to emit light toward the person's body, wherein the light receivers in the second array are configured to receive light from light emitters in the second array after this light has interacted with the person's body tissue, and wherein the spectra of light rays received by light receivers in the first and second arrays are analyzed in order to measure the person's hydration level; (f) a data processor; (g) a data transceiver; and (h) a battery.

With respect to specific components, the wearable device in FIG. 12 comprises: oval or elliptical housing 1202; proximal arcuate band 1203; distal arcuate band 1201; a first array of light emitters (including 1205) and light receivers (including 1204) on the proximal arcuate band; a second array of light emitters (including 1208) and light receivers (including 1209) on the distal arcuate band; data processor 1211; data transceiver 1207; battery 1210; and a buckle (or clasp, clip, pin, or snap) 1206. Relevant example variations discussed in other places in this disclosure or in priority-linked disclosures can also be applied to this example.

Figure 13:
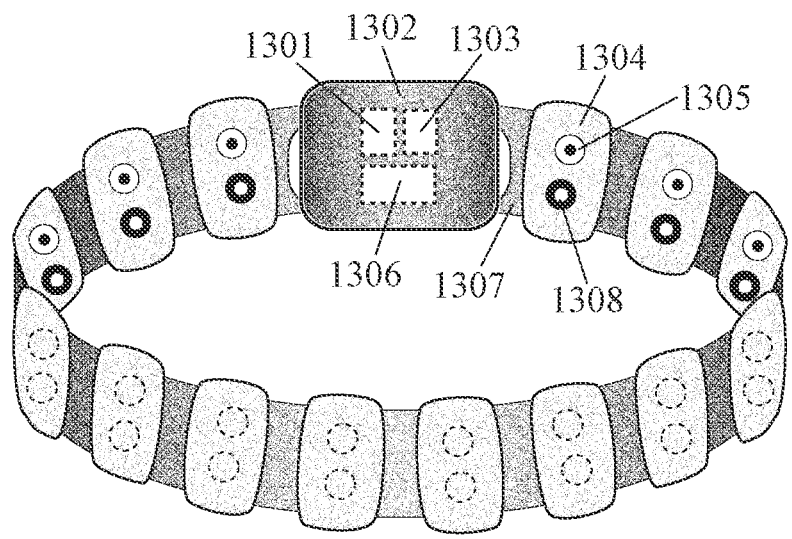
FIGS. 13 and 14 show a device with secondary electronics housings on a band.
Figure 14:
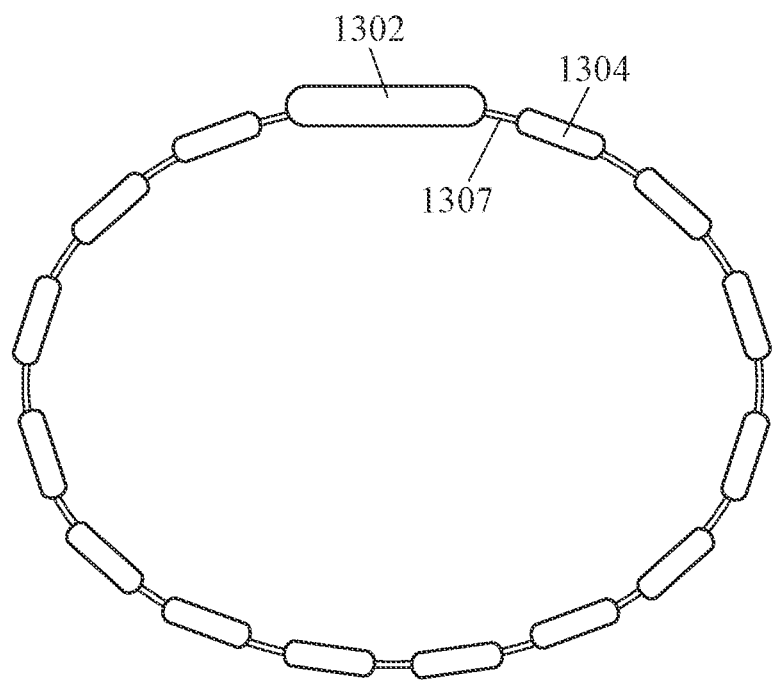

FIGS. 13 and 14 show two different views of an example of how this invention can be embodied in a wearable band (such as a smart watch) for measuring a person's hydration level. FIG. 13 shows an opaque, oblique, side view of this wearable band (e.g. smart watch). FIG. 14 shows a top-down, outline view of this wearable band (e.g. smart watch). The wearable band (e.g. smart watch) has: a primary electronics housing on the dorsal surface worn on a person's wrist and/or arm; and a circumferential or annular series of secondary electronics housings. The circumferential or annular series of secondary electronics housings are connected to each other by flexible members selected from the group consisting of: bands, straps, strips, swatches, wires, cords, threads, joints, and chain links. These housings and flexible members form an arcuate band which spans at least half of the circumference of a person's wrist and/or arm. In this example, each secondary electronics housing has both a light emitter and a light receiver, collectively creating a circumferential or annular array of light emitters and light receivers. This wearable band can function as a smart watch with hydration sensors on housings distributed around the watch band.

FIGS. 13 and 14 show a wearable band (such as a smart watch) for measuring a person's hydration level comprising: (a) a primary electronics housing which is configured to be worn on the dorsal surface of a person's wrist and/or arm; (b) a circumferential or annular series of secondary electronics housings, wherein a secondary electronics housing has both a light emitter and a light receiver, wherein the light emitter emits light toward the surface of the person's wrist and/or arm, wherein the light receiver receives light from the light emitter after this light has interacted with the person's body, and wherein the spectrum of light received by a light receiver is analyzed in order to measure the person's hydration level; and (c) a circumferential or annular series of flexible members; wherein the flexible members are selected from the group consisting of bands, straps, strips, swatches, wires, cords, threads, joints, and chain links; wherein the flexible members connect the primary electronics housing the and secondary electronics housings into an arcuate wearable band which spans at least half of the circumference of a person's wrist and/or arm.

With respect to specific components, the wearable band (e.g. smart watch) shown in FIGS. 13 and 14 comprises: a primary electronics housing (1302); secondary electronics housings (such as 1304); light emitters (such as 1305); light receivers (such as 1308); flexible members (such as 1307) which connect the housings into an arcuate band; a data processor (1301); a data transceiver (1303); and a battery (1306). In an example, the primary electronics housing can include a watch display on its outward-facing surface so that this wearable band can function as a smart watch. In an example, the series of flexible members and secondary electronics housings can function as a watch band. In an example, a primary electronics housing can be larger than a secondary electronics housing. In an example, light from a circumferential or annular array of light emitters can interact with the person's body by reflecting off body tissue and/or by being transmitted through body tissue. In an example, such reflection or transmission changes the spectrum of light rays and these changes in light spectra can be used to measure the person's hydration level.

In an example, a primary electronics housing and/or a secondary electronics housing can be rigid. In an example, a primary electronics housing and/or a secondary electronics housing can be flexible, but less flexible than the flexible members which connect them. In an example, a primary electronics housing and/or a secondary electronics housing can be flat. In an example, a primary electronics housing and/or a secondary electronics housing can be curved. In an example, flexible members (e.g. bands, straps, strips, swatches, wires, cords, threads, joints, or chain links) which connect electronic housings can include electromagnetic energy pathways which enable electromagnetic communication between housings.

In an example, secondary electronics housings can be reversibly connected to a band and/or each other. In an example, secondary electronics housings can be modular. In this example, there are a discontinuous series of flexible members which connect electronics housings. In an example, there can be a single, continuous flexible band which connects electronics housings. In an example, secondary electronics housings can be reversibly connected to a single, continuous flexible band.

In this example, there is one light emitter and one light receiver on each secondary electronics housing. In an example, a first subset of secondary electronics housings can have just a light emitter and a second subset of secondary electronics housings can have just a light receiver. In an example, a first housing in a pair of adjacent secondary electronics housings can have a light emitter and a second housing in that pair can have a light receiver. In an example, there can be an array of multiple light emitters on a single electronics housing. In an example, a single secondary electronics housing can include a circular and/or polygonal array of light emitters around a central light receiver. In an example, a single secondary electronics housing can include a nested and/or concentric array of light emitters around a central light receiver.

In this example, secondary electronics housings have rounded rectangular shapes. In an example, secondary electronics housings can have circular, oval, or elliptical shapes. In this example, there are over a dozen secondary electronics housings which are relatively evenly distributed around the circumference of a band (apart from the primary electronics housing). In an example, there can be an even number of secondary electronics housings around a band. In an example, there can be 2, 4, or 6 secondary electronics housing around a band. In an example, there can be 8, 10, or 12 secondary electronics housing around a band. In an example, secondary electronics housings can be unevenly distributed around a band. In an example, secondary electronics housings can be disproportionately located and/or clustered on the dorsal and/or ventral portions of a band.

Food consumption includes consumption of liquid beverages. In an example, a food-consumption sensor can detect a person's consumption of water. In an example, a wearable food-consumption sensor can be a near-infrared spectroscopic sensor. In an example, a wearable food-consumption sensor can collect data concerning light energy that is reflected from a person's body and/or absorbed by the person's body. In an example, an arcuate wrist-worn device can have a circumferentially or annularly distributed array of near-infrared spectroscopic sensors. In an example, near-infrared spectroscopic sensors can be distributed along different locations on the circumference of the device. In another example, an array of near-infrared spectroscopic sensors can be distributed along the circumference of an arcuate wrist-worn band or strap. In an example, an arcuate wrist-worn device can have a two-dimensional array of spectroscopic sensors. Sensors in a two-dimensional array can differ in location circumferentially or annularly (they are at different locations around the circumference of a wearable device) and laterally (they are at different locations along axes which are perpendicular to the circumference of the device). In an example, sensors in a two-dimensional sensor array can be spectroscopic sensors which are each configured to measure the spectrum of light energy reflected from (and/or absorbed by) tissue of a person's arm.

In an example, an arcuate wearable device for measuring a person's hydration level can comprise: a primary electronics housing which is configured to be worn on the dorsal surface of a person's wrist and/or arm; a circumferential or annular series of secondary electronics housings, wherein a secondary electronics housing has both a light emitter and a light receiver, wherein the light emitter emits light toward the surface of the person's wrist and/or arm, wherein the light receiver receives light from the light emitter after this light has interacted with the person's body, and wherein the spectrum of light received by a light receiver is analyzed in order to measure a person's hydration level; and a circumferential or annular series of flexible members; wherein the flexible members are selected from the group consisting of bands, straps, strips, swatches, wires, cords, threads, joints, and chain links; wherein the flexible members connect the primary electronics housing and the secondary electronics housings into an arcuate wearable band which spans at least half of the circumference of a person's wrist and/or arm.

In an example, a light emitter and a light receiver together can comprise a near-infrared spectroscopic sensor. In an example, a near-infrared spectroscopic sensor can be used to monitor a person's water consumption. In an example, a circumferential or annular array of light emitters can be configured to span at least half of the circumference of a person's wrist and/or arm. In an example, a circumferential or annular array of light receivers can be configured to span at least half of the circumference of a person's wrist and/or arm.

In an example: a first subset of one or more light emitters selected from the array can have a first average polar coordinate and emits light at a first point in time, wherein a second subset of one or more light emitters selected from the array can have a second average polar coordinate and emit light at a second point in time, and wherein the second average coordinate can differ from the first average coordinate by at least 5 degrees; and wherein the light receivers can be configured to receive light from the first subset of light emitters at a first point in time after light from this subset has interacted with the person's body tissue, wherein the light receivers can be configured to receive light from the second subset of light emitters at a second point in time after light from this subset has interacted with the person's body tissue.

In an example, a primary electronics housing can further comprise a display. In an example, secondary electronics housings can be modular and reversibly connected to the device. In an example, this device can have between 2 and 6 secondary electronics housings. In an example, this device can have more than 6 secondary electronics housings. In an example, at least one of the secondary electronics housings can include a circular or polygonal array of light emitters around a central light receiver. In an example, secondary electronics housings are disproportionately located and/or clustered on dorsal and/ventral portions of the device. Relevant example variations discussed in other places in this disclosure or in priority-linked disclosures can also be applied to this example.

Figure 15:
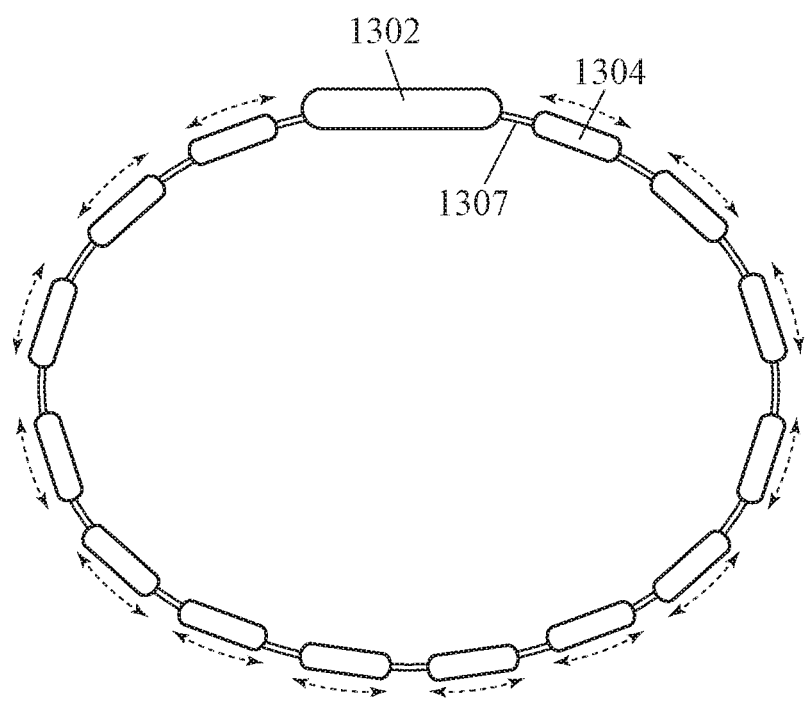
FIG. 15 shows a device with circumferentially-adjustable secondary electronics housings on a band.
Figure 16:
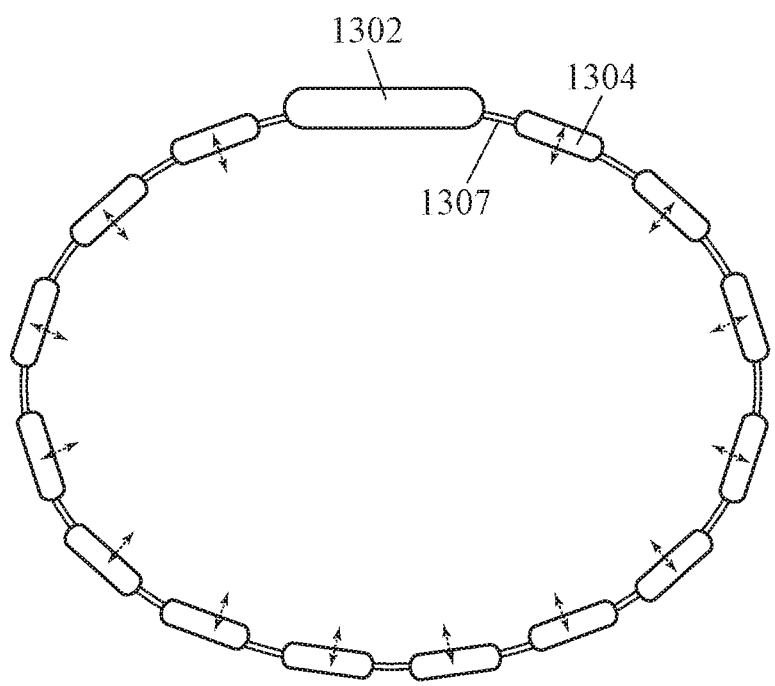
FIG. 16 shows a device with inwardly-adjustable secondary electronics housings on a band.

FIGS. 15 and 16 show two additional top-down outline views of the wearable band that was introduced in FIGS. 13 and 14. FIGS. 15 and 16 show how the locations of secondary electronics housings can be adjusted circumferentially or annularly and radially in order to improve hydration measurement.

FIG. 15 shows how secondary electronics housings can be slid clockwise or counter-clockwise around a portion of a circumference of the band. Adjusting the circumferential locations and/or polar coordinates of secondary electronics housings in this manner can customize the circumferential placement of light emitters and/or light receivers for optimal measurement of body hydration. This can enable customization of light sensor placement for a particular person's anatomy and/or for a particular activity. For example, if someone has a blood vessel which spans their wrist in a particular circumferential location and/or polar coordinate, then a secondary electronics housing (and thus a light emitter and/or light receiver) can be slid to this location and/or coordinate in order to optimally collect hydration information concerning this vessel.

In an example, the positioning of a secondary electronics housing along the circumference of a wearable band can be done manually. In an example, such positioning can be guided by a feedback loop. In an example, such positioning can be done automatically (e.g. by an electromagnetic actuator). In an example, this band can further comprise a locking mechanism which locks a secondary electronics housing in place once it has been slid to an optimal location. In an example, each secondary electronics housing can have an unlocking/locking mechanism, wherein the housing can be slid back and forth along the circumference of the band when the mechanism is unlocked and the housing is held in place at a particular coordinate when the mechanism is locked.

In an example, the positioning of a light emitter and/or light receiver along the circumference of a wearable band can be done manually. In an example, such positioning can be guided by a feedback loop. In an example, such positioning can be done automatically (e.g. by an electromagnetic actuator). In an example, this band can further comprise a locking mechanism which locks a light emitter and/or light receiver in place once it has been slid to an optimal location. In an example, each light emitter and/or light receiver can have an unlocking/locking mechanism, wherein the light emitter and/or light receiver can be slid back and forth along the circumference of the band when the mechanism is unlocked and the light emitter and/or light receiver is held in place at a particular polar coordinate when the mechanism is locked.

FIG. 16 shows how secondary electronics housings can be moved radially inward (closer to the surface of a person's body) or outward (farther from the surface of the person's body). This movement can also be seen as moving inward or outward along a radial spoke which extends outward from the cross-sectional centroid of the person's wrist and/or arm. Adjusting the radial locations of secondary electronics housings in this manner can be done to customize the closeness of light emitters and/or light receivers to the person's body surface at different locations for optimal hydration measurement.

Radial adjustment of secondary electronics housings can enable customization of light sensor placement for a particular person's anatomy and/or for a particular activity. For example, if someone's wrist and/or arm has an asymmetric circumferential shape, then the radial locations of different secondary electronics housings around the circumference of the band can be differentially adjusted to get the optimal fit for body hydration measurement. As another example, if someone is going to start a very vigorous activity, then secondary electronics housings can be moved inward to achieve a tighter fit so that the band does not slide around. In an example, such radial adjustment can be automatic, such as in response to motion detected by a motion sensor.

In an example, radial adjustment of the location of a secondary electronics housing can be done by rotating a threaded portion of the housing. In an example, radial adjustment of the location of a secondary electronics housing can be done by inflating a member which is part of the housing or flexible band. In an example, radial adjustment of the location of a secondary electronics housing can be done by an electromagnetic actuator which is part of the housing or flexible band. In an example, radial adjustment of the location of a secondary electronics housing can be done by a hydraulic piston which is part of the housing or flexible band.

In an example, radial adjustment of the location of a light emitter and/or receiver can be done by rotating a threaded portion of the housing. In an example, radial adjustment of the location of a light emitter and/or receiver can be done by inflating a member which is part of the housing or flexible band. In an example, radial adjustment of the location of a light emitter and/or receiver can be done by an electromagnetic actuator which is part of the housing or flexible band. In an example, radial adjustment of the location of a light emitter and/or receiver can be done by a hydraulic piston which is part of the housing or flexible band. Relevant example variations discussed in other places in this disclosure or in priority-linked disclosures can also be applied to this example.

Figure 17:
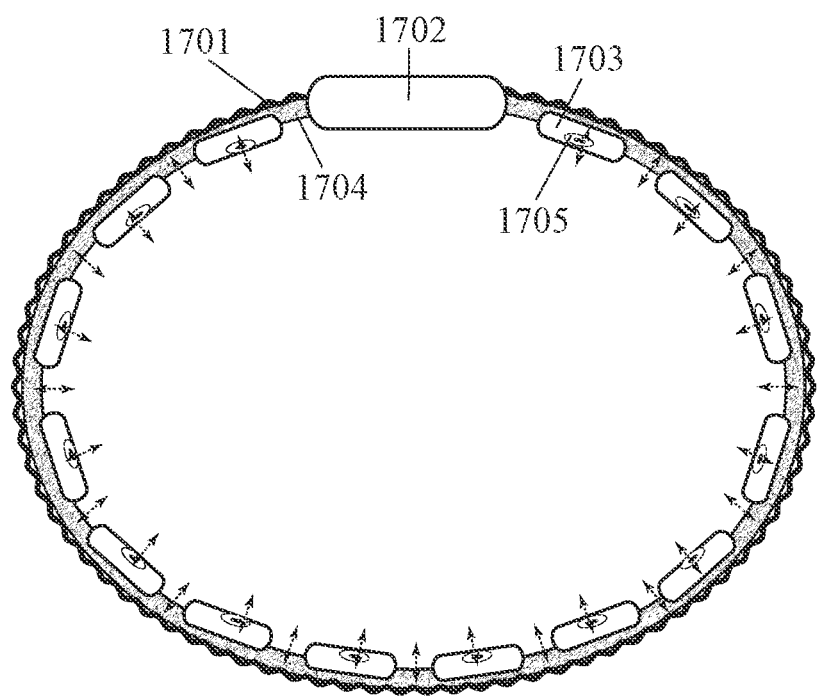
FIG. 17 shows a device with inwardly-adjustable secondary electronics housings which are adjusted by inflation.

FIG. 17 shows another example of how this invention can be embodied in a wearable band for measuring a person's hydration level. This wearable band has an inner ring or layer which is inflated or deflated to adjust the proximity (or contact pressure) of electronic housings (and thus light emitters and/or light receivers on those housings) with respect to the surface of a person's body. This wearable band comprises: (a) an inflatable inner ring or layer; (b) an outer ring or layer which spans at least half of the circumference of a person's finger, wrist, and/or arm; (c) a circumferential or annular array of electronic housings with light emitters and/or light receivers which are connected to the inflatable inner ring or layer, wherein light emitters direct light toward the surface of a person's body, wherein light receivers receive light from the light emitters after this light has interacted with body tissue, wherein light spectra received by light receivers are analyzed in order to measure the person's hydration level, and wherein the proximity of light emitters and/or light receivers to the surface of the person's body is adjusted by inflation or deflation of the inflatable inner ring or layer.

In an example, this wearable band can also comprise a primary electronics housing which includes an electronic display. In an example, this wearable band can function as a smart watch with an inflatable band to adjust the proximity of light sensors to the person's body. In an example, the inner ring or layer can be manually inflated or deflated. In an example, the inner ring or layer can be automatically inflated or deflated. In an example, the inner ring or layer can be automatically inflated based on vigorous motion detected by a motion sensor, so that the band is less likely to shift or rotate during vigorous motion. With respect to specific components, FIG. 17 shows a wearable band for measuring a person's hydration level comprising: an inflatable inner ring or layer 1704; an outer ring or layer 1701; a circumferential or annular array of electronic housings (including 1703); light emitters and/or light receivers (including 1705);

and a primary electronics housing 1702. In an example, this band can further comprise: an electronic display on the primary electronics housing; a data processor; a data transceiver; and a battery. Relevant example variations discussed in other places in this disclosure or in priority-linked disclosures can also be applied to this example.

Figure 18:
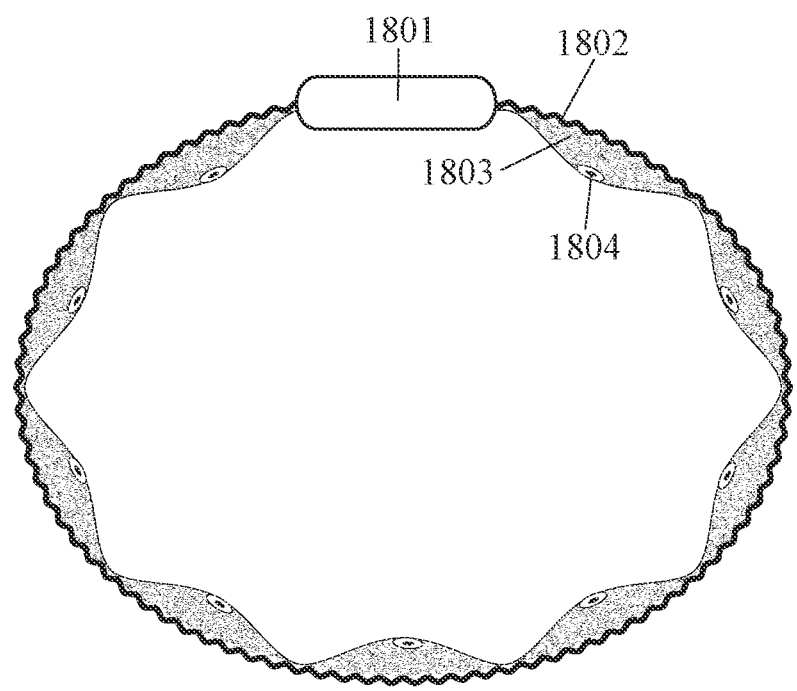
FIG. 18 shows a device whose band has compressible radial undulations.

FIG. 18 shows another example of how this invention can be embodied in a wearable band for measuring a person's hydration level. This wearable band has sinusoidal radial undulations in depth and a circumferential or annular array of light emitters and/or light receivers on the inward-extending portions of these radial undulations. This wearable band comprises: (a) a band with radial undulations in depth which is configured to span at least half of the circumference of a person's finger, wrist, and/or arm; and (b) a circumferential or annular array of light emitters and/or light receivers which are located on the inward-extending portions of these radial undulations. In an example, these radial undulations can be sinusoidal. In an example, these radial undulations can be soft and compressible. In an example, this band can further comprise: an electronics housing; an electronic display; a data processor; a data transceiver; and a battery. With respect to specific components, the wearable band shown in FIG. 18 comprises: inner ring or layer 1803 with radial undulations; outer ring or layer 1802; light emitter and/or receiver 1804; and electronics housing 1801. Relevant example variations discussed in other places in this disclosure or in priority-linked disclosures can also be applied to this example.

Figure 19:
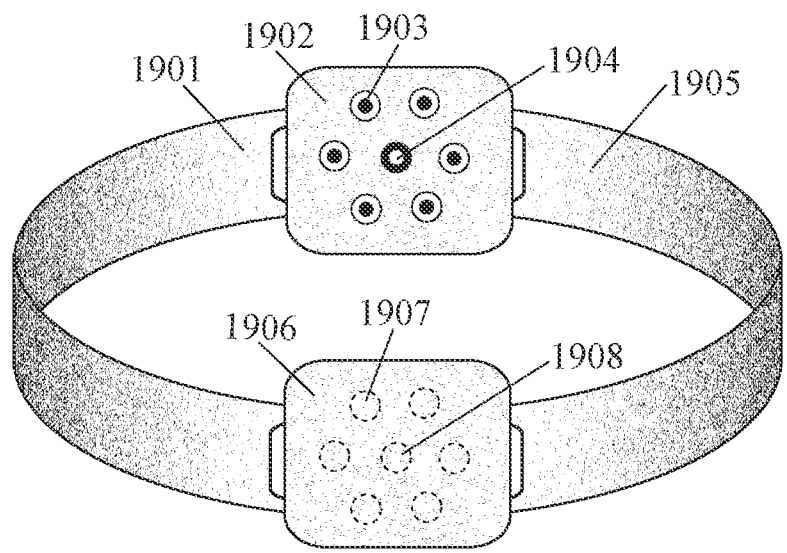
FIG. 19 shows a device with one dorsal electronics housing and one ventral electronics housing.

FIG. 19 shows another example of how this invention can be embodied in a wearable band (such as a smart watch) for measuring a person's hydration level. This wearable band (e.g. smart watch) has: a first electronics housing which is configured to be worn on the dorsal side of a person's wrist and/or arm; a first light emitter and a first light receiver on the first electronics housing, wherein the first light emitter emits light toward the surface of the person's wrist and/or arm, and wherein the first light receiver receives light from the first light emitter after this light has interacted with the person's body tissue; a second electronics housing which is configured to be worn on the ventral side of a person's wrist and/or arm; a second light emitter and a second light receiver on the second electronics housing, wherein the second light emitter emits light toward the surface of the person's wrist and/or arm, and wherein the second light receiver receives light from the second light emitter after this light has interacted with the person's body tissue, and wherein the spectra of light rays received by the first light receiver and by the second light receiver are analyzed in order to measure the person's hydration level; and one or more flexible members which connect the first electronics housing and the second electronics housing, wherein these flexible members are selected from the group consisting of bands, straps, strips, swatches, wires, cords, threads, joints, and chain links.

With respect to specific components, the wearable band (e.g. smart watch) in FIG. 19 comprises: first electronics housing 1902; first light emitter 1903; first light receiver 1904; second electronics housing 1906; second light emitter 1907; second light receiver 1908; and flexible members 1901 and 1905. In an example, an electronics housing can have a rounded rectangular shape. In an example, an electronics housing can have a circular, oval, or elliptical shape. In an example, an electronics housing can further comprise an electronic display on its outward-facing side. In an example, an electronics housing can have a circular or polygonal array of light emitters around a central light receiver. In an example, an electronics housing can have a nested and/or concentric array of light emitters around a central light receiver. Relevant example variations discussed in other places in this disclosure or in priority-linked disclosures can also be applied to this example.

Figure 20:
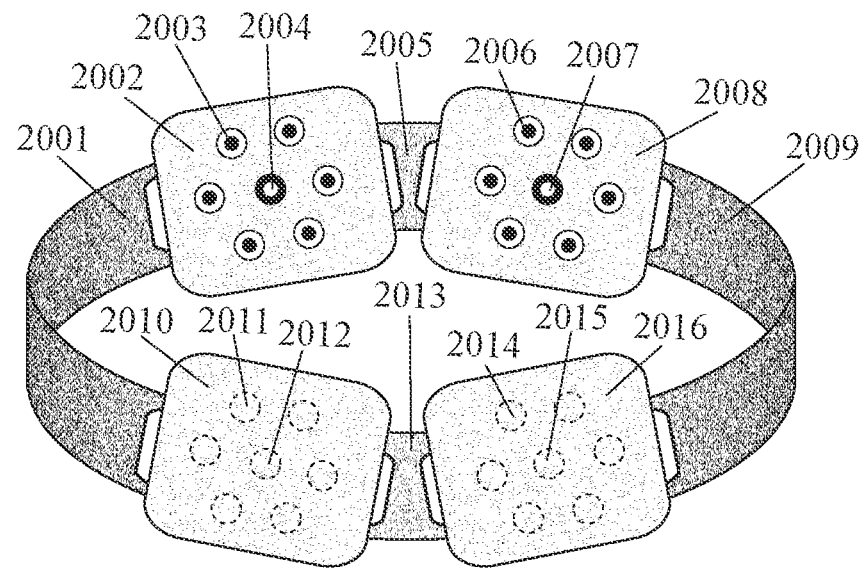
FIG. 20 shows a device with two dorsal electronics housings and two ventral electronics housings.

FIG. 20 shows another example of how this invention can be embodied in a wearable band for measuring a person's hydration level. This wearable band has: a first electronics housing which is configured to be worn on a first half of the dorsal side of a person's wrist and/or arm; a first light emitter and a first light receiver on the first electronics housing, wherein the first light emitter emits light toward the surface of the person's wrist and/or arm, and wherein the first light receiver receives light from the first light emitter after this light has interacted with the person's body tissue; a second electronics housing which is configured to be worn on a second half of the dorsal side of a person's wrist and/or arm; a second light emitter and a second light receiver on the second electronics housing, wherein the second light emitter emits light toward the surface of the person's wrist and/or arm, and wherein the second light receiver receives light from the second light emitter after this light has interacted with the person's body tissue; a third electronics housing which is configured to be worn on a first half of the ventral side of a person's wrist and/or arm; a third light emitter and a third light receiver on the third electronics housing, wherein the third light emitter emits light toward the surface of the person's wrist and/or arm, and wherein the third light receiver receives light from the third light emitter after this light has interacted with the person's body tissue; a fourth electronics housing which is configured to be worn on a second half of the ventral side of a person's wrist and/or arm; a fourth light emitter and a fourth light receiver on the fourth electronics housing, wherein the fourth light emitter emits light toward the surface of the person's wrist and/or arm, and wherein the fourth light receiver receives light from the fourth light emitter after this light has interacted with the person's body tissue; and wherein the spectra of light rays received by the light receivers are analyzed in order to measure the person's hydration level; and one or more flexible members which connect the electronics housings, wherein these flexible members are selected from the group consisting of bands, straps, strips, swatches, wires, cords, threads, joints, and chain links.

With respect to specific components, the wearable band in FIG. 20 comprises: first electronics housing 2002; first light emitter 2003; first light receiver 2004; second electronics housing 2008; second light emitter 2006; second light receiver 2007; third electronics housing 2010; third light emitter 2011; third light receiver 2012; fourth electronics housing 2016; fourth light emitter 2014; fourth light receiver 2015; and flexible members 2001, 2005, 2009, and 2013. In an example, an electronics housing can have a rounded rectangular shape. In an example, an electronics housing can have a circular, oval, or elliptical shape. In an example, an electronics housing can further comprise an electronic display on its outward-facing side. In an example, an electronics housing can have a circular or polygonal array of light emitters around a central light receiver. In an example, an electronics housing can have a nested and/or concentric array of light emitters around a central light receiver. Relevant example variations discussed in other places in this disclosure or in priority-linked disclosures can also be applied to this example.

Figure 21:
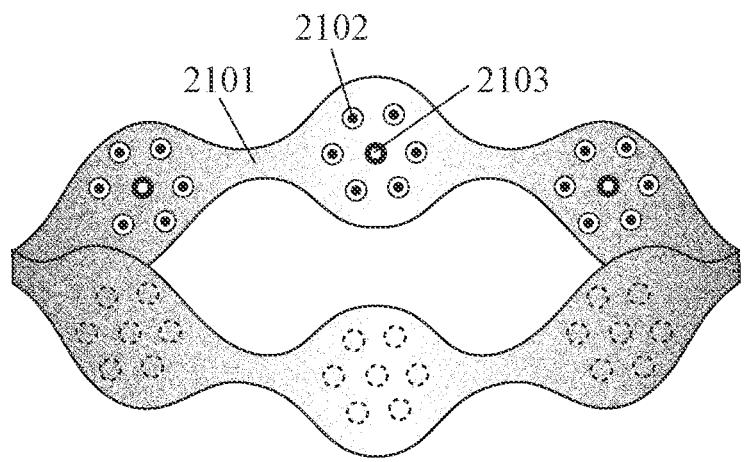
FIG. 21 shows a device with sinusoidal undulations in width.

FIG. 21 shows another example of how this invention can be embodied in a wearable band for measuring a person's hydration level. This wearable band has sinusoidal undulations in width, wherein light emitters and/or light receivers are located on the wider portions of band undulations. This example is a wearable band for measuring a person's hydration level comprising: a wearable band which is configured to span at least half of the circumference of a person's wrist and/or arm, wherein the wearable band has undulations in width; a plurality of light emitters, wherein the light emitters are located on the wider portions of wearable band undulations, and wherein the light emitters emit light toward the surface of the person's wrist and/or arm; a plurality of light receivers, wherein the light emitters are located on the wider portions of wearable band undulations, and wherein the light receivers receive light from the light emitters after this light has interacted with the person's body, and wherein the spectra of light rays received by light receivers are analyzed in order to measure the person's hydration level.

With respect to specific components, the wearable band shown in FIG. 21 includes: undulating wearable band 2101; a plurality of light emitters (including 2102); and a plurality of light receivers (including 2013). In an example, an undulating wearable band can have sinusoidal undulations in width. In the example shown here, a wearable band has six sinusoidal undulations in width. In an example, a wearable band can have an even number of undulations in width. In an example, a wearable band can have 4, 6, or 8 undulations in width. In an example, a wearable band can have an odd number of undulations in width. In an example, a wearable band can have 5, 7, or 9 undulations in width. In an example, an undulating band can have ten or more undulations in width. In an example, an undulating band can have narrow portions with a first width and wide portions with a second width, wherein the second width is at least 50% larger than the first width. In an example, the second width can be at least twice the first width. In an example, width undulations can span only a portion of the circumference of a wearable band.

In an example, a wide portion of an undulating wearable band can have a single light emitter or light receiver. In an example, a wide portion of an undulating wearable band can have both a light emitter and a light receiver. In an example, a wide portion of an undulating wearable band can have a circular or polygonal array of light emitters around a central light receiver. In an example, an undulating wearable band can comprise electromagnetic energy pathways which connect light emitters and light receivers around its circumference. In an example, an undulating wearable band can further comprise a data processor, data transceiver, and battery. In an example, an undulating wearable band can further comprise an electronic display. In an example, an undulating band can function as the band for a smart watch. Relevant example variations discussed in other places in this disclosure or in priority-linked disclosures can also be applied to this example.

Figure 22:
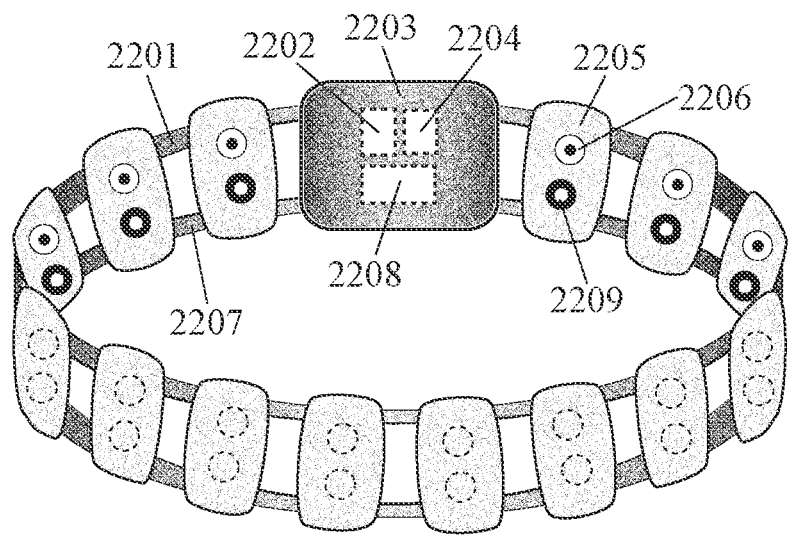
FIGS. 22 and 23 show a device with secondary electronics housings which are interconnected by parallel bands.
Figure 23:
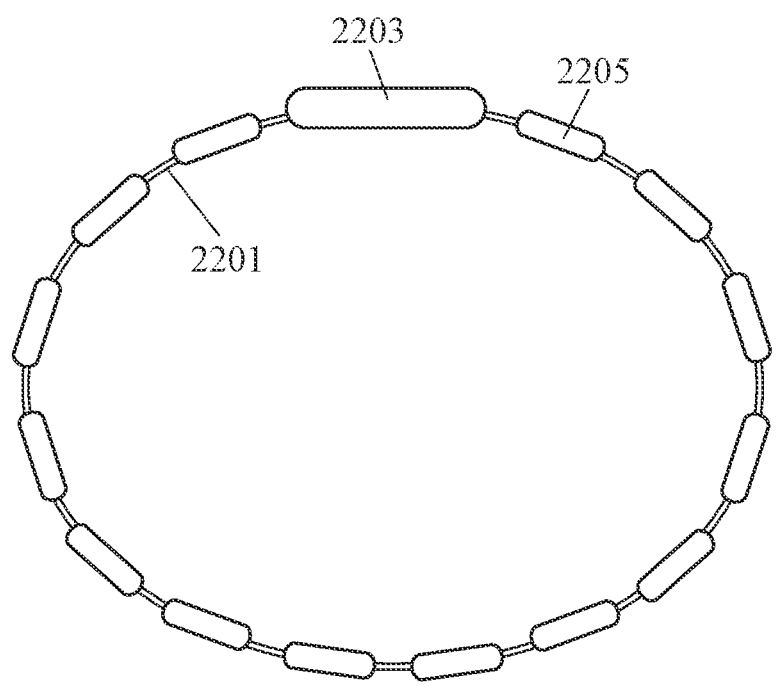
Figure 24:
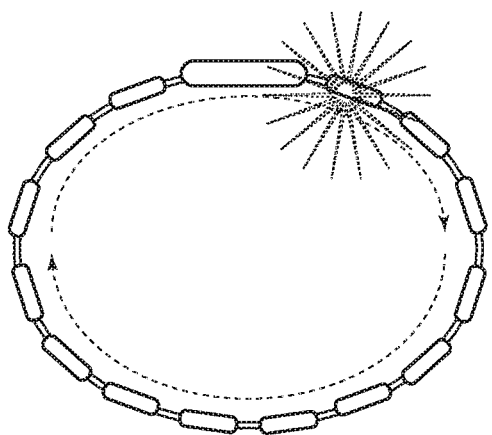
FIGS. 24 through 29 show six sequential views of a device with a circumferential emitter array of secondary electronics housings.
Figure 25:
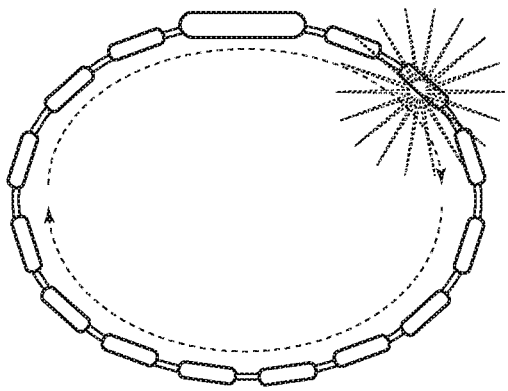
Figure 26:
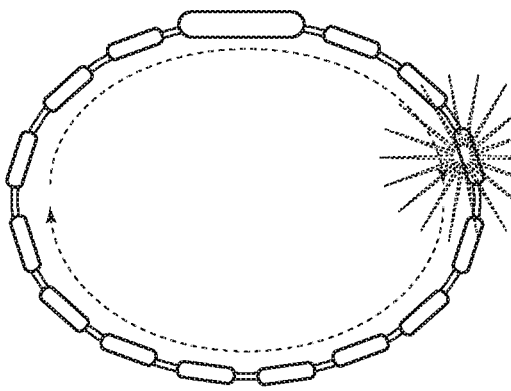
Figure 27:
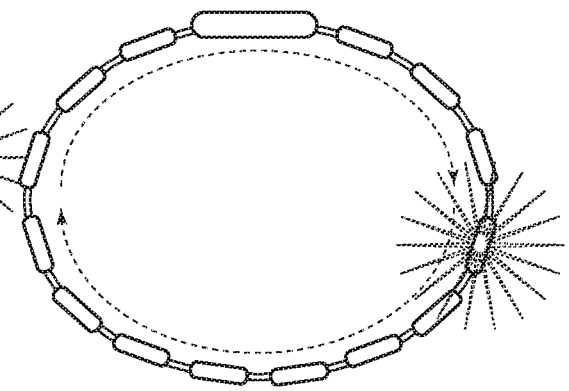
Figure 28:
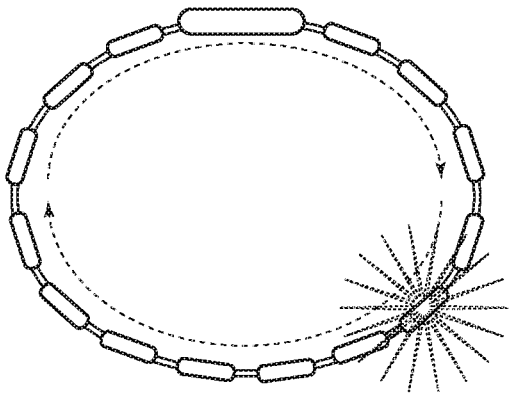
Figure 29:
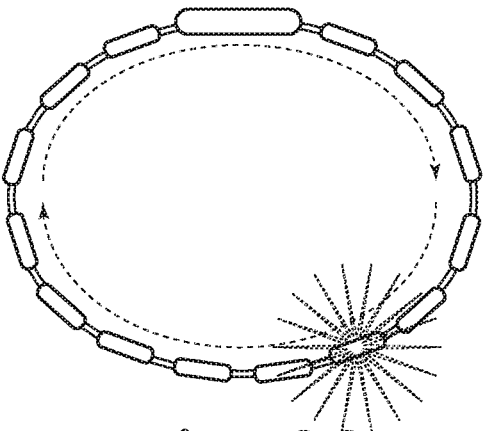

FIGS. 22 and 23 show a wearable band (such as a smart watch) that is similar to the one shown in FIGS. 13 and 14 except that pairs of electronic housings are connected by two bands with a gap between them. This can allow for more airflow to skin under the wearable band. FIG. 22 shows an opaque, oblique, side view of this wearable band (e.g. smart watch). FIG. 23 shows a top-down, outline view of this wearable band (e.g. smart watch). This wearable band (e.g. smart watch) has a primary electronics housing on the dorsal surface on a person's wrist and/or arm; and a circumferential or annular series of secondary electronics housings. The circumferential or annular series of secondary electronics housings are each connected to each other by two flexible members which are separated from each other by a gap. Flexible members are selected from the group consisting of: bands, straps, strips, swatches, wires, cords, threads, joints, and chain links. These housings and flexible members form an arcuate band which spans at least half of the circumference of a person's wrist and/or arm. In this example, each secondary electronics housing has both a light emitter and a light receiver, forming a circumferential or annular array of light emitters and light receivers. This wearable band can function as a smart watch with hydration sensors on housings distributed around the watch band.

FIGS. 22 and 23 show a wearable band (such as a smart watch) for measuring a person's hydration level comprising: (a) a primary electronics housing which is configured to be worn on the dorsal surface of a person's wrist and/or arm; (b) a circumferential or annular series of secondary electronics housings, wherein a secondary electronics housing has both a light emitter and a light receiver, wherein the light emitter emits light toward the surface of the person's wrist and/or arm, wherein the light receiver receives light from the light emitter after this light has interacted with the person's body, and wherein the spectrum of light received by a light receiver is analyzed in order to measure the person's hydration level; and (c) a circumferential or annular series of pairs of flexible members; wherein a pair of flexible members separated from each other by a gap connect a pair of electronics housings; wherein the flexible members are selected from the group consisting of bands, straps, strips, swatches, wires, cords, threads, joints, and chain links; and wherein the flexible members connect the primary electronics housing and the secondary electronics housings into an arcuate wearable band which spans at least half of the circumference of a person's wrist and/or arm.

With respect to specific components, the wearable band (e.g. smart watch) shown in FIGS. 22 and 23 comprises: a primary electronics housing (2203); secondary electronics housings (such as 2205); light emitters (such as 2206); light receivers (such as 2209); paired flexible members (such as 2201 and 2207) which connect pairs of housings; a data processor (2202); a data transceiver (2204); and a battery (2208). In an example, the primary electronics housing can include a watch display on its outward-facing surface so that this wearable band can function as a smart watch. In an example, the series of flexible members and secondary electronics housings can function as a watch band. In an example, a primary electronics housing can be larger than a secondary electronics housing. In an example, light from a circumferential or annular array of light emitters can interact with the person's body by reflecting off body tissue and/or by being transmitted through body tissue. In an example, such reflection or transmission changes the spectrum of light rays and these changes in light spectra can be used to measure the person's hydration level. Relevant example variations discussed in other places in this disclosure or in priority-linked disclosures can also be applied to this example.

FIGS. 24 through 29 show six sequential, top-down, outline views of a wearable band with a circumferential or annular array of light emitters on secondary electronics housings, such as the band introduced in FIGS. 13 and 14, as these light emitters are activated in a clockwise sequence. The first six time periods in the sequence are shown in FIGS. 24 through 29, but it is to be understood that this sequence can continue around the entire circumference of the wearable band. Sequential activation (i.e. lighting) of light emitters in a circumferential or annular array can enable measurement of body hydration at different tissue locations and depths within a cross-section of a person's finger, wrist, and/or arm.

A band with a circumferential or annular array of light emitters can have important advantages over a band that just has a light emitter and light receiver in a particular location, such as on the back of the enclosure for a smart watch display. For example, if a wearable band is shifted or rotated with respect to a person's finger, wrist, and/or arm, then at least some subset of the light emitters and/or receivers in a circumferential or annular array will remain in contact with the person's body even if there are gaps between the band and body at some locations. Also, if a particular tissue area or anatomical feature is of particular importance for body hydration measurement, then at least one light emitter and/or light receiver will be near this area or feature even if the band rotates. Also, sequential activation of a circumferential or annular array of light emitters can enable creation of a two-dimensional image of analyte concentration in a cross-section of a person's finger, wrist, and/or arm. Such an image can be useful for diagnostic and monitoring purposes. Relevant example variations discussed in other places in this disclosure or in priority-linked disclosures can also be applied to this example.

FIG. 30 shows how "proximal-to-distal" and "circumferential" axes can be defined on a wearable band, but does not show a complete embodiment of this invention. FIG. 30 shows how the term "proximal-to-distal" can be defined with respect to a band which is worn on a person's wrist, finger, or ankle. The term "proximal" when applied to a person's wrist or finger means "closer to the person's shoulder when the arm is extended" and the term "distal" means "farther from the person's shoulder when the arm is extended." The term "proximal" when applied to a person's ankle means "closer to the person's hip when the leg is extended" and the term "distal" means "farther from the person's hip when the leg is extended." A proximal-to-distal axis can be defined for a band worn on the wrist, finger, or ankle using these definitions of proximal and distal. The left side of FIG. 30 shows a straight-line proximal-to-distal axis (labeled with the words "proximal" and "distal") for band 3001 which can be worn on a person's wrist, finger, or ankle.

FIG. 30 also shows how the term "circumferential" can be defined with respect to a band which is worn on a person's wrist, finger, or ankle. Circumferential refers to the cross-sectional perimeter of the part of the body (e.g. wrist, finger, or ankle) around which the band is worn. In an example, this cross-sectional perimeter can be perpendicular to the central proximal-to-distal axis of the part of the body (e.g. wrist, finger, or ankle). The upper portion of FIG. 30 shows an arcuate circumferential axis (labeled with the word "circumferential") for band 3001 which is worn on a person's wrist, finger, or ankle. In an example, movement in one direction or the other along the circumferential axis can be referred to as clockwise or counter-clockwise movement or, alternatively, as movement to the right or to the left.

FIG. 30 also shows how compass (or polar) or clock-hour coordinates be defined around a band's circumferential axis. These compass or clock-hour coordinates are shown in a circle around band 3001. Compass coordinates are shown in degrees, from 0 degrees, around the full circle, and then back to 0 degrees (which can also be called 360 degrees). Clock-hour coordinates are shown in hours, from 12 o'clock, around the full circle, and then back to 12 o'clock. In an example, the 0-degree (or 12 o'clock) location on the circumferential axis of a band can be the central frontal (or ventral or anterior) location on a wrist (around which a traditional watch face would be usually centered) or the central frontal (or ventral or anterior) location on an ankle.

FIG. 31 shows an example of an arcuate wearable device for measuring a person's hydration level with a single energy emitter and a single energy receiver which are both along the same circumferential line of a band. Specifically, FIG. 31 shows an oblique-side-perspective view of an arcuate wearable device for measuring body hydration level comprising: arcuate band 3101 which is configured to span (some or all of) the circumferential perimeter of a part of a person's body (such as a wrist, arm, finger, ankle, and/or leg); energy emitter 3106 (identified with a plus sign) which is configured to emit energy toward the part of the person's body; energy receiver 3107 (identified with a negative sign) which is configured to receive energy from the energy emitter after that energy has passed through and/or been reflected from the part of the person's body; data processor 3104 which receives data from the energy receiver which is analyzed in order to measure the person's body hydration level; energy source 3103 which provides energy to the energy emitter and/or to the data processor; and data transmitter 3105 which transmits data from the data processor to a remote device and/or remote location. This example further comprises another (type of) biometric or environmental sensor 3102.

In the example in FIG. 31, there is a single energy emitter 3106 and a single energy receiver 3107 which are circumferentially or annularly aligned; both are located along the same circumferential line of band 3101. In this example, energy emitter 3106 is between the 330-degree and 0-degree locations and energy receiver 3107 is between the 0-degree and 30-degree locations. In this example, energy emitter 3106 and energy receiver 3107 are separated by less than 1" or by less than 60 degrees of the band circumference. In another example, the locations of the energy emitter and the energy receiver can be reversed. In another example, an energy emitter, an energy receiver, or both can be part of a housing which is attached to the band, rather than part of the band itself. Other example variations and component elaborations discussed elsewhere in this disclosure (or in other disclosures within the priority-linked family) can also be applied to this example.

FIG. 32 shows an example of this invention with a single energy emitter and a single energy receiver which are both along the same proximal-to-distal line of a band. In this example, the energy emitter is more proximal than the energy receiver. In another example, the locations of the energy emitter and the energy receiver can be reversed.

Specifically, FIG. 32 shows an oblique-side-perspective view of an arcuate wearable device for measuring body hydration level comprising: arcuate band 3201 which is configured to span (some or all of) the circumferential perimeter of a part of a person's body (such as a wrist, arm, finger, ankle, and/or leg); energy emitter 3206 (identified with a plus sign) which is configured to emit energy toward the part of the person's body; energy receiver 3207 (identified with a negative sign) which is configured to receive energy from the energy emitter after that energy has passed through and/or been reflected from the part of the person's body; data processor 3204 which receives data from the energy receiver which is analyzed in order to measure the person's body hydration level; energy source 3203 which provides energy to the energy emitter and/or to the data processor; and data transmitter 3205 which transmits data from the data processor to a remote device and/or remote location.

This example further comprises another (type of) biometric or environmental sensor 3202. In another example, an energy emitter and/or an energy receiver can be part of a housing which is attached to the band. Other example variations and component elaborations discussed elsewhere in this disclosure (or in other disclosures within the priority-linked family) can also be applied to this example.

FIG. 33 shows an example of this invention with a single energy emitter and two energy receivers which are all along the same circumferential line of a wearable arcuate band. In this example, the energy emitter is located between the two energy receivers. In this example, the energy emitter is located midway between the two energy receivers.

Specifically, FIG. 33 shows an oblique-side-perspective view of an arcuate wearable device for measuring body hydration level comprising: arcuate band 3301 which is configured to span (some or all of) the circumferential perimeter of a part of a person's body (such as a wrist, arm, finger, ankle, and/or leg); energy emitter 3307 (identified with a plus sign) which is configured to emit energy toward the part of the person's body; first energy receiver 3306 (identified with a negative sign) which is configured to receive energy from the energy emitter after that energy has passed through and/or been reflected from the part of the person's body; second energy receiver 3308 (identified with a negative sign) which is configured to receive energy from the energy emitter after that energy has passed through and/or been reflected from the part of the person's body, wherein the energy emitter is located between the first energy receiver and the second energy receiver; data processor 3304 which receives data from the energy receivers which is analyzed in order to measure the person's body hydration level; energy source 3303 which provides energy to the energy emitter and/or to the data processor; and data transmitter 3305 which transmits data from the data processor to a remote device and/or remote location.

This example further comprises another (type of) biometric or environmental sensor 3302. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 34 shows an example of this invention with two energy emitters and a single energy receiver which are all along the same circumferential line of a wearable arcuate band. In this example, the energy receiver is located between the two energy emitters. In this example, the energy receiver is located midway between the two energy emitters. In an example, different energy emitters can emit energy at different times and/or in a chronological sequence.

Specifically, FIG. 34 shows an oblique-side-perspective view of an arcuate wearable device for measuring body hydration level comprising: arcuate band 3401 which is configured to span (some or all of) the circumferential perimeter of a part of a person's body (such as a wrist, arm, finger, ankle, and/or leg); first energy emitter 3406 (identified with a plus sign) which is configured to emit energy toward the part of the person's body; second energy emitter 3408 (identified with a plus sign) which is configured to emit energy toward the part of the person's body; energy receiver 3407 (identified with a negative sign) which is configured to receive energy from the first energy emitter and/or the second energy emitter after that energy has passed through and/or been reflected from the part of the person's body, wherein the energy receiver is located between the first energy emitter and the second energy emitter; data processor 3404 which receives data from the energy receiver which is analyzed in order to measure the person's body hydration level; energy source 3403 which provides energy to the energy emitter and/or to the data processor; and data transmitter 3405 which transmits data from the data processor to a remote device and/or remote location.

This example further comprises another (type of) biometric or environmental sensor 3402. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 35 shows an example of this invention with a single energy emitter and two energy receivers along the same circumferential line of a wearable arcuate band, wherein the energy emitter is to one side (e.g. clockwise or clockwise-clockwise, or to the right or left) of the two energy receivers.

Specifically, FIG. 35 shows an oblique-side-perspective view of an arcuate wearable device for measuring body hydration level comprising: arcuate band 3501 which is configured to span (some or all of) the circumferential perimeter of a part of a person's body (such as a wrist, arm, finger, ankle, and/or leg); energy emitter 3506 (identified with a plus sign) which is configured to emit energy toward the part of the person's body; first energy receiver 3507 (identified with a negative sign) which is configured to receive energy from the energy emitter after that energy has passed through and/or been reflected from the part of the person's body; second energy receiver 3508 (identified with a negative sign) which is configured to receive energy from the energy emitter after that energy has passed through and/or been reflected from the part of the person's body, wherein the energy emitter is to one side (e.g. clockwise or counter-clockwise, or to the right or left) of the first energy receiver and the second energy receiver; data processor 3504 which receives data from the energy receivers which is analyzed in order to measure the person's body hydration level; energy source 3503 which provides energy to the energy emitter and/or to the data processor; and data transmitter 3505 which transmits data from the data processor to a remote device and/or remote location.

This example further comprises another (type of) biometric or environmental sensor 3502. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 36 shows an example of this invention with a single energy receiver and two energy emitters along the same circumferential line of a wearable arcuate band, wherein the energy receiver is to one side (e.g. clockwise or clockwise-clockwise, or to the right or left) of the two energy emitters. In an example, different energy emitters can emit energy at different times and/or in a chronological sequence.

Specifically, FIG. 36 shows an oblique-side-perspective view of an arcuate wearable device for measuring body hydration level comprising: arcuate band 3601 which is configured to span (some or all of) the circumferential perimeter of a part of a person's body (such as a wrist, arm, finger, ankle, and/or leg); first energy emitter 3607 (identified with a plus sign) which is configured to emit energy toward the part of the person's body; second energy emitter 3608 (identified with a plus sign) which is configured to emit energy toward the part of the person's body; energy receiver 3606 (identified with a negative sign) which is configured to receive energy from the first energy emitter and/or the second energy emitter after that energy has passed through and/or been reflected from the part of the person's body, wherein the energy receiver is to one side (e.g. clockwise or counter-clockwise, or to the right or left) of the first energy emitter and the second energy emitter; data processor 3604 which receives data from the energy receiver which is analyzed in order to measure the person's body hydration level; energy source 3603 which provides energy to the energy emitter and/or to the data processor; and data transmitter 3605 which transmits data from the data processor to a remote device and/or remote location.

This example further comprises another (type of) biometric or environmental sensor 3602. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 37 shows an example of this invention with a single central energy emitter and a plurality of energy receivers configured around the central energy emitter. In this example, energy receivers are configured in a polygonal (or approximately circular) array around the central energy emitter. In this example, energy receivers are configured in a rectangular array around the central energy emitter. In this example, the energy receivers comprise the vertexes of a polygonal (or approximately circular) array. In this example, the energy receivers comprise the vertexes of a rectangular array.

Specifically, FIG. 37 shows an oblique-side-perspective view of an arcuate wearable device for measuring body hydration level comprising: an arcuate band 3701 which is configured to span (some or all of) the circumferential perimeter of a part of a person's body (such as a wrist, arm, finger, ankle, and/or leg); a central energy emitter 3708 (identified with a plus sign) which is configured to emit energy toward the part of the person's body; a plurality of energy receivers 3706, 3707, 3709, and 3710 (identified with negative signs) which are configured to receive energy from the energy emitter after that energy has passed through and/or been reflected from the part of the person's body, wherein this plurality of energy receivers is configured in a (polygonal or circular) array around the central energy emitter; a data processor 3704 which receives data from the energy receivers which is analyzed in order to measure the person's body hydration level; an energy source 3703 which provides energy to the energy emitter and/or to the data processor; and a data transmitter 3705 which transmits data from the data processor to a remote device and/or remote location.

This example further comprises another (type of) biometric or environmental sensor 3702. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 38 shows an example of this invention with a single central energy receiver and a plurality of energy emitters configured around the central energy receiver. In this example, energy emitters are configured in a polygonal (or approximately circular) array around the central energy receiver. In this example, energy emitters are configured in a rectangular array around the central energy receiver. In this example, the energy emitters comprise the vertexes of a polygonal (or approximately circular) array. In this example, the energy emitters comprise the vertexes of a rectangular array. In an example, different energy emitters can emit energy at different times and/or in a chronological sequence.

Specifically, FIG. 38 shows an oblique-side-perspective view of an arcuate wearable device for measuring body hydration level comprising: an arcuate band 3801 which is configured to span (some or all of) the circumferential perimeter of a part of a person's body (such as a wrist, arm, finger, ankle, and/or leg); a plurality of energy emitters 3806, 3807, 3809, and 3810 (identified with positive signs) which are configured to emit energy toward the part of the person's body; a central energy receiver 3808 (identified with a negative sign) which is configured to receive energy from the energy emitters after that energy has passed through and/or been reflected from the part of the person's body, wherein the plurality of energy emitters is configured in a (polygonal or circular) array around the central energy receiver; a data processor 3804 which receives data from the energy receiver which is analyzed in order to measure the person's body hydration level; an energy source 3803 which provides energy to the energy emitter and/or to the data processor; and a data transmitter 3805 which transmits data from the data processor to a remote device and/or remote location.

This example further comprises another (type of) biometric or environmental sensor 3802. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 39 shows an example of this invention with a single central energy emitter and a plurality of energy receivers configured around the central energy emitter. In this example, energy receivers are configured in a circular (approximately-circular octagonal) array around the central energy emitter. In this example, the energy receivers comprise the vertexes of an (approximately-circular octagonal) array.

Specifically, FIG. 39 shows an oblique-side-perspective view of an arcuate wearable device for measuring body hydration level comprising: an arcuate band 3901 which is configured to span (some or all of) the circumferential perimeter of a part of a person's body (such as a wrist, arm, finger, ankle, and/or leg); a central energy emitter 3909 (identified with a plus sign) which is configured to emit energy toward the part of the person's body; a plurality of energy receivers 3906, 3907, 3908, 3910, 3911, 3912, 3913, and 3914 (identified with negative signs) which are configured to receive energy from the energy emitter after that energy has passed through and/or been reflected from the part of the person's body, wherein the plurality of energy receivers is configured in a circular (or approximately-circular polygonal) array around the central energy emitter; a data processor 3904 which receives data from the energy receivers which is analyzed in order to measure the person's body hydration level; an energy source 3903 which provides energy to the energy emitter and/or to the data processor; and a data transmitter 3905 which transmits data from the data processor to a remote device and/or remote location.

This example further comprises another (type of) biometric or environmental sensor 3902. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 40 shows an example of this invention with a central energy receiver and a plurality of energy emitters configured around the central energy receiver. In this example, energy emitters are configured in a circular (approximately-circular octagonal) array around the central energy receiver. In this example, the energy emitters comprise the vertexes of an approximately-circular octagonal array. In an example, different energy emitters can emit energy at different times and/or in a chronological sequence.

Specifically, FIG. 40 shows an oblique-side-perspective view of an arcuate wearable device for measuring body hydration level comprising: an arcuate band 4001 which is configured to span (some or all of) the circumferential perimeter of a part of a person's body (such as a wrist, arm, finger, ankle, and/or leg); a plurality of energy emitters 4006, 4007, 4008, 4010, 4011, 4012, 4013, and 4014 (identified with plus signs) which are configured to emit energy toward the part of the person's body; a central energy receiver 4009 (identified with a negative sign) which is configured to receive energy from the energy emitters after that energy has passed through and/or been reflected from the part of the person's body, wherein the plurality of energy emitters is configured in a circular (or approximately-circular polygonal) array around the central energy receiver; a data processor 4004 which receives data from the energy receiver which is analyzed in order to measure the person's body hydration level; an energy source 4003 which provides energy to the energy emitter and/or to the data processor; and a data transmitter 4005 which transmits data from the data processor to a remote device and/or remote location.

This example further comprises another (type of) biometric or environmental sensor 4002. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 41 shows an example of this invention with a central energy emitter and a plurality of (more than four) energy receivers along the same circumferential line of a wearable arcuate band, wherein the central energy emitter is centrally located with respect to the energy receivers. In this example, there are eight energy receivers in total, four on each side of the central energy emitter. In this example, the energy receivers and the central energy emitter are evenly spaced around a portion of the circumference of a band. In this example, the energy receivers and the central energy emitter are each the same distance from the closest energy receiver or energy emitter.

Specifically, FIG. 41 shows an oblique-side-perspective view of an arcuate wearable device for measuring body hydration level comprising: arcuate band 4101 which is configured to span (some or all of) the circumferential perimeter of a part of a person's body (such as a wrist, arm, finger, ankle, and/or leg); central energy emitter 4110 (identified with a plus sign) which is configured to emit energy toward the part of the person's body; a plurality of (more than four) energy emitters 4106, 4107, 4108, 4109, 4111, 4112, 4113, and 4114 (identified with negative signs) which are configured to receive energy from the central energy emitter after that energy has passed through and/or been reflected from the part of the person's body, wherein the central energy emitter and the energy emitters are all along the same circumferential line of the band, and wherein the central energy emitter is centrally located with respect to the energy emitters; data processor 4104 which receives data from the energy receivers which is analyzed in order to measure the person's body hydration level; energy source 4103 which provides energy to the central energy emitter and/or to the data processor; and data transmitter 4105 which transmits data from the data processor to a remote device and/or remote location.

This example further comprises another (type of) biometric or environmental sensor 4102. In another example, one or more energy emitters and/or receivers can be part of a housing which is attached to the band instead of being part of the band itself. In an example, the central energy emitter and the energy receivers can be distributed around the circumference of a band, but not all be along the same circumferential line. Other example variations and component elaborations discussed elsewhere in this disclosure (or in other disclosures within the priority-linked family) can also be applied to this example.

FIG. 42 shows an example of this invention with a central energy receiver and a plurality of (more than four) energy emitters along the same circumferential line of a wearable arcuate band, wherein the central energy receiver is centrally located with respect to the energy emitters. In this example, there are eight energy emitters in total, four on each side of the central energy receiver. In this example, the energy emitters and the central energy receiver are evenly spaced around a portion of the circumference of a band. In this example, the energy emitters and the central energy receiver are each the same distance from the closest energy emitter or energy receiver. In an example, different energy emitters can emit energy at different times and/or in a chronological sequence.

Specifically, FIG. 42 shows an oblique-side-perspective view of an arcuate wearable device for measuring body hydration level comprising: arcuate band 4201 which is configured to span (some or all of) the circumferential perimeter of a part of a person's body (such as a wrist, arm, finger, ankle, and/or leg); a plurality of (more than four) energy emitters 4206, 4207, 4208, 4209, 4211, 4212, 4213, and 4214 (identified with plus signs) which are configured to emit energy toward the part of the person's body; a central energy receiver 4210 (identified with a negative sign) which is configured to receive energy from the energy emitters after that energy has passed through and/or been reflected from the part of the person's body, wherein the central energy receiver and the energy receivers are all along the same circumferential line of the band, and wherein the central energy receiver is centrally located with respect to the energy receivers; a data processor 4204 which receives data from the energy receiver which is analyzed in order to measure the person's body hydration level; an energy source 4203 which provides energy to the central energy emitter and/or to the data processor; and a data transmitter 4205 which transmits data from the data processor to a remote device and/or remote location.

This example further comprises another (type of) biometric or environmental sensor 4202. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 43 shows an example of this invention with a plurality of energy emitters and a plurality of energy receivers which are all along the same circumferential line of a wearable arcuate band. In this example, there are multiple pairs of energy emitters and energy receivers along the same circumferential line of a wearable arcuate band. In this example, there are at least two pairs of energy emitters and energy receivers along a circumferential line of a wearable arcuate band. In this example, there are four pairs of energy emitters and energy receivers along a circumferential line of a wearable arcuate band. In this example, there are alternating energy emitters and energy receivers along a circumferential line of a wearable arcuate band. In an example, different energy emitters can emit energy at different times and/or in a chronological sequence.

Specifically, FIG. 43 shows an oblique-side-perspective view of an arcuate wearable device for measuring body hydration level comprising: arcuate band 4301 which is configured to span (some or all of) the circumferential perimeter of a part of a person's body (such as a wrist, arm, finger, ankle, and/or leg); a plurality of energy emitters 4307, 4309, 4311, and 4313 (identified with plus signs) which are configured to emit energy toward the part of the person's body; a plurality of energy receivers 4306, 4308, 4310, 4312, and 4314 (identified with negative signs) which are configured to receive energy from the plurality of energy emitters after that energy has passed through and/or been reflected from the part of the person's body, wherein the energy emitters and the energy receivers are all along the same circumferential line of the band, and wherein the energy emitters and the energy receivers alternate sequentially along the circumferential line of the band; a data processor 4304 which receives data from the energy receivers which is analyzed in order to measure the person's body hydration level; an energy source 4303 which provides energy to the central energy emitter and/or to the data processor; and a data transmitter 4305 which transmits data from the data processor to a remote device and/or remote location.

FIG. 43 also shows an oblique-side-perspective view of an arcuate wearable device for measuring body hydration level comprising: arcuate band 4301 which is configured to span (some or all of) the circumferential perimeter of a part of a person's body (such as a wrist, arm, finger, ankle, and/or leg); a plurality of pairs of energy emitters 4307, 4309, 4311, and 4313 (identified with plus signs) and energy receivers 4306, 4308, 4310, and 4312 (identified with negative signs), wherein the energy emitters are configured to emit energy toward the part of the person's body, wherein the energy receivers receive energy from the plurality of energy emitters after that energy has passed through and/or been reflected from the part of the person's body, wherein the pairs of energy emitters and energy receivers are along the same circumferential line of the band; a data processor 4304 which receives data from the energy receivers which is analyzed in order to measure the person's body hydration level; an energy source 4303 which provides energy to the central energy emitter and/or to the data processor; and a data transmitter 4305 which transmits data from the data processor to a remote device and/or remote location.

This example further comprises another (type of) biometric or environmental sensor 4302. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 44 shows an example of this invention with a first plurality of energy emitters and energy receivers along a first circumferential line of a wearable arcuate band and a second plurality of energy emitters and energy receivers along a second circumferential line of the wearable arcuate band. In this example, there is a first set of multiple pairs of energy emitters and energy receivers along a first circumferential line of a wearable arcuate band and a second set of multiple pairs of energy emitters and energy receivers along a second circumferential line of a wearable arcuate band. In this example, there is a first set of alternating energy emitters and energy receivers along a first circumferential line of a wearable arcuate band and a second set of alternating energy emitters and energy receivers along a second circumferential line of a wearable arcuate band. In an example, different energy emitters can emit energy at different times and/or in a chronological sequence.

Specifically, FIG. 44 shows an oblique-side-perspective view of an arcuate wearable device for measuring body hydration level comprising: arcuate band 4401 which is configured to span (some or all of) the circumferential perimeter of a part of a person's body (such as a wrist, arm, finger, ankle, and/or leg); a first plurality of energy emitters 4407, 4409, 4411, and 4413 (identified with plus signs) and energy receivers 4406, 4408, 4410, 4412, and 4414 (identified with negative signs) along a first circumferential line of the arcuate band; a second plurality of energy emitters 4423, 4421, 4419, 4417, and 4415 (identified with plus signs) and energy receivers 4422, 4420, 4418, and 4416 (identified with negative signs) along a second circumferential line of the arcuate band, wherein energy emitters are configured to emit energy toward the part of the person's body, and wherein energy receivers are configured to receive energy from energy emitters after that energy has passed through and/or been reflected from the part of the person's body; a data processor 4404 which receives data from the energy receivers which is analyzed in order to measure the person's body hydration level; an energy source 4403 which provides energy to the energy emitters and/or to the data processor; and a data transmitter 4405 which transmits data from the data processor to a remote device and/or remote location.

This example further comprises another (type of) biometric or environmental sensor 4402. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 45 shows an example of this invention with a plurality of energy emitters along a first circumferential line of a wearable arcuate band and a plurality of energy receivers along a second circumferential line of the wearable arcuate band. In an example, different energy emitters can emit energy at different times and/or in a chronological sequence.

Specifically, FIG. 45 shows an oblique-side-perspective view of an arcuate wearable device for measuring body hydration level comprising: arcuate band 4501 which is configured to span (some or all of) the circumferential perimeter of a part of a person's body (such as a wrist, arm, finger, ankle, and/or leg); a plurality of energy emitters 4506, 4507, 4508, 4509, 4510, 4511, 4512, 4513, and 4514 (identified with plus signs) along a first circumferential line of the arcuate band, wherein energy emitters are configured to emit energy toward the part of the person's body; a plurality of energy receivers 4523, 4522, 4521, 4520, 4519, 4518, 4517, 4516, and 4515 (identified with negative signs) along a second circumferential line of the arcuate band, wherein energy receivers are configured to receive energy from energy emitters after that energy has passed through and/or been reflected from the part of the person's body; a data processor 4504 which receives data from the energy receivers which is analyzed in order to measure the person's body hydration level; an energy source 4503 which provides energy to the energy emitters and/or to the data processor; and a data transmitter 4505 which transmits data from the data processor to a remote device and/or remote location.

This example further comprises another (type of) biometric or environmental sensor 4502. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 46 shows an example of this invention comprising: a single energy emitter and a single energy receiver which are both located along the same circumferential line of an arcuate band; and an energy barrier around the energy receiver. The energy barrier reduces energy transmission from the energy emitter to the energy receiver apart from energy transmission through body tissue. In this example, the energy barrier is circular and fully encircles the energy receiver. In examples wherein the energy which is emitted and received is light energy, then the energy barrier can be opaque. In an example, an energy barrier can be made from opaque compressible material or an opaque inflatable member.

Specifically, FIG. 46 shows an oblique-side-perspective view of an arcuate wearable device for measuring body hydration level comprising: arcuate band 4601 which is configured to span (some or all of) the circumferential perimeter of a part of a person's body (such as a wrist, arm, finger, ankle, and/or leg); energy emitter 4606 (identified with a plus sign) which is configured to emit energy toward the part of the person's body; energy receiver 4607 (identified with a negative sign) which is configured to receive energy from the energy emitter after that energy has passed through and/or been reflected from the part of the person's body; energy barrier 4608 between the energy emitter and the energy receiver, wherein the energy barrier is configured to reduce energy transmission from the energy emitter to the energy receiver apart from energy transmission through the person's body and wherein the energy barrier encircles the energy receiver; data processor 4604 which receives data from the energy receiver which is analyzed in order to measure the person's body hydration level; energy source 4603 which provides energy to the energy emitter and/or to the data processor; and data transmitter 4605 which transmits data from the data processor to a remote device and/or remote location.

This example further comprises another (type of) biometric or environmental sensor 4602. In another example, an energy emitter, an energy receiver, or both can be part of a housing which is attached to the band, rather than part of the band itself. Other example variations and component elaborations discussed elsewhere in this disclosure (or in other disclosures within the priority-linked family) can also be applied to this example.

FIG. 47 shows an example of this invention comprising: a single energy emitter and a single energy receiver which are both located along the same circumferential line of an arcuate band; an energy barrier around the energy emitter, and an energy barrier around the energy receiver. The energy barriers reduce energy transmission from the energy emitter to the energy receiver apart from energy transmission through body tissue. In this example, the energy barriers are circular. In examples wherein the energy which is emitted and received is light energy, energy barriers can be opaque. In an example, energy barriers can be made from opaque compressible material or opaque inflatable members.

Specifically, FIG. 47 shows an oblique-side-perspective view of an arcuate wearable device for measuring body hydration level comprising: arcuate band 4701 which is configured to span (some or all of) the circumferential perimeter of a part of a person's body (such as a wrist, arm, finger, ankle, and/or leg); energy emitter 4707 (identified with a plus sign) which is configured to emit energy toward the part of the person's body; energy receiver 4708 (identified with a negative sign) which is configured to receive energy from the energy emitter after that energy has passed through and/or been reflected from the part of the person's body; first compressible energy barrier 4706 around the energy emitter; and second compressible energy barrier 4709 around the energy receiver; data processor 4704 which receives data from the energy receiver which is analyzed in order to measure the person's body hydration level; energy source 4703 which provides energy to the energy emitter and/or to the data processor; and data transmitter 4705 which transmits data from the data processor to a remote device and/or remote location.

This example further comprises another (type of) biometric or environmental sensor 4702. In another example, an energy emitter, an energy receiver, or both can be part of a housing which is attached to the band, rather than part of the band itself. Other example variations and component elaborations discussed elsewhere in this disclosure (or in other disclosures within the priority-linked family) can also be applied to this example.

FIG. 48 shows an example of this invention comprising a single energy emitter and a single energy receiver (which are both located along the same circumferential line of an arcuate band) and a proximal-to-distal energy barrier between them. The energy barrier reduces energy transmission from the energy emitter to the energy receiver apart from energy transmission through body tissue. In this example, the energy barrier is linear and midway between the energy emitter and the energy receiver. In examples wherein the energy which is emitted and received is light energy, then the energy barrier can be opaque. In an example, an energy barrier can be made from opaque compressible material or an opaque inflatable member.

Specifically, FIG. 48 shows an oblique-side-perspective view of an arcuate wearable device for measuring body hydration level comprising: arcuate band 4801 which is configured to span (some or all of) the circumferential perimeter of a part of a person's body (such as a wrist, arm, finger, ankle, and/or leg); energy emitter 4806 (identified with a plus sign) which is configured to emit energy toward the part of the person's body; energy receiver 4807 (identified with a negative sign) which is configured to receive energy from the energy emitter after that energy has passed through and/or been reflected from the part of the person's body; a proximal-to-distal energy barrier 4808 (midway) between the energy emitter and the energy receiver; data processor 4804 which receives data from the energy receiver which is analyzed in order to measure the person's body hydration level; energy source 4803 which provides energy to the energy emitter and/or to the data processor; and data transmitter 4805 which transmits data from the data processor to a remote device and/or remote location.

This example further comprises another (type of) biometric or environmental sensor 4802. In another example, an energy emitter, an energy receiver, or both can be part of a housing which is attached to the band, rather than part of the band itself. Other example variations and component elaborations discussed elsewhere in this disclosure (or in other disclosures within the priority-linked family) can also be applied to this example.

FIG. 49 shows an example of this invention comprising a single energy emitter and a single energy receiver (which are both located along the same circumferential line of an arcuate band) and three proximal-to-distal energy barriers. In this example, there is a first energy barrier between the emitter and receiver, a second energy barrier to the left of the emitter and receiver, and a third energy barrier to the right of the emitter and receiver. In an example, energy barriers can be made from opaque compressible material or opaque inflatable members. In this example, each of the three energy barriers is proximal-to-distal and linear.

Specifically, FIG. 49 shows an oblique-side-perspective view of an arcuate wearable device for measuring body hydration level comprising: arcuate band 4901 which is configured to span (some or all of) the circumferential perimeter of a part of a person's body (such as a wrist, arm, finger, ankle, and/or leg); an energy emitter 4907 (identified with a plus sign) which is configured to emit energy toward the part of the person's body; an energy receiver 4909 (identified with a negative sign) which is configured to receive energy from the energy emitter after that energy has passed through and/or been reflected from the part of the person's body; a first energy barrier 4906 between the energy emitter and the energy receiver; a second energy barrier 4908 to the left of (or counter-clockwise from) the energy emitter and the energy receiver; a third energy barrier 4910 to the right of (or clockwise from) the energy emitter and the energy receiver; a data processor 4904 which receives data from the energy receiver which is analyzed in order to measure the person's body hydration level; an energy source 4903 which provides energy to the energy emitter and/or to the data processor; and a data transmitter 4905 which transmits data from the data processor to a remote device and/or remote location.

This example further comprises another (type of) biometric or environmental sensor 4902. In another example, an energy emitter, an energy receiver, or both can be part of a housing which is attached to the band, rather than part of the band itself. Other example variations and component elaborations discussed elsewhere in this disclosure (or in other disclosures within the priority-linked family) can also be applied to this example.

FIG. 50 shows an example of this invention with a single energy emitter, two energy receivers, and two energy barriers (one surrounding each energy receiver). In this example, the energy emitter is located between the two energy receivers. In this example, the energy emitter is located midway between the two energy receivers. The energy barriers reduce energy transmission from the energy emitter to the energy receiver apart from energy transmission through body tissue. In this example, the energy barriers are circular. In an example, the energy barriers can be made from opaque compressible material or opaque inflatable members.

Specifically, FIG. 50 shows an oblique-side-perspective view of an arcuate wearable device for measuring body hydration level comprising: arcuate band 5001 which is configured to span (some or all of) the circumferential perimeter of a part of a person's body (such as a wrist, arm, finger, ankle, and/or leg); energy emitter 5008 (identified with a plus sign) which is configured to emit energy toward the part of the person's body; first energy receiver 5007 (identified with a negative sign) which is configured to receive energy from the energy emitter after that energy has passed through and/or been reflected from the part of the person's body; second energy receiver 5009 (identified with a negative sign) which is configured to receive energy from the energy emitter after that energy has passed through and/or been reflected from the part of the person's body, wherein the energy emitter is located between the first energy receiver and the second energy receiver; first energy barrier 5006 around the first energy receiver; second energy barrier 5010 around the second energy receiver; data processor 5004 which receives data from the energy receivers which is analyzed in order to measure the person's body hydration level; energy source 5003 which provides energy to the energy emitter and/or to the data processor; and data transmitter 5005 which transmits data from the data processor to a remote device and/or remote location.

This example further comprises another (type of) biometric or environmental sensor 5002. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 51 shows an example of this invention with a single energy emitter, two energy receivers, and four proximal-to-distal energy barriers. In this example, the energy emitter is located between the two energy receivers. In this example, the energy emitter is located midway between the two energy receivers. The energy barriers reduce energy transmission from the energy emitter to the energy receiver apart from energy transmission through body tissue. In an example, the energy barriers can be made from opaque compressible material or opaque inflatable members.

Specifically, FIG. 51 shows an oblique-side-perspective view of an arcuate wearable device for measuring body hydration level comprising: arcuate band 5101 which is configured to span (some or all of) the circumferential perimeter of a part of a person's body (such as a wrist, arm, finger, ankle, and/or leg); an energy emitter 5109 (identified with a plus sign) which is configured to emit energy toward the part of the person's body; a first energy receiver 5107 (identified with a negative sign) which is configured to receive energy from the energy emitter after that energy has passed through and/or been reflected from the part of the person's body; a second energy receiver 5111 (identified with a negative sign) which is configured to receive energy from the energy emitter after that energy has passed through and/or been reflected from the part of the person's body, wherein the energy emitter is located between the first energy receiver and the second energy receiver; a first energy barrier 5106 to the left of the energy receivers and the energy emitter; a second energy barrier 5108 between the first energy receiver and the energy emitter; a third energy barrier 5110 between the second energy receiver and the energy emitter; a fourth energy barrier 5112 to the right of the energy receivers and the energy emitter; a data processor 5104 which receives data from the energy receivers which is analyzed in order to measure the person's body hydration level; an energy source 5103 which provides energy to the energy emitter and/or to the data processor; and a data transmitter 5105 which transmits data from the data processor to a remote device and/or remote location.

This example further comprises another (type of) biometric or environmental sensor 5102. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 52 shows an example of this invention with a single central energy emitter, a plurality of energy receivers around the central energy emitter, and an energy barrier between the central energy emitter and the plurality of energy receivers. In this example, energy receivers are configured in a circular (or approximately-circular polygonal) array around the central energy emitter. In this example, the energy barrier is arcuate. In this example, the energy barrier is circular. In an example wherein the type of energy that is emitted and received is light energy, the energy barrier can be opaque. In an example wherein the type of energy that is emitted and received is light energy, the energy barrier can be made from a compressible material (such as foam) or an inflated member (such as a balloon).

Specifically, FIG. 52 shows an oblique-side-perspective view of an arcuate wearable device for measuring body hydration level comprising: an arcuate band 5201 which is configured to span (some or all of) the circumferential perimeter of a part of a person's body (such as a wrist, arm, finger, ankle, and/or leg); a central energy emitter 5209 (identified with a plus sign) which is configured to emit energy toward the part of the person's body; a plurality of energy receivers 5206, 5207, 5208, 5210, 5211, 5212, 5213, and 5214 (identified with negative signs) which are configured to receive energy from the energy emitter after that energy has passed through and/or been reflected from the part of the person's body, wherein the plurality of energy receivers is configured in a circular (or approximately-circular polygonal) array around the central energy emitter; an energy barrier 5215 between the central energy emitter and the plurality of energy receivers; a data processor 5204 which receives data from the energy receivers which is analyzed in order to measure the person's body hydration level; an energy source 5203 which provides energy to the energy emitter and/or to the data processor; and a data transmitter 5205 which transmits data from the data processor to a remote device and/or remote location.

This example further comprises another (type of) biometric or environmental sensor 5202. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 53 shows an example of this invention with a single central energy emitter, a plurality of energy receivers configured around the central energy emitter, a first energy barrier between the central energy emitter and the plurality of energy receivers, and a second energy barrier around the plurality of energy receivers. In this example, energy receivers are configured in a circular (or approximately-circular polygonal) array around the central energy emitter. In this example, the energy barriers are arcuate. In this example, the energy barriers are circular. In an example wherein the type of energy that is emitted and received is light energy, the energy barriers can be opaque. In an example wherein the type of energy that is emitted and received is light energy, the energy barriers can be made from a compressible material (such as foam) or inflated members (such as balloons).

Specifically, FIG. 53 shows an oblique-side-perspective view of an arcuate wearable device for measuring body hydration level comprising: an arcuate band 5301 which is configured to span (some or all of) the circumferential perimeter of a part of a person's body (such as a wrist, arm, finger, ankle, and/or leg); a central energy emitter 5309 (identified with a plus sign) which is configured to emit energy toward the part of the person's body; a plurality of energy receivers 5306, 5307, 5308, 5310, 5311, 5312, 5313, and 5314 (identified with negative signs) which are configured to receive energy from the energy emitter after that energy has passed through and/or been reflected from the part of the person's body, wherein the plurality of energy receivers is configured in a circular (or approximately-circular polygonal) array around the central energy emitter; a first energy barrier 5315 between the central energy emitter and the plurality of energy receivers; a second energy barrier 5316 around the plurality of energy receivers; a data processor 5304 which receives data from the energy receivers which is analyzed in order to measure the person's body hydration level; an energy source 5303 which provides energy to the energy emitter and/or to the data processor; and a data transmitter 5305 which transmits data from the data processor to a remote device and/or remote location.

This example further comprises another (type of) biometric or environmental sensor 5302. In another example, one or more energy emitters and/or receivers can be part of a housing which is attached to the band instead of being part of the band itself. Other example variations and component elaborations discussed elsewhere in this disclosure (or in other disclosures within the priority-linked family) can also be applied to this example.

FIG. 54 shows an example of this invention with a first set of energy emitters and energy receivers along a first circumferential line of a wearable arcuate band, a second set of energy emitters and energy receivers along a second circumferential line of the wearable arcuate band, and a third set of energy emitters and energy receivers along a third circumferential line of the wearable arcuate band. In an example, these circumferential lines are parallel to each other. In an example, there are at least three energy emitters and/or energy receivers in each set. In an example, different energy emitters can emit energy at different times and/or in a chronological sequence.

In this example, energy emitters and energy receivers alternate along a circumferential line. In this example, there is an alternating sequence of energy emitters and energy receivers along a circumferential line. In this example, there are multiple triads of energy emitters and energy receivers in the first, second, and third sets, wherein a triad is aligned along the same proximal-to-distal line. In an example, there can be at least two energy emitters and two energy receivers in each set. In an example, there can be at least four energy emitters and four energy receivers in each set. In an example, energy emitters and energy receivers can be evenly-spaced within each set along a circumferential line. In this example, energy emitters and energy receivers can also be evenly-spaced between sets.

In this example, there is an arcuate array of energy emitters and energy receivers on an arcuate wearable band wherein this array has a circumferential axis (along which there are nine energy emitters and/or energy receivers) and a proximal-to-distal axis (along which there are three energy emitters and/or energy receivers). In an example, there can be an arcuate array of energy emitters and energy receivers on an arcuate wearable band wherein this array has a circumferential axis (along which there are at least three energy emitters and/or energy receivers) and a proximal-to-distal axis (along which there are at least two energy emitters and/or energy receivers).

In this example, there is an arcuate array of energy emitters and energy receivers on an arcuate wearable band wherein this array includes three parallel circumferential lines (along each of which there are nine energy emitters and/or energy receivers) and three parallel proximal-to-distal lines (along each of which there are three energy emitters and/or energy receivers). In an example, there can be an arcuate array of energy emitters and energy receivers on an arcuate wearable band wherein this array includes at least two parallel circumferential lines (along each of which there at least three energy emitters and/or energy receivers) and at least two parallel proximal-to-distal lines (along each of which there are at least two energy emitters and/or energy receivers).

Specifically, FIG. 54 shows an oblique-side-perspective view of an arcuate wearable device for measuring body hydration level comprising: arcuate band 5401 which is configured to span (some or all of) the circumferential perimeter of a part of a person's body (such as a wrist, arm, finger, ankle, and/or leg); a first set of three or more energy emitters (including 5409) and/or energy receivers (including 5408) along a first circumferential line of the arcuate band; a second set of three or more energy emitters (including 5407) and/or energy receivers (including 5410) along a second circumferential line of the arcuate band; a third set of three or more energy emitters (including 5411) and/or energy receivers (including 5406) along a third circumferential line of the arcuate band, wherein energy emitters are configured to emit energy toward the part of the person's body, and wherein energy receivers are configured to receive energy from energy emitters after that energy has passed through and/or been reflected from the part of the person's body; a data processor 5404 which receives data from the energy receivers which is analyzed in order to measure the person's body hydration level; an energy source 5403 which provides energy to the central energy emitter and/or to the data processor; and a data transmitter 5405 which transmits data from the data processor to a remote device and/or remote location.

This example further comprises another (type of) biometric or environmental sensor 5402. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 55 shows an example of this invention with a first set of energy emitters and energy receivers along a first circumferential line of a wearable arcuate band, a second set of energy emitters and energy receivers along a second circumferential line of the wearable arcuate band, a third set of energy emitters and energy receivers along a third circumferential line of the wearable arcuate band, a plurality of circumferential or annular energy barriers between sets, and a plurality of proximal-to-distal energy barriers between energy emitters and/or energy receivers within sets. In an example in which the type of energy emitted and received is light energy, energy barriers can be opaque and/or compressible. In an example, different energy emitters can emit energy at different times and/or in a chronological sequence.

In this example, energy emitters and energy receivers alternate along a circumferential line. In this example, there is an alternating sequence of energy emitters and energy receivers along a circumferential line. In this example, there are multiple triads of energy emitters and energy receivers in the first, second, and third sets, wherein each triad is aligned along the same proximal-to-distal lines. In an example, there can be at least two energy emitters and two energy receivers in each set. In an example, there can be at least four energy emitters and four energy receivers in each set. In an example, energy emitters and energy receivers can be evenly-spaced within each set along a circumferential line. In this example, energy emitters and energy receivers can also be evenly-spaced between sets.

In this example, there is an arcuate array of energy emitters and energy receivers on an arcuate wearable band wherein this array has a circumferential axis (along which there are nine energy emitters and/or energy receivers) and a proximal-to-distal axis (along which there are three energy emitters and/or energy receivers). In an example, there can be an arcuate array of energy emitters and energy receivers on an arcuate wearable band wherein this array has a circumferential axis (along which there are at least three energy emitters and/or energy receivers) and a proximal-to-distal axis (along which there are at least two energy emitters and/or energy receivers).

In this example, there is an arcuate array of energy emitters and energy receivers on an arcuate wearable band wherein this array includes three parallel circumferential lines (along each of which there are nine energy emitters and/or energy receivers) and three parallel proximal-to-distal lines (along each of which there are three energy emitters and/or energy receivers). In an example, there can be an arcuate array of energy emitters and energy receivers on an arcuate wearable band wherein this array includes at least two parallel circumferential lines (along each of which there at least three energy emitters and/or energy receivers) and at least two parallel proximal-to-distal lines (along each of which there are at least two energy emitters and/or energy receivers).

Specifically, FIG. 55 shows an oblique-side-perspective view of an arcuate wearable device for measuring body hydration level comprising: arcuate band 5501 which is configured to span (some or all of) the circumferential perimeter of a part of a person's body (such as a wrist, arm, finger, ankle, and/or leg); a first set of three or more energy emitters (including 5509) and/or energy receivers (including 5508) along a first circumferential line of the arcuate band; a second set of three or more energy emitters (including 5507) and/or energy receivers (including 5510) along a second circumferential line of the arcuate band; a third set of three or more energy emitters (including 5511) and/or energy receivers (including 5506) along a third circumferential line of the arcuate band, wherein energy emitters are configured to emit energy toward the part of the person's body, and wherein energy receivers are configured to receive energy from energy emitters after that energy has passed through and/or been reflected from the part of the person's body; a plurality of circumferential or annular energy barriers (including 5513 and 5514) between the sets (e.g. a first circumferential or annular barrier between the first set and the second set and a second circumferential or annular barrier between the second set and the third set); a plurality of proximal-to-distal energy barriers (including 5512) between the energy emitters and/or energy receivers within sets; a data processor 5504 which receives data from the energy receivers which is analyzed in order to measure the person's body hydration level; an energy source 5503 which provides energy to the central energy emitter and/or to the data processor; and a data transmitter 5505 which transmits data from the data processor to a remote device and/or remote location.

This example further comprises another (type of) biometric or environmental sensor 5502. In another example, one or more energy emitters and/or receivers can be part of a housing which is attached to the band instead of being part of the band itself. In an example, the central energy receiver and the energy emitters can be distributed around the circumference of a band, but not all be along the same circumferential line. Other example variations and component elaborations discussed elsewhere in this disclosure (or in other disclosures within the priority-linked family) can also be applied to this example.

FIG. 56 shows an example of this invention with a single energy emitter and single energy receiver (which are on same circumferential line of a band) and an energy guide between the energy emitter and the energy receiver. In this example, the energy guide is a spit-ring resonator. In this example, the energy emitter emits (and receives reflected) microwave energy and the energy receiver receives microwave energy. In this example, the transmission of microwave energy from the energy emitter to the energy receiver is affected by the resonance of the split-ring resonator between them which, in turn, is affected by the permittivity of nearby body tissue which, in turn, is affected by body hydration level. In this example, the body hydration level of the person wearing this device can be estimated by analyzing the transmission of microwave energy from the energy emitter to the energy receiver (and also reflected back to the energy emitter).

Specifically, FIG. 56 shows an oblique-side-perspective view of an arcuate wearable device for measuring body hydration level comprising: arcuate band 5601 which is configured to span (some or all of) the circumferential perimeter of a part of a person's body (such as a wrist, arm, finger, ankle, and/or leg); energy emitter 5606 (identified with a plus sign) which is configured to emit energy toward the part of the person's body; energy receiver 5608 (identified with a negative sign) which is configured to receive energy from the energy emitter; energy guide 5607 between the energy emitter and the energy receiver, wherein transmission of energy from the energy emitter to the energy receiver through the energy guide is affected by the body hydration level of the person; data processor 5604 which receives data from the energy receiver which is analyzed in order to measure the person's body hydration level; energy source 5603 which provides energy to the energy emitter and/or to the data processor; and data transmitter 5605 which transmits data from the data processor to a remote device and/or remote location.

This example further comprises another (type of) biometric or environmental sensor 5602. In another example, an energy emitter, an energy receiver, or both can be part of a housing which is attached to the band, rather than part of the band itself.

In this example, the energy emitter and energy receiver can emit and receive microwave energy. In this example, the energy guide can be a split-ring resonator. Accordingly, FIG. 56 can also show an oblique-side-perspective view of an arcuate wearable device for measuring body hydration level comprising: arcuate band 5601 which is configured to span (some or all of) the circumferential perimeter of a part of a person's body (such as a wrist, arm, finger, ankle, and/or leg); microwave energy emitter 5606 (identified with a plus sign) which is configured to emit microwave energy toward the part of the person's body; microwave energy receiver 5608 (identified with a negative sign) which is configured to receive microwave energy from the energy emitter; split-ring resonator 5607 between the microwave energy emitter and the microwave energy receiver, wherein transmission of microwave energy from the microwave energy emitter to the microwave energy receiver through the split-ring resonator is affected by the body hydration level of the person; data processor 5604 which receives data from the microwave energy receiver and/or microwave emitter which is analyzed in order to measure the person's body hydration level; energy source 5603 which provides energy to the microwave energy emitter and/or to the data processor; and data transmitter 5605 which transmits data from the data processor to a remote device and/or remote location.

This example further comprises another (type of) biometric or environmental sensor 5602. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 57 shows an example of this invention with a single microwave energy emitter and two microwave energy receivers on the same circumferential line of a band, a first split-ring resonator between the microwave energy emitter and the first microwave energy receiver, and a second split-ring resonator between the microwave energy emitter and the second microwave energy receiver. In this example, the transmission of microwave energy from the energy emitter to the energy receivers is affected by resonances of the split-ring resonators which, in turn, are affected by the permittivity of nearby body tissue which, in turn, is affected by body hydration level. In this example, the body hydration level of the person wearing this device can be estimated by analyzing the transmission of microwave energy from the energy emitter to the energy receivers (and/or reflected back to the energy emitter).

Specifically, FIG. 57 shows an oblique-side-perspective view of an arcuate wearable device for measuring body hydration level comprising: arcuate band 5701 which is configured to span (some or all of) the circumferential perimeter of a part of a person's body (such as a wrist, arm, finger, ankle, and/or leg); microwave energy emitter 5708 (identified with a plus sign) which is configured to emit microwave energy toward the part of the person's body; first microwave energy receiver 5706 (identified with a negative sign) which is configured to receive microwave energy from the microwave energy emitter; second microwave energy receiver 5710 (identified with a negative sign) which is configured to receive microwave energy from the microwave energy emitter; first split-ring resonator 5707 between the microwave energy emitter and the first microwave energy receiver, wherein transmission of microwave energy from the microwave energy emitter to the first microwave energy receiver through the first split-ring resonator is affected by body hydration level of the person; second split-ring resonator 5709 between the microwave energy emitter and the second microwave energy receiver, wherein transmission of microwave energy from the microwave energy emitter to the second microwave energy receiver through the second split-ring resonator is affected by body hydration level of the person; data processor 5704 which receives data from the microwave energy receivers and/or microwave emitter which is analyzed in order to measure the person's body hydration level; energy source 5703 which provides energy to the microwave energy emitter and/or to the data processor; and data transmitter 5705 which transmits data from the data processor to a remote device and/or remote location.

This example further comprises another (type of) biometric or environmental sensor 5702. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 58 shows an example of this invention with two microwave energy emitters and a single microwave energy receiver on the same circumferential line of a band, a first split-ring resonator between the first microwave energy emitter and the microwave energy receiver, and a second split-ring resonator between the second microwave energy emitter and the microwave energy receiver. In this example, the transmission of microwave energy from the energy emitters to the energy receiver is affected by the resonances of the split-ring resonators which, in turn, are affected by the permittivity of nearby body tissue which, in turn, is affected by body hydration level. In this example, the body hydration level of the person wearing this device can be estimated by analyzing the transmission of microwave energy from the energy emitters to the energy receiver (and/or reflected back to the energy emitter). In an example, different microwave energy emitters can emit microwave energy at different times and/or in a chronological sequence.

Specifically, FIG. 58 shows an oblique-side-perspective view of an arcuate wearable device for measuring body hydration level comprising: arcuate band 5801 which is configured to span (some or all of) the circumferential perimeter of a part of a person's body (such as a wrist, arm, finger, ankle, and/or leg); first microwave energy emitter 5806 (identified with a plus sign) which is configured to emit microwave energy toward the part of the person's body; second microwave energy emitter 5810 (identified with a plus sign) which is configured to emit microwave energy toward the part of the person's body; microwave energy receiver 5808 (identified with a negative sign) which is configured to receive microwave energy from the microwave energy emitters; first split-ring resonator 5807 between the first microwave energy emitter and the microwave energy receiver, wherein transmission of microwave energy from the first microwave energy emitter to the microwave energy receiver through the first split-ring resonator is affected by the body hydration level of the person; second split-ring resonator 5809 between the second microwave energy emitter and the microwave energy receiver, wherein transmission of microwave energy from the second microwave energy emitter to the microwave energy receiver through the second split-ring resonator is affected by the body hydration level of the person; data processor 5804 which receives data from the microwave energy receiver and/or microwave emitters which is analyzed in order to measure the person's body hydration level; energy source 5803 which provides energy to the microwave energy emitters and/or to the data processor; and data transmitter 5805 which transmits data from the data processor to a remote device and/or remote location.

This example further comprises another (type of) biometric or environmental sensor 5802. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 59 shows an example of this invention: with a microwave energy emitter and a microwave energy receiver on the same circumferential line of an arcuate wearable band; and with two nested (and concentric) split-ring resonators between the microwave energy emitter and the microwave energy receiver. In this example, the transmission of microwave energy from the energy emitter to the energy receiver is affected by the resonances of the nested split-ring resonators which, in turn, are affected by the permittivity of nearby body tissue which, in turn, is affected by body hydration level. In this example, the body hydration level of the person wearing this device can be estimated by analyzing the transmission of microwave energy from the energy emitter to the energy receiver (and/or reflected back to the energy emitter).

Specifically, FIG. 59 shows an oblique-side-perspective view of an arcuate wearable device for measuring body hydration level comprising: arcuate band 5901 which is configured to span (some or all of) the circumferential perimeter of a part of a person's body (such as a wrist, arm, finger, ankle, and/or leg); microwave energy emitter 5906 (identified with a plus sign) which is configured to emit microwave energy toward the part of the person's body; microwave energy receiver 5909 (identified with a negative sign) which is configured to receive microwave energy from the microwave energy emitter; first split-ring resonator 5907 between the microwave energy emitter and the microwave energy receiver, wherein transmission of microwave energy from the microwave energy emitter to the microwave energy receiver through the first split-ring resonator is affected by the body hydration level of the person; second split-ring resonator 5908 between the microwave energy emitter and the microwave energy receiver, wherein transmission of microwave energy from the microwave energy emitter to the microwave energy receiver through the second split-ring resonator is affected by the body hydration level of the person, and wherein the second split-ring resonator is nested (in a concentric manner) within the first spit-ring resonator; data processor 5904 which receives data from the microwave energy receiver and/or microwave emitter which is analyzed in order to measure the person's body hydration level; energy source 5903 which provides energy to the microwave energy emitters and/or to the data processor; and data transmitter 5905 which transmits data from the data processor to a remote device and/or remote location.

This example further comprises another (type of) biometric or environmental sensor 5902. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 60 shows an example of this invention: with a microwave energy emitter and a microwave energy receiver on the same circumferential line of an arcuate wearable band; and with two stacked (and parallel) split-ring resonators between the microwave energy emitter and the microwave energy receiver. In this example, the transmission of microwave energy from the energy emitter to the energy receiver is affected by the resonances of the stacked split-ring resonators which, in turn, are affected by the permittivity of nearby body tissue which, in turn, is affected by body hydration level. In this example, the body hydration level of the person wearing this device can be estimated by analyzing the transmission of microwave energy from the energy emitter to the energy receiver (and/or reflected back to the energy emitter).

Specifically, FIG. 60 shows an oblique-side-perspective view of an arcuate wearable device for measuring body hydration level comprising: arcuate band 6001 which is configured to span (some or all of) the circumferential perimeter of a part of a person's body (such as a wrist, arm, finger, ankle, and/or leg); microwave energy emitter 6006 (identified with a plus sign) which is configured to emit microwave energy toward the part of the person's body; microwave energy receiver 6008 (identified with a negative sign) which is configured to receive microwave energy from the microwave energy emitter; first split-ring resonator 6007 between the microwave energy emitter and the microwave energy receiver, wherein transmission of microwave energy from the microwave energy emitter to the microwave energy receiver through the first split-ring resonator is affected by the body hydration level of the person; second split-ring resonator 6009 between the microwave energy emitter and the microwave energy receiver, wherein transmission of microwave energy from the microwave energy emitter to the microwave energy receiver through the second split-ring resonator is affected by the body hydration level of the person, and wherein the second split-ring resonator is stacked above (e.g. parallel to) the first spit-ring resonator; data processor 6004 which receives data from the microwave energy receiver and/or microwave emitter which is analyzed in order to measure the person's body hydration level; energy source 6003 which provides energy to the microwave energy emitters and/or to the data processor; and data transmitter 6005 which transmits data from the data processor to a remote device and/or remote location.

This example further comprises another (type of) biometric or environmental sensor 6002. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 61 shows an example of this invention with a plurality of sets, wherein each set comprises: a microwave energy emitter, a microwave energy receiver, and a split-ring resonator between the microwave energy emitter and the microwave energy receiver. In this example, there are three such sets. In another example, there can be four or more such sets distributed around the circumference of an arcuate wearable band. In this example, the sets are along the same circumferential line of an arcuate wearable band. In an example, the transmission of microwave energy from a microwave energy emitter to a microwave energy receiver in each set is affected by the resonance of the split-ring resonator in that set which, in turn, is affected by the permittivity of nearby body tissue which, in turn, is affected by body hydration level. In this example, the body hydration level of the person wearing this device can be estimated by analyzing the transmission of microwave energy from microwave energy emitters to microwave energy receivers (and/or reflected back to energy emitters) in the plurality of sets. In an example, microwave energy emitters in different sets can emit microwave energy at different times and/or in a chronological sequence.

Specifically, FIG. 61 shows an oblique-side-perspective view of an arcuate wearable device for measuring body hydration level comprising: an arcuate band 6101 which is configured to span (some or all of) the circumferential perimeter of a part of a person's body (such as a wrist, arm, finger, ankle, and/or leg); a plurality of microwave sensor sets, wherein each microwave sensor set further comprises a microwave energy emitter (such as 6106, 6109, and 6112) which is configured to emit microwave energy toward the part of the person's body, a microwave energy receiver (such as 6108, 6111, and 6114) which is configured to receive microwave energy from the microwave energy emitter, and a split ring resonator (such as 6107, 6110, and 6113) between the microwave energy emitter and the microwave energy receiver; a data processor 6104 which receives data from the microwave energy receivers and/or microwave emitters which is analyzed in order to measure the person's body hydration level; an energy source 6103 which provides energy to the microwave energy emitters and/or to the data processor; and a data transmitter 6105 which transmits data from the data processor to a remote device and/or remote location.

This example further comprises another (type of) biometric or environmental sensor 6102. In another example, a microwave energy emitter, a microwave energy receiver, and/or a split-ring resonator can be part of a housing which is attached to the band, rather than part of the band itself. Other example variations and component elaborations discussed elsewhere in this disclosure (or in other disclosures within the priority-linked family) can also be applied to this example.

FIG. 62 shows an example of this invention with an energy emitter and an energy receiver which are part of a housing which is held onto a person's body by an arcuate wearable band. In an example, the housing and band can comprise a smart watch, fitness band, or wearable hydration monitor. In this example, the energy emitter and the energy receiver are located along the same circumferential line (of the device comprising the housing and band). In an alternative example, an energy emitter and energy receiver can be located along the same proximal-to-distal line (of a device). In an example, the housing can be more rigid (e.g.

less flexible) than the arcuate band. In an example, an energy emitter and an energy receiver can be located on the inward-facing (body-facing) side of a housing. In an example, the opposite (outward-facing) side of a housing can comprise a computer display and/or screen. In an example, the type of energy that is emitted and received can be light energy. In an example, the type of energy that is emitted and received can be (non-light-spectrum) electromagnetic energy.

Specifically, FIG. 62 shows an oblique-side-perspective view of an arcuate wearable device for measuring body hydration level comprising: an arcuate band 6201 which is configured to span (some or all of) the circumferential perimeter of a part of a person's body (such as a wrist, arm, finger, ankle, and/or leg); a housing 6207 which is attached to the arcuate band; an energy emitter 6206 which is held by the housing and configured to emit energy toward the part of the person's body; an energy receiver 6208 which is held by the housing and configured to receive energy from the energy emitter; a data processor 6204 which receives data from the energy receiver which is analyzed in order to measure the person's body hydration level; an energy source 6203 which provides energy to the energy emitter and/or to the data processor; and a data transmitter 6205 which transmits data from the data processor to a remote device and/or remote location. This example further comprises another (type of) biometric or environmental sensor 6202. Other example variations and component elaborations discussed elsewhere in this disclosure (or in other disclosures within the priority-linked family) can also be applied to this example.

FIG. 63 shows an example of this invention with an energy emitter and an energy receiver and other electronic components (e.g. energy source, data processor, data transmitter, and other type of sensor) which are all part of a housing which is held onto a person's body by an arcuate wearable band. In an example, the housing and band can comprise a smart watch, fitness band, or wearable hydration monitor. In this example, the energy emitter and the energy receiver are located along the same circumferential line (of the device comprising the housing and band). In an alternative example, an energy emitter and energy receiver can be located along the same proximal-to-distal line (of a device). In an example, the housing can be more rigid (e.g. less flexible) than the arcuate band. In an example, an energy emitter and an energy receiver can be located on the inward-facing (body-facing) side of a housing. In an example, the opposite (outward-facing) side of a housing can comprise a computer display and/or screen. In an example, the type of energy that is emitted and received can be light energy. In an example, the type of energy that is emitted and received can be (non-light-spectrum) electromagnetic energy.

Specifically, FIG. 63 shows an oblique-side-perspective view of an arcuate wearable device for measuring body hydration level comprising: an arcuate band 6301 which is configured to span (some or all of) the circumferential perimeter of a part of a person's body (such as a wrist, arm, finger, ankle, and/or leg); a housing 6307 which is attached to the arcuate band; an energy emitter 6306 which is held by the housing and configured to emit energy toward the part of the person's body; an energy receiver 6308 which is held by the housing and configured to receive energy from the energy emitter; a data processor 6304 which is held by the housing and receives data from the energy receiver which is analyzed in order to measure the person's body hydration level; an energy source 6303 which is held by the housing and provides energy to the energy emitters and/or to the data processor; and a data transmitter 6305 which is held by the housing and transmits data from the data processor to a remote device and/or remote location. This example further comprises another (type of) biometric or environmental sensor 6302. Other example variations and component elaborations discussed elsewhere in this disclosure (or in other disclosures within the priority-linked family) can also be applied to this example.

FIG. 64 shows an example of this invention with: a housing that is attached to a wearable arcuate band; and a plurality of energy emitters and a central energy receiver which are held by this housing. In this example, the energy emitters and energy receiver are all on the same circumferential line of the device, wherein the device comprises the housing as well as the arcuate band. In an example, the housing and band can comprise a smart watch, fitness band, or wearable hydration monitor. In an example, the energy emitters and energy receiver can be located on the inward-facing (body-facing) side of a housing. In an example, the opposite (outward-facing) side of a housing can comprise a computer display and/or screen. In this example, the central energy receiver is centrally located with respect to the energy emitters. In this example, there are two energy emitters on each side (clockwise or counter-clockwise, right or left) of the central energy receiver. In an example, different energy emitters can emit energy at different times and/or in a chronological sequence. In an example, the type of energy that is emitted and received can be light energy. In an example, the type of energy that is emitted and received can be (non-light-spectrum) electromagnetic energy.

Specifically, FIG. 64 shows an oblique-side-perspective view of an arcuate wearable device for measuring body hydration level comprising: an arcuate band 6401 which is configured to span (some or all of) the circumferential perimeter of a part of a person's body (such as a wrist, arm, finger, ankle, and/or leg); a housing 6408 which is attached to the arcuate band; a plurality of energy emitters (6406, 6407, 6410, and 6411) which are held by the housing and configured to emit energy toward the part of the person's body; a central energy receiver 6409 which is held by the housing and configured to receive energy from the energy emitters, wherein the plurality of energy emitters and the central energy receiver are all located along the same circumferential line, and wherein the central energy receiver is centrally located with respect to the plurality of energy emitters; a data processor 6404 which is held by the housing and receives data from the energy receiver which is analyzed in order to measure the person's body hydration level; an energy source 6403 which is held by the housing and provides energy to the energy emitters and/or to the data processor; and a data transmitter 6405 which is held by the housing and transmits data from the data processor to a remote device and/or remote location. This example further comprises another (type of) biometric or environmental sensor 6402. Other example variations and component elaborations discussed elsewhere in this disclosure (or in other disclosures within the priority-linked family) can also be applied to this example.

FIG. 65 shows an example of this invention with: a housing that is attached to a wearable arcuate band; and a plurality of energy emitters and central energy receiver which are held by this housing. In an example, energy emitters can encircle the energy receiver. In an example, energy emitters can be arranged in an (approximately-circular) polygonal array around the central energy receiver. In an example, the housing and band can comprise a smart watch, fitness band, or wearable hydration monitor. In an example, the energy emitters and energy receiver can be located on the inward-facing (body-facing) side of a housing. In an example, the opposite (outward-facing) side of a housing can comprise a computer display and/or screen.

In this example, the central energy receiver is centrally located with respect to the energy emitters. In this example, there are eight energy emitters around the central energy receiver. In an example, different energy emitters can emit energy at different times and/or in a chronological sequence. In an example, the type of energy that is emitted and received can be light energy. In an example, the type of energy that is emitted and received can be (non-light-spectrum) electromagnetic energy.

Specifically, FIG. 65 shows an oblique-side-perspective view of an arcuate wearable device for measuring body hydration level comprising: an arcuate band 6501 which is configured to span (some or all of) the circumferential perimeter of a part of a person's body (such as a wrist, arm, finger, ankle, and/or leg); a housing 6509 which is attached to the arcuate band; a plurality of energy emitters (6506, 6507, 6508, 6511, 6512, 6513, 6514, and 6515) which are held by the housing and configured to emit energy toward the part of the person's body; a central energy receiver 6510 which is held by the housing and configured to receive energy from the energy emitters, wherein the plurality of energy emitters are around the central energy receiver (in an approximately-circular polygonal array); a data processor 6504 which is held by the housing and receives data from the energy receiver which is analyzed in order to measure the person's body hydration level; an energy source 6503 which is held by the housing and provides energy to the energy emitters and/or to the data processor; and a data transmitter 6505 which is held by the housing and transmits data from the data processor to a remote device and/or remote location. This example further comprises another (type of) biometric or environmental sensor 6502. Other example variations and component elaborations discussed elsewhere in this disclosure (or in other disclosures within the priority-linked family) can also be applied to this example.

FIG. 66 shows an example of this invention with multiple connected segments (or housings) which comprise (parts of) an arcuate wearable band, wherein each segment (or housing) holds an energy emitter and an energy receiver. In this example, there are five connected segments which span approximately half of the circumference of a band. In an example, there can be more than five connected segments and they can span a greater portion of the band circumference. In this example, an energy emitter and an energy receiver on a segment are on same proximal-to-distal line. In an alternative example, an energy emitter and an energy receiver on a segment can be on the same circumferential line. In an example, different energy emitters can emit energy at different times and/or in a chronological sequence. In an example, the type of energy that is emitted and received can be light energy. In an example, the type of energy that is emitted and received can be (non-light-spectrum) electromagnetic energy.

Specifically, FIG. 66 shows an oblique-side-perspective view of an arcuate wearable device for measuring body hydration level comprising: an arcuate band 6601 which is configured to span (some or all of) the circumferential perimeter of a part of a person's body (such as a wrist, arm, finger, ankle, and/or leg); a plurality of segments (or housings) 6603, 6605, 6607, 6612, and 6613 which are attached to (and/or comprise) the arcuate band, wherein each segment (or housing) holds an energy emitter 6604, 6606, 6609, 6611, and 6613 and an energy receiver 6602, 6620, 6618, 6616, and 6615; a data processor 6604 which receives data from the energy receivers which is analyzed in order to measure the person's body hydration level; an energy source 6603 which provides energy to the energy emitters and/or to the data processor; and a data transmitter 6605 which transmits data from the data processor to a remote device and/or remote location. This example further comprises another (type of) biometric or environmental sensor 6602. Other example variations and component elaborations discussed elsewhere in this disclosure (or in other disclosures within the priority-linked family) can also be applied to this example.

In an example, this invention can be embodied in an arcuate wearable device for measuring body hydration level comprising: a plurality of flexibly-connected segments which collectively form an arcuate wearable band which is configured to span (some or all of) the circumferential perimeter of a part of a person's body (such as a wrist, arm, finger, ankle, and/or leg), wherein each segment (or housing) holds an energy emitter and an energy receiver; a data processor which receives data from the energy receivers which is analyzed in order to measure the person's body hydration level; an energy source which provides energy to the energy emitters and/or to the data processor; and a data transmitter which transmits data from the data processor to a remote device and/or remote location. Other example variations and component elaborations discussed elsewhere in this disclosure (or in other disclosures within the priority-linked family) can also be applied to this example.

FIG. 67 shows an example of a wearable glucose monitor comprising: an energy emitter and an energy receiver for measuring body glucose level; and also a fluid-based glucose sensor for measuring body glucose level. In an example, body glucose level is measured less frequently with the fluid-based glucose sensor than with the energy emitter and energy receiver. In an example, measurement of body glucose level with the fluid-based glucose sensor can be used to calibrate measurement of body glucose level with the energy emitter and energy receiver. In an example, a fluid-based glucose sensor can withdraw small samples of interstitial fluid or blood through a small catheter or needle for analysis of glucose level.

In an example, the type of energy that is emitted by the energy emitter and received by the energy receiver can be light energy. In an example, the type of energy that is emitted by the energy emitter and received by the energy receiver can be (non-light-spectrum) electromagnetic energy. In this example, the energy emitter, energy receiver, and fluid-based glucose sensor are held in place by a housing which is attached to an arcuate band. In another example, these components can be directly part of an arcuate band.

Specifically, FIG. 67 shows an oblique-side-perspective view of wearable glucose monitor comprising: an arcuate band 6701 which is configured to span (some or all of) the circumferential perimeter of a part of a person's body (such as a wrist, arm, finger, ankle, and/or leg); a housing 6702 which is attached to the arcuate band; an energy emitter 6703 which is held by the housing and configured to emit energy toward the part of the person's body; an energy receiver 6705 which is held by the housing and configured to receive energy from the energy emitter; a fluid-based glucose sensor 6704 which is held by the housing; a data processor 6707 which receives data from the energy receiver and data from the fluid-based glucose sensor which are analyzed in order to measure the person's body glucose level; an energy source 6708 which provides energy to the energy emitter, the fluid-based glucose sensor, and/or to the data processor; and a data transmitter 6706 which transmits data from the data processor to a remote device and/or remote location. This example further comprises another (type of) biometric or environmental sensor 6709.

In an example, a wearable glucose monitor can comprise: an arcuate band which is configured to span (some or all of) the circumferential perimeter of a part of a person's body (such as a wrist, arm, finger, ankle, and/or leg); an energy emitter which is configured to emit energy toward the part of the person's body; an energy receiver which is configured to receive energy from the energy emitter; a fluid-based glucose sensor; a data processor which receives data from the energy receiver and data from the fluid-based glucose sensor which are analyzed in order to measure the person's body glucose level; an energy source which provides energy to the energy emitter, the fluid-based glucose sensor, and/or to the data processor; and a data transmitter which transmits data from the data processor to a remote device and/or remote location. This example can further comprise another (type of) biometric or environmental sensor. Other example variations and component elaborations discussed elsewhere in this disclosure (or in other disclosures within the priority-linked family) can also be applied to this example.

FIG. 68 shows an example of a wearable device for measuring body hydration level with a plurality of close-fitting spectroscopic sensors. This figure shows the device from a side perspective, as it would appear encircling a lateral cross-section of a person's wrist (or other portion of the person's arm). Described generally, the example shown in FIG. 68 is an arcuate wrist-worn device with a circumferentially or annularly distributed array of spectroscopic sensors. A series of circumference-center-facing spectroscopic sensors are distributed along different locations on a portion of the circumference of the device. In this example, the array of sensors is distributed along the circumference-center-facing surface of an enclosure which is on the anterior (upper) portion of the device. In another example, an array of sensors can be distributed along the circumference-center-facing surface of a band or strap.

Having a circumferentially or annularly distributed array of sensors allows a wearable device to record spectroscopic measurements from different locations along the circumference of a person's wrist. This can help to find the best location on a person's wrist from which to most-accurately record spectroscopic measurements. Having a circumferentially or annularly distributed array of sensors can also enable a device to record spectroscopic measurements from substantially the same location on a person's wrist, even if the device is unintentionally slid, shifted, and/or partially-rotated around the person's wrist. A different primary sensor can selected to record data when the device slides, shifts, and/or rotates. This can help to reduce spectroscopic measurement errors when the device is slid, shifted, and/or partially-rotated around a person's wrist.

More specifically, the example shown in FIG. 68 is a wearable device for measuring body hydration level with a plurality of close-fitting spectroscopic sensors comprising: (a) an attachment member, such as a strap or band, which is configured to span at least a portion of the circumference of a person's arm; (b) an enclosure which is part of (or attached to) the attachment member; (c) a first spectroscopic sensor at a first location in the enclosure which is configured to record data concerning the person's arm tissue; and (d) a second spectroscopic sensor at a second location in the enclosure which is configured to record data concerning the person's arm tissue, wherein the distance along the circumference of the device from the first location to second location is at least a quarter inch.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure. In an example, first and second spectroscopic sensors can be spectroscopic sensors which are each configured to measure the spectrum of light energy reflected from (and/or absorbed by) tissue of the person's arm.

With respect to specific components, the example shown in FIG. 68 includes: strap (or band) 6801, strap (or band) connector 6802, enclosure 6803, and spectroscopic sensors 6804, 6805, 6806, 6807, and 6808. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 69 shows another example of a wearable device for measuring body hydration level with a plurality of close-fitting spectroscopic sensors. This figure shows the device from a side perspective, as it would appear encircling a lateral cross-section of a person's wrist (or other portion of the person's arm).

The example shown in FIG. 69 is like the one shown in FIG. 68 except that different sensors in the array of sensors direct light energy onto the surface of an arm at different angles relative to an enclosure. Having an array of sensors which direct light energy onto the surface of the arm at different angles relative to an enclosure can enable a device to record spectroscopic measurements with substantially the same angle of incidence, even if the enclosure is tilted with respect to the surface of the person's wrist. A different primary sensor with a different angle of light projection can be selected to record data when the enclosure is tilted. For example, when an enclosure is parallel to the surface of the person's wrist, then a sensor with a 90-degree light projection angle (relative to the enclosure) can be selected so that light is projected onto the surface of the arm in a perpendicular manner. However, when the enclosure is tilted at a 20-degree angle relative to the surface of the person's wrist, then a sensor with a 70-degree angle (relative to the enclosure) can be selected so that light is again projected onto the surface of the arm in a perpendicular manner.

The example shown in FIG. 69 is a wearable device for measuring body hydration level with a plurality of close-fitting spectroscopic sensors comprising: (a) an attachment member, such as a strap or band, which is configured to span at least a portion of the circumference of a person's arm; (b) an enclosure which is part of (or attached to) the attachment member; (c) a first spectroscopic sensor in the enclosure which is configured to project a beam of light onto the arm surface at a first angle relative to the enclosure; and (d) a second spectroscopic sensor in the enclosure which is configured to project a beam of light onto the arm surface at a second angle relative to the enclosure, wherein the first angle differs from the second angle by at least 10 degrees.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure.

With respect to specific components, the example shown in FIG. 69 includes: strap (or band) 6901, strap (or band) connector 6902, enclosure 6903, and spectroscopic sensors 6904, 6905, 6906, 6907, and 6908. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 70 shows an example of a wearable device for measuring body hydration level with a close-fitting spectroscopic sensor. This figure shows the device from a side perspective, as it would appear encircling a lateral cross-section of a person's wrist (or other portion of the person's arm).

Described generally, the example shown in FIG. 70 is an arcuate wrist-worn device with a rotating light-projecting spectroscopic sensor, wherein rotation of this sensor changes the angle at which it projects light onto the surface of a person's arm. In this example, the rotating light-projecting spectroscopic sensor is on the circumference-center-facing surface of an enclosure which is on the anterior (upper) portion of the device. In another example, such a sensor can be on the circumference-center-facing surface of a band or strap.

Having a rotating light-projecting spectroscopic sensor can enable a device to record spectroscopic measurements with substantially the same angle of incidence, even if an enclosure is tilted with respect to the surface of the person's wrist. For example, when the enclosure is parallel to the surface of the person's wrist, then the rotating sensor is automatically rotated to project light at a 90-degree angle (relative to the enclosure) so that light is projected onto the surface of the arm in a perpendicular manner. However, when the enclosure is tilted at a 20-degree angle relative to the surface of the person's wrist, then the rotating sensor is automatically rotated to project light at a 70-degree angle (relative to the enclosure) so that light is again projected onto the surface of the arm in a perpendicular manner.

The example shown in FIG. 70 is a wearable device for measuring body hydration level with a close-fitting spectroscopic sensor comprising: (a) an attachment member, such as a strap or band, which is configured to span at least a portion of the circumference of a person's arm; (b) an enclosure which is part of (or attached to) the attachment member; and (c) a rotating light-projecting spectroscopic sensor, wherein this sensor can be rotated relative to the enclosure and wherein rotation of this sensor relative to the enclosure changes the angle at which the sensor projects light onto the surface of a person's arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure.

With respect to specific components, the example shown in FIG. 70 includes: strap (or band) 7001, strap (or band) connector 7002, enclosure 7003, rotating member 7004, and light-projecting spectroscopic sensor 7005. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 71 shows another example of a wearable device for measuring body hydration level with a plurality of close-fitting spectroscopic sensors. This figure shows the device from a non-perpendicular lateral perspective, as it would appear encircling a lateral cross-section of a person's wrist (or other portion of the person's arm).

Described generally, the example shown in FIG. 71 is an arcuate wrist-worn device with a two-dimensional array of spectroscopic sensors. Sensors in this two-dimensional array differ in location circumferentially or annularly (they are at different locations around the circumference of the device) and laterally (they are at different locations along axes which are perpendicular to the circumference of the device). In this example, the two-dimensional sensor array is part of the circumference-center-facing surface of an enclosure which is on the anterior (upper) portion of the device. In another example, a two-dimensional sensor array can be on the circumference-center-facing surface of a band or strap.

Having a two-dimensional sensor array allows a wearable device to record spectroscopic measurements from multiple locations on a person's wrist. This can help to find the best location on a person's wrist from which to most-accurately record spectroscopic measurements. Having a two-dimensional sensor array can also enable a device to record spectroscopic measurements from substantially the same location on a person's wrist even if the device is rotated around the person's wrist or slid up or down the person's arm. A different primary sensor can be automatically selected to record data when the device rotates or slides.

More specifically, the example shown in FIG. 71 is a wearable device for measuring body hydration level with a plurality of close-fitting spectroscopic sensors comprising: (a) an attachment member, such as a strap or band, which is configured to span at least a portion of the circumference of a person's arm; (b) an enclosure which is part of (or attached to) the attachment member; and (c) a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure. In an example, sensors in a two-dimensional sensor array can be spectroscopic sensors which are each configured to measure the spectrum of light energy reflected from (and/or absorbed by) tissue of the person's arm.

With respect to specific components, the example shown in FIG. 71 includes: a strap (or band) 7101, a strap (or band) connector 7102, an enclosure 7103, and a two-dimensional spectroscopic sensor array which includes sensor 7104. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 72 shows another example of a wearable device for measuring body hydration level with a plurality of close-fitting spectroscopic sensors. This figure shows the device from a side perspective, as it would appear encircling a lateral cross-section of a person's wrist (or other portion of the person's arm).

Described generally, the example shown in FIG. 72 is an arcuate wrist-worn device with a plurality of spectroscopic sensors, wherein each of these sensors is pushed toward the surface of an arm in order to stay in close contact with the surface of the arm even if the enclosure is shifted or tilted away from the surface of the arm. In this example, the spectroscopic sensors are on the circumference-center-facing portion of an enclosure. In this example, each of the spectroscopic sensors is pushed toward the surface of the arm by a spring mechanism. In another example, each of the spectroscopic sensors can be pushed toward the surface by a hydraulic mechanism, a pneumatic mechanism, or a microscale electromagnetic actuator.

More specifically, the example shown in FIG. 72 is a wearable device for measuring body hydration level with a plurality of close-fitting spectroscopic sensors comprising: (a) an attachment member, such as a strap or band, which is configured to span at least a portion of the circumference of a person's arm; (b) an enclosure which is part of (or attached to) the attachment member; and (c) a plurality of sensors which are part of the enclosure, wherein each sensor in this plurality of sensors is configured to be pushed toward the surface of the arm by a spring mechanism in order to keep the sensor in close contact with the surface of the arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed. In an example, sensors of this device can be spectroscopic sensors which are each configured to measure the spectrum of light energy reflected from (and/or absorbed by) tissue of the person's arm.

With respect to specific components, the example shown in FIG. 72 includes: a strap (or band) 7201; a strap (or band) connector 7202; an enclosure 7203; a plurality of spectroscopic sensors (7207, 7208, and 7209); and a plurality of spring mechanisms (7204, 7205, and 7206) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 73 shows another example of a wearable device for measuring body hydration level with a plurality of close-fitting spectroscopic sensors. This figure shows the device from a side perspective, as it would appear encircling a lateral cross-section of a person's wrist (or other portion of the person's arm). The example shown in FIG. 73 is similar to the one shown in FIG. 72, except that the enclosure housing spectroscopic sensors in FIG. 73 has a curved circumference-center-facing surface rather than a flat circumference-center-facing surface.

With respect to specific components, the example shown in FIG. 73 includes: a strap (or band) 7301; a strap (or band) connector 7302; an enclosure 7303; a plurality of spectroscopic sensors (7307, 7308, and 7309); and a plurality of spring mechanisms (7304, 7305, and 7306) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 74 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 74 is an arcuate wrist-worn device with a spectroscopic sensor which is located on a circumference-center-facing portion of an enclosure, wherein this circumference-center-facing portion tilts on a central inflated portion of the enclosure so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen), a central inflated portion (which can be a balloon), and an inner-facing portion (which houses the spectroscopic sensor). In an example, a central inflated portion can be sandwiched between a rigid outward-facing portion and a rigid circumference-center-facing portion. In an example, the circumference-center-facing portion can tilt with respect to the outward-facing portion as the device tilts with respect to the surface of the person's arm.

Having a spectroscopic sensor located on a circumference-center-facing portion of an enclosure which tilts on a central inflated portion can help to keep the spectroscopic sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 74 is a wearable device for measuring body hydration level with one or more close-fitting spectroscopic sensors comprising: (a) an attachment member, such as a strap or band, which is configured to span at least a portion of the circumference of a person's arm; (b) an enclosure which is part of (or attached to) the attachment member, wherein this enclosure further comprises a rigid outward facing portion, an inflated central portion, and a rigid circumference-center-facing portion, wherein the rigid circumference-center-facing portion tilts relative to the rigid outward facing portion; and (c) a spectroscopic sensor in the circumference-center-facing portion which is configured to record data concerning the person's arm tissue.

In an example, there can be a display screen on the outward-facing surface of the enclosure. In an example, the central portion of an enclosure can be filled with a liquid or gel rather than inflated with a gas. In an example, there can be more than one spectroscopic sensor on the rigid circumference-center-facing portion. In an example, a spectroscopic sensor can measure the spectrum of light energy reflected from (and/or absorbed by) tissue of the person's arm.

With respect to specific components, the example shown in FIG. 74 includes: strap (or band) 7401, strap (or band) connector 7402, outward facing portion 7403 of an enclosure, circumference-center-facing portion 7404 of the enclosure, inflated central portion 7405 of the enclosure, and a spectroscopic sensor 7406 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 75 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 75 is an arcuate wrist-worn device with a spectroscopic sensor which is located on a circumference-center-facing portion of an enclosure, wherein this circumference-center-facing portion pivots around an axis so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen) and an inner-facing portion (which houses the spectroscopic sensor).

In this example, a circumference-center-facing portion which houses a spectroscopic sensor pivots around a central axis when the device tilts with respect to the surface of the person's arm. Having a spectroscopic sensor located on a circumference-center-facing portion of an enclosure which pivots around an axis can help to keep the spectroscopic sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 75 is a wearable device for measuring body hydration level with one or more close-fitting spectroscopic sensors comprising: (a) an attachment member, such as a strap or band, which is configured to span at least a portion of the circumference of a person's arm; (b) an enclosure which is part of (or attached to) the attachment member, wherein this enclosure further comprises an outward facing portion and a circumference-center-facing portion, wherein the rigid inward (or center) pivots around a central axis with respect to the outward facing portion; and (c) a spectroscopic sensor in the circumference-center-facing portion which is configured to record data concerning the person's arm tissue.

In this example, the central axis around which the circumference-center-facing portion pivots is perpendicular to the circumference of the device. In another example, the central axis around which the circumference-center-facing portion pivots can be parallel or tangential to the circumference of the device. In an example, there can be a display screen on the outward-facing surface of the enclosure. In an example, there can be more than one spectroscopic sensor on the circumference-center-facing portion of the enclosure. In an example, a spectroscopic sensor can measure the spectrum of light energy reflected from (and/or absorbed by) tissue of the person's arm.

With respect to specific components, the example shown in FIG. 75 includes: strap (or band) 7501, strap (or band) connector 7502, outward facing portion 7503 of an enclosure, circumference-center-facing portion 7504 of the enclosure, axis 7505 around which circumference-center-facing portion 7504 pivots; and a spectroscopic sensor 7506 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 76 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 76 is a wrist-worn device with a spectroscopic sensor located on an enclosure, wherein the enclosure is pushed toward the surface of a person's arm by spring mechanisms so that the sensor remains in close contact with the arm's surface even if the rest of the device shifts away from the arm's surface. In this example, the enclosure is on the anterior (upper) portion of the device circumference.

The example shown in FIG. 76 can also be expressed as a wearable device for measuring body hydration level with one or more close-fitting spectroscopic sensors comprising: (a) an attachment member, such as a strap or band, which is configured to span at least a portion of the circumference of a person's arm; (b) an enclosure which is part of (or attached to) the attachment member; (c) one or more spring mechanisms which push the enclosure inward toward the circumference center of the device; and (d) a spectroscopic sensor in the enclosure which is configured to record data concerning the person's arm tissue.

In this example, there are two spring mechanisms which push the enclosure inward toward the surface of a person's arm. In this example, these spring mechanisms are located at the places where the enclosure is connected to a strap or band. In an example, there can be a display screen on the outward-facing surface of the enclosure. In an example, there can be more than one spectroscopic sensor on the circumference-center-facing portion of the enclosure. In an example, a spectroscopic sensor can measure the spectrum of light energy reflected from (and/or absorbed by) tissue of the person's arm.

With respect to specific components, the example shown in FIG. 76 includes: strap (or band) 7601, strap (or band) connector 7602, first spring mechanism 7603, second spring mechanism 7604, enclosure 7605 which is pushed inward (toward the circumference center of the device) by spring mechanisms 7603 and 7604, and spectroscopic sensor 7606. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 77 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, this example is a wrist-worn device with an elastic member (such as a balloon) that is filled with a fluid, gel, or gas and a spectroscopic sensor which is attached to the circumference-center-facing wall of this elastic member. Having a spectroscopic sensor attached to the circumference-center-facing wall of an elastic member can help to keep the sensor in close contact with the surface of a person's arm, even if other components of the device are shifted or tilted away from the arm's surface. In an example, an elastic member can be part of an enclosure which is attached to an arm by a strap. In an example, such an enclosure can be positioned on the anterior (upper) portion of the device circumference.

The example shown in FIG. 77 can also be expressed as a wearable device for measuring body hydration level with one or more close-fitting spectroscopic sensors comprising: (a) an attachment member, such as a strap or band, which is configured to span at least a portion of the circumference of a person's arm; (b) an enclosure which is part of (or attached to) the attachment member; (c) an elastic member filled with a fluid, gel, or gas which is attached to (or part of) the enclosure; and (d) a spectroscopic sensor which is configured to record data concerning the person's arm tissue, wherein this sensor is attached to a circumference-center-facing wall of the elastic member.

In an example, there can be a display screen on the outward facing surface of an enclosure. In an example, there can be more than one spectroscopic sensor on the circumference-center-facing wall of an elastic member. In an example, a spectroscopic sensor can measure the spectrum of light energy reflected from (and/or absorbed by) tissue of the person's arm.

With respect to specific components, the example shown in FIG. 77 includes: strap (or band) 7701; strap (or band) connector 7702; enclosure 7703; elastic member 7704 which is filled with a fluid, gel, or gas; and spectroscopic sensor 7705 which is attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 78 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example shown in FIG. 78 is like the one shown in FIG. 77, except that in FIG. 78 there are multiple spectroscopic sensors on the circumference-center-facing wall of an elastic member. In FIG. 78, there are three spectroscopic sensors.

With respect to specific components, the example shown in FIG. 78 includes: strap (or band) 7801; strap (or band) connector 7802; enclosure 7803; elastic member 7804 which is filled with a fluid, gel, or gas; and spectroscopic sensors 7805, 7806, and 7807 which are attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 79 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example shown in FIG. 79 is like the one shown in FIG. 77, except that in FIG. 79 there is also a micropump which can pump fluid, gel, or gas into (or out of) the elastic member. This enables (automatic) adjustment of the size and/or internal pressure of the elastic member in order to better maintain proximity of the sensor to the surface of the person's arm.

With respect to specific components, the example shown in FIG. 79 includes: strap (or band) 7901; strap (or band) connector 7902; enclosure 7903; elastic member 7904 which is filled with a fluid, gel, or gas; spectroscopic sensor 7905 which is attached to the circumference-center-facing wall of the elastic member; and micropump 7906 which pumps fluid, gel, or gas into (or out of) the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 80 shows another example of a wearable device for measuring body hydration level with one or more close-fitting spectroscopic sensors. This figure shows the device from a side perspective, as it would appear encircling a lateral cross-section of a person's wrist (or other portion of the person's arm). This wrist-worn device comprises: an attachment member which is configured to span at least a portion of the circumference of a person's arm; one or more elastic members filled with a flowable substance, wherein these elastic members are part of (or attached to) the circumference-center-facing surface of the attachment member; and one or more spectroscopic sensors, wherein each sensor is part of (or attached to) a circumference-center-facing wall of an elastic member.

The design of this device keeps spectroscopic sensors close to the surface of a person's arm, even if portions of the device shift away from the surface of the person's arm. The interiors of the elastic members on which these sensors are located are under modest pressure so that these elastic members expand when they are moved away from the arm surface and these elastic members are compressed when they are moved toward the arm surface.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, an attachment member can be attached to a person's arm by stretching it circumferentially or annularly and sliding it over the person's hand onto the arm. In an example, an attachment member can be attached to a person's arm by applying force to pull two ends of the member apart in order to slip the member over the arm; the two ends then retract back towards each other when device is on the arm and the force is removed.

In an example, an elastic member can be a balloon or other elastic substance-filled compartment. In an example, the flowable substance inside an elastic member can be a fluid, gel, or gas. In this example, there are two elastic members on the attachment member. In this example, the elastic members are symmetrically located with respect to a central cross-section of the device. In an example, there can be a plurality of elastic members (with attached spectroscopic sensors) which are distributed around the circumference of an attachment member and/or the device. In this example, a device can also include an enclosure which further comprises a display screen. In an example, a spectroscopic sensor can measure the spectrum of light energy reflected from (and/or absorbed by) tissue of the person's arm.

With respect to specific components, the example shown in FIG. 80 includes: band 8001; band connector 8002; enclosure 8003; first elastic member 8004 which is filled with a fluid, gel, or gas; first spectroscopic sensor 8005 which is attached to the circumference-center-facing wall of the first elastic member; second elastic member 8006 which is filled with a fluid, gel, or gas; and second spectroscopic sensor 8007 which is attached to the circumference-center-facing wall of the second elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 81 shows another example of a wearable device for measuring body hydration level with one or more close-fitting spectroscopic sensors. This figure shows the device from a side perspective, as it would appear encircling a lateral cross-section of a person's wrist (or other portion of the person's arm). This wrist-worn device comprises: (a) an attachment member which is configured to span at least a portion of the circumference of a person's arm; (b) an enclosure which is part of (or attached to) the attachment member; (c) one or more torus-shaped elastic members filled with a flowable substance, wherein these elastic members are part of (or attached to) the enclosure; and (d) one or more spectroscopic sensors, wherein each sensor is located in the central hole of a torus-shaped elastic member.

In an example, an attachment member can be a strap, band, bracelet, ring, armlet, cuff, or sleeve. In an example, an enclosure can further comprise a display screen on its outer surface. In an example, a torus-shaped elastic member can be a balloon which is filled with a fluid, gel, or gas. In an example, a spectroscopic sensor can measure the spectrum of light energy reflected from (and/or absorbed by) tissue of the person's arm.

With respect to specific components, the example shown in FIG. 81 includes: band 8101; band connector 8102; enclosure 8103; torus-shaped elastic members 8104, 8105, and 8106; and spectroscopic sensors 8107, 8108, and 8109 which are each located in the central opening (or hole) of a torus-shaped elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 82 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example in FIG. 82 like the one shown in FIG. 81, except that the example in FIG. 82 also includes channels through which a fluid, gel, or gas can flow between the torus-shaped elastic members.

With respect to specific components, the example shown in FIG. 82 includes: band 8201; band connector 8202; enclosure 8203; torus-shaped elastic members 8204, 8205, and 8206; spectroscopic sensors 8207, 8208, and 8209 which are each located in the central opening (or hole) of a torus-shaped elastic member; and channels 8210 and 8211 through which fluid, gel, or gas can flow between the torus-shaped elastic members. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 83 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example in FIG. 83 like the one shown in FIG. 80, except that the example in FIG. 83 also includes elastic members on the outward-facing surface of the attachment member and channels through which fluid, gel, or gas can flow from circumference-center-facing elastic members to outward-facing elastic members, or vice versa.

This wrist-worn device comprises: (a) an attachment member which is configured to span at least a portion of the circumference of a person's arm; (b) at least one circumference-center-facing elastic member, wherein this member is filled with a flowable substance, and wherein this elastic member is part of (or attached to) the circumference-center-facing surface of the attachment member; (c) at least one outward-facing elastic member, wherein this member is filled with the flowable substance, and wherein this elastic member is part of (or attached to) the outward-facing surface of the attachment member; (d) a channel through which the flowable substance can flow between the circumference-center-facing elastic member and the outward-facing elastic member; and (e) a spectroscopic sensor which is part of (or attached to) the circumference-center-facing wall of the circumference-center-facing elastic member.

In an example, an attachment member can be a strap, band, bracelet, ring, armlet, cuff, or sleeve. In an example, one or both of the elastic members can be a balloon or other elastic substance-filled compartment. In an example, the flowable substance inside an elastic member can be a fluid, gel, or gas. In an example, a spectroscopic sensor can measure the spectrum of light energy reflected from (and/or absorbed by) tissue of the person's arm.

With respect to specific components, the example shown in FIG. 83 includes: band 8301; band connector 8302; enclosure 8303; outward-facing elastic members 8304 and 8308, which are filled with a fluid, gel, or gas; circumference-center-facing elastic members 8306 and 8310, which are filled with the fluid, gel, or gas; channels 8305 and 8309 through which the fluid, gel, or gas can flow from an outward-facing elastic member to a circumference-center-facing elastic member, or vice versa; and spectroscopic sensors 8307 and 8311 which are each attached to a circumference-center-facing wall of a circumference-center-facing elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 84 shows another example of a wearable device for measuring body hydration level with one or more close-fitting spectroscopic sensors. This figure shows the device from a side perspective, as it would appear encircling a lateral cross-section of a person's wrist (or other portion of the person's arm). A general description of the example in FIG. 84 can be expressed as a wrist-worn device with spectroscopic sensors on circumferentially or annularly-sliding members, wherein these circumferentially or annularly-sliding members are slid along the circumference of the device in order to adjust the positions from which the spectroscopic sensors measure data concerning arm tissue. Such moveable sensors enable a user to find the best positions around the circumference of the device from which to collect data for a selected application.

This wrist-worn device comprises: (a) an attachment member which is configured to span at least a portion of the circumference of a person's arm; (b) at least one circumferentially or annularly-sliding member, wherein this member is slid along the circumference of the attachment member; and (c) at least one a spectroscopic sensor which is part of (or attached to) the circumferentially or annularly-sliding member and collects data concerning arm tissue.

In an example, a sliding member can laterally-encircle an attachment member in order to keep the sliding member on the attachment member. In an example, the ends of a sliding member can curve around the sides of an attachment member in order to keep the sliding member on the attachment member. In an example, there can be a circumferential or annular array on an attachment member into which a sliding member fits in order to keep the sliding member on the attachment member. In an example, a spring or other compressive mechanism on a sliding member can engage the attachment member in order to keep the sliding member on the attachment member. In an example, pressing on the top or sides of a sliding member frees it to slide along the attachment member and releasing this pressure causes the sliding member to stop sliding (and remain at a selected location on the attachment member). In an example, data from a spectroscopic sensor on the sliding member can be analyzed in real time in order to identify the optimal location along the circumference of the attachment member from which to collect data. In an example, an attachment member can be a strap, band, bracelet, ring, armlet, cuff, or sleeve. In an example, a spectroscopic sensor can measure the spectrum of light energy reflected from (and/or absorbed by) tissue of the person's arm.

With respect to specific components, the example shown in FIG. 84 includes: band 8401; band connector 8402; enclosure 8403; circumferentially or annularly-sliding members 8404 and 8406, wherein these members slide along the circumference of the band; and spectroscopic sensors 8405 and 8407 which are each part of (or attached to) a circumferentially or annularly-sliding member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 85 shows another example of a wearable device for measuring body hydration level with one or more close-fitting spectroscopic sensors. This figure shows the device from a non-perpendicular lateral perspective, as it would appear encircling a lateral cross-section of a person's wrist (or other portion of the person's arm).

A general description of the example in FIG. 85 can be expressed as a wrist-worn device with a spectroscopic sensor on a rotating member, wherein rotation of the rotating member moves the spectroscopic sensor in a circular manner. In an example, the circular path in which a sensor moves is configured to be in a plane which is substantially tangential to the surface of a person's arm. In an example, a user can manually rotate the rotating member in order to find the optimal location from which to have the sensor collect data. In an example, a device can automatically rotate the rotating member in order to find the optimal location from which to have the sensor collect data. In an example, a device can automatically rotate the rotating member in order to maintain the optimal sensor location if the device is unintentionally shifted with respect to the arm's surface. In an example, a device can automatically rotate the rotating member in order to collect data from multiple locations for more comprehensive and/or accurate analysis.

In this example, a wearable device for measuring body hydration level with one or more close-fitting spectroscopic sensors comprises: (a) an attachment member which is configured to span at least a portion of the circumference of a person's arm; (b) an enclosure which is part of (or attached to) the attachment member; (c) a rotating member which is part of (or attached to) the enclosure; and (d) a spectroscopic sensor which is part of (or attached to) the rotating member, wherein this spectroscopic sensor is configured to collect data concerning a person's arm tissue, and wherein this spectroscopic sensor moves in a circular path when the rotating member is rotated.

In an example, an attachment member can be a strap, band, bracelet, ring, armlet, cuff, or sleeve. In an example, a rotating member can be a circular member which fits into a hole or recess in an enclosure. In an example, a rotating member can be manually moved by a user in order to find the best location from which to have a sensor collect data. In an example, a rotating member can be automatically moved by an actuator in the device in order to find the best location from which to have a sensor collect data. In an example, a rotating member can be automatically moved by an actuator in the device in order to maintain the best sensor location when an enclosure is unintentionally shifted with respect to the arm's surface. In an example, a rotating member can be automatically moved by an actuator in order to collect data from multiple locations for more comprehensive and/or accurate analysis. In an example, a spectroscopic sensor can measure the spectrum of light energy reflected from (and/or absorbed by) tissue of the person's arm.

With respect to specific components, the example shown in FIG. 85 includes: band 8501; band connector 8502; enclosure 8503; rotating member 8504 which is part of (or attached to) the enclosure; and spectroscopic sensor 8505 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 86 shows another example of a wearable device for measuring body hydration level with one or more close-fitting spectroscopic sensors. This figure shows the device from a non-perpendicular lateral perspective, as it would appear encircling a lateral cross-section of a person's wrist (or other portion of the person's arm).

A general description of the example shown in FIG. 86 can be expressed as a wrist-worn device with a spectroscopic sensor on a threaded rotating member, wherein rotation of the threaded rotating member adjusts the distance between the spectroscopic sensor and the surface of a person's arm. In an example, a user can manually rotate the rotating member in order to find the optimal distance between the sensor and the arm's surface from which to have the sensor collect data. In an example, a device can automatically (e.g. with an actuator) rotate the rotating member in order to find the optimal distance between the sensor and the arm's surface from which to have the sensor collect data. In an example, a device can automatically (e.g. with an actuator) rotate the rotating member to maintain the optimal distance between a sensor and the arm's surface if the enclosure is unintentionally shifted with respect to the arm's surface.

In this example, a wearable device for measuring body hydration level with one or more close-fitting spectroscopic sensors comprises: (a) an attachment member which is configured to span at least a portion of the circumference of a person's arm; (b) an enclosure which is attached to (or part of) the attachment member; (c) a threaded rotating member which is attached to (or part of) the enclosure, wherein rotation of the threaded rotating member changes the distance between the threaded rotating member and the circumferential center of the device; and (d) a spectroscopic sensor which is attached to (or part of) the threaded rotating member, wherein this spectroscopic sensor is configured to collects data concerning a person's arm tissue, and wherein rotation of the threaded rotating member changes the distance between the spectroscopic sensor and the circumferential center of the device. In an example, rotation of the threaded rotating member is also configured to change the distance between the spectroscopic sensor and the surface of the person's arm.

In an example, an attachment member can be a strap, band, bracelet, ring, armlet, cuff, or sleeve. In an example, a threaded rotating member can have a spiral thread around its circumference which fits into a complementary spiral thread in a hole or recess in the enclosure. In an example, a threaded rotating member can be manually moved by a user in order to find the best distance between a sensor and the arm's surface from which to collect data. In an example, a threaded rotating member can be automatically moved by an actuator in the device in order to find the best distance between a sensor and the arm's surface from which to collect data. In an example, a threaded rotating member can be automatically moved by an actuator in the device in order to maintain the best distance between a sensor and the arm's surface when the location of an enclosure with respect to the arm's surface is unintentionally shifted. In an example, a spectroscopic sensor can measure the spectrum of light energy reflected from (and/or absorbed by) tissue of the person's arm.

With respect to specific components, the example shown in FIG. 86 includes: band 8601; band connector 8602; enclosure 8603; threaded rotating member 8604 with spiral thread 8605 which is part of (or attached to) the enclosure; and spectroscopic sensor 8606 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 87 shows another example of a wearable device for measuring body hydration level with one or more close-fitting spectroscopic sensors. This figure shows the device from a non-perpendicular lateral perspective, as it would appear encircling a lateral cross-section of a person's wrist (or other portion of the person's arm). The example shown in FIG. 87 can be described as a wrist-worn device with a spectroscopic sensor, wherein the location of this sensor can be moved along an X axis and/or along a Y axis, wherein the X axis is substantially tangential to the circumference of the device, and wherein the Y axis is perpendicular to the X axis.

In an example, a user can manually move a sensor along these X and/or Y axes in order to find the optimal location from which to collect data concerning arm tissue. In an example, the device can automatically move a sensor (e.g. with an actuator) along these X and/or Y axes in order to find the optimal location from which to collect data concerning arm tissue. In an example, the device can automatically move a sensor (e.g. with an actuator) along these X and/or Y axes in order to keep the sensor at the optimal location even if the device is unintentionally shifted with respect to the arm's surface. In an example, the device can automatically move a sensor (e.g. with an actuator) along these X and/or Y axes in order to collect data from various locations for more comprehensive or accurate analysis.

In this example, a wearable device for measuring body hydration level with one or more close-fitting spectroscopic sensors comprises: (a) an attachment member which is configured to span at least a portion of the circumference of a person's arm; (b) an enclosure which is attached to (or part of) the attachment member; (c) a spectroscopic sensor which is configured to collect data concerning arm tissue; (d) a first moving member whose movement moves the spectroscopic sensor along an X axis, wherein this X axis is substantially tangential to the circumference of the device; and (e) a second moving member whose movement moves the spectroscopic sensor along an Y axis, wherein this Y axis is perpendicular to the X axis.

In an example, an attachment member can be a strap, band, bracelet, ring, armlet, cuff, or sleeve. In an example, a spectroscopic sensor can be attached to a circumference-center-facing portion of an enclosure. In an example, first and second moving members can be sliding members. In an example, a first moving member can be a strip on an enclosure which slides along the X axis. In an example, a second moving member can be a strip on an enclosure which slides along the Y axis. In another example, first and second moving members can be rotating members. In an example, a spectroscopic sensor can measure the spectrum of light energy reflected from (and/or absorbed by) tissue of the person's arm.

With respect to specific components, the example shown in FIG. 87 includes: band 8701; band connector 8702; enclosure 8703; first sliding member 8704 which slides along an X axis, wherein the X axis is substantially tangential to the circumference of the device; second sliding member 8705 which slides along an Y axis, wherein the Y axis is substantially perpendicular to the X axis; and spectroscopic sensor 8706 which is configured to collect data concerning arm tissue, wherein the X and Y coordinates of spectroscopic sensor 8706 are changed by moving the first and second sliding members, respectively. In a variation on this example, both an enclosure and Y axis can be arcuate. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 88 shows another example of a wearable device for measuring body hydration level with one or more close-fitting spectroscopic sensors. This figure shows the device from a non-perpendicular lateral perspective, as it would appear encircling a lateral cross-section of a person's wrist (or other portion of the person's arm). The example shown in FIG. 88 can be described as a wrist-worn device with: two parallel bands which are connected to each other on the anterior (upper) surface of the wrist; and a spectroscopic sensor which slides (back and forth) along the strip which connects the two bands.

In an example, a user can manually slide the spectroscopic sensor (back and forth) along the strip connecting the two bands in order to find the optimal location from which to collect data concerning arm tissue. In an example, the device can automatically slide the spectroscopic sensor (back and forth) along the strip connecting the two bands in order to find the optimal location from which to collect data concerning arm tissue. In an example, the device can automatically slide the spectroscopic sensor (back and forth) along the strip connecting the two bands in order to collect data from different locations for more comprehensive or accurate analysis.

In this example, a wearable device for measuring body hydration level with one or more close-fitting spectroscopic sensors comprises: (a) two substantially-parallel bands which are each configured to span at least a portion of the circumference of a person's arm; (b) a connecting strip which is configured to connect the two bands to each other on the anterior (upper) surface of the arm; (c) a moving enclosure which slides (back and forth) along the connecting strip; and (d) a spectroscopic sensor which is configured to collect data concerning arm tissue, wherein this spectroscopic sensor is part of (or attached to) the moving enclosure. In an example, a spectroscopic sensor can measure the spectrum of light energy reflected from (and/or absorbed by) tissue of the person's arm.

With respect to specific components, the example shown in FIG. 88 includes: first band 8801; second band 8802; connecting strip 8803 which connects the first and second bands; sliding enclosure 8804 which slides (back and forth) along the connecting strip; and spectroscopic sensor 8805 which is configured to collect data concerning arm tissue, wherein this spectroscopic sensor is part of (or attached to) the sliding enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 89 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 89 is an arcuate wrist-worn device with a light-projecting spectroscopic sensor on a rotating ball. Rotating the ball changes the angle at which the spectroscopic sensor projects light onto the surface of a person's arm. The ball can be rotated in different directions so that the range of possible projection beams comprises a conic or frustal shape in three-dimensional space. Having a light-projecting spectroscopic sensor on a rotating ball can enable a device to record spectroscopic measurements with substantially the same angle of incidence, even if an enclosure is tilted with respect to the surface of the person's arm.

The example shown in FIG. 89 is a wearable device for measuring body hydration level with a close-fitting spectroscopic sensor comprising: (a) an attachment member, such as a strap or band, which is configured to span at least a portion of the circumference of a person's arm; (b) an enclosure which is part of (or attached to) the attachment member; (c) a rotating ball which is part of (or attached to) the enclosure; and (d) a light-projecting spectroscopic sensor which is part of (or attached to) the rotating ball.

In an example, an attachment member can be a strap, band, bracelet, ring, armlet, cuff, or sleeve. In an example, the circumference-center-facing surface of an enclosure can be substantially flat. In an example, the circumference-center-facing surface of an enclosure can be curved. In an example, there can be a display screen on the outward-facing surface of an enclosure. In an example, the rotating ball can fit into the enclosure like a ball-and-socket joint. In an example, the device can further comprise one or more actuators which move the rotating ball.

With respect to specific components, the example shown in FIG. 89 includes: strap 8901, strap connector 8902, enclosure 8903, rotating ball 8904, and spectroscopic sensor 8905 which emits beam of light 8906. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 90 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 90 is a wearable device for measuring body hydration level with a flexible circumferentially or annularly-undulating band with spectroscopic sensors on the proximal portions of undulating waves. A band with such a flexible circumferentially or annularly-undulating structure can help to keep a plurality of spectroscopic sensors in close proximity to the surface of a person's arm. In an example, an attachment member can be a strap, band, bracelet, ring, or armlet. In an example, a circumferentially or annularly-undulating attachment member can have a repeating wave pattern. In an example, a circumferentially or annularly-undulating attachment member can have a sinusoidal wave pattern.

The example shown in FIG. 90 is a wearable device for measuring body hydration level with a close-fitting spectroscopic sensor comprising: (a) a circumferentially or annularly-undulating attachment member which is configured to span at least a portion of the circumference of a person's arm; and (b) a plurality of spectroscopic sensors which collect data concerning arm tissue, wherein each spectroscopic sensor is located at the proximal portion of an undulation, and wherein the proximal portion of an undulation is the portion of an undulating wave which is closest to the circumferential center of the device.

With respect to specific components, the example shown in FIG. 90 includes: circumferentially or annularly-undulating band 9001, band connector 9002, enclosure 9003, first spectroscopic sensor 9004 at the proximal portion of a first wave in the circumferentially or annularly-undulating band, and second spectroscopic sensor 9005 at the proximal portion of a second wave in the circumferentially or annularly-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 91 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 91 is a wearable device for measuring body hydration level with a flexible circumferentially or annularly-undulating band with six waves and spectroscopic sensors on the proximal portions of some or all of these waves.

A band with a circumferentially or annularly-undulating structure can help to keep a plurality of spectroscopic sensors in close proximity to the surface of a person's arm. Further, a band with six waves can engage the sides of a person's wrist with two symmetrically-opposite waves to resist rotational shifting better than a circular or oval band. This can help to reduce measurement errors caused by movement of spectroscopic sensors. In an example, a circumferentially or annularly-undulating attachment member can be a strap, band, bracelet, ring, or armlet. In an example, a circumferentially or annularly-undulating attachment member can have a repeating wave pattern. In an example, a circumferentially or annularly-undulating attachment member can have a sinusoidal wave pattern.

The example shown in FIG. 91 is a wearable device for measuring body hydration level with one or more close-fitting spectroscopic sensors comprising: (a) a circumferentially or annularly-undulating attachment member with six waves which is configured to span the circumference of a person's arm; and (b) a plurality of spectroscopic sensors which collect data concerning arm tissue, wherein each spectroscopic sensor is located at the proximal portion of an undulation, and wherein the proximal portion of an undulation is the portion of an undulating wave which is closest to the circumferential center of the device.

With respect to specific components, the example shown in FIG. 91 includes: circumferentially or annularly-undulating band 9101 with six waves, band connector 9102, a first spectroscopic sensor 9103 at the proximal portion of a first wave in the circumferentially or annularly-undulating band, a second spectroscopic sensor 9105 at the proximal portion of a second wave in the circumferentially or annularly-undulating band, and a third spectroscopic sensor 9106 at the proximal portion of a third wave in the circumferentially or annularly-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 92 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. Described generally, the example shown in FIG. 92 is a wearable device for measuring body hydration level with a laterally-undulating band and spectroscopic sensors. Lateral undulations are waves which are substantially perpendicular to the plane containing the band circumference. In an example, a band can have sinusoidal lateral undulations.

The example shown in FIG. 92 is a wearable device for measuring body hydration level with one or more close-fitting spectroscopic sensors comprising: (a) a laterally-undulating attachment member which is configured to span at least a portion of the circumference of a person's arm, wherein lateral undulations are waves which are substantially perpendicular to the plane containing the circumference of the attachment member; and (b) one or more spectroscopic sensors which collect data concerning arm tissue, wherein these spectroscopic sensors are part of (or attached to) the laterally-undulating attachment member.

With respect to specific components, the example shown in FIG. 92 includes: laterally-undulating strap 9201; display screen 9202; and spectroscopic sensors including 9203 and 9204. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 93 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 93 is a wearable device for an arm with one or more spectroscopic sensors in an enclosure and an attachment member (such as a strap, band, bracelet, or cuff) which attaches the enclosure to the arm, wherein this attachment member has relatively-elastic portions connected to the enclosure and relatively-inelastic portions elsewhere. This structure can help to keep the enclosure and sensors fitting closely against the arm. This, in turn, can enable more-consistent collection of data concerning body hydration levels. Many "elderly" people (which at many Silicon Valley companies is apparently anyone over the age of 39) do not realize that they are becoming dehydrated until an adverse health event occurs.

In an example, the device in FIG. 93 can be specified as a wearable device for measuring body hydration level with one or more close-fitting spectroscopic sensors comprising: (a) an attachment member which is configured to span at least 60% of the circumference of a person's arm, wherein this attachment member further comprises—one or more elastic portions which are configured to span the anterior (upper) surface of a person's arm and one or more inelastic portions which are configured to span the posterior (lower) surface of the person's arm; (b) an enclosure which is connected to the elastic portions of the attachment member; and (c) one or more spectroscopic sensors which collect data concerning arm tissue which are part of (or attached to) the enclosure.

In an alternative example, a wearable device for measuring body hydration level with one or more close-fitting spectroscopic sensors can comprise: (a) an attachment member which is configured to span at least 60% of the circumference of a person's arm, wherein this attachment member further comprises—one or more elastic portions which are configured to span the posterior (lower) surface of a person's arm and one or more inelastic portions which are configured to span the anterior (upper) surface of the person's arm; (b) an enclosure which is connected to the elastic portions of the attachment member; and (c) one or more spectroscopic sensors which collect data concerning arm tissue which are part of (or attached to) the enclosure.

In an example, an elastic portion of an attachment member can be an elastic strap or band. In an example, an elastic portion of an attachment member can be made from elastic fabric. In an example, an elastic portion of an attachment member can have a first elasticity level, an inelastic portion of an attachment member can have a second elasticity level, and the first elasticity level can be greater than the second elasticity level. In an example, a first elastic portion of an attachment member can be directly connected to a first side of an enclosure and a second elastic portion of an attachment member can be directly connected to a second (opposite) side of the enclosure. In an example, a first elastic portion of an attachment member can be indirectly connected to a first side of an enclosure and a second elastic portion of an attachment member can be indirectly connected to a second (opposite) side of the enclosure.

In an example, the device in FIG. 93 can be specified as a wearable device for measuring body hydration level with one or more close-fitting spectroscopic sensors comprising: (a) an attachment member which is configured to span at least 60% of the circumference of a person's arm wherein this attachment member further comprises: two elastic portions which are configured to span a first portion of the circumference of a person's arm; and two inelastic portions which are configured to span a second portion of the circumference of the person's arm; (b) an enclosure which is connected between the two elastic portions; (c) a clip, buckle, clasp, pin, or hook-and-eye mechanism between the two inelastic portions; and d) one or more spectroscopic sensors which collect data concerning arm tissue which are part of (or attached to) the enclosure.

In an example, the device in FIG. 93 can be specified as a wearable device for measuring body hydration level with one or more close-fitting spectroscopic sensors comprising: (a) an attachment member which is configured to span at least 60% of the circumference of a person's arm wherein this attachment member further comprises: two elastic portions of the attachment member which are configured to span a portion of the circumference of a person's arm; and one or more inelastic portions which comprise the remainder of the attachment member; (b) an enclosure which is connected between the two elastic portions; (c) one or more spectroscopic sensors which collect data concerning arm tissue which are part of (or attached to) the enclosure.

In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member. In an example, two elastic portions can be configured to collectively span at least 20% of the circumference of a person's arm. In an example, two elastic portions can be configured to collectively span at least 20% of the circumference of an attachment member. In an example, two inelastic portions can be configured to collectively span at least 20% of the circumference of a person's arm. In an example, two inelastic portions can be configured to collectively span at least 20% of the circumference of an attachment member.

In an example, a first definition of polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is (clockwise) midway between the 0-degree and 180-degree positions. A 270-degree position is diametrically opposite the 90-degree position.

Using this first definition of polar coordinates, the device in FIG. 93 can be specified as a wearable device for measuring body hydration level with one or more close-fitting spectroscopic sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is configured to be worn (clockwise) between the 270-degree and 90-degree positions; and (c) one or more spectroscopic sensors which collect data concerning arm tissue which are part of (or attached to) the enclosure.

Using this first definition of polar coordinates, the device in FIG. 93 can also be specified as a wearable device for measuring body hydration level with one or more close-fitting spectroscopic sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions; and (c) one or more spectroscopic sensors which collect data concerning arm tissue which are part of (or attached to) the enclosure.

Alternatively, a second definition of polar (or compass) coordinates can be defined for the circumference of such a device relative to the position of an enclosure. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position.

Using this second definition of polar coordinates, the device in FIG. 93 can be specified as a wearable device for measuring body hydration level with one or more close-fitting spectroscopic sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions of the attachment member; and (c) one or more spectroscopic sensors which collect data concerning arm tissue which are part of (or attached to) the enclosure. In an example, a spectroscopic sensor can measure the spectrum of light energy reflected from (and/or absorbed by) tissue of the person's arm.

With respect to specific components, the example shown in FIG. 93 includes: inelastic portion 9301 of an attachment member; elastic portion 9302 of an attachment member; elastic portion 9303 of an attachment member; inelastic portion 9304 of an attachment member; attachment member connector 9305; enclosure 9306; and spectroscopic sensors 9307 and 9308. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 94 shows another example of a wearable device for measuring body hydration level with one or more close-fitting spectroscopic sensors. This figure shows the device from a side perspective, as it would appear encircling a lateral cross-section of a person's wrist (or other portion of the person's arm). Described generally, the example shown in FIG. 94 is a wearable device for measuring body hydration level with one or more spectroscopic sensors in an enclosure and an attachment member (such as a strap, band, bracelet, or cuff) which attaches the enclosure to the arm, wherein the attachment member is configured to have elastic portions spanning the lateral surfaces of the arm and inelastic portions spanning the anterior (upper) and posterior (lower) surfaces of the arm. This structure can help to keep the enclosure and sensors from rotating around the arm. This, in turn, can enable more-consistent collection of data concerning arm tissue.

In an example, the device in FIG. 94 can be specified as a wearable device for measuring body hydration level with one or more close-fitting spectroscopic sensors comprising: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the anterior (upper) portion of the arm; and (c) one or more spectroscopic sensors which collect data concerning arm tissue which are part of (or attached to) the enclosure.

In another example, a wearable device for measuring body hydration level with one or more close-fitting spectroscopic sensors can comprise: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the posterior (lower) portion of the arm; and (c) one or more spectroscopic sensors which collect data concerning arm tissue which are part of (or attached to) the enclosure.

In an example, a first inelastic portion of an attachment member can be connected to a first side of an enclosure and a second inelastic portion of an attachment member can be connected to a second side of the enclosure. In an example, an elastic portion can have a first level of elasticity, an inelastic portion can have a second level of elasticity, and the first level is greater than the second level. In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member.

In an example, polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is clockwise midway between the 0-degree and 180-degree positions. A 270-degree position is diametrically opposite the 90-degree position.

In an example, the device in FIG. 94 can be specified as a wearable device for measuring body hydration level with one or more close-fitting spectroscopic sensors comprising: (a) an attachment member which is configured to span at least 60% of the circumference of a person's arm wherein this attachment member further comprises—a inelastic first portion with a first level of elasticity which spans at least 35 degrees (clockwise) between the 270-degree and 90-degree positions; an inelastic second portion with a second level of elasticity which spans at least 35 degrees (clockwise) between the 90-degree and 270-degree positions, an elastic third portion with a third level of elasticity which spans at least 35 degrees (clockwise) between the 180-degree and 0-degree positions, an elastic fourth portion with a fourth level of elasticity which spans at least 35 degrees (clockwise) between the 0-degree and 180-degree positions, and wherein each of the first and second elasticity levels is lower than each of the third and fourth elasticity levels; (b) an enclosure that is connected between the inelastic first portion and the inelastic second portion; and (c) one or more spectroscopic sensors which collect data concerning arm tissue which are part of (or attached to) the enclosure.

In an alternative example, polar (or compass) coordinates can be defined for the circumference of such a device relative to the position of an enclosure on the device. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position. In an example, a spectroscopic sensor can measure the spectrum of light energy reflected from (and/or absorbed by) tissue of the person's arm.

With respect to specific components, the example shown in FIG. 94 includes: inelastic portion 9401 of an attachment member; elastic portion 9402 of an attachment member; inelastic portion 9403 of an attachment member; inelastic portion 9404 of an attachment member; elastic portion 9405 of an attachment member; inelastic portion 9406 of an attachment member; attachment member connector 9407; enclosure 9408; and spectroscopic sensors 9409 and 9410. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 95 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. This can be seen as a top-down view of a further-specified variation of the example that was shown from a side perspective in FIG. 93.

The example shown in FIG. 95 can be described generally as a wearable device for measuring body hydration level with one or more spectroscopic sensors in an enclosure and an attachment member (such as a band, strap, bracelet, or cuff) which holds the enclosure on a person's arm, wherein there are rectangular, rounded rectangular, or plano-concave elastic portions of the attachment member which are connected to the enclosure and wherein the rest of the attachment member is inelastic. Such a structure can help to keep the enclosure and sensors close against the arm surface. This, in turn, can enable more-consistent collection of data concerning arm tissue.

In an example, the device in FIG. 95 can be specified as a wearable device for measuring body hydration level with one or more close-fitting spectroscopic sensors comprising: (a) an attachment member which is configured to span at least 60% of the circumference of a person's arm, wherein this attachment member further comprises—a first elastic portion with a first elasticity level, a second elastic portion with a second elasticity level, and an inelastic portion with a third elasticity level, wherein the third elasticity level is less than each of the first and second elasticity levels; (b) an enclosure which is connected between the first and second elastic portions; and (c) one or more spectroscopic sensors which collect data concerning arm tissue which are part of (or attached to) the enclosure.

In an example, the device in FIG. 95 can be specified as a wearable device for measuring body hydration level with one or more close-fitting spectroscopic sensors comprising: (a) an attachment member which is configured to span at least 60% of the circumference of a person's arm, wherein this attachment member further comprises—a first plano-concave elastic portion with a first elasticity level, a second plano-concave elastic portion with a second elasticity level, and an inelastic portion with a third elasticity level, wherein the third elasticity level is less than each of the first and second elasticity levels; (b) an enclosure which is connected between the first and second plano-concave elastic portions; and (c) one or more spectroscopic sensors which collect data concerning arm tissue which are part of (or attached to) the enclosure.

In an example, the device in FIG. 95 can be specified as a wearable device for measuring body hydration level with one or more close-fitting spectroscopic sensors comprising: (a) an enclosure which is configured to be worn on a person's arm; (b) one or more spectroscopic sensors which collect data concerning arm tissue which are part of (or attached to) the enclosure; (c) two elastic members which are attached to the enclosure, wherein these elastic members are configured to collectively span at least 20% of the circumference of the arm, and wherein these elastic attachment members have first and second elasticity levels, respectively; and (d) one or more inelastic members which are attached to the two elastic attachment members, wherein these inelastic members collectively span at least 40% of the circumference of the arm, and wherein these inelastic members have a third elasticity level which is less than each of the first and second elasticity levels.

In an example, an elastic member can have a shape which is selected from the group consisting of: rectangular; rounded rectangle; plano-concave; and section of a cylinder. In an example, the device in FIG. 95 can be specified as a wearable device for measuring body hydration level with one or more close-fitting spectroscopic sensors comprising: (a) an attachment member which is configured to span at least 60% of the circumference of a person's arm, wherein this attachment member further comprises—two symmetric plano-concave elastic portions, with first and second elasticity levels respectively, and an inelastic portion with a third elasticity level, wherein the third elasticity level is less than each of the first and second elasticity levels; (b) an enclosure which is connected to the concave sides of the two symmetric plano-concave elastic portions of the attachment member; and (c) one or more spectroscopic sensors which collect data concerning arm tissue which are part of (or attached to) the enclosure.

In an example, an attachment member can be a band, strap, bracelet, bangle, armlet, cuff, or sleeve. In an example, an elastic portion of an attachment member can be made from elastic and/or stretchable fabric. In an example, an enclosure can be arcuate. In an example, an enclosure can be circular. In an example, a device can further comprise a display screen on the outward-facing surface of an enclosure. In an example, a spectroscopic sensor can measure the spectrum of light energy reflected from (and/or absorbed by) tissue of a person's arm.

With respect to specific components, the example shown in FIG. 95 includes: first elastic portion 9502 of an attachment member; second elastic portion 9503 of an attachment member; first inelastic portion 9501 of an attachment member; second inelastic portion 9504 of an attachment member; enclosure 9505 with a display screen on its outward-facing surface; and spectroscopic sensors 9506 and 9507. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 96 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 96 is like the one shown in FIG. 95 except that in FIG. 96 the elastic portions are tapered (narrower in width) as they approach their connections with the enclosure.

With respect to specific components, the example shown in FIG. 96 includes: first tapered (width-varying) elastic portion 9602 of an attachment member; second tapered (width-varying) elastic portion 9603 of an attachment member; first inelastic portion 9601 of an attachment member; second inelastic portion 9604 of an attachment member; enclosure 9605 with a display screen on its outward-facing surface; and spectroscopic sensors 9606 and 9607. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 97 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 97 is like the one shown in FIG. 95 except that in FIG. 97 there are four elastic portions, two connected to each side of the enclosure. Further, each elastic portion has a shape which is triangular and/or pennant shaped.

The example shown in FIG. 97 is a wearable device for measuring body hydration level with one or more close-fitting spectroscopic sensors comprising: (a) an attachment member which is configured to span at least 60% of the circumference of a person's arm, wherein this attachment member further comprises—four tapered (width-varying) elastic portions, wherein these elastic portions have a first elasticity level, and wherein these elastic portions are configured to be worn on the anterior (upper) portion of a person's arm; and one or more inelastic portions which comprise the remainder of the attachment member, wherein these inelastic portions have a second elasticity level which is less than the first elasticity level; (b) an enclosure, wherein a first side of the enclosure is connected to tapered ends of two of the four elastic portions of the attachment member and wherein a second (opposite) side of the enclosure is connected to tapered ends of the other two of the four elastic portions of the attachment member; and (c) one or more spectroscopic sensors which collect data concerning arm tissue, wherein these sensors are part of (or attached to) the enclosure.

With respect to specific components, the example shown in FIG. 97 includes: first, second, third, and fourth tapered elastic portions (9702, 9703, 9704, and 9705) of an attachment member; first and second inelastic portions (9701 and 9706) of an attachment member; enclosure 9707 with a display screen on its outward-facing surface; and spectroscopic sensors 9708 and 9709. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 98 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 98 is like the one shown in FIG. 95 except that in FIG. 98 there are two elastic portions on each side of the enclosure which criss-cross each other, forming an "X" on each side of the enclosure. This design can help to keep the enclosure and sensors close to the surface of the arm for more consistent collection of data.

The example shown in FIG. 98 is a wearable device for measuring body hydration level with one or more close-fitting spectroscopic sensors comprising: (a) an enclosure which is configured to be worn on a person's arm; (b) one or more spectroscopic sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, wherein the portion of the attachment member that connects to the enclosure includes elastic bands (or straps) on each side of the enclosure which criss-cross each other. In an example, the criss-crossing bands (or straps) on each side of the enclosure form an "X" on each side of the enclosure.

With respect to specific components, the example shown in FIG. 98 includes: inelastic portion 9801 of the attachment member; inelastic portion 9802 of the attachment member; enclosure 9803 with an outward-facing display screen; spectroscopic sensors 9804 and 9805; and elastic bands (or straps) 9806, 9807, 9808, 9809, 9810, and 9811. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 99 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 99 is like the one shown in FIG. 95 except that in FIG. 99 there are two parallel elastic bands (or straps) connected to the enclosure. This design can help to keep the enclosure and sensors close to the surface of the arm for more consistent collection of data.

The example shown in FIG. 99 is a wearable device for measuring body hydration level with one or more close-fitting spectroscopic sensors comprising: (a) an enclosure which is configured to be worn on a person's arm; (b) one or more spectroscopic sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes two parallel elastic bands (or straps) connected to the enclosure.

With respect to specific components, the example shown in FIG. 99 includes: inelastic portion 9901 of the attachment member; inelastic portion 9902 of the attachment member; enclosure 9903 with an outward-facing display screen; spectroscopic sensors 9904 and 9905; and two parallel elastic bands (or straps) 9906 and 9907. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 100 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 100 is like the one shown in FIG. 95 except that in FIG. 100 there are three parallel elastic bands (or straps) connected to the enclosure. This design can help to keep the enclosure and sensors close to the surface of the arm for more consistent collection of data.

The example shown in FIG. 100 is a wearable device for measuring body hydration level with one or more close-fitting spectroscopic sensors comprising: (a) an enclosure which is configured to be worn on a person's arm; (b) one or more spectroscopic sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes three parallel elastic bands (or straps) connected to the enclosure.

With respect to specific components, the example shown in FIG. 100 includes: inelastic portion 10001 of the attachment member; inelastic portion 10002 of the attachment member; enclosure 10003 with an outward-facing display screen; spectroscopic sensors 10004 and 10005; and three parallel elastic bands (or straps) 10006, 10007, and 10008. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 101 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 101 is like the one shown in FIG. 100 except that the three elastic bands (or straps) are not parallel.

With respect to specific components, the example shown in FIG. 101 includes: inelastic portion 10101 of the attachment member; inelastic portion 10102 of the attachment member; enclosure 10103 with an outward-facing display screen; spectroscopic sensors 10104 and 10105; and three elastic bands (or straps) 10106, 10107, and 10108. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 102 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 102 can be generally described as an arm-worn device with spectroscopic sensors in an enclosure, wherein the enclosure is suspended on the surface of the arm by four elastic bands, and wherein each elastic band is individually connected to one of four points which are equally-spaced around the circumference of the enclosure. This enclosure suspension design can help to keep the sensors close to the surface of the arm for more consistent collection of data.

The example shown in FIG. 102 can be specified as a wearable device for measuring body hydration level with one or more close-fitting spectroscopic sensors comprising: (a) an arcuate enclosure which is configured to be worn on a person's arm; (b) one or more spectroscopic sensors which collect data concerning arm tissue, wherein these sensors are part of (or attached to) the enclosure; and (c) four elastic bands (or straps), each of which is connected to one of four points which are equally spaced around the circumference of the enclosure. In an example, each of the four elastic bands (or straps) can have one end which is connected to the enclosure and one end which is connected to an inelastic band, strap, bracelet, or armlet which is configured to span at least 50% of the circumference of the arm.

In another example, a wearable device for measuring body hydration level with one or more close-fitting spectroscopic sensors can comprise: (a) a quadrilateral enclosure which is configured to be worn on a person's arm; (b) one or more spectroscopic sensors which collect data concerning arm tissue, wherein these sensors are part of (or attached to) the enclosure; and (c) four elastic bands (or straps), each of which is connected to one side of the enclosure. In an example, each of the four elastic bands (or straps) can have one end which is connected to the enclosure and one end which is connected to an inelastic band, strap, bracelet, or armlet which is configured to span at least 50% of the circumference of the arm.

With respect to specific components, the example shown in FIG. 102 includes: inelastic portion 10201 of the attachment member; inelastic portion 10202 of the attachment member; enclosure 10203 with an outward-facing display screen; spectroscopic sensors 10204 and 10205; and four elastic bands (or straps) 10206, 10207, 10208, and 10209. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 103 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 103 can be generally described as an arm-worn device with spectroscopic sensors in an enclosure, wherein the enclosure is suspended on the surface of the arm by four elastic suspension bands (or straps) connected to three parallel attachment bands or straps which encircle the arm. This enclosure suspension design can help to keep the sensors close to the surface of the arm for more consistent collection of data.

The example shown in FIG. 103 can be specified as a wearable device for measuring body hydration level with one or more close-fitting spectroscopic sensors comprising: (a) an enclosure which is configured to be worn on a person's arm; (b) one or more spectroscopic sensors which collect data concerning arm tissue, wherein these sensors are part of (or attached to) the enclosure; and (c) three parallel attachment bands, including proximal, middle, distal attachment bands; wherein each of the three parallel attachment bands is configured to span at least 60% of the circumference of the arm; and (d) four elastic suspension bands, wherein the four suspension bands are connected to the four sides of the enclosure, respectively; wherein two of the suspension bands are also connected to the proximal attachment band and the distal attachment band, respectively; and wherein the other two of the suspension bands are also connected to the middle attachment band. In an example, the word "strap" can be substituted for the word "band" in the above specification.

With respect to specific components, the example shown in FIG. 103 includes: a distal attachment band 10301, ends 10302 and 10303 of a middle attachment band, proximal attachment band 10304, enclosure 10305 with outward-facing display screen, spectroscopic sensors 10306 and 10307, and four suspension bands 10308, 10309, 10310, and 10311. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 104 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 104 can be described as a wrist-worn device with a gimbaled enclosure that contains one or more spectroscopic sensors. The gimbal mechanism around the enclosure enables the enclosure and sensors to remain relatively flat against the surface of the arm, even if the device shifts, rotates, and/or twists on the person's arm. This can help to maintain consistent measurement of data from the arm.

The example in FIG. 104 can be specified as a wearable device for measuring body hydration level with one or more close-fitting spectroscopic sensors comprising: (a) an attachment member which is configured to span at least 60% of the circumference of a person's arm; (b) a gimbal mechanism which is connected to the attachment member, wherein this gimbal mechanism further comprises two or more concentric rings which are axially connected so that they can move relative to each other; (c) an enclosure within the most central concentric ring of the gimbal mechanism; and (d) one or more spectroscopic sensors which are part of (or attached to) the enclosure, wherein these spectroscopic sensors are configured to collect data concerning arm tissue.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm even though the ends are not connected to each other.

In an example, a gimbal mechanism can comprise two concentric (inner and outer) rings which pivot relative to each other, wherein these rings are connected by one or more axles at opposite sides of the inner ring. In an example, a gimbal mechanism can comprise three concentric (inner, central, and outer) rings which pivot relative to each other, wherein the outer and central rings are connected by one or more axles at a first set of opposite sides of the central ring, wherein the central and inner rings are connected by one or more axles at a second set of opposite sides of the central ring, and wherein the second set is at locations which are rotated around the circumference of the center ring by 90-degrees relative to the locations of the first set. In an example, a spectroscopic sensor can measure the spectrum of light energy reflected from (and/or absorbed by) tissue of the person's arm.

In an example, an enclosure can further comprise a display screen which is seen on the outward-facing surface of the enclosure. In an example, the enclosure can be circular. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

With respect to specific components, the example shown in FIG. 104 includes: first portion 10401 of an attachment member; second portion 10402 of the attachment member; enclosure 10403 with an outward-facing display screen; spectroscopic sensors 10404 and 10405 within the enclosure; inner ring 10406, central ring 10407, and outer ring 10408 of a gimbal mechanism; first set of axles 10409 and 10410 connecting the inner ring and the central ring; and second set of axles 10411 and 10412 connecting the central ring and the outer ring.

FIG. 105 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 105 is a wrist-worn device with an enclosure containing one or more spectroscopic sensors, wherein this enclosure is suspended by a radial plurality of elastic (and/or stretchable or springy) suspension members which connect to locations on the circumference of the enclosure. In an example, this design can be called a "sunburst suspension system" because the elastic (and/or stretchable or springy) suspension members look like the radial sunrays in a traditional "sunburst" drawing. The "sunburst suspension" design enables the enclosure and sensors to remain relatively flat against the surface of the arm, even if the device shifts, rotates, and/or twists on the person's arm. This can help to maintain consistent measurement of data from the arm.

The example in FIG. 105 can be specified as a wearable device for measuring body hydration level with one or more close-fitting spectroscopic sensors comprising: (a) an attachment member which is configured to span at least 60% of the circumference of a person's arm; (b) an enclosure; (c) one or more spectroscopic sensors which are part of (or attached to) the enclosure, wherein these spectroscopic sensors are configured to collect data concerning arm tissue; and (d) a plurality of elastic (and/or stretchable or springy) suspension members, wherein these suspension members flexibly connect the enclosure to the attachment member, wherein each of these suspension members is connected at one end to a location on the circumference of the enclosure and connected at its other end to the attachment member, and wherein the longitudinal axis of each of the suspension members is substantially parallel with a virtual radial spoke outward from the center of the enclosure.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm, even though the ends of the attachment member are not connected to each other.

In an example, an enclosure can be circular. In an example, an enclosure can further comprise a display screen which is seen on the outward-facing surface of the enclosure. In an example, a spectroscopic sensor can measure the spectrum of light energy reflected from (and/or absorbed by) tissue of the person's arm.

In an example, a suspension member can be a spring. In an example, a suspension member can be an elastic band or strap. In an example, the locations on the circumference of the enclosure to which the suspension members are connected can be evenly distributed around the circumference of the enclosure. In an example, there can be four suspension members. In an example, there can be six suspension members. In an example, there can be eight suspension members. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

With respect to specific components, the example shown in FIG. 105 includes: first portion 10501 of an attachment member; second portion 10502 of the attachment member; enclosure 10503 with an outward-facing display screen; spectroscopic sensors 10504 and 10505 within the enclosure; a plurality of spring suspension members, including 10506; and ring 10507.

FIG. 106 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 106 is a flexible arm-worn device with two arcuate enclosures which contain spectroscopic sensors.

The example in FIG. 106 can be specified as a wearable device for measuring body hydration level with one or more close-fitting spectroscopic sensors comprising: (a) a flexible attachment member which is configured to span at least 60% of the circumference of a person's arm; (b) a first arcuate enclosure whose center is at a first location on the circumference of the flexible attachment member; (c) a first spectroscopic sensor which is part of (or attached to) the first arcuate enclosure, wherein this first spectroscopic sensor is configured to collect data concerning arm tissue; (d) a second arcuate enclosure whose center is at a second location on the circumference of the flexible attachment member, wherein the distance between the first and second locations is greater than one-half inch; and (e) a second spectroscopic sensor which is part of (or attached to) the second arcuate enclosure, wherein this second spectroscopic sensor is configured to collect data concerning arm tissue.

In an example, a flexible attachment member can be a strap, band, bracelet, bangle, chain, ring, armlet, cuff, gauntlet, or sleeve. In an example, a flexible attachment member can stretch to span the entire circumference of a person's arm. In an example, a flexible attachment member can have two ends which connect to each other to hold the attachment member onto a person's arm. In an example, a flexible attachment member can be sufficiently rigid and/or resilient in shape that it has ends which hold onto the person's arm, even though the ends of the attachment member are not connected to each other.

In an example, an arcuate enclosure containing a spectroscopic sensor can be circular. In an example, this device can further comprise a display screen between the two arcuate enclosures. In an alternative example, each of the arcuate enclosures can have a display screen on its outward-facing side. In an example, a spectroscopic sensor can measure the spectrum of light energy reflected from (and/or absorbed by) tissue of the person's arm.

With respect to specific components, the example shown in FIG. 106 includes: flexible attachment member 10601; central display screen 10602; first arcuate enclosure 10603; first spectroscopic sensor 10604; second arcuate enclosure 10605; and second spectroscopic sensor 10606. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure or in priority-linked disclosures can also apply to this example.

FIG. 107 shows another example of a wearable device for measuring body hydration level with one or more close-fitting spectroscopic sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. The example shown in FIG. 107 can be described as an arm-worn device with an arcuate enclosure to which a strap or band is connected diagonally.

The example in FIG. 107 can be specified as a wearable device for measuring body hydration level with one or more close-fitting spectroscopic sensors comprising: (a) an arcuate enclosure which is configured to be worn on a person's arm; (b) one or more spectroscopic sensors which are configured to collect data concerning arm tissue and which are part of (or attached to) the arcuate enclosure; and (c) an attachment member which is configured to span at least 60% of the circumference of a person's arm, wherein a first portion of this attachment member is connected to the arcuate enclosure between the 12 o'clock and 3 o'clock positions (or 0-degree and 90-degree positions using compass coordinates) of the circumference of the enclosure; and wherein a second portion of this attachment member is connected to the arcuate enclosure between the 6 o'clock and 9 o'clock positions (or 180-degree and 270-degree positions using compass coordinates) of the circumference of the enclosure.

With respect to specific components, the example shown in FIG. 107 includes: attachment member 10701; enclosure 10702 with an outward-facing display screen; and spectroscopic sensors 10703 and 10704 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 108 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 108 can be colorfully described as a "two gummi worm" design—because it looks like two gummi worms crawling in a symmetric manner around portions of the circumference of an enclosure.

The example in FIG. 108 can be specified as a wearable device for measuring body hydration level with one or more close-fitting spectroscopic sensors comprising: (a) an arcuate enclosure which is configured to be worn on a person's arm; (b) one or more spectroscopic sensors which are configured to collect data concerning arm tissue and which are part of (or attached to) the arcuate enclosure; and (c) an attachment member which is configured to span at least 60% of the circumference of a person's arm, wherein a first portion of this attachment member spans most of the circumference of the arcuate enclosure between the 10 o'clock and 2 o'clock positions (or 300-degree and 60-degree positions using compass coordinates); and wherein a second portion of this attachment member spans most of the circumference of the arcuate enclosure between the 4 o'clock and 8 o'clock positions (or 120-degree and 240-degree positions using compass coordinates).

With respect to specific components, the example shown in FIG. 108 includes: first portion 10801 of an attachment member; second portion 10802 of an attachment member; enclosure 10803 with an outward-facing display screen; and spectroscopic sensors 10804 and 10805 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 109 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 109 can be generally described as an arm-worn device with a bifurcating band, wherein one branch of the band is connected to a display screen and the other branch of the band is connected to a circumferentially or annularly-sliding enclosure which contains one or more spectroscopic sensors. Having spectroscopic sensors on a separate circumferentially or annularly-sliding enclosure enables adjustment of the circumferential location from which data is collected, without changing the location of a display screen.

The example in FIG. 109 can be specified as a wearable device for measuring body hydration level with one or more close-fitting spectroscopic sensors comprising: (a) an attachment member which is configured to span at least 60% of the circumference of a person's arm, wherein this attachment member has a first circumferential portion which bifurcates into a first branch and a second branch, and wherein this attachment member has a second circumferential portion in which the first branch and the second branch reconverge; (b) a display screen which is connected to the first branch of the attachment member; (c) a circumferentially or annularly-sliding enclosure which is connected to the second branch of the attachment member; and (d) one or more spectroscopic sensors which are configured to collect data concerning arm tissue and which are part of (or attached to) the circumferentially or annularly-sliding enclosure.

With respect to specific components, the example shown in FIG. 109 includes: bifurcating attachment member 10901; display screen 10902 on a first branch of the attachment member; circumferentially or annularly-sliding enclosure 10903 on a second branch of the attachment member; and spectroscopic sensor 10904 within the circumferentially or annularly-sliding enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 110 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner.

The example in FIG. 110 can be specified as a wearable device for measuring body hydration level with one or more close-fitting spectroscopic sensors comprising: (a) an attachment member which is configured to span at least 60% of the circumference of a person's arm, wherein this attachment member further comprises a plurality of various-shaped (rigid) polygons which are inter-connected by flexible strips and/or joints; (b) an enclosure which is connected to the attachment member; and (c) one or more spectroscopic sensors which are configured to collect data concerning arm tissue and which are part of (or attached to) the enclosure. Such a design can help to keep the enclosure (and thus the sensors) flat against the surface of the person's arm, even if the attachment member shifts, twists, or rotates.

In an example, a majority of the various-shaped polygons can have five sides. In an example, a majority of the various-shaped polygons can have six sides. In an example, a majority of the various-shaped polygons can have unequal sides. In an example, a majority of the various-shaped polygons can have unequal angles between sides. In an example, sides of the various-shaped polygons can be inter-connected by strips of flexible fabric. In an example, sides of the various-shaped polygons can be inter-connected by hinge joints. In an example, the enclosure can have a display screen on its outward-facing surface.

With respect to specific components, the example shown in FIG. 110 includes: a plurality of various-shaped inter-connected polygons, including polygon 11001; a plurality of flexible joints, including joint 11002; an arcuate enclosure 11003 which further comprises a display screen on its outward-facing surface; and spectroscopic sensors 11004 and 11005 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 111 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. In this example, an attachment member has a honeycomb configuration. This can help to keep the enclosure (and thus the sensors) flat against the surface of the person's arm, even if the attachment member shifts, twists, or rotates.

The example in FIG. 111 can be specified as a wearable device for measuring body hydration level with one or more close-fitting spectroscopic sensors comprising: (a) an attachment member which is configured to span at least 60% of the circumference of a person's arm, wherein this attachment member further comprises a plurality of flexibly-connected (rigid) hexagons; (b) an enclosure which is connected to the attachment member; and (c) one or more spectroscopic sensors which are configured to collect data concerning arm tissue and which are part of (or attached to) the enclosure.

With respect to specific components, the example shown in FIG. 111 includes: a plurality of hexagons, including hexagon 11101; a plurality of flexible joints, including joint 11102; an arcuate enclosure 11103 which further comprises a display screen on its outward-facing surface; and spectroscopic sensors 11104 and 11105 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 112 shows another example of a wearable device for measuring body hydration level with one or more close-fitting spectroscopic sensors. This figure shows the device from a side perspective, as it would appear encircling a lateral cross-section of a person's wrist (or other portion of the person's arm). In this example, one or more spectroscopic sensors are located on a portion of the device which is diametrically-opposite (e.g. symmetric relative to the circumferential center of the device) from the portion of the device which includes a display screen. In an example, one or more spectroscopic sensors can be configured to be worn on the posterior (lower) surface of an arm and a display screen can be configured to be worn on the anterior (upper) surface of the arm, or vice versa.

The specific example in FIG. 112 can be specified as a wearable device for measuring body hydration level with one or more close-fitting spectroscopic sensors comprising: (a) an attachment member which is configured to span at least 60% of the circumference of a person's arm, wherein this attachment member further comprises a first portion with a first elasticity level spanning completely or partially (clockwise) between the 9 o'clock and 3 o'clock (or 270-degree and 90-degree) positions around the device circumference and a second portion with a second elasticity level spanning completely or partially (clockwise) between the 3 o'clock and 9 o'clock (or 90-degree and 270-degree) positions around the device circumference, wherein the second elasticity level is greater than the first elasticity level; (b) a display screen which is part of (or connected to) the first portion of the attachment member; (c) an enclosure which is part of (or connected to) the second portion of the attachment member; and (d) one or more spectroscopic sensors which are configured to collect data concerning arm tissue and which are part of (or attached to) the enclosure.

In an example, the display screen can be centrally located with respect to the first portion of the attachment member. In an example, the center of the display screen can be located at the 12 o'clock (or 0-degrees) position on the circumference of the device. In an example, the enclosure can be centrally located with respect to the second portion of the attachment member. In an example, the center of the display screen can be located at the 6 o'clock (or 180-degrees) position on the circumference of the device.

With respect to specific components, the example shown in FIG. 112 includes: elastic segments 11201 and 11204 of an attachment member; inelastic segments 11202 and 11203 of an attachment member; display screen 11205; enclosure 11206; and spectroscopic sensor 11207. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 113 shows another example of a wearable device for measuring body hydration level with one or more close-fitting spectroscopic sensors. This figure shows the device from a side perspective, as it would appear encircling a lateral cross-section of a person's wrist (or other portion of the person's arm). In this example, one or more spectroscopic sensors are located on a portion of the device which is diametrically-opposite (e.g. symmetric relative to the circumferential center of the device) from the portion of the device which includes a display screen and there is a connector (such as a buckle, clip, clasp, pin, plug, or hook-and-eye mechanism) on the device between the sensors and the screen.

The example in FIG. 113 can be specified as a wearable device for measuring body hydration level with one or more close-fitting spectroscopic sensors comprising: (a) an attachment member which is configured to span at least 60% of the circumference of a person's arm; (b) a display screen which is part of (or connected to) the attachment member at a first location along the circumference of the device; (c) an enclosure which is part of (or connected to) the attachment member at a second location along the circumference of the device, wherein the second location is on the opposite side of the device (e.g. through the circumferential center of the device) from the first location; (d) one or more spectroscopic sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

The example in FIG. 113 can also be specified as a wearable device for measuring body hydration level with one or more close-fitting spectroscopic sensors comprising: (a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member; (d) one or more spectroscopic sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 113 includes: segments 11301, 11302, and 11303 of an attachment member; connector 11304; display screen 11305; enclosure 11306; and spectroscopic sensor 11307. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 114 shows another example of a wearable device for measuring body hydration level with one or more close-fitting spectroscopic sensors. This figure shows the device from a side perspective, as it would appear encircling a lateral cross-section of a person's wrist (or other portion of the person's arm). In this example, there are one or more spectroscopic sensors which are opposite a display screen, a connector between the sensors and the screen, and a hinge which is opposite the connector. If portions of an attachment member connecting these components are relatively rigid, then this example can be called a "clam shell" design.

The example in FIG. 114 can be specified as a wearable device for measuring body hydration level with one or more close-fitting spectroscopic sensors comprising: (a) an attachment member which is configured to span at least 60% of the circumference of a person's arm; (b) a display screen which is part of (or connected to) the attachment member at a first location around the circumference of the device; (c) an enclosure which is part of (or connected to) the attachment member at a second location around the circumference of the device, wherein the second location is on the opposite (e.g. through the circumferential center) side of the device from the first location; (d) one or more spectroscopic sensors which are configured to collect data concerning arm tissue and which are part of (or attached to) the enclosure; and (e) a connector which connects two ends of the attachment member to each other at a third location around the circumference of the device, wherein this third location is between the first and second locations; (f) a hinge (or joint) which connects two portions of the attachment member to each other at a fourth location around the circumference of the device, wherein this fourth location is on the opposite (e.g. through the circumferential center) side of the device from the third location.

The example in FIG. 114 can also be specified as a wearable device for measuring body hydration level with one or more close-fitting spectroscopic sensors comprising:

(a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member; (d) one or more spectroscopic sensors which are configured to collect data concerning arm tissue and which are part of (or attached to) the enclosure; (e) a connector which connects two ends of the attachment member to each other, wherein this connector is located between the 7 o'clock and 11 o'clock (or 210-degree and 330-degree) positions on the circumference of the attachment member; and (f) a hinge which connects two portions of the attachment member to each other, wherein this hinge is located between the 1 o'clock and 5 o'clock (or 30-degree and 150-degree) positions on the circumference of the attachment member.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 114 includes: segments 11401, 11402, and 11403 of an attachment member; connector 11404; hinge 11405; display screen 11406; enclosure 11407; and spectroscopic sensor 11408. In an example, this device can further comprise one or more components selected from the group consisting of: a data processor; a battery and/or energy harvesting unit; a display screen; a data transmitter; and a data receiver. Relevant embodiment variations discussed with respect to FIG. 104 or elsewhere in this disclosure can also be applied to this example.

FIG. 115 shows another example of a wearable device for measuring body hydration level with one or more close-fitting spectroscopic sensors. This figure shows the device from a side perspective, as it would appear encircling a lateral cross-section of a person's wrist (or other portion of the person's arm). This example is similar to the one shown in FIG. 114 except a spectroscopic sensor is on the center-facing surface of a compressible member.

With respect to specific components, the example shown in FIG. 115 includes: segments 11501, 11502, and 11503 of an attachment member; connector 11504; hinge 11505; display screen 11506; compressible member 11507; and spectroscopic sensor 11508. In an example, this device can further comprise one or more components selected from the group consisting of: a data processor; a battery and/or energy harvesting unit; a display screen; a data transmitter; and a data receiver.

In an example, a compressible member can be an elastic member which is filled with a fluid, gel, or gas. In an example, a compressible member can be a pneumatic or hydraulic chamber which is filled with a fluid, gel, or gas. In an example, a compressible member can be a balloon. In an example, a compressible member can be made from compressible foam. Relevant embodiment variations discussed with respect to FIG. 114 or elsewhere in this disclosure can also be applied to this example.

FIG. 116 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. Described generally, the example shown in FIG. 116 is a hydration-sensing device with proximal and distal arcuate display screens which are attached to a person's arm by a band, wherein the band has one holes on each side of a virtual line connecting the centers of the two displays.

Described more specifically, the example shown in FIG. 116 is a wearable device for measuring body hydration level with one or more close-fitting spectroscopic sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) an attachment member which attaches the proximal arcuate display screen and the distal arcuate display screen to the person's arm, wherein this attachment member has one hole on each side of a virtual line connecting the center of the proximal arcuate display screen and the center of the distal arcuate display screen; and (d) one or more spectroscopic sensors which are configured to collect data concerning arm tissue.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, holes on each side of this virtual line can be circular. In an example, the area of a hole in an attachment member can be half of the area of a display screen. In an example, the area of a hole in an attachment member can be the same as the area of a display screen. In an example, the area of a hole in an attachment member can be between 50% and 100% of the area of a display screen.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

Specific components in the example shown in FIG. 116 include: attachment member 11601 which has a hole on each side of a central longitudinal axis of the anterior (upper) surface of an arm; distal display screen 11602; proximal display screen 11604; and spectroscopic sensors 11603 and 11605. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 117 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. Described generally, the example shown in FIG. 117 is an arm-worn hydration-sensing device with: proximal and distal arcuate display screens; and right and left side enclosures with spectroscopic sensors.

Described more specifically, the example shown in FIG. 117 is a wearable device for measuring body hydration level with one or more close-fitting spectroscopic sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) a right-side enclosure, wherein the center of this right-side enclosure is to the right of a virtual line connecting the center of the proximal arcuate display screen and the center of the distal arcuate display screen, and wherein this right-side enclosure further comprises a spectroscopic sensor that is configured to collect data concerning arm tissue; (d) a left-side enclosure, wherein the center of this left-side enclosure is to the left of a virtual line connecting the center of the proximal arcuate display screen and the center of the distal arcuate display screen, and wherein this left-side enclosure further comprises a spectroscopic sensor that is configured to collect data concerning arm tissue; and (e) an attachment member which attaches the proximal arcuate display screen, the distal arcuate display screen, the right-side enclosure, and the left-side enclosure to the person's arm.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

Specific components in the example shown in FIG. 117 include: attachment member 11701; distal display screen 11702; proximal display screen 11703; right-side enclosure 11706 with spectroscopic sensor 11707; and left-side enclosure 11704 with spectroscopic sensor 11705. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 118 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. Described generally, the example shown in FIG. 118 is an arm-worn hydration-sensing device with proximal and distal arcuate display screens which are circumferentially or annularly attached to an arm by a bifurcating band (or strap) and also connected to each other by a band (or strap) along the central longitudinal axis of the anterior (upper) surface of the arm.

Described more specifically, the example shown in FIG. 118 is a wearable device for measuring body hydration level with one or more close-fitting spectroscopic sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more spectroscopic sensors that are configured to collect data concerning arm tissue; (d) a bifurcated attachment member, wherein this bifurcated attachment member bifurcates into a proximal and distal branches as it spans the anterior (upper) surface of the person's arm, wherein these proximal and distal branches reconverge as the bifurcated attachment member further spans the anterior (upper) surface of the person's arm, wherein the proximal branch is configured to attach the proximal arcuate display screen to the person's arm, and wherein the distal branch is configured to attach the distal arcuate display screen to the person's arm; and (e) an inter-display connecting band (or strip) which connects the proximal arcuate display screen to the distal arcuate display screen.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an inter-display connecting band (or strip) connecting the center of a proximal display screen and the center of a distal display screen can parallel to the longitudinal axis of the arm.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

Specific components in the example shown in FIG. 118 include: bifurcated attachment member 11801; distal display screen 11802; proximal display screen 11804; spectroscopic sensors 11803 and 11805; and inter-display connecting band 11806. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 119 shows another example of a wearable device for measuring body hydration level with one or more close-fitting spectroscopic sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. Described generally, the example shown in FIG. 119 is an arm-worn hydration-sensing device with proximal and distal arcuate display screens which are attached to a person's arm by a band with an "S"-shaped portion spanning the anterior (upper) portion of the arm.

Described more specifically, the example shown in FIG. 119 is a wearable device for measuring body hydration level with one or more close-fitting spectroscopic sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more spectroscopic sensors that are configured to collect data concerning arm tissue; (d) a attachment member which is attached to the right side of the proximal arcuate display screen and to the left side of the distal arcuate display screen; (e) an inter-display connecting band which connects the distal portion of the proximal display screen to the proximal portion of the distal arcuate display screen.

Alternatively, a wearable device for measuring body hydration level with one or more close-fitting spectroscopic sensors can comprise: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more spectroscopic sensors that are configured to collect data concerning arm tissue; (d) a attachment member which is attached to the left side of the proximal arcuate display screen and to the right side of the distal arcuate display screen; (e) an inter-display band which connects the distal portion of the proximal display screen to the proximal portion of the distal arcuate display screen.

In an example, an attachment member can be a strap, band, bracelet, bangle, ring, armlet, gauntlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

Specific components in the example shown in FIG. 119 include: attachment member 11901; connector 11902; distal display screen 11903; proximal display screen 11905; spectroscopic sensors 11904 and 11906; and inter-display band 11907. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 120 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 120 can be described as a wearable device with two bands which encircle an arm, wherein these two bands are movably-attached to each other in a manner which allows a second band (with spectroscopic sensors) to be rotated relative to a first band. Such rotation enables adjustment of the locations of one or more spectroscopic sensors relative to the arm in order to improve collection of data from arm tissue.

More specifically, the example shown in FIG. 120 is a wearable device for measuring body hydration level with one or more close-fitting spectroscopic sensors comprising: (a) a first band which is configured to span at least 60% of the circumference of a person's arm; (b) a second band which is configured to span at least 60% of the circumference of the person's arm, wherein the first band and the second band are attached to each other by a mechanism that enables the second band to be circumferentially or annularly-rotated relative to the first band; and (c) one or more spectroscopic sensors which are configured to collect data concerning arm tissue, wherein these spectroscopic sensors are part of (or attached to) the second band.

More generally, the example shown in FIG. 120 is a wearable device for measuring body hydration level with one or more close-fitting spectroscopic sensors comprising: (a) a first attachment member which is configured to span at least 60% of the circumference of a person's arm; (b) a second attachment member which is configured to span at least 60% of the circumference of the person's arm, wherein the first attachment member and the second attachment member are attached to each other by a mechanism that enables the second attachment member to be circumferentially or annularly-rotated relative to the first attachment member; and (c) one or more spectroscopic sensors which are configured to collect data concerning arm tissue, wherein these spectroscopic sensors are part of (or attached to) the second attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a first attachment member can be attached to a person's arm in a relatively-fixed manner, so that it does not substantively rotate and/or shift around the circumference of the arm. In an example, a second attachment member can be attached to a person's arm in a relatively-loose manner, so that it can rotate around the circumference of the arm. In an example, a second attachment member can be attached (or connected) to the first attachment member by a connection mechanism which enables the second attachment member to be rotated around the circumference of the person's arm (relative to the first attachment member).

When the second attachment member contains one or more spectroscopic sensors, rotation of the second attachment member also rotates these sensors relative to the circumference of the arm. This enables a user to find the optimal locations around the circumference of the arm from which to collect data for a selected application. In an example, this device can further include a locking mechanism which locks the location of the second attachment member relative to the first attachment member when the optimal location for sensors is found. In an example, a connection mechanism between the two attachment members can be a ball-bearing mechanism. In an example, a connection mechanism can be a sliding tongue-and-groove (or tongue-and-slot) mechanism. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, a first attachment member can include a display screen on its outward-facing surface. In an example, this device can function as a smart watch. Relevant embodiment variations discussed elsewhere in this disclosure can also be applied to this example. Specific components in the example shown in FIG. 120 include: first band 12001; second band 12002; display screen 12003; and spectroscopic sensors including 12004.

FIG. 121 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 121 is like the one shown in FIG. 120, except that in FIG. 121 there are three bands instead of two and spectroscopic sensors are on a central band which rotates relative to distal and proximal bands. Such rotation enables adjustment of the locations of one or more spectroscopic sensors relative to the arm in order to improve collection of data from arm tissue.

The example shown in FIG. 121 is a wearable device for measuring body hydration level with one or more close-fitting spectroscopic sensors comprising: (a) a distal attachment member which is configured to span at least 60% of the circumference of a person's arm; (b) a proximal attachment member which is configured to span at least 60% of the circumference of a person's arm; (c) a central attachment member which is configured to span at least 60% of the circumference of the person's arm, wherein this central attachment member is between the distal and proximal attachment members, and wherein this central attachment member is circumferentially or annularly-rotated relative to the distal and proximal attachment members; and (d) one or more spectroscopic sensors which are configured to collect data concerning arm tissue, wherein these spectroscopic sensors are part of (or attached to) the central attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, distal and proximal attachment members can be attached to a person's arm in a relatively-fixed manner, so that they do not substantively rotate and/or shift around the circumference of the arm. In an example, a central attachment member can be attached to a person's arm in a relatively-loose manner, so that it can rotate around the circumference of the arm. In an example, a central attachment member can be attached (or connected) to the distal and proximal attachment members by a connection mechanism which enables the second attachment member to be rotated around the circumference of the person's arm.

When a central attachment member contains one or more spectroscopic sensors, rotation of the central attachment member also rotates these sensors relative to the circumference of the arm. This enables a user to find the optimal locations around the circumference of the arm from which to collect data for a selected application. In an example, this device can further include a locking mechanism which locks the location of the central attachment member relative to the distal and proximal attachment members when the optimal location for sensors is found. In an example, a connection mechanism between the two attachment members can be a ball-bearing mechanism. In an example, a connection mechanism can be a sliding tongue-and-groove (or tongue-and-slot) mechanism. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, a distal and/or proximal attachment member can include a display screen on an outward-facing surface. In an example, this device can function as a smart watch. Relevant embodiment variations discussed elsewhere in this disclosure can also be applied to this example. Specific components in the example shown in FIG. 121 include: distal band 12101; central band 12102; proximal band 12103; display screens 12104 and 12105; and spectroscopic sensors including 12106.

FIG. 122 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 122 can be described as an arm-wearable device with a relatively-rigid band and a relatively-elastic band, wherein each of these bands spans at least 60% of the circumference of a person's arm, wherein these bands are connected to each other, and wherein there are spectroscopic sensors on the relatively-elastic band.

More specifically, the example shown in FIG. 122 is a wearable device for measuring body hydration level with one or more close-fitting spectroscopic sensors comprising: (a) an inelastic attachment member which is configured to span at least 60% of the circumference of a person's arm, wherein this inelastic attachment member has a first elasticity level; (b) an elastic attachment member which is configured to span at least 60% of the circumference of a person's arm, wherein this elastic attachment member has a second elasticity level, wherein the second elasticity level is greater than the first elasticity level, and wherein the elastic attachment member is connected to the inelastic attachment member; and (c) one or more spectroscopic sensors which are configured to collect data concerning arm tissue, wherein these spectroscopic sensors are part of (or attached to) the elastic attachment member.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 122 include: inelastic band 12201; elastic band 12202; display screen 12203; and spectroscopic sensors including 12204.

FIG. 123 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example shown in FIG. 123 can be described as an arm-wearable device with two or more modular and connectable bands, wherein each band spans at least 60% of the circumference of a person's arm, and wherein one or more of these bands house spectroscopic sensors.

More specifically, the example shown in FIG. 123 is a wearable device for measuring body hydration level with one or more close-fitting spectroscopic sensors comprising: (a) a first modular band which is configured to span at least 60% of the circumference of a person's arm; (b) a second modular band which is configured to span at least 60% of the circumference of a person's arm, wherein the first modular band and the second modular band have a first configuration in which they are not connected to each other and are not worn by a person, wherein the first band and the second band have a second configuration wherein they are connected to each other and worn on a person's arm, and wherein the first band and the second band can be changed from the first configuration to the second configuration by the person who wears them, and wherein the first band and the second band can be changed back from the second configuration to the first configuration by the person who wears them; and (c) one or more spectroscopic sensors which are configured to collect data concerning arm tissue, wherein these spectroscopic sensors are part of (or attached to) one or both of the modular bands.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 123 include: first modular band 12301; second modular band 12302; temporary connectors 12303 and 12304; and display screens 12305 and 12306.

FIG. 124 shows another example of a wearable device for measuring body hydration level with one or more close-fitting spectroscopic sensors. This figure shows the device from a side perspective, as it would appear encircling a lateral cross-section of a person's arm.

The example in FIG. 124 can be described as an arm-wearable device with a partial-circumferential inner elastic band and spectroscopic sensors. Such a device can have an outer inelastic band with a first elasticity level which spans a first percentage of the arm circumference and an inner elastic band with a second elasticity level which spans a second percentage of the arm circumference—wherein the second percentage is less than the first percentage and the second elasticity level is greater than the first elasticity level. In the example shown in FIG. 124, an outer inelastic band (and display screen) spans the entire arm circumference and a semi-circular inner elastic band (interior relative to the outer inelastic band) spans only half of the arm circumference. This design can provide an overall semi-rigid structure (for housing a display screen), but can also keep spectroscopic sensors close against the surface of the arm for consistent collection of data.

More specifically, the example shown in FIG. 124 is a wearable device for measuring body hydration level with one or more close-fitting spectroscopic sensors comprising: (a) an outer inelastic band which is configured to span a first percentage of a person's arm and which has a first elasticity level; (b) an inner elastic band which is configured to span a second percentage of a person's arm and which has a second elasticity level, wherein this inner elastic band is configured to be closer to the surface of the arm than the outer inelastic band, wherein the second percentage is less than the first percentage, and wherein the second elasticity level is greater than the first elasticity level; and (c) one or more spectroscopic sensors which are configured to collect data concerning arm tissue, wherein these spectroscopic sensors are part of (or attached to) the inner elastic band.

Alternatively, the example shown in FIG. 124 can be specified as a wearable device for measuring body hydration level with one or more close-fitting spectroscopic sensors comprising: (a) an outer inelastic band with a first arcuate length and a first elasticity level; (b) an inner elastic band with a second arcuate length and a second elasticity level, wherein this inner elastic band is located on the concave side of the outer elastic band, wherein the second percentage is less than the first percentage, and wherein the second elasticity level is greater than the first elasticity level; and (c) one or more spectroscopic sensors which are configured to collect data concerning arm tissue, wherein these spectroscopic sensors are part of (or attached to) the inner elastic band.

In an example, the word "ring", "strap", "bracelet", "bangle", "armlet", "sleeve", or "cuff" can be substituted for the word "band" in the above specifications. In an example, an outer inelastic band can span Y % of the circumference of a person's arm and an inner elastic band can span X % of the circumference of a person's arm, wherein Y % is at least 20 percentage points greater than X %. In an example, Y % can be 75% and X % can be 50%. In an example, the ends of the inner elastic band can be attached to the outer inelastic band. In an example, an inner elastic band can be configured to span the anterior (upper) surface of a person's arm. In an example, an inner elastic band can be configured to span the posterior (lower) surface of a person's arm.

In an example, an outer inelastic band can be attached to a person's arm by connecting two ends of an outer inelastic band with a clasp, clip, buckle, hook, pin, plug, or hook-and-eye mechanism. In an example, an outer inelastic band can be attached to a person's arm by stretching and sliding it over the person's hand onto the arm. In an example, an outer inelastic band can be attached to a person's arm by applying force to pull two ends apart to slip the member over the arm, wherein the two ends retract back towards each other when the force is removed. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 124 include: four segments (12401, 12402, 12404, and 12405) of an outer inelastic band; inner elastic band 12407; spectroscopic sensors (12408, 12409, and 12410); outer elastic band clasp 12403; and display screen 12406.

FIG. 125 shows another example of a wearable device for measuring body hydration level with one or more close-fitting spectroscopic sensors. This figure shows the device from a side perspective, as it would appear encircling a lateral cross-section of a person's wrist (or other portion of their arm). The example in FIG. 125 is like the one shown in FIG. 124, except that in FIG. 125 the outer inelastic band is sufficiently resilient that its ends hold onto the person's arm without the need for a clasp. The outer inelastic band can be attached to a person's arm by applying force to pull two ends apart to slip the member over the arm, wherein the two ends retract back towards each other when the force is removed.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 125 include: four segments (12501, 12502, 12504, and 12505) of an outer inelastic band; inner elastic band 12507; spectroscopic sensors (12508, 12509, and 12510); and display screen 12506.

FIG. 126 shows another example of a wearable device for measuring body hydration level with one or more close-fitting spectroscopic sensors. This figure shows the device from a side perspective, as it would appear encircling a lateral cross-section of a person's arm. The example in FIG. 126 can be described as an arm-wearable device with an outer arcuate inelastic band, an inner arcuate elastic band, and spectroscopic sensors which are part of the inner band. This design can provide an overall semi-rigid structure (e.g. to hold a rigid display screen in place) and also keep spectroscopic sensors close against the surface of the arm for consistent collection of data.

The example shown in FIG. 126 can be specified as a wearable device for measuring body hydration level with one or more close-fitting spectroscopic sensors comprising: (a) an outer arcuate inelastic band which is configured to span at least 60% of the circumference of a person's arm and which has a first elasticity level; (b) an inner arcuate elastic band which is located on (and attached to) the concave side of the outer arcuate band and which has a second elasticity level, wherein the second elasticity level is greater than the first elasticity level; and (c) one or more spectroscopic sensors which are configured to collect data concerning arm tissue, wherein these spectroscopic sensors are part of (or attached to) the inner arcuate elastic band. In various examples, a ring, strap, bracelet, bangle, armlet, sleeve, or cuff can be substituted for a band.

Alternatively, the example shown in FIG. 126 can be specified as a wearable device for measuring body hydration level with one or more close-fitting spectroscopic sensors comprising: (a) an outer arcuate inelastic band, wherein this outer arcuate inelastic band is configured to span at least 60% of the circumference of a person's arm, wherein this outer arcuate inelastic band is configured to be a first average distance from the surface of the person's arm, and wherein this outer arcuate inelastic band has a first elasticity level; (b) an inner arcuate elastic band, wherein this inner arcuate elastic band is attached to the outer arcuate inelastic band, wherein this inner arcuate elastic band is configured to be an second average distance from the surface of the person's arm, wherein this inner arcuate elastic band has a second elasticity level, wherein the second average distance is less than the first average distance, and wherein the second elasticity level is greater than the first elasticity level; and (c) one or more spectroscopic sensors which are configured to collect data concerning arm tissue, wherein these spectroscopic sensors are part of (or attached to) the inner arcuate elastic band. In various examples, a ring, strap, bracelet, bangle, armlet, sleeve, or cuff can be substituted for a band.

In an example, an outer arcuate inelastic band can be attached to a person's arm by connecting two ends of the outer inelastic band with a clasp, clip, buckle, hook, pin, plug, or hook-and-eye mechanism. In an example, an outer arcuate inelastic band can be attached to a person's arm by stretching and sliding it over the person's hand onto the arm. In an example, an outer arcuate inelastic band can be attached to a person's arm by applying force to pull two ends apart to slip the member over the arm, wherein the two ends retract back towards each other when the force is removed. In an example, an inner arcuate elastic band can be made from a stretchable fabric. In an example, an inner arcuate elastic band can be attached to an outer arcuate inelastic band at the ends of the arcuate inelastic band. In an example, an inner arcuate elastic band can be attached to an outer arcuate inelastic band near mid-points of segments of the outer arcuate inelastic band. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 126 include: four segments (12601, 12602, 12604, and 12605) of an outer inelastic band; inner elastic band 12607; spectroscopic sensors (12608, 12609, and 12610); and display screen 12606.

FIG. 127 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example in FIG. 127 can be described as an arm-wearable device with an outer rigid "clam shell" structure to hold a display screen in place and an inner arcuate elastic band to keep spectroscopic sensors close against the surface of the arm.

The example shown in FIG. 127 can be specified as a wearable device for measuring body hydration level with one or more close-fitting spectroscopic sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an arcuate elastic band which is located within the concavity of the clam shell structure and is attached to the clam shell structure; and (c) one or more spectroscopic sensors which are configured to collect data concerning arm tissue, wherein these spectroscopic sensors are part of (or attached to) the arcuate elastic band.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism. In an example, an inner arcuate elastic band can be made from a stretchable fabric. In an example, an inner arcuate elastic band can be attached to an upper half-circumferential portion of a clam shell structure. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 127 include: two segments 12702 and 12703 of an upper half-circumferential portion of a clam shell structure; a lower half-circumferential portion 12701 of the clam shell structure; a joint (or hinge) 12704 between the upper and lower portions of the clam shell structure; a reversible connector 12705 between the upper and lower portions of the clam shell structure; an inner elastic band 12707; spectroscopic sensors 12708, 12709, and 12710; and display screen 12706.

FIG. 128 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example in FIG. 128 is like the one shown in FIG. 127, except that in FIG. 128 an inner arcuate elastic band spans the posterior (lower) surface of a person's arm. Specific components in the example shown in FIG. 128 include: two segments 12802 and 12803 of an upper half-circumferential portion of a clam shell structure; a lower half-circumferential portion 12801 of the clam shell structure; a joint (or hinge) 12804 between the upper and lower portions of the clam shell structure; a reversible connector 12805 between the upper and lower portions of the clam shell structure; an inner elastic band 12807; spectroscopic sensors 12808, 12809, and 12810; and display screen 12806.

FIG. 129 shows another example of a wearable device for measuring body hydration level with one or more close-fitting spectroscopic sensors. This figure shows the device from a side perspective, as it would appear encircling a lateral cross-section of a person's wrist (or other portion of the person's arm). The example in FIG. 129 can be described as an arm-wearable device with an outer rigid "clam shell" structure and inward-facing flexible undulations to keep spectroscopic sensors close against the surface of the arm.

The example shown in FIG. 129 can be specified as a wearable device for measuring body hydration level with one or more close-fitting spectroscopic sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an inward-facing undulating member which is part of (or attached to) the clam shell structure; and (c) one or more spectroscopic sensors which are configured to collect data concerning arm tissue, wherein these spectroscopic sensors are part of (or attached to) the undulating member.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism.

In an example, an inward-facing undulating member can have a sinusoidal shape. In an example, an inward-facing undulating member can be flexible and/or compressible. In an example, an inward-facing undulating member can be elastic and filled with a liquid, gel, or gas. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 129 include: two segments 12902 and 12903 of an upper half-circumferential portion of a clam shell structure; a lower half-circumferential portion 12901 of the clam shell structure; a joint (or hinge) 12904 between the upper and lower portions of the clam shell structure; a reversible connector 12905 between the upper and lower portions of the clam shell structure; inward-facing undulating members including 12907 and 12908; spectroscopic sensors including 12909 and 12910; and display screen 12906.

FIG. 130 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example in FIG. 130 can be described as an arm-wearable device with two display screens suspended by an elastic material between two arcuate bands.

The example shown in FIG. 130 can be specified as a wearable device for measuring body hydration level with one or more close-fitting spectroscopic sensors comprising: (a) a distal arcuate band which is configured to span at least 60% of the circumference of a person's arm; (b) a proximal arcuate band which is configured to span at least 60% of the circumference of a person's arm, wherein distal is defined as further from a person's shoulder and proximal is defined as closer to the person's shoulder; (c) an elastic member that is between the distal arcuate band and the proximal arcuate band which connects the distal actuate band to the proximal arcuate band; and (d) two arcuate display screens between the distal arcuate band and the proximal arcuate band, wherein these display screens are attached to the elastic member; and (e) one or more spectroscopic sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic member can be made from elastic fabric. In an example, an elastic member can be an elastic mesh. In an example, an elastic member can have four arcuate sides: two convex sides and two concave sides. In an example, one concave side can connect to the distal arcuate band and the other concave side can connect to the proximal band. In an example, two convex sides can be between the two bands. In an example, an elastic member can completely surround the perimeters of two display screens. In an example, an elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands. In an example, spectroscopic sensors can be part of (or attached to) display screens and/or enclosures which house display screens. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 130 include: distal arcuate band 13001; proximal arcuate band 13002; elastic member 13003 between the two arcuate bands; display screens 13004 and 13005 suspended by the elastic member; and spectroscopic sensors 13006 and 13007.

FIG. 131 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example in FIG. 131 can be described as an arm-wearable device with two display screens which are suspended by elastic straps between two arcuate bands.

The example shown in FIG. 131 can be specified as a wearable device for measuring body hydration level with one or more close-fitting spectroscopic sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a plurality of elastic straps between the distal arcuate band and the proximal arcuate band which connect the distal actuate band to the proximal arcuate band; and (d) two arcuate display screens between the distal arcuate band and the proximal arcuate band, wherein these display screens are attached to the plurality of elastic straps; and (e) one or more spectroscopic sensors which are configured to collect data concerning arm tissue. In an example, a ring, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic strap can be made from elastic fabric. In an example, an elastic strap can be an elastic mesh. In an example, each display screen can be connected to three elastic straps. In an example, each display screen can be connected to three elastic straps with connection points which are substantially equidistant around the circumference of a display screen. In an example, each arcuate band can be connected to two elastic straps. In an example, two display screens can be connected by one elastic strap. In an example, there can be five elastic straps in total. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands. In an example, spectroscopic sensors can be part of (or attached to) display screens and/or enclosures which house display screens. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 131 include: distal arcuate band 13101; proximal arcuate band 13102; a plurality of elastic straps including 13103, 13104, 13105, 13106, and 13107; display screens 13108 and 13110 suspended by the elastic straps; and spectroscopic sensors 13109 and 13111.

FIG. 132 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example in FIG. 132 can be described as an arm-wearable device with two display screens whose centers are at 12 o'clock and 6 o'clock positions around a circular band on the anterior (upper) surface of an arm.

The example shown in FIG. 132 can be specified as a wearable device for measuring body hydration level with one or more close-fitting spectroscopic sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a distal display screen on the distal arcuate band; (d) a proximal display screen on the proximal arcuate band; (e) a right circle-segment band which connects the right side of the distal display screen to the right side of the proximal display screen; (f) a left circle-segment band which connects the left side of the distal display screen to the left side of the proximal display screen; and (g) one or more spectroscopic sensors which are configured to collect data concerning arm tissue.

In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands. In an example, spectroscopic sensors can be part of (or attached to) display screens and/or enclosures which house display screens. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 132 include: portions 13201 and 13202 of a distal arcuate band; portions 13203 and 13204 of a proximal arcuate band; display screens 13207 and 13209; right circle-segment band 13206; left circle-segment band 13205; and spectroscopic sensors 13208 and 13210.

FIG. 133 shows another example of a wearable device for measuring body hydration level with one or more close-fitting spectroscopic sensors. This figure shows the device from a top-down perspective, as it would appear spanning the anterior (upper) surface of a person's wrist (or other portion of the person's arm) in a circumferential manner. The example in FIG. 133 can be described as an arm-wearable device with two display screens suspended by an oval (or elliptical or circular) elastic member between two arcuate bands.

The example shown in FIG. 133 can be specified as a wearable device for measuring body hydration level with one or more close-fitting spectroscopic sensors comprising: (a) a distal arcuate band which is configured to span at least 60% of the circumference of a person's arm; (s) a proximal arcuate band which is configured to span at least 60% of the circumference of a person's arm, wherein distal is defined as further from a person's shoulder and proximal is defined as closer to the person's shoulder; (t) an oval (or elliptical or circular) elastic member that is between the distal arcuate band and the proximal arcuate band which connects the distal actuate band to the proximal arcuate band; and (r) two arcuate display screens between the distal arcuate band and the proximal arcuate band, wherein these display screens are attached to the oval (or elliptical or circular) elastic member; and (o) one or more spectroscopic sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an oval (or elliptical or circular) elastic member can be made from elastic fabric. In an example, an oval (or elliptical or circular) elastic member can be an elastic mesh. In an example, an oval (or elliptical or circular) elastic member can completely surround the perimeters of two display screens. In an example, an oval (or elliptical or circular) elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands. In an example, spectroscopic sensors can be part of (or attached to) display screens and/or enclosures which house display screens. In an example, a spectroscopic sensor can measure the spectrum of light energy reflected from (and/or absorbed by) tissue of the person's arm.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 133 include: distal arcuate band 13301; proximal arcuate band 13302; oval (or elliptical or circular) elastic member 13303 between the two arcuate bands; display screens 13304 and 13305 suspended by the oval (or elliptical or circular) elastic member; and spectroscopic sensors 13306 and 13307.

I claim:

1. An arcuate wearable device for measuring a person's hydration level comprising:
    a primary electronics housing which is configured to be worn on a dorsal surface of a person's wrist and/or arm;
    a circumferential or annular series of secondary electronics housings, wherein at least one of the secondary electronics housings includes a circular or polygonal array of light emitters around a central light receiver, wherein the light emitters are configured to emit light toward the surface of a person's wrist and/or arm, and wherein the light receiver is configured to receive the light emitted from the light emitters after interaction with the person's wrist and/or arm;
    a circumferential or annular series of flexible members; wherein the flexible members are selected from the group consisting of: bands, straps, strips, swatches, wires, cords, threads, joints, and chain links; wherein the flexible members connect the primary electronics housing and the secondary electronics housings into an arcuate wearable band which spans at least half of the circumference of the person's wrist and/or arm; and
    a data processor which is configured to analyze the spectrum of light received by the light receiver in order to measure the person's hydration level.

* * * * *